US010252997B2

(12) United States Patent
Mizojiri et al.

(10) Patent No.: US 10,252,997 B2
(45) Date of Patent: Apr. 9, 2019

(54) MONOCYCLIC COMPOUND

(71) Applicant: Takeda Pharmaceutical Company Limited, Chuo-ku, Osaka-shi, Osaka (JP)

(72) Inventors: Ryo Mizojiri, Kanagawa (JP);
Moriteru Asano, Kanagawa (JP);
Daisuke Tomita, Kanagawa (JP);
Hiroshi Banno, Kanagawa (JP);
Michiko Tawada, Kanagawa (JP);
Noriyuki Nii, Kanagawa (JP); Krista E. Gipson, Medford, MA (US);
Hironobu Maezaki, Kanagawa (JP);
Shuntarou Tsuchiya, Kanagawa (JP);
Mayumi Imai, Kanagawa (JP);
Yuichiro Amano, Kanagawa (JP)

(73) Assignee: Takeda Pharmaceutical Company Limited, Osaka (JP)

(*) Notice: Subject to any disclaimer, the term of this patent is extended or adjusted under 35 U.S.C. 154(b) by 0 days.

(21) Appl. No.: 15/563,128

(22) PCT Filed: Mar. 30, 2016

(86) PCT No.: PCT/JP2016/060326
§ 371 (c)(1),
(2) Date: Sep. 29, 2017

(87) PCT Pub. No.: WO2016/159049
PCT Pub. Date: Oct. 6, 2016

(65) Prior Publication Data
US 2018/0079723 A1 Mar. 22, 2018

(30) Foreign Application Priority Data
Mar. 31, 2015 (JP) .................. 2015-071614

(51) Int. Cl.
| | |
|---|---|
| *C07D 213/65* | (2006.01) |
| *A61K 31/165* | (2006.01) |
| *A61K 31/167* | (2006.01) |
| *A61K 31/277* | (2006.01) |
| *A61K 31/381* | (2006.01) |
| *A61K 31/402* | (2006.01) |
| *A61K 31/415* | (2006.01) |
| *A61K 31/42* | (2006.01) |
| *A61K 31/421* | (2006.01) |
| *A61K 31/426* | (2006.01) |
| *A61K 31/427* | (2006.01) |
| *A61K 31/44* | (2006.01) |

(Continued)

(52) U.S. Cl.
CPC .......... *C07D 213/65* (2013.01); *A61K 31/165* (2013.01); *A61K 31/167* (2013.01); *A61K 31/277* (2013.01); *A61K 31/381* (2013.01); *A61K 31/402* (2013.01); *A61K 31/415* (2013.01); *A61K 31/42* (2013.01); *A61K 31/421* (2013.01); *A61K 31/426* (2013.01); *A61K 31/427* (2013.01); *A61K 31/44* (2013.01); *A61K 31/444* (2013.01); *A61K 31/4412* (2013.01); *A61K 31/4436* (2013.01); *A61K 31/4439* (2013.01); *A61K 31/451* (2013.01); *A61K 31/454* (2013.01); *A61K 31/4965* (2013.01); *A61K 31/50* (2013.01); *A61K 31/501* (2013.01); *A61K 31/505* (2013.01); *A61K 31/506* (2013.01); *C07C 233/18* (2013.01); *C07C 233/25* (2013.01); *C07C 233/47* (2013.01); *C07C 255/54* (2013.01); *C07D 207/08* (2013.01); *C07D 207/12* (2013.01); *C07D 211/44* (2013.01); *C07D 211/46* (2013.01); *C07D 213/643* (2013.01); *C07D 213/69* (2013.01); *C07D 213/74* (2013.01); *C07D 213/75* (2013.01); *C07D 213/81* (2013.01); *C07D 231/12* (2013.01); *C07D 237/14* (2013.01); *C07D 239/34* (2013.01); *C07D 241/18* (2013.01); *C07D 261/08* (2013.01); *C07D 263/32* (2013.01); *C07D 263/42* (2013.01); *C07D 277/34* (2013.01); *C07D 333/20* (2013.01); *C07D 401/04* (2013.01); *C07D 401/12* (2013.01); *C07D 409/04* (2013.01); *C07D 413/04* (2013.01); *C07D 417/04* (2013.01); *C07C 2601/02* (2017.05); *C07C 2601/14* (2017.05); *C12N 9/99* (2013.01); *C12N 15/09* (2013.01)

(58) Field of Classification Search
CPC .................................................. C07D 213/65
USPC ........................................................ 546/296
See application file for complete search history.

(56) References Cited

U.S. PATENT DOCUMENTS

| | | |
|---|---|---|
| 6,399,629 B1 | 6/2002 | Chamberland et al. |
| 2005/0245530 A1 | 11/2005 | Borzilleri et al. |

(Continued)

FOREIGN PATENT DOCUMENTS

| | | |
|---|---|---|
| WO | WO 00/001714 A1 | 1/2000 |
| WO | WO 2005/117867 A2 | 12/2005 |

(Continued)

OTHER PUBLICATIONS

Bhadauriya et al., "Identification of dual Acetyl-CoA carboxylases 1 and 2 inhibitors by pharmacophore based virtual screening and molecular docking approach," Mol. Divers, 2013, 17:139-149.

(Continued)

*Primary Examiner* — Taofiq A Solola
(74) *Attorney, Agent, or Firm* — Foley & Lardner LLP

(57) ABSTRACT

The present invention relates to a compound which may be useful as an agent for the prophylaxis or treatment of cancer, hepatitis, hepatic fibrosis, fatty liver and the like.

6 Claims, 2 Drawing Sheets
Specification includes a Sequence Listing.

(51) Int. Cl.
*A61K 31/4412* (2006.01)
*A61K 31/4436* (2006.01)
*A61K 31/4439* (2006.01)
*A61K 31/444* (2006.01)
*A61K 31/451* (2006.01)
*A61K 31/454* (2006.01)
*A61K 31/4965* (2006.01)
*A61K 31/50* (2006.01)
*A61K 31/501* (2006.01)
*A61K 31/505* (2006.01)
*A61K 31/506* (2006.01)
*C07D 213/75* (2006.01)
*C07D 213/81* (2006.01)
*C07D 231/12* (2006.01)
*C07D 333/20* (2006.01)
*C07D 401/04* (2006.01)
*C07D 237/14* (2006.01)
*C07D 239/34* (2006.01)
*C07D 409/04* (2006.01)
*C07D 413/04* (2006.01)
*C07D 241/18* (2006.01)
*C07D 417/04* (2006.01)
*C07C 233/18* (2006.01)
*C07C 233/47* (2006.01)
*C07D 261/08* (2006.01)
*C07D 263/32* (2006.01)
*C07D 263/42* (2006.01)
*C07D 207/08* (2006.01)
*C07D 207/12* (2006.01)
*C07D 277/34* (2006.01)
*C07D 211/44* (2006.01)
*C07D 213/643* (2006.01)
*C07D 213/69* (2006.01)
*C07C 233/25* (2006.01)
*C07C 255/54* (2006.01)
*C07D 211/46* (2006.01)
*C07D 213/74* (2006.01)
*C07D 401/12* (2006.01)
*C12N 9/99* (2006.01)
*C12N 15/09* (2006.01)

(56) References Cited

U.S. PATENT DOCUMENTS

| | | |
|---|---|---|
| 2007/0219251 A1 | 9/2007 | Gu et al. |
| 2007/0225332 A1 | 9/2007 | Gu et al. |
| 2009/0054436 A1 | 2/2009 | Borzilleri et al. |
| 2010/0183606 A1 | 7/2010 | Borzilleri et al. |
| 2011/0183998 A1 | 7/2011 | Zoller et al. |
| 2014/0275199 A1 | 9/2014 | Liu et al. |
| 2015/0246938 A1 | 9/2015 | Matsumura et al. |

FOREIGN PATENT DOCUMENTS

| | | |
|---|---|---|
| WO | WO 2007/095602 A2 | 8/2007 |
| WO | WO 2007/095603 A2 | 8/2007 |
| WO | WO 2010/003624 A2 | 1/2010 |
| WO | WO 2012/090219 A2 | 7/2012 |
| WO | WO 2012/108478 A1 | 8/2012 |
| WO | WO 2013/017600 A1 | 2/2013 |
| WO | WO 2013/035827 A1 | 3/2013 |
| WO | WO 2016/084816 A1 | 6/2016 |

OTHER PUBLICATIONS

Chonan et al., "Discovery of novel (4-piperidinyl)-piperazines as potent and orally active acetyl-CoA carboxylase 1/2 non-selective inhibitors: F-Boc and triF-Boc groups are acid-stable bioisosteres for the Boc group," Bioorganic & Medicinal Chemistry, 2011, 19:1580-1593.

Gu et al, ,"N-{3-[2-(4-Alkoxyphenoxy)thiazol-5-yl]-1-methylprop-2-ynyl}carboxy Derivatives as Acetyl-CoA Carboxylase Inhibitors—Improvement of Cardiovascular and Neurological Liabilities via Structural Modifications," J. Med. Chem., 2007, 50:1078-1082.

Haque et al., "Potent biphenyl- and 3-phenyl pyridine-based inhibitors of acetyl-CoA carboxylase," Bioorganic & Medicinal Chemistry Letters, 2009, 19:5872-5876.

MONOCYCLIC COMPOUND

TECHNICAL FIELD

The present invention relates to a monocyclic compound having an acetyl-CoA carboxylase (in the present specification, sometimes to be abbreviated as ACC) inhibitory action, which may be useful for the prophylaxis or treatment of cancer, hepatitis, hepatic fibrosis, fatty liver and the like.

BACKGROUND OF THE INVENTION

ACC is involved in ATP-dependent carboxylation of acetyl-CoA to malonyl-CoA, which is a rate-limiting step in fatty acid synthesis. This reaction proceeds in two half reactions, that is, a biotin carboxylase reaction and a carboxyltransferase reaction. Malonyl-CoA is a carbon donor in the synthesis and elongation reaction of long chain fatty acids and is also a regulator of the palmitoyl CoA carnitine shuttle system involved in mitochondrial oxidation of long chain fatty acids.

ACC exists as two isozymes, that is, ACC1 present in adipogenic tissues such as liver and fat, and ACC2 present in oxidized tissues such as liver, heart and skeletal muscle. ACC1 and ACC2 are encoded by different genes.

ACC1 is abundantly present in the cytoplasm and controls de novo synthesis of fatty acids. Malonyl-CoA, which is a product thereof, acts as a substrate for fatty acid synthase (FASN) and is used for the biosynthesis of long chain fatty acids, phospholipids, triglycerides (TG) and the like. On the other hand, ACC2 is abundantly present in the mitochondrial outer membrane, and controls fatty acid oxidation. Malonyl-CoA, which is a product thereof, inhibits uptake of fatty acid into mitochondria and inhibits fatty acid oxidation in mitochondria, based on the feedback inhibition of carnitine palmitoyl transferase-1 (CPT-1).

In many cancer cells, de novo fatty acid synthesis is flourishing regardless of the number of exogenous fatty acids compared to normal cells. It is already known that several lipid metabolic enzymes, such as FASN, promote the development and malignancy of cancer, and these are expected to become new target molecules for cancer treatment. It is also known that ACC1 is highly expressed in a wide variety of cancer cells. Therefore, inhibition of the biosynthesis of fatty acid in cancer cells by inhibition of ACC1 is extremely useful for the prophylaxis and treatment of cancer. In fact, as a compound having ACC1 inhibitory activity and cancer cell proliferation inhibitory activity, the compound described in patent document 1 is known.

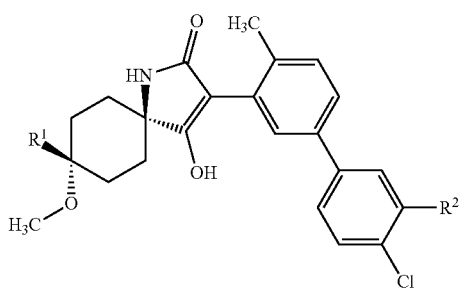

(I)

wherein each symbol is as defined in the document.

On the other hand, ACC1 is present in lipogenic tissues such as liver and fat, and controls fatty acid synthesis. Therefore, inhibition of ACC1 reduces fatty acid synthesis and is extremely useful for the prophylaxis or treatment of metabolic syndrome, obesity, hypertension, diabetes, metabolic disorders such as cardiovascular diseases associated with atherosclerosis and the like.

Patent Document 2 discloses the following compound having an ACC inhibitory action, which is useful for the prophylaxis or treatment of obesity and the like.

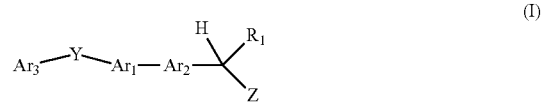

(I)

wherein each symbol is as defined in the document.

Patent Document 3 discloses the following compound having an ACC inhibitory action, which is useful for the prophylaxis or treatment of obesity and the like.

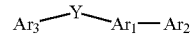

wherein each symbol is as defined in the document.

Patent Document 4 discloses the following compound having an ACC inhibitory action, which is useful for the prophylaxis or treatment of obesity and the like.

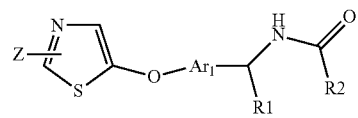

wherein each symbol is as defined in the document.

Non-Patent Document 1 discloses the following compound as an ACC inhibitor.

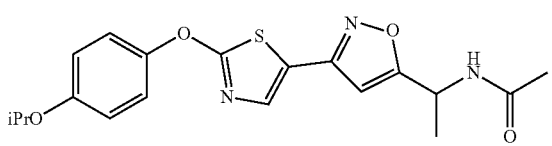 [SMILES: CC(=O)NC(C)c1cc(-c2cnc(Oc3ccc(OC(C)C)cc3)s2)no1]

Non-Patent Document 2 discloses the following compound as an ACC inhibitor.

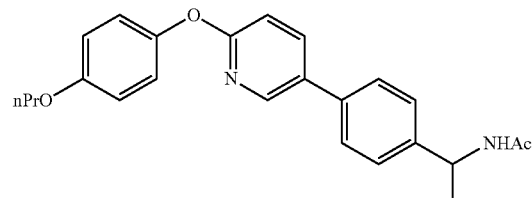

Non-Patent Document 3 discloses the following compound as an ACC1/2 non-selective inhibitor.

Non-Patent Document 4 discloses the following compound as an ACC inhibitor.

DOCUMENT LIST

Patent Document

Patent Document 1: WO 2013/017600
Patent Document 2: WO 2007/095602
Patent Document 3: WO 2007/095603
Patent Document 4: WO 2012/090219

Non-Patent Document

Non-Patent Document 1: Journal of Medicinal Chemistry, 50, (2007), pp. 1078-1082
Non-Patent Document 2: Bioorganic & Medicinal Chemistry Letters, 19, (2009), pp. 5872-5876
Non-Patent Document 3: Bioorganic & Medicinal Chemistry, 19, (2011), pp. 1580-1593
Non-Patent Document 4: Molecular Diversity, 17, (2013), pp. 139-149

SUMMARY OF THE INVENTION

Problems to be Solved by the Invention

An object of the present invention is to provide a compound having a superior ACC inhibitory action, which is fully acceptable as a medicament.

Means of Solving the Problems

The present inventors have found for the first time that a compound represented by the following formula (I) or a salt thereof [hereinafter sometimes to be referred to as compound (I)] has a ACC inhibitory action, which may be useful for the prophylaxis or treatment of cancer, hepatitis, hepatic fibrosis, fatty liver and the like. Based on this finding, the present inventors have conducted intensive studies and completed the present invention.

Accordingly, the present invention provides the following.

[1] A compound represented by the formula (I):

wherein
$R^1$ is
(1) a $C_{1-6}$ alkyl group optionally substituted by halogen atom(s),
(2) an optionally substituted $C_{3-6}$ cycloalkyl group,
(3) an optionally substituted $C_{1-6}$ alkoxy group, or
(4) an amino group optionally mono- or di-substituted by optionally substituted $C_{1-6}$ alkyl group(s);
$R^2$ is a $C_{1-6}$ alkyl group optionally substituted by halogen atom(s) or an optionally substituted $C_{3-6}$ cycloalkyl group;
X is —C($R^3$)($R^4$)—, —CO— or —O—;
Y is —C($R^5$)($R^6$)—O—, —O—C($R^5$)($R^6$)—, —C($R^7$)($R^8$)—C($R^9$)($R^{10}$)—, —$NR^{11}$—CO— or —CO—$NR^{11}$—;
$R^3$, $R^4$, $R^5$, $R^6$, $R^7$, $R^8$, $R^9$, $R^{10}$ and $R^{11}$ are each independently a hydrogen atom or a substituent, or $R^8$ and $R^{10}$ in combination optionally form, together with the adjacent carbon atoms, an optionally further substituted $C_{3-4}$ cycloalkane, or $R^8$ and $R^{10}$ in combination optionally form a bond;
Ring Q, Ring R and Ring S are each independently an optionally further substituted 5- or 6-membered ring;
m and n are each independently 1 or 2, and m+n is 2 or 3; and
p and q are each independently 0 or 1, and p+q is 1,
or a salt thereof (hereinafter sometimes to be referred to as compound (I)).
[2] The compound or salt of [1], wherein
$R^3$ and $R^4$ are each independently a hydrogen atom or an optionally substituted hydroxy group;
$R^5$ and $R^6$ are both hydrogen atoms;
$R^7$ and $R^8$ are each independently a hydrogen atom or an optionally substituted $C_{1-6}$ alkyl group;
$R^9$ and $R^{10}$ are both hydrogen atoms; and
$R^{11}$ is a hydrogen atom or an optionally substituted $C_{1-6}$ alkyl group; or
$R^8$ and $R^{10}$ in combination optionally form, together with the adjacent carbon atoms, an optionally further substituted $C_{3-4}$ cycloalkane, or $R^8$ and $R^{10}$ in combination optionally form a bond.
[3] The compound or salt of [1], wherein
$R^1$ is a $C_{1-6}$ alkyl group or an amino group;
$R^2$ is a $C_{1-6}$ alkyl group;
$R^3$ and $R^4$ are each independently a hydrogen atom or a hydroxy group;
$R^5$ and $R^6$ are both hydrogen atoms;
$R^7$ and $R^8$ are each independently a hydrogen atom or a $C_{1-6}$ alkyl group;
$R^9$ and $R^{10}$ are both hydrogen atoms;
$R^{11}$ is a hydrogen atom or a $C_{1-6}$ alkyl group; or
$R^8$ and $R^{10}$ in combination optionally form, together with the adjacent carbon atoms, a $C_{3-4}$ cycloalkane, or $R^8$ and $R^{10}$ in combination optionally form a bond;
Ring Q is a 5- or 6-membered ring optionally substituted by 1 to 3 substituents selected from (a) a halogen atom, (b) a cyano group and (c) a $C_{1-6}$ alkyl group;
Ring R is a 5- or 6-membered ring optionally substituted by 1 to 3 substituents selected from (a) a halogen atom,
(b) an oxo group,
(c) a $C_{1-6}$ alkyl group, and
(d) a $C_{1-6}$ alkoxy group optionally substituted by 1 to 3 substituents selected from (i) a halogen atom and (ii) a $C_{3-10}$ cycloalkyl group optionally substituted by 1 to 3 halogen atoms; and Ring S is a 5- or 6-membered ring optionally substituted by 1 to 3 substituents selected from
(a) a halogen atom,
(b) an optionally halogenated $C_{1-6}$ alkyl group, and
(c) a $C_{1-6}$ alkoxy group.

[4] The compound or salt of [1], wherein X is —CO— or —O—.

[5] N-((2S)-1-((2-(4-(3-(Cyclopropylmethoxy)phenoxy)phenyl)-1,3-oxazol-5-yl)oxy)propan-2-yl)acetamide or a salt thereof.

[6] N-(1-(6-((4-(3-(Cyclopropylmethoxy)phenoxy)-2,6-difluorobenzyl)oxy)pyridin-3-yl)ethyl)acetamide or a salt thereof.

[7] 1-((2S)-1-((2-(4-(3-(Cyclopropylmethoxy)phenoxy)phenyl)-1,3-oxazol-5-yl)oxy)propan-2-yl)urea or a salt thereof.

[8] A medicament comprising the compound or salt of [1].

[9] The medicament of [8], which is an ACC1 inhibitor.

[10] The medicament of [8], which is an agent for the prophylaxis or treatment of cancer.

[11] The medicament of [8], which is an agent for the prophylaxis or treatment of hepatitis, hepatic fibrosis or fatty liver.

[12] A method of inhibiting ACC1 in a mammal, which comprises administering an effective amount of the compound or salt of [1] to the mammal.

[13] A method for the prophylaxis or treatment of cancer in a mammal, which comprises administering an effective amount of the compound or salt of [1] to the mammal.

[14] A method for the prophylaxis or treatment of hepatitis, hepatic fibrosis or fatty liver in a mammal, which comprises administering an effective amount of the compound or salt of [1] to the mammal.

[15] The compound or salt of [1] for use in the prophylaxis or treatment of cancer.

[16] The compound or salt of [1] for use in the prophylaxis or treatment of hepatitis, hepatic fibrosis or fatty liver.

[17] Use of the compound or salt of [1] for the production of an agent for the prophylaxis or treatment of cancer.

[18] Use of the compound or salt of [1] for the production of an agent for the prophylaxis or treatment of hepatitis, hepatic fibrosis or fatty liver.

Effect of the Invention

Compound (I) may have a superior ACC inhibitory action and may be useful as an agent for the prophylaxis or treatment of cancer, hepatitis, hepatic fibrosis, fatty liver and the like.

DETAILED DESCRIPTION OF THE INVENTION

Figure 1:
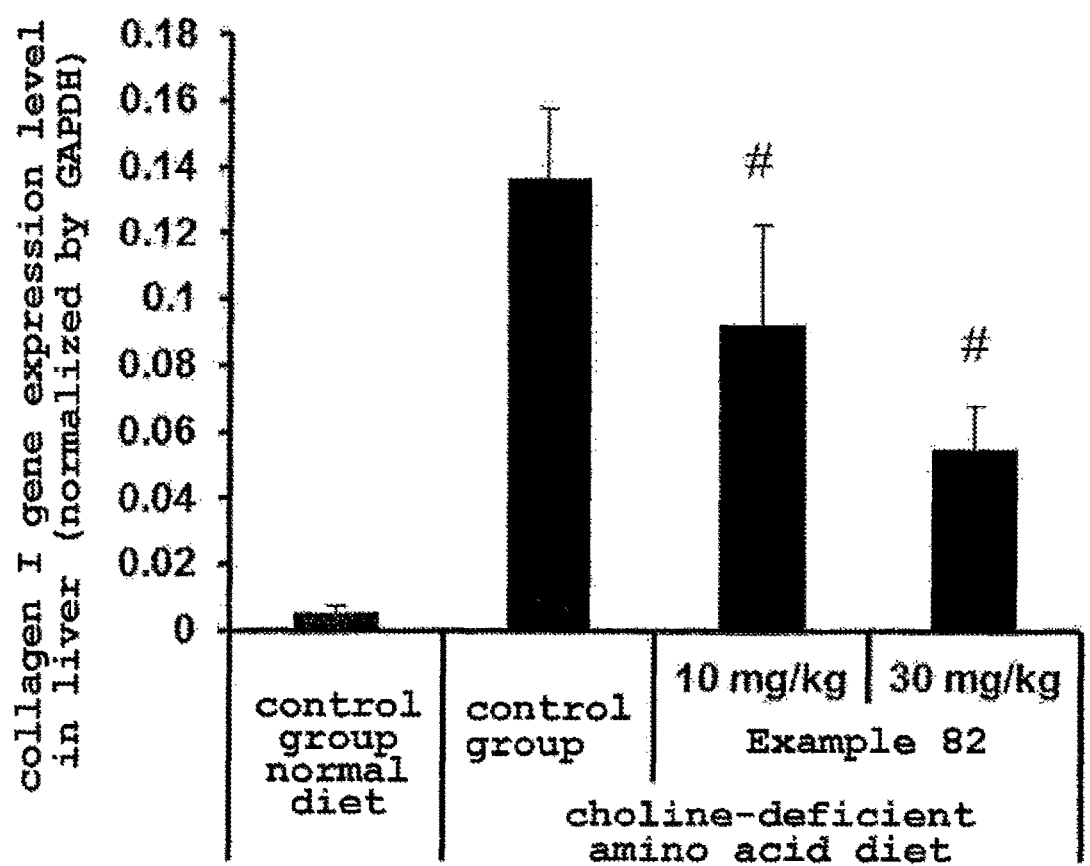
FIG. 1 shows the inhibitory effect of the present compound on liver fibrosis caused by non-alcoholic steatohepatitis.

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,

(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkyl-sulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "optionally halogenated $C_{3-10}$ cycloalkyloxy group" include a $C_{3-10}$ cycloalkyloxy group optionally having 1 to 7, preferably 1 to 5 halogen atoms. Specific examples thereof include cyclopropyloxy, 2,2-difluorocyclopropyloxy, cyclobutyloxy, 3,3-difluorocyclobutyloxy, cyclopentyloxy, 3,3-difluorocyclopentyloxy, 3,3,4-trifluorocyclopentyloxy, cyclohexyloxy, 3-fluorocyclohexyloxy, 4,4-difluorocyclohexyloxy, cycloheptyloxy and cyclooctyloxy.

The definition of each symbol in the formula (I) is explained in detail in the following.

$R^1$ is a $C_{1-6}$ alkyl group optionally substituted by halogen atom(s), an optionally substituted $C_{3-6}$ cycloalkyl group, an optionally substituted $C_{1-6}$ alkoxy group, or an amino group optionally mono- or di-substituted by optionally substituted $C_{1-6}$ alkyl group(s).

Examples of the "$C_{3-6}$ cycloalkyl group" of the "optionally substituted $C_{3-6}$ cycloalkyl group" represented by $R^1$ include groups having 3 to 6 carbon atoms, from among the above-mentioned "$C_{3-10}$ cycloalkyl group".

The "$C_{3-6}$ cycloalkyl group" of the "optionally substituted $C_{3-6}$ cycloalkyl group" represented by $R^1$ is optionally substituted by substituent(s) selected from the above-mentioned Substituent Group A at substitutable position(s). The number of the substituents is, for example, 1 to 3. When the number of the substituents is 2 or more, the respective substituents may be the same or different.

The "$C_{1-6}$ alkoxy group" of the "optionally substituted $C_{1-6}$ alkoxy group" represented by $R^1$ is optionally substituted by substituent(s) selected from the above-mentioned Substituent Group A at substitutable position(s). The number of the substituents is, for example, 1 to 3. When the number of the substituents is 2 or more, the respective substituents may be the same or different.

The "$C_{1-6}$ alkyl group" of the "optionally substituted $C_{1-6}$ alkyl group" of the "amino group optionally mono- or di-substituted by optionally substituted $C_{1-6}$ alkyl group(s)" represented by $R^1$ is optionally substituted by substituent(s) selected from the above-mentioned Substituent Group A at substitutable position(s). The number of the substituents is, for example, 1 to 3. When the number of the substituents is 2 or more, the respective substituents may be the same or different.

$R^1$ is preferably a $C_{1-6}$ alkyl group (e.g., methyl) optionally substituted by halogen atom(s), or an amino group optionally mono- or di-substituted by optionally substituted $C_{1-6}$ alkyl group(s).

$R^1$ is more preferably
(1) a $C_{1-6}$ alkyl group (e.g., methyl), or
(2) an amino group.

$R^2$ is a $C_{1-6}$ alkyl group optionally substituted by halogen atom(s) or an optionally substituted $C_{3-6}$ cycloalkyl group.

Examples of the "$C_{3-6}$ cycloalkyl group" of the "optionally substituted $C_{3-6}$ cycloalkyl group" represented by $R^2$ include groups having 3 to 6 carbon atoms, from among the above-mentioned "$C_{3-10}$ cycloalkyl group".

The "$C_{3-6}$ cycloalkyl group" of the "optionally substituted $C_{3-6}$ cycloalkyl group" represented by $R^2$ is optionally substituted by substituent(s) selected from the above-mentioned Substituent Group A at substitutable position(s). The number of the substituents is, for example, 1 to 3. When the number of the substituents is 2 or more, the respective substituents may be the same or different.

$R^2$ is preferably a $C_{1-6}$ alkyl group (e.g., methyl) optionally substituted by halogen atom(s).

$R^2$ is more preferably a $C_{1-6}$ alkyl group (e.g., methyl).

X is —C($R^3$)($R^4$)—, —CO— or —O—.

Y is —C($R^5$)($R^6$)—O—, —O—C($R^5$)($R^6$)—, —C($R^7$)($R^8$)—C($R^9$)($R^{10}$)—, —NR$^{11}$—CO— or —CO—NR$^{11}$—.

$R^3$, $R^4$, $R^5$, $R^6$, $R^7$, $R^8$, $R^9$, $R^{10}$ and $R^{11}$ are each independently a hydrogen atom or a substituent, and $R^8$ and $R^{10}$ in combination optionally form, together with the adjacent carbon atoms, an optionally further substituted $C_{3-4}$ cycloalkane or $R^8$ and $R^{10}$ in combination optionally form a bond.

Examples of the "$C_{3-4}$ cycloalkane" of the "optionally substituted $C_{3-4}$ cycloalkane" formed by $R^8$ and $R^{10}$ in combination together with the adjacent carbon atoms include cyclopropane and cyclobutane.

The "$C_{3-4}$ cycloalkane" of the "optionally substituted $C_{3-4}$ cycloalkane" formed by $R^8$ and $R^{10}$ in combination together with the adjacent carbon atoms is optionally substituted by substituent(s) selected from the above-mentioned Substituent Group A at substitutable position(s). The number of the substituents is, for example, 1 to 3. When the number of the substituents is 2 or more, the respective substituents may be the same or different.

X is preferably —C($R^3$)($R^4$)—, —CO— or —O— wherein $R^3$ and $R^4$ is each independently a hydrogen atom or an optionally substituted hydroxy group.

X is more preferably —C($R^3$)($R^4$)—, —CO— or —O— wherein $R^3$ and $R^4$ is each independently a hydrogen atom or a hydroxy group.

X is further more preferably —C($R^3$)($R^4$)—, —CO— or —O— wherein $R^3$ and $R^4$ are both hydrogen atoms.

X is still more preferably —CO— or —O—.

X is particularly preferably —O—.

Y is preferably —C($R^5$)($R^6$)—O—, —O—C($R^5$)($R^6$)—, —C($R^7$)($R^8$)—C($R^9$)($R^{10}$)—, —NR$^{11}$—CO— or —CO—NR$^{11}$— wherein $R^5$ and $R^6$ are both hydrogen atoms, $R^7$ and $R^8$ are each independently a hydrogen atom or an optionally substituted $C_{1-6}$ alkyl group (e.g., methyl), $R^9$ and $R^{10}$ are both hydrogen atoms, and $R^{11}$ is a hydrogen atom or an optionally substituted $C_{1-6}$ alkyl group (e.g., methyl), or $R^8$ and $R^{10}$ in combination optionally form, together with the adjacent carbon atoms, an optionally further substituted $C_{3-4}$ cycloalkane (e.g., cyclopropane), or $R^8$ and $R^{10}$ in combination optionally form a bond.

Y is more preferably —C($R^5$)($R^6$)—O—, —O—C($R^5$)($R^6$)—, —C($R^7$)($R^8$)—C($R^9$)($R^{10}$)—, —NR$^{11}$—CO— or —CO—NR$^{11}$— wherein $R^5$ and $R^6$ are both hydrogen atoms, $R^7$ and $R^8$ are each independently a hydrogen atom or a $C_{1-6}$ alkyl group (e.g., methyl), $R^9$ and $R^{10}$ are both hydrogen atoms, and $R^{11}$ is a hydrogen atom or a $C_{1-6}$ alkyl group (e.g., methyl), or $R^8$ and $R^{10}$ in combination optionally form, together with the adjacent carbon atoms, a $C_{3-4}$ cycloalkane (e.g., cyclopropane), or $R^8$ and $R^{10}$ in combination optionally form a bond.

Y is further more preferably —C($R^5$)($R^6$)—O—, —O—C($R^5$)($R^6$)—, —C($R^7$)($R^8$)—C($R^9$)($R^{10}$)— or —NR$^{11}$—CO— wherein $R^5$ and $R^6$ are both hydrogen atoms, $R^7$ and $R^8$ are each independently a hydrogen atom or a $C_{1-6}$ alkyl group (e.g., methyl), $R^9$ and $R^{10}$ are both hydrogen atoms, and $R^{11}$ is a hydrogen atom or a $C_{1-6}$ alkyl group (e.g., methyl), or $R^8$ and $R^{10}$ in combination optionally form, together with the adjacent carbon atoms, a $C_{3-4}$ cycloalkane (e.g., cyclopropane), or $R^8$ and $R^{10}$ in combination optionally form a bond.

Y is still more preferably —C($R^5$)($R^6$)—O— wherein $R^5$ and $R^6$ are both hydrogen atoms.

In another embodiment, Y is preferably —C($R^5$)($R^6$)—O—, —O—C($R^5$)($R^6$)— or —C($R^7$)($R^8$)—C($R^9$)($R^{10}$)— wherein $R^5$, $R^6$, $R^7$, $R^8$, $R^9$ and $R^{10}$ are each independently a hydrogen atom or a substituent.

In this embodiment, preferably $R^5$ and $R^6$ are both hydrogen atoms, $R^7$ and $R^8$ are each independently a hydrogen atom or a $C_{1-6}$ alkyl group (e.g., methyl), and $R^9$ and $R^{10}$ are both hydrogen atoms.

Ring Q, Ring R and Ring S are each independently an optionally further substituted 5- or 6-membered ring.

Examples of the "5- or 6-membered ring" of the "optionally further substituted 5- or 6-membered ring" represented by Ring Q, Ring R or Ring S include benzene, a $C_{5-6}$ cycloalkane, a $C_{5-6}$ cycloalkene, a 5- to 6-membered monocyclic aromatic heterocycle and a 5- to 6-membered monocyclic non-aromatic heterocycle.

Examples of the above-mentioned $C_{5-6}$ cycloalkane include 5- to 6-membered groups, from among the above-mentioned "$C_{3-10}$ cycloalkane".

Examples of the above-mentioned $C_{5-6}$ cycloalkene include 5- to 6-membered groups, from among the above-mentioned "$C_{3-10}$ cycloalkene".

Examples of the above-mentioned 5- to 6-membered monocyclic aromatic heterocycle include 5- to 6-membered monocyclic groups, from among the above-mentioned "aromatic heterocycle".

Examples of the above-mentioned 5- to 6-membered monocyclic non-aromatic heterocycle include 5- to 6-membered monocyclic groups, from among the above-mentioned "non-aromatic heterocycle".

The "5- or 6-membered ring" of the "optionally further substituted 5- or 6-membered ring" represented by Ring Q is optionally further substituted by substituent(s) selected from the above-mentioned Substituent Group A, in addition to —O-Ring R and —(Y)$_q$—, at substitutable position(s). The number of the substituents is, for example, 1 to 3. When the number of the substituents is 2 or more, the respective substituents may be the same or different. In addition, Substituent Group A is optionally further substituted by substituent(s) selected from Substituent Group A. The number of the substituents is, for example, 1 to 3. When the number of the substituents is 2 or more, the respective substituents may be the same or different.

Ring Q is preferably optionally substituted benzene, an optionally substituted $C_{5-6}$ cycloalkane (preferably cyclohexane), an optionally substituted 5- to 6-membered monocyclic aromatic heterocycle (preferably pyridine, pyrimidine, pyridazine, oxazole, thiazole), or an optionally substituted 5- to 6-membered monocyclic non-aromatic heterocycle (preferably piperidine), more preferably optionally substituted benzene, or an optionally substituted 5- to 6-membered monocyclic aromatic heterocycle (preferably pyridine), further more preferably optionally substituted benzene.

Specifically, Ring Q is preferably a 5- or 6-membered ring (preferably benzene, a 5- or 6-membered monocyclic aromatic heterocycle (preferably pyridine, pyrimidine, pyridazine, oxazole, thiazole), a 5- or 6-membered monocyclic non-aromatic heterocycle (preferably piperidine) or a $C_{5-6}$ cycloalkane (preferably cyclohexane)) optionally substituted by 1 to 3 substituents selected from
  (a) a halogen atom (e.g., a fluorine atom, a chlorine atom, a bromine atom),
  (b) a cyano group, and
  (c) a $C_{1-6}$ alkyl group (e.g., methyl)
[preferably
(1) benzene optionally substituted by 1 to 3 substituents selected from
  (a) a halogen atom (e.g., a fluorine atom, a chlorine atom, a bromine atom),
  (b) a cyano group, and
  (c) a $C_{1-6}$ alkyl group (e.g., methyl),
(2) a 5- or 6-membered monocyclic aromatic heterocycle (preferably pyridine, pyrimidine, pyridazine, oxazole, thiazole) optionally substituted by 1 to 3 $C_{1-6}$ alkyl groups (e.g., methyl),
(3) a 5- or 6-membered monocyclic non-aromatic heterocycle (preferably piperidine), or
(4) a $C_{5-6}$ cycloalkane (preferably cyclohexane)].

Ring Q is more preferably benzene or a 5- or 6-membered monocyclic aromatic heterocycle (preferably pyridine), each of which is optionally substituted by 1 to 3 substituents selected from
  (a) a halogen atom (e.g., a fluorine atom), and
  (b) a $C_{1-6}$ alkyl group (e.g., methyl)
[preferably
(1) benzene optionally substituted by 1 to 3 halogen atoms (e.g., a fluorine atom), or
(2) a 5 or 6-membered monocyclic aromatic heterocycle (preferably pyridine) optionally substituted by 1 to 3 $C_{1-6}$ alkyl groups (e.g., methyl)].

Ring Q is further more preferably benzene optionally substituted by 1 to 3 halogen atoms (e.g., a fluorine atom).

The "5- or 6-membered ring" of the "optionally further substituted 5- or 6-membered ring" represented by Ring R is optionally further substituted by substituent(s) selected from the above-mentioned Substituent Group A, in addition to —O-Ring Q-, at substitutable position(s). The number of the substituents is, for example, 1 to 3. When the number of the substituents is 2 or more, the respective substituents may be the same or different. In addition, Substituent Group A is optionally further substituted by substituent(s) selected from Substituent Group A. The number of the substituents is, for example, 1 to 3. When the number of the substituents is 2 or more, the respective substituents may be the same or different.

Ring R is preferably optionally substituted benzene, an optionally substituted 5- to 6-membered monocyclic aromatic heterocycle (preferably pyridine), or an optionally substituted 5- to 6-membered monocyclic non-aromatic heterocycle (preferably dihydropyridine),
more preferably optionally substituted benzene.

Specifically, Ring R is preferably a 5- or 6-membered ring (preferably benzene, a 5- or 6-membered monocyclic aromatic heterocycle (preferably pyridine) or a 5- or 6-membered monocyclic non-aromatic heterocycle (preferably dihydropyridine)) optionally substituted by 1 to 3 substituents selected from
  (a) a halogen atom (e.g., a fluorine atom),
  (b) an oxo group,
  (c) a $C_{1-6}$ alkyl group (e.g., pentyl), and
  (d) a $C_{1-6}$ alkoxy group (e.g., methoxy, propoxy) optionally substituted by 1 to 3 substituents selected from
    (i) a halogen atom (e.g., a fluorine atom), and
    (ii) a $C_{3-10}$ cycloalkyl group (e.g., cyclopropyl) optionally substituted by 1 to 3 halogen atoms (e.g., a fluorine atom)
[preferably
(1) benzene optionally substituted by 1 to 3 substituents selected from
  (a) a halogen atom (e.g., a fluorine atom), and
  (b) a $C_{1-6}$ alkoxy group (e.g., methoxy, propoxy) optionally substituted by 1 to 3 substituents selected from
    (i) a halogen atom (e.g., a fluorine atom), and
    (ii) a $C_{3-10}$ cycloalkyl group (e.g., cyclopropyl) optionally substituted by 1 to 3 halogen atoms (e.g., a fluorine atom),
(2) a 5- or 6-membered monocyclic aromatic heterocycle (preferably pyridine) optionally substituted by 1 to 3 $C_{1-6}$ alkoxy groups (e.g., methoxy) optionally substituted by 1 to 3 $C_{3-10}$ cycloalkyl groups (e.g., cyclopropyl), or
(3) a 5- or 6-membered monocyclic non-aromatic heterocycle (preferably dihydropyridine) optionally substituted by 1 to 3 substituents selected from
  (a) an oxo group, and
  (b) a $C_{1-6}$ alkyl group (e.g., pentyl)].

Ring R is more preferably benzene optionally substituted by 1 to 3 $C_{1-6}$ alkoxy groups (e.g., methoxy) optionally substituted by 1 to 3 $C_{3-10}$ cycloalkyl groups (e.g., cyclopropyl). Ring R is particularly preferably benzene substituted by $C_{3-10}$ cycloalkyl-$C_{1-6}$ alkoxy group(s) (preferably cyclopropylmethoxy).

The "5- or 6-membered ring" of the "optionally further substituted 5- or 6-membered ring" represented by Ring S is optionally further substituted by substituent(s) selected from the above-mentioned Substituent Group A, in addition to —$(Y)_q$— and —$(X—CH_2)_p$—, at substitutable position(s). The number of the substituents is, for example, 1 to 3. When the number of the substituents is 2 or more, the respective substituents may be the same or different. In addition, Substituent Group A is optionally further substituted by substituent(s) selected from Substituent Group A. The number of the substituents is, for example, 1 to 3. When the number of the substituents is 2 or more, the respective substituents may be the same or different.

Ring S is preferably optionally substituted benzene, an optionally substituted $C_{5-6}$ cycloalkane (preferably cyclohexane), an optionally substituted 5- to 6-membered monocyclic aromatic heterocycle (preferably pyridine, pyrimidine, pyrazine, pyridazine, thiophene, pyrazole, oxazole, isoxazole, oxadiazole, thiazole), or an optionally substituted 5- to 6-membered monocyclic non-aromatic heterocycle (preferably pyrrolidine, piperidine),
more preferably optionally substituted benzene, or an optionally substituted 5- to 6-membered monocyclic aromatic heterocycle (preferably pyridine, pyrazine, pyridazine, pyrazole, oxazole, isoxazole),
further more preferably an optionally substituted 5- to 6-membered monocyclic aromatic heterocycle (preferably pyridine, oxazole).

Specifically, Ring S is preferably a 5- or 6-membered ring (preferably benzene, a 5- or 6-membered monocyclic aromatic heterocycle (preferably pyridine, pyrimidine, pyrazine, pyridazine, thiophene, pyrazole, oxazole, isoxazole, oxadiazole, thiazole), a 5- or 6-membered monocyclic non-aromatic heterocycle (preferably pyrrolidine, piperidine) or a $C_{5-6}$ cycloalkane (preferably cyclohexane)) optionally substituted by 1 to 3 substituents selected from (a) a halogen atom (e.g., a fluorine atom, a chlorine atom),
(b) an optionally halogenated $C_{1-6}$ alkyl group (e.g., methyl, trifluoromethyl), and
(c) a $C_{1-6}$ alkoxy group (e.g., methoxy)
[preferably
(1) benzene optionally substituted by 1 to 3 substituents selected from
(a) a halogen atom (e.g., a fluorine atom, a chlorine atom),
(b) an optionally halogenated $C_{1-6}$ alkyl group (e.g., methyl, trifluoromethyl), and
(c) a $C_{1-6}$ alkoxy group (e.g., methoxy),
(2) a 5- or 6-membered monocyclic aromatic heterocycle (preferably pyridine, pyrimidine, pyrazine, pyridazine, thiophene, pyrazole, oxazole, isoxazole, oxadiazole, thiazole) optionally substituted by 1 to 3 substituents selected from
(a) a halogen atom (e.g., a fluorine atom), and
(b) an optionally halogenated $C_{1-6}$ alkyl group (e.g., methyl, trifluoromethyl),
(3) a 5- or 6-membered monocyclic non-aromatic heterocycle (preferably pyrrolidine, piperidine), or
(4) a $C_{5-6}$ cycloalkane (preferably cyclohexane)].

Ring S is more preferably benzene or a 5- or 6-membered monocyclic aromatic heterocycle (preferably pyridine, pyrazine, pyridazine, pyrazole, oxazole, isoxazole), each of which is optionally substituted by 1 to 3 halogen atoms (e.g., a fluorine atom)
[preferably
(1) benzene, or
(2) a 5- or 6-membered monocyclic aromatic heterocycle (preferably pyridine, pyrazine, pyridazine, pyrazole, oxazole, isoxazole) optionally substituted by 1 to 3 halogen atoms (e.g., a fluorine atom)].

Ring S is further more preferably a 5- or 6-membered monocyclic aromatic heterocycle (preferably pyridine, oxazole).

m and n are each independently 1 or 2, and m+n is 2 or 3.

The combination (m, n) of m and n is preferably (1, 1), (2, 1) or (1, 2), more preferably (1, 1) or (2, 1).

p and q are each independently 0 or 1, and p+q is 1.

The combination (p, q) of p and q is preferably (0, 1) or (1, 0), more preferably (1, 0).

Preferable examples of compound (I) include the following compounds.

[Compound A]
Compound (I) wherein
$R^1$ is a $C_{1-6}$ alkyl group (e.g., methyl) optionally substituted by halogen atom(s), or an amino group optionally mono- or di-substituted by optionally substituted $C_{1-6}$ alkyl group(s);
$R^2$ is a $C_{1-6}$ alkyl group (e.g., methyl) optionally substituted by halogen atom(s);
X is —C($R^3$)($R^4$)—, —CO— or —O—;
$R^3$ and $R^4$ are each independently a hydrogen atom or an optionally substituted hydroxy group;
Y is —C($R^5$)($R^6$)—O—, —O—C($R^5$)($R^6$)—, —C($R^7$)($R^8$)—C($R^9$)($R^{10}$)—, —$NR^{11}$—CO— or —CO—$NR^{11}$—;
$R^5$ and $R^6$ are both hydrogen atoms;
$R^7$ and $R^8$ are each independently a hydrogen atom or an optionally substituted $C_{1-6}$ alkyl group (e.g., methyl);
$R^9$ and $R^{10}$ are both hydrogen atoms;
$R^{11}$ is a hydrogen atom or an optionally substituted $C_{1-6}$ alkyl group (e.g., methyl); or
$R^8$ and $R^{10}$ in combination optionally form, together with the adjacent carbon atoms, an optionally further substituted $C_{3-4}$ cycloalkane (e.g., cyclopropane), or $R^8$ and $R^{10}$ in combination optionally form a bond;

Ring Q is optionally substituted benzene, an optionally substituted $C_{5-6}$ cycloalkane (preferably cyclohexane), an optionally substituted 5- to 6-membered monocyclic aromatic heterocycle (preferably pyridine, pyrimidine, pyridazine, oxazole, thiazole), or an optionally substituted 5- to 6-membered monocyclic non-aromatic heterocycle (preferably piperidine);

Ring R is optionally substituted benzene, an optionally substituted 5- to 6-membered monocyclic aromatic heterocycle (preferably pyridine), or an optionally substituted 5- to 6-membered monocyclic non-aromatic heterocycle (preferably dihydropyridine);

Ring S is optionally substituted benzene, an optionally substituted $C_{5-6}$ cycloalkane (preferably cyclohexane), an optionally substituted 5- to 6-membered monocyclic aromatic heterocycle (preferably pyridine, pyrimidine, pyrazine, pyridazine, thiophene, pyrazole, oxazole, isoxazole, oxadiazole, thiazole), or an optionally substituted 5- to 6-membered monocyclic non-aromatic heterocycle (preferably pyrrolidine, piperidine);

m and n are each independently 1 or 2, and m+n is 2 or 3 (the combination (m, n) of m and n is preferably (1, 1), (2, 1) or (1, 2)); and p and q are each independently 0 or 1, and p+q is 1 (the combination (p, q) of p and q is preferably (0, 1) or (1, 0)).

[Compound B]
Compound (I) wherein
$R^1$ is
(1) a $C_{1-6}$ alkyl group (e.g., methyl), or
(2) an amino group;
$R^2$ is a $C_{1-6}$ alkyl group (e.g., methyl);
X is —C($R^3$)($R^4$)—, —CO— or —O—;
$R^3$ and $R^4$ are each independently a hydrogen atom or a hydroxy group;
Y is —C($R^5$)($R^6$)—O—, —O—C($R^5$)($R^6$)—, —C($R^7$)($R^8$)—C($R^9$)($R^{10}$)—, —$NR^{11}$—CO— or —CO—$NR^{11}$—;
$R^5$ and $R^6$ are both hydrogen atoms;
$R^7$ and $R^8$ are each independently a hydrogen atom or a $C_{1-6}$ alkyl group (e.g., methyl);
$R^9$ and $R^{10}$ are both hydrogen atoms;
$R^{11}$ is a hydrogen atom or a $C_{1-6}$ alkyl group (e.g., methyl); or
$R^8$ and $R^{10}$ in combination optionally form, together with the adjacent carbon atoms, a $C_{3-4}$ cycloalkane (e.g., cyclopropane), or $R^8$ and $R^{10}$ in combination optionally form a bond;

Ring Q is a 5- or 6-membered ring (preferably benzene, a 5- or 6-membered monocyclic aromatic heterocycle (preferably pyridine, pyrimidine, pyridazine, oxazole, thiazole), a 5- or 6-membered monocyclic non-aromatic heterocycle (preferably piperidine) or a $C_{5-6}$ cycloalkane (preferably cyclohexane)) optionally substituted by 1 to 3 substituents selected from
(a) a halogen atom (e.g., a fluorine atom, a chlorine atom, a bromine atom),
(b) a cyano group, and
(c) a $C_{1-6}$ alkyl group (e.g., methyl)
[preferably
(1) benzene optionally substituted by 1 to 3 substituents selected from
(a) a halogen atom (e.g., a fluorine atom, a chlorine atom, a bromine atom),
(b) a cyano group, and
(c) a $C_{1-6}$ alkyl group (e.g., methyl),
(2) a 5- or 6-membered monocyclic aromatic heterocycle (preferably pyridine, pyrimidine, pyridazine, oxazole, thiazole) optionally substituted by 1 to 3 $C_{1-6}$ alkyl groups (e.g., methyl), (3) a 5- or 6-membered monocyclic non-aromatic heterocycle (preferably piperidine), or
(4) a $C_{5-6}$ cycloalkane (preferably cyclohexane)]; Ring R is a 5- or 6-membered ring (preferably benzene, a 5- or 6-membered monocyclic aromatic heterocycle (preferably pyridine) or a 5- or 6-membered monocyclic non-aromatic heterocycle (preferably dihydropyridine)) optionally substituted by 1 to 3 substituents selected from
  (a) a halogen atom (e.g., a fluorine atom),
  (b) an oxo group,
  (c) a $C_{1-6}$ alkyl group (e.g., pentyl), and
  (d) a $C_{1-6}$ alkoxy group (e.g., methoxy, propoxy) optionally substituted by 1 to 3 substituents selected from
    (i) a halogen atom (e.g., a fluorine atom), and
    (ii) a $C_{3-10}$ cycloalkyl group (e.g., cyclopropyl) optionally substituted by 1 to 3 halogen atoms (e.g., a fluorine atom)
[preferably
(1) benzene optionally substituted by 1 to 3 substituents selected from
  (a) a halogen atom (e.g., a fluorine atom), and
  (b) a $C_{1-6}$ alkoxy group (e.g., methoxy, propoxy) optionally substituted by 1 to 3 substituents selected from
    (i) a halogen atom (e.g., a fluorine atom), and
    (ii) a $C_{3-10}$ cycloalkyl group (e.g., cyclopropyl) optionally substituted by 1 to 3 halogen atoms (e.g., a fluorine atom),
(2) a 5- or 6-membered monocyclic aromatic heterocycle (preferably pyridine) optionally substituted by 1 to 3 $C_{1-6}$ alkoxy groups (e.g., methoxy) optionally substituted by 1 to 3 $C_{3-10}$ cycloalkyl groups (e.g., cyclopropyl), or
(3) a 5- or 6-membered monocyclic non-aromatic heterocycle (preferably dihydropyridine) optionally substituted by 1 to 3 substituents selected from
  (a) an oxo group, and
  (b) a $C_{1-6}$ alkyl group (e.g., pentyl)];
Ring S is a 5- or 6-membered ring (preferably benzene, a 5- or 6-membered monocyclic aromatic heterocycle (preferably pyridine, pyrimidine, pyrazine, pyridazine, thiophene, pyrazole, oxazole, isoxazole, oxadiazole, thiazole), a 5- or 6-membered monocyclic non-aromatic heterocycle (preferably pyrrolidine, piperidine) or a $C_{5-6}$ cycloalkane (preferably cyclohexane)) optionally substituted by 1 to 3 substituents selected from
  (a) a halogen atom (e.g., a fluorine atom, a chlorine atom),
  (b) an optionally halogenated $C_{1-6}$ alkyl group (e.g., methyl, trifluoromethyl), and
  (c) a $C_{1-6}$ alkoxy group (e.g., methoxy)
[preferably
(1) benzene optionally substituted by 1 to 3 substituents selected from
  (a) a halogen atom (e.g., a fluorine atom, a chlorine atom),
  (b) an optionally halogenated $C_{1-6}$ alkyl group (e.g., methyl, trifluoromethyl), and
  (c) a $C_{1-6}$ alkoxy group (e.g., methoxy),
(2) a 5- or 6-membered monocyclic aromatic heterocycle (preferably pyridine, pyrimidine, pyrazine, pyridazine, thiophene, pyrazole, oxazole, isoxazole, oxadiazole, thiazole) optionally substituted by 1 to 3 substituents selected from
  (a) a halogen atom (e.g., a fluorine atom), and
  (b) an optionally halogenated $C_{1-6}$ alkyl group (e.g., methyl, trifluoromethyl), (3) a 5- or 6-membered monocyclic non-aromatic heterocycle (preferably pyrrolidine, piperidine), or
(4) a $C_{5-6}$ cycloalkane (preferably cyclohexane)];
m and n are each independently 1 or 2, and m+n is 2 or 3 (the combination (m, n) of m and n is preferably (1, 1), (2, 1) or (1, 2)); and
p and q are each independently 0 or 1, and p+q is 1 (the combination (p, q) of p and q is preferably (0, 1) or (1, 0)).
[Compound C-1]
Compound (I) wherein
$R^1$ is
  (1) a $C_{1-6}$ alkyl group (e.g., methyl), or
  (2) an amino group;
$R^2$ is a $C_{1-6}$ alkyl group (e.g., methyl);
X is —C($R^3$)($R^4$)—, —CO— or —O—;
$R^3$ and $R^4$ are both hydrogen atoms;
Y is —C($R^5$)($R^6$)—O—;
$R^5$ and $R^6$ are both hydrogen atoms;
Ring Q is benzene or a 5- or 6-membered monocyclic aromatic heterocycle (preferably pyridine), each of which is optionally substituted by 1 to 3 substituents selected from
  (a) a halogen atom (e.g., a fluorine atom), and
  (b) a $C_{1-6}$ alkyl group (e.g., methyl)
[preferably
(1) benzene optionally substituted by 1 to 3 halogen atoms (e.g., a fluorine atom), or
(2) a 5- or 6-membered monocyclic aromatic heterocycle (preferably pyridine) optionally substituted by 1 to 3 $C_{1-6}$ alkyl groups (e.g., methyl)];
Ring R is benzene optionally substituted by 1 to 3 $C_{1-6}$ alkoxy groups (e.g., methoxy) optionally substituted by 1 to 3 $C_{3-10}$ cycloalkyl groups (e.g., cyclopropyl);
Ring S is benzene or a 5- or 6-membered monocyclic aromatic heterocycle (preferably pyridine, pyrazine, pyridazine, pyrazole, oxazole, isoxazole), each of which is optionally substituted by 1 to 3 halogen atoms (e.g., a fluorine atom)
[preferably
(1) benzene, or
(2) a 5- or 6-membered monocyclic aromatic heterocycle (preferably pyridine, pyrazine, pyridazine, pyrazole, oxazole, isoxazole) optionally substituted by 1 to 3 halogen atoms (e.g., a fluorine atom)];
m and n are each independently 1 or 2, and m+n is 2 or 3 (the combination (m, n) of m and n is preferably (1, 1) or (2, 1)); and
p and q are each independently 0 or 1, and p+q is 1 (the combination (p, q) of p and q is preferably (0, 1) or (1, 0)).
[Compound C-2]
Compound (I) wherein
$R^1$ is
  (1) a $C_{1-6}$ alkyl group (e.g., methyl), or
  (2) an amino group;
$R^2$ is a $C_{1-6}$ alkyl group (e.g., methyl);
X is —C($R^3$)($R^4$)—, —CO— or —O—;
$R^3$ and $R^4$ are both hydrogen atoms;
Ring Q is benzene or a 5- or 6-membered monocyclic aromatic heterocycle (preferably pyridine), each of which is optionally substituted by 1 to 3 $C_{1-6}$ alkyl groups (e.g., methyl)
[preferably
(1) benzene, or
(2) a 5- or 6-membered monocyclic aromatic heterocycle (preferably pyridine) optionally substituted by 1 to 3 $C_{1-6}$ alkyl groups (e.g., methyl)];
Ring R is benzene optionally substituted by 1 to 3 $C_{1-6}$ alkoxy groups (e.g., methoxy) optionally substituted by 1 to 3 $C_{3-10}$ cycloalkyl groups (e.g., cyclopropyl);
Ring S is a 5-membered monocyclic aromatic heterocycle (preferably pyrazole, oxazole, isoxazole);

m and n are both 1; and
p is 1, and q is 0.
[Compound C-3]
Compound (I) wherein
$R^1$ is a $C_{1-6}$ alkyl group (e.g., methyl);
$R^2$ is a $C_{1-6}$ alkyl group (e.g., methyl);
Y is —C($R^5$)($R^6$)—O—;
$R^5$ and $R^6$ are both hydrogen atoms;
Ring Q is benzene optionally substituted by 1 to 3 halogen atoms (e.g., a fluorine atom);
Ring R is benzene optionally substituted by 1 to 3 $C_{1-6}$ alkoxy groups (e.g., methoxy) optionally substituted by 1 to 3 $C_{3-10}$ cycloalkyl groups (e.g., cyclopropyl);
Ring S is benzene or a 6-membered monocyclic aromatic heterocycle (preferably pyridine, pyrazine, pyridazine), each of which is optionally substituted by 1 to 3 halogen atoms (e.g., a fluorine atom)
[preferably
(1) benzene, or
(2) a 6-membered monocyclic aromatic heterocycle (preferably pyridine, pyrazine, pyridazine) optionally substituted by 1 to 3 halogen atoms (e.g., a fluorine atom)];
m is 1, and n is 2; and
p is 0, and q is 1.
[Compound D-1]
Compound (I) wherein
$R^1$ is
(1) a $C_{1-6}$ alkyl group (e.g., methyl), or
(2) an amino group;
$R^2$ is a $C_{1-6}$ alkyl group (e.g., methyl);
X is —O—;
Y is —C($R^5$)($R^6$)—O—;
$R^5$ and $R^6$ are both hydrogen atoms;
Ring Q is benzene optionally substituted by 1 to 3 halogen atoms (e.g., a fluorine atom);
Ring R is benzene optionally substituted by 1 to 3 $C_{1-6}$ alkoxy groups (e.g., methoxy) optionally substituted by 1 to 3 $C_{3-10}$ cycloalkyl groups (e.g., cyclopropyl);
Ring S is a 5- or 6-membered monocyclic aromatic heterocycle (preferably pyridine, oxazole);
m and n are each independently 1 or 2, and m+n is 2 or 3 (the combination (m, n) of m and n is preferably (1, 1) or (2, 1)); and
p and q are each independently 0 or 1, and p+q is 1 (the combination (p, q) of p and q is preferably (0, 1) or (1, 0)).
[Compound D-2]
Compound (I) wherein
$R^1$ is
(1) a $C_{1-6}$ alkyl group (e.g., methyl), or
(2) an amino group;
$R^2$ is a $C_{1-6}$ alkyl group (e.g., methyl);
X is —O—;
Ring Q is benzene;
Ring R is benzene optionally substituted by 1 to 3 $C_{1-6}$ alkoxy groups (e.g., methoxy) optionally substituted by 1 to 3 $C_{3-10}$ cycloalkyl groups (e.g., cyclopropyl);
Ring S is a 5-membered monocyclic aromatic heterocycle (preferably oxazole);
m and n are both 1; and
p is 1, and q is 0.
[Compound D-3]
Compound (I) wherein
$R^1$ is a $C_{1-6}$ alkyl group (e.g., methyl);
$R^2$ is a $C_{1-6}$ alkyl group (e.g., methyl);
Y is —C($R^5$)($R^6$)—O—;
$R^5$ and $R^6$ are both hydrogen atoms;

Ring Q is benzene optionally substituted by 1 to 3 halogen atoms (e.g., a fluorine atom);
Ring R is benzene optionally substituted by 1 to 3 $C_{1-6}$ alkoxy groups (e.g., methoxy) optionally substituted by 1 to 3 $C_{3-10}$ cycloalkyl groups (e.g., cyclopropyl);
Ring S is a 6-membered monocyclic aromatic heterocycle (preferably pyridine);
m is 1, and n is 2; and
p is 0, and q is 1.
[Compound E]
N-((2S)-1-((2-(4-(3-(cyclopropylmethoxy)phenoxy)phenyl)-1,3-oxazol-5-yl)oxy)propan-2-yl)acetamide or a salt thereof. N-(1-(6-((4-(3-(cyclopropylmethoxy)phenoxy)-2,6-difluorobenzyl)oxy)pyridin-3-yl)ethyl)acetamide (preferably N-((1S)-(6-((4-(3-(cyclopropylmethoxy)phenoxy)-2,6-difluorobenzyl)oxy)pyridin-3-yl)ethyl)acetamide) or a salt thereof.
1-((2S)-1-((2-(4-(3-(cyclopropylmethoxy)phenoxy)phenyl)-1,3-oxazol-5-yl)oxy)propan-2-yl)urea or a salt thereof.
Specific examples of compound (I) include the below-mentioned compounds of Examples 1 to 115.
A salt of the compound represented by the formula (I) is preferably a pharmacologically acceptable salt. Examples of such salt include salts with inorganic base, salts with organic base, salts with inorganic acid, salts with organic acid, and salts with basic or acidic amino acid.
Preferable examples of the salt with inorganic base include alkali metal salts such as sodium salt, potassium salt and the like; alkaline earth metal salts such as calcium salt, magnesium salt and the like; aluminum salt; and ammonium salt.
Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine and N,N-dibenzylethylenediamine.
Preferable examples of the salt with inorganic acid include salts with hydrogen chloride, hydrogen bromide, nitric acid, sulfuric acid and phosphoric acid.
Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid.
Preferable examples of the salt with basic amino acid include salts with arginine, lysine and ornithine.
Preferable examples of the salt with acidic amino acid include salts with aspartic acid and glutamic acid.
Compound (I) may be used in the form of a prodrug.
A prodrug of compound (I) means a compound which is converted to compound (I) by a reaction due to an enzyme, an gastric acid, etc. under the physiological condition in the living body, that is, a compound which is converted to compound (I) by oxidation, reduction, hydrolysis, etc. due to an enzyme; a compound which is converted to compound (I) by hydrolysis etc. due to gastric acid, etc.
Examples of the prodrug of compound (I) include a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation);
a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation);

a compound obtained by subjecting a carboxy group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methyl amidation etc.)

and the like. These compounds can be produced from compound (I) according to a method known per se.

A prodrug for compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

In the present specification, a prodrug may be in the form of a salt. Examples of the salt include those exemplified as the above-mentioned salt of the compound represented by the formula (I).

Compound (I) may be labeled with an isotope (e.g., $^3$H, $^{13}$C, $^{14}$C, $^{18}$F, $^{35}$S, $^{125}$I) and the like.

Compound (I) labeled with or substituted by an isotope may be used, for example, as a tracer (PET tracer) in Positron Emission Tomography (PET), and useful in the field of medical diagnosis and the like.

Compound (I) may be a hydrate or a non-hydrate, and a non-solvate or a solvate.

Compound (I) also encompasses a deuterium conversion form wherein $^1$H is converted to $^2$H(D).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability). The cocrystal and cocrystal salt can be produced by cocrystallization method known per se.

Compound (I) or a prodrug thereof (hereinafter sometimes to be abbreviated simply as the compound of the present invention) is expected to have low toxicity, and may be used safely as an agent for the prophylaxis or treatment of various diseases mentioned below in a mammal (e.g., human, mouse, rat, rabbit, dog, cat, bovine, horse, swine, monkey) directly or in the form of a pharmaceutical composition (hereinafter sometimes to be abbreviated as the medicament of the present invention) by admixing with a pharmacologically acceptable carrier and the like.

Examples of the pharmacologically acceptable carrier include various organic or inorganic carrier substances conventionally used as preparation materials, which are added as excipient, lubricant, binder or disintegrant for solid preparations; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethylstarch, light anhydrous silicic acid and low-substituted hydroxypropylcellulose.

Preferable examples of the solvent include water for injection, physiological saline, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include paraoxybenzoates, chlorobutanol, benzyl alcohol, phenethyl alcohol, dehydroacetic acid and sorbic acid.

Preferable examples of the antioxidant include sulfites, ascorbates.

Preferable examples of the colorant include aqueous food tar colors (e.g., food colors such as Food Red No. 2 and No. 3, Food Yellow No. 4 and No. 5, Food Blue No. 1 and No. 2, etc.), water insoluble lake dye (e.g., aluminum salt of the above-mentioned aqueous food tar color) and natural dye (e.g., β-carotene, chlorophyll, ferric oxide red).

Preferable examples of the sweetening agent include sodium saccharin, dipotassium glycyrrhizinate, aspartame and stevia.

Examples of the medicament of the present invention include tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop, and they are orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

These preparations may be controlled-release preparations such as immediate-release preparations, sustained-release preparations and the like (e.g., sustained-release microcapsule).

The medicament of the present invention can be produced by a method conventionally used in the technical field of pharmaceutical preparation, for example, the method described in the Japanese Pharmacopoeia.

While the content of the compound of the present invention in the medicament of the present invention varies depending on the dosage form, dose of the compound of the present invention, and the like, it is, for example, about 0.1 to 100 wt %.

During production of an oral preparation, coating may be applied as necessary for the purpose of masking of taste, enteric property or durability.

Examples of the coating base to be used for coating include sugar coating base, water-soluble film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax may be used in combination.

Examples of the water-soluble film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)].

The above-mentioned coating bases may be used after mixing with two or more kinds thereof at appropriate ratios. For coating, for example, a light shielding agent such as titanium oxide, ferric oxide can be used.

The compound of the present invention is expected to show low toxicity (e.g., acute toxicity, chronic toxicity, genetic toxicity, reproductive toxicity, pneumotoxicity, carcinogenicity and the like) and have a few side effects. Therefore, it can be used as an agent for the prophylaxis or treatment or a diagnostic of various diseases in a mammal.

The compound of the present invention may have an ACC (particularly, ACC1) inhibitory activity, and may be used as an agent for the prophylaxis or treatment of cancer, a cancer growth inhibitor, a cancer metastasis inhibitor and the like. In addition, the compound of the present invention may be used as an agent for the prophylaxis or treatment of ACC (particularly, ACC1) dependent diseases.

The compound of the present invention (particularly, the above-mentioned compound B, compound C, compound D and compound E) may be useful as a selective inhibitor of ACC1. Here, the "selective" means that the inhibitory activity against ACC1 is higher than that against ACC2.

The compound of the present invention may be used as a medicament such as an agent for the prophylaxis or treatment of diseases potentially influenced by ACC (particularly, ACC1), for example, cancer [e.g., colorectal cancer (e.g., colon cancer, rectal cancer, anus cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), pharynx cancer, larynx cancer, esophageal cancer, gastric cancer (e.g., papillary adenocarcinoma, mucinous adenocarcinoma, adenosquamous carcinoma), duodenal cancer, small intestinal cancer, breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), testis tumor, prostate cancer (e.g., hormone-dependent prostate cancer, non-hormone dependent prostate cancer, castration-resistant prostate cancer), liver cancer (e.g., hepatocellular cancer, primary liver cancer, extrahepatic bile duct cancer), thyroid cancer (e.g., medullary thyroid carcinoma), renal cancer (e.g., renal cell carcinoma, transitional cell carcinoma in kidney and urinary duct), uterine cancer (e.g., uterine cervix cancer, uterine body cancer, uterus sarcoma), gestational choriocarcinoma, brain tumor (e.g., medulloblastoma, glioma, pineal astrocytoma, pilocytic astrocytoma, diffuse astrocytoma, anaplastic astrocytoma, pituitary adenoma), retinoblastoma, skin cancer (e.g., basalioma, malignant melanoma), sarcoma (e.g., rhabdomyosarcoma, leiomyosarcoma, soft-tissue sarcoma, spindle cell sarcoma), malignant bone tumor, urinary bladder cancer, blood cancer (e.g., multiple myeloma, leukemia, malignant lymphoma, Hodgkin's disease, chronic myeloproliferative disease), primary unknown cancer]; a cancer growth inhibitor; a cancer metastasis inhibitor; an apoptosis promoter; an agent for the treatment of precancerous lesion (e.g., myelodysplastic syndrome); and the like.

In addition, the compound of the present invention may be used as an agent for the prophylaxis or treatment of angiogenesis, diabetic retinopathy, rheumatoid arthritis, psoriasis, atherosclerosis, restenosis, cardiac failure, Kaposi's sarcoma, COPD (chronic obstructive pulmonary diseases), cystic fibrosis, pain, asthma, endometriosis, cystic kidney, inflammation such as nephritis, hepatitis, dermatitis, osteoarthritis and the like, hypertension and the like.

Among these, the compound of the present invention may be effective for colorectal cancer, lung cancer, pancreatic cancer, gastric cancer, breast cancer, ovarian cancer, prostate cancer, liver cancer, thyroid cancer, renal cancer, brain tumor, melanoma, urinary bladder cancer, and hematologic cancer. Particularly, the compound of the present invention is effective for melanoma, thyroid cancer, lung cancer, colorectal cancer, ovarian cancer, prostate cancer, renal cancer and colorectal cancer.

In addition, the compound of the present invention may be used as an agent for the prophylaxis or treatment of obesity, diabetes (e.g., type 1 diabetes, type 2 diabetes, gestational diabetes, obese diabetes), hyperlipidemia (e.g., hypertriglyceridemia, hypercholesterolemia, high LDL-cholesterolemia, hypoHDL-emia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (pathology having three or more selected from hypertriglyceridemia, low HDL cholesterol (HDL-C), hypertension, abdomen obesity and impaired glucose tolerance), sarcopenia and the like.

Also, the compound of the present invention may also be used as a body weight increase inhibitor or an agent for the prophylaxis or treatment of metabolic syndrome of mammals.

Furthermore, the compound of the present invention can also be used, for example, as an agent for the prophylaxis or treatment of osteoporosis, cachexia (e.g., carcinomatous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrosis syndrome, hypertensive nephrosclerosis, terminal renal disorder), muscular dystrophy, myocardial infarction, angina pectoris, cerebrovascular disorder (e.g., cerebral infarction, cerebral apoplexy), Alzheimer's disease, Parkinson's disease, anxiety, dementia, insulin resistance syndrome, syndrome X, hyperinsulinemia, sensory abnormality in hyperinsulinemia, acute or chronic diarrhea, inflammatory disease (e.g., chronic rheumatoid arthritis, spondylitis deformans, osteoarthritis, lumbago, gout, postoperative or posttraumatic inflammation, swelling, neuralgia, pharyngolaryngitis, cystitis, hepatitis (including non-alcoholic steatohepatitis), liver fibrosis, pneumonia, pancreatitis, enteritis, inflammatory bowel disease (including inflammatory colitis), ulcerative colitis, stomach mucosal injury (including stomach mucosal injury caused by aspirin)), small intestine mucosal injury, malabsorption, testis dysfunction, visceral obesity syndrome and sarcopenia.

Particularly, the compound of the present invention may be useful as an agent for the prophylaxis or treatment of hepatitis, hepatic fibrosis, fatty liver and the like, due to an ACC1 selective inhibitory action.

While the dose of the compound of the present invention may vary depending on the subject of administration, administration route, target disease, symptom and the like, for example, for oral administration of the compound of the present invention to an adult cancer patient, it is generally about 0.01 to 100 mg/kg body weight, preferably about 0.1 to 30 mg/kg body weight, further preferably about 0.5 to 10 mg/kg body weight for one dose, which may be administered once to 3 times a day.

With the aim of enhancing the action of the compound of the present invention or decreasing the dose of the compound and the like, the compound may be used in combination with other drug. Specifically, the compound of the present invention may be used in combination with drugs such as hormonal therapeutic agent, chemotherapeutic agent, immunotherapeutic agent or medicament inhibiting actions of cell growth factor and receptor thereof and the like. In the following, a drug that can be used in combination with the compound of the present invention is to be abbreviated as a "concomitant drug".

As the "hormonal therapeutic agent", for example, fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate, toremifene citrate), pill preparation, mepitiostane, testrolactone, aminoglutethimide, LH-RH agonist (e.g., goserelin acetate, buserelin, leuprorelin acetate), droloxifene, epitiostanol, ethinylestradiol sulfonate, aromatase inhibitor (e.g., fadrozole hydrochloride, anastrozole, retrozole, exemestane, vorozole, formestane), anti-androgen (e.g., flutamide, bicartamide, nilutamide, enzalutamide), 5α-reductase inhibitor (e.g., finasteride, epristeride, dutasteride), adrenocortical hormone drug (e.g., dexamethasone, predonisolone, betamethasone, triamcinolone, dutasteride), androgen synthesis inhibitor (e.g., abiraterone), retinoid and drugs that retard retinoid metabolism (e.g., liarozole) are used.

As the "chemotherapeutic agent", for example, alkylating agents, metabolic antagonists, antitumor antibiotics, and plant-derived antitumor drugs are used.

As the "alkylating agent", for example, nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and DDS preparations thereof are used.

As the "metabolic antagonist", for example, mercaptopurine, 6-mercaptopurine riboside, thioinosine, methotrexate, pemetrexed, enocitabine, cytarabine, cytarabine ocfosfate, ancitabine hydrochloride, 5-FU drug (e.g., fluorouracil, tegafur, UFT, doxifluridine, carmofur, gallocitabine, emitefur, capecitabine), aminopterin, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, tiazofurin, ambamustine, bendamustine, and DDS preparations thereof are used.

As the "antitumor antibiotic", for example, actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, and DDS preparations thereof (e.g., doxorubicin-containing PEG liposome) are used.

As the "plant-derived antitumor agent", for example, etoposide, etoposide phosphate, vinblastine sulfate, vincristine sulfate, vindesine sulfate, teniposide, paclitaxel, docetaxel, cabazitaxel, vinorelbine, and DDS preparations thereof are used.

As the "immunotherapeutic agent", biological response modifiers (e.g., picibanil, krestin, schizophyllan, lentinan, ubenimex, interferon, interleukin, macrophage colony stimulating factor, granulocyte colony stimulating factor, erythropoietin, lymphotoxin, BCG vaccine, *corynebacterium parvum*, levamisole, polysaccharide K, procodazole and anti-CTLA4 antibody (e.g., ipilimumab, tremelimumab), anti-PD-1 antibody (e.g., nivolumab, pembrolizumab), anti-PD-L1 antibody)) are used.

The "cell growth factors" in the "medicament inhibiting actions of cell growth factor and receptor thereof" may be any substance that promotes cell proliferation, which is normally peptide having not more than 20,000 molecular weight, and capable of exhibiting the activity at low concentrations by binding to a receptor, and specifically
(1) EGF (epidermal growth factor) or substances possessing substantially the same activity as EGF (e.g., TGFα);
(2) insulin or substances possessing substantially the same activity as insulin (e.g., insulin, IGF (insulin-like growth factor)-1, IGF-2),
(3) FGF (fibroblast growth factor) or substances possessing substantially the same activity as FGF (e.g., acidic FGF, basic FGF, KGF (keratinocyte growth factor), FGF-10), and
(4) other cell growth factors (e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin); and the like are used.

The "cell growth factor receptor" may be any receptor capable of binding to the above-mentioned cell growth factors, and specifically, EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2), PDGF receptor, and the like are used.

As the "medicament inhibiting actions of cell growth factor and receptor thereof", for example, EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor inhibitor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Smo inhibitor, ALK inhibitor, ROR1 inhibitor, Trk inhibitor, Ret inhibitor, mTOR inhibitor, Aurora inhibitor, PLK inhibitor, MEK (MEK1/2) inhibitor, MET inhibitor, CDK inhibitor, Akt inhibitor, ERK inhibitor, PI3K inhibitor and the like are used. As such medicament, more specifically, anti-VEGF antibody (e.g., Bevacizumab, Ramucurumab), anti-HER2 antibody (e.g., Trastuzumab, Pertuzumab), anti-EGFR antibody (e.g., Cetuximab, Panitumumab, Matuzumab, Nimotuzumab), anti-HGF antibody, Imatinib, Erlotinib, Gefitinib, Sorafenib, Sunitinib, Dasatinib, Lapatinib, Vatalanib, Ibrutinib, Bosutinib, Cabozantinib, Crizotinib, Alectinib, Vismodegib, Axitinib, Motesanib, Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, Tozasertib, 2-[N-[3-[4-[5-[N-(3-fluorophenyl)carbamoylmethyl]-1H-pyrazol-3-ylamino]quinazolin-7-yloxy]propyl]-N-ethylamino] ethyl phosphate (AZD-1152), 4-[9-chloro-7-(2,6-difluorophenyl)-5H-primido[5,4-d][2]benzazepin-2-ylamino]benzoic acid, N-[2-methoxy-5-[(E)-2-(2,4,6-trimethoxyphenyl)vinylsulfonylmethyl]phenyl]glycine sodium salt (ON-1910Na), Volasertib, Selumetinib, Trametinib, N-[2(R),3-dihydroxypropoxy]-3,4-difluoro-2-(2-fluoro-4-iodophenylamino)benzamide (PD-0325901), Bosutinib, Regorafenib, Afatinib, Idelalisib, Ceritinib, Dabrafenib and the like are used.

Besides the above-mentioned medicaments, L-asparaginase, L-arginase, arginine deiminase, aceglatone, procarbazine hydrochloride, protoporphyrin-cobalt complex salt, mercuric hematoporphyrin-sodium, topoisomerase I inhibitor (e.g., irinotecan, topotecan, indotecan, Indimitecan), topoisomerase II inhibitor (e.g., sobuzoxane), differentiation-inducing factor (e.g., retinoid, vitamin D), other angiogenesis inhibitor (e.g., fumagillin, shark extract, COX-2 inhibitor), α-blocker (e.g., tamsulosin hydrochloride), bisphosphonic acid (e.g., pamidronate, zoledronate), thalidomide, lenalidomide, pomalidomide, 5-azacytidine, decitabine, proteasome inhibitor (e.g., bortezomib, carfilzomib, ixazomib), NEDD8 inhibitor (e.g., Pevonedistat), UAE inhibitor, PARP inhibitor (e.g., Olaparib, Niraparib, Veliparib), antitumor antibodies such as anti-CD20 antibody (e.g., Rituximab, Obinutuzumab), anti-CCR4 antibody (e.g., Mogamulizumab) and the like, antibody drug complexes (e.g., Trastuzumab emtansine, Brentuximab vedotin) and the like can also be used.

In addition, the compound of the present invention can also be used in combination with medicaments such as therapeutic or prophylactic agents for non-alcoholic fatty liver disease (NAFLD), therapeutic agents for diabetes, therapeutic agents for diabetic complications, therapeutic agents for hyperlipidemia, antihypertensive agents, antiobesity agents, diuretics, antithrombotic agents, therapeutic agents for liver diseases and the like.

As the therapeutic or prophylactic agents for NAFLD, obeticholic acid, saroglitazar, simtuzumab, emricasan, eicosapentaenoic acid, cenicriviroc, GFT-505, aramchol, tipelukast, GS-4997, GR-MD-02, NGM-282, BMS-986036, IMM124E, ARI-3037MO, KD-025, VK-2809, ND-L02-s0201 (HSP47 siRNA), TRX-318, CEM-101, LJN-452, JKB-121, NDI-010976, AZD-4076, DS-102, PRX-106, A-4250, IONIS-DGAT2Rx, NC-101, PXS4728A, DUR-928, CAT-213, Px-102, VBY-376, MGL-3196, SHP-626 and the like are used.

As the "therapeutic agents for diabetes", insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, the compound described in WO 2007/013694, WO 2007/018314, WO 2008/093639 or WO 2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [e.g., sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Alogliptin or a salt thereof (preferably, benzoate), trelagliptin or a salt thereof (preferably, succinate), Vildagliptin, Sitagliptin, Saxagliptin, BI1356, GRC8200, MP-513, PF-00734200, PHX1149, SK-0403, ALS2-0426, TA-6666, TS-021, KRP-104, β3 agonists (e.g., N-5984), GPR40 agonists (e.g., fasiglifam, the compound described in WO 2004/041266, WO 2004/

106276, WO 2005/063729, WO 2005/063725, WO 2005/087710, WO 2005/095338, WO 2007/013689 or WO 2008/001931), GLP-1 receptor agonists (e.g., GLP-1, GLP-1MR preparation, Liraglutide, Exenatide, AVE-0010, BIM-51077, Aib(8,35)hGLP-1(7,37)NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or an agonist thereof, IKK inhibitors (e.g., AS-2868), leptin resistance improving drugs, somatostatin receptor agonists, glucokinase activators (e.g., Piragliatin, AZD1656, AZD6370, TTP-355, the compound described in WO 2006/112549, WO 2007/028135, WO 2008/047821, WO 2008/050821, WO 2008/136428 or WO2008/156757), GIP (Glucose-dependent insulinotropic peptide), GPR119 agonist (e.g., PSN821, MBX-2982, APD597), FGF21, FGF analogue and the like are used.

As the "therapeutic agents for diabetic complications", aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF, neurophin production-secretion promoters thereof (e.g., 4-(4-chlorophenyl)-2-(2-methyl-1-imidazolyl)-5-[3-(2-methylphenoxy)propyl]oxazole) described in WO 01/14372, a compound described in WO 2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, Pregabalin), serotonin-noradrenaline re-uptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1(ASK-1) inhibitors and the like are used.

As the "therapeutic agent for hyperlipidemia", HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., a compound described in WO 97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., cohlestyramine), probucol, nicotinic acid drugs (e.g., nicomol, niceritrol, niaspan), ethyl icosapentate, phytosterols (e.g., soysterol, γ-oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like are used.

Examples of the "antihypertensive agent" include angiotensin converting enzyme inhibitors (e.g., captopril, enalapril, delapril etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, amlodipine, cilnidipine and the like), β blockers (e.g., metoprolol, atenolol, propranolol, carvedilol, pindolol), clonidine and the like.

Examples of the "antiobesity agent" include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor modulators, GABA modulators (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylating enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearoyl-CoA desaturase inhibitors, microsomal triglyceride transfer protein inhibitors (e.g., R-256918), Na-glucose cotransporter inhibitors (e.g., JNJ-28431754, remogliflozin), NFκ inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821, MBX-2982, APD597), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine and pig; human GLP-1 preparations genetically synthesized using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine and pig; human FGF21 preparations genetically synthesized using *Escherichia coli* or yeast; fragments or derivatives of FGF21)), anorexigenic agents (e.g., P-57) and the like.

Examples of the "diuretics" include xanthine derivatives (e.g., theobromine sodium salicylate, theobromine calcium salicylate etc.), thiazide preparations (e.g., ethiazide, cyclopenthiazide, trichloromethiazide, hydrochlorothiazide, hydroflumethiazide, benzylhydrochlorothiazide, penflutizide, poly5thiazide, methyclothiazide etc.), antialdosterone preparations (e.g., spironolactone, triamterene etc.), carbonic anhydrase inhibitors (e.g., acetazolamide etc.), chlorobenzenesulfonamide agents (e.g., chlortalidone, mefruside, indapamide etc.), azosemide, isosorbide, ethacrynic acid, piretanide, bumetanide, furosemide and the like.

Examples of the "antithrombotic agent" include heparins (e.g., heparin sodium, heparin calcium, enoxaparin sodium, dalteparin sodium), warfarins (e.g., warfarin potassium), anti-thrombin drugs (e.g., argatroban, dabigatran), FXa inhibitors (e.g., rivaroxaban, apixaban, edoxaban, YM150, compound described in WO 02/06234, WO 2004/048363, WO 2005/030740, WO 2005/058823 or WO 2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the "therapeutic agents for liver diseases" include viral hepatitis drug (e.g., interferon preparation (e.g., interferon alpha-2a, PEGylated interferon alpha-2a, interferon alfacon-1, natural interferon, interferon beta-1a, omega interferon), Ribavirin, telaprevir, sofosbuvir, ledipasvir, entecavir and the like), antioxidant (vitamin E preparation and the like), liver protecting agent (ursodeoxycholic acid, glycyrrhizin, glucuronic acid and the like), therapeutic drugs for liver cancer (sorafenib and the like), immunosuppressant (steroids such as predonisolone and the like, azathioprine and the like), therapeutic drug for decompensated liver cirrhosis (spironolactone, furosemide, amino acid preparation, vitamin K preparation and the like) and the like.

The administration time of the above-mentioned concomitant drug is not limited, and the compound of the present invention and the concomitant drug may be administered to an administration subject simultaneously, or may be administered at different times. The dosage of the concomitant drug may be determined according to the dosage clinically used, and can be appropriately selected depending on the administration subject, administration route, diseases, combination thereof and the like.

The administration mode of the concomitant drug is not particularly limited, and the compound of the present invention and the concomitant drug only need to be combined on administration. Examples of such administration mode include the following:
(1) administration of a single preparation obtained by simultaneously processing the compound of the present invention and the concomitant drug,
(2) simultaneous administration of two kinds of preparations of the compound of the present invention and the concomitant drug, which have been separately produced, by the same administration route,
(3) administration of two kinds of preparations of the compound of the present invention and the concomitant drug, which have been separately produced, by the same administration route in a staggered manner,
(4) simultaneous administration of two kinds of preparations of the compound of the present invention and the concomitant drug, which have been separately produced, by different administration routes,
(5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug may be appropriately selected depending on the administration subject, administration route(s), diseases and the like.

In addition, the compound of the present invention may also be used in combination with a non-medication therapy. Specific examples of the non-medication therapy include (1) operation; (2) hypertensive chemical therapy using angiotensin II and the like; (3) gene therapy; (4) hyperthermic therapy; (5) cryotherapy; (6) laser ablation method; and (7) radiation therapy.

The production method of the compound of the present invention is explained in the following.

The starting materials and reagents used in each step in the following production method, and the compounds obtained therein each may form a salt. Examples of the salt include those similar to the above-mentioned salts of the compound of the present invention, and the like.

When the compound obtained in each step is a free compound, it can be converted to a desired salt according to a method known per se. Conversely, when the compound obtained in each step is a salt, it can be converted to a free form or a desired other kind of salt according to a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

The starting materials and reagent compounds used in each step can be produced according to a method known per se. When these compounds are commercially available, the commercially available products can be used as they are.

In the reaction of each step, while the reaction time varies depending on the reagents and solvents to be used, unless otherwise specified, it is generally 1 min-48 hr, preferably 10 min-8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm-20 atm, preferably 1 atm-3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature −300° C., preferably 50° C.-250° C. While the reaction time varies depending on the reagents and solvents to be used, unless otherwise specified, it is generally 1 min-48 hr, preferably 1 min-8 hr.

In the reaction of each step, unless otherwise specified, a reagent is used in 0.5 equivalent-20 equivalents, preferably 0.8 equivalent-5 equivalents, relative to the substrate. When a reagent is used as a catalyst, the reagent is used in 0.001 equivalent-1 equivalent, preferably 0.01 equivalent-0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and water.

The above-mentioned solvent can be used in a mixture of two or more kinds thereof in an appropriate ratio.

When a base is used in the reaction of each step, for example, bases shown below or those described in Examples are used.

inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropyl amide, lithium hexamethyl disilazide and the like; and
organic lithiums: n-butyllithium and the like.

When an acid or acidic catalyst is used in the reaction of each step, for example, acids and acidic catalysts shown below or those described in Examples are used.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; and
Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, t-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as t-butylcarbonate and the like, and the like.

Examples of the protecting group of the carbonyl group of aldehyde include acetal protecting groups such as dimethyl acetal and the like; cyclic acetal protecting groups such as cyclic 1,3-dioxane and the like, and the like.

Examples of the protecting group of the carbonyl group of ketone include ketal protecting groups such as dimethyl ketal and the like; cyclic ketal protecting groups such as cyclic 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic hetero ring such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid, and the like. When a carbon-carbon double bond or triple bond is reduced, a method using a catalyst such as palladium-carbon, Lindlar catalyst and the like is used.

When an oxidation reaction is performed in each step, examples of an oxidant to be used include peracids such as m-chloroperbenzoic acid (mCPBA), hydrogen peroxide, t-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5,6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include phosphonoacetic acid esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include a combination of Lewis acid and acid chloride and a combination of Lewis acid and alkylating agents (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include arylmagnesium halides such as phenylmagnesium bromide and the like; and alkylmagnesium halides such as methylmagnesium bromide and the like. The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5,4,0]undec-7-ene (DBU), a method using trimethylsilyl azide and the Lewis acid and the like can be employed.

When a reductive amination reaction is performed in each step, examples of the reducing agent to be used include sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia, primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and triphenylphosphine are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1'-carbonyldiimidazole (CDI) and the like; diphenylphosphoryl azide (DPPA); benzotriazol-1-yloxy-trisdimethylaminophosphonium salt (BOP reagent); 2-chloro-1-methylpyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; a combination thereof and the like. When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine) palladium(II), dichlorobis(triethylphosphine)palladium(II), tris(dibenzylideneacetone)dipalladium(0), 1,1'-bis(diphenylphosphino)ferrocene palladium(II) chloride, palladium (II) acetate and the like; nickel compounds such as tetrakis (triphenylphosphine)nickel(0) and the like; rhodium compounds such as tris(triphenylphosphine)rhodium(III) chloride and the like; a cobalt compound; copper compounds such as copper oxide, copper(I) iodide and the like; a platinum compound and the like. A base may be further added to the reaction and examples of such base include inorganic bases and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid and the like for bromination. In addition, a method of obtaining a halogenated alkyl form from alcohol by reacting with triphenylphosphine and carbon tetrachloride or carbon tetrabromide, and the like may be used. Alternatively, a method of synthesizing a halogenated alkyl form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethyl phosphite, tri(isopropyl) phosphite and the like.

When a sulfonate esterification reaction is performed in each step, examples of the sulfonylating agent to be used include methanesulfonyl chloride, p-toluenesulfonyl chloride, methanesulfonic anhydride, p-toluenesulfonic anhydride and the like.

When a hydrolysis reaction is performed in each step, an acid or a base is used as the reagent. In addition, when an acid hydrolysis reaction of t-butyl ester is performed, formic acid, triethylsilane and the like are sometimes added to reductively trap the by-produced t-butyl cation.

When a dehydrating reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

Specific examples of the solvent to be used for the reaction of each step also include the following.

Examples of the "aromatic amines" include pyridine, imidazole and 2,6-lutidine.

Examples of the "tertiary amines" include triethylamine, diisopropylethylamine, N-methylmorpholine, 1,8-diazabicyclo[5.4.0]undec-7-ene] (DBU), 1,5-diazabicyclo[4.3.0]non-5-ene (DBN) and 1,1,3,3-tetramethylguanidine.

Examples of the "Lewis acids" include boron trifluoride diethyl ether complex, titanium tetrachloride, aluminium chloride, trifluoroacetic anhydride and trifluoromethanesulfonic anhydride.

Unless otherwise specified, each symbol in the formulas is as defined above. Moreover, in each formula, unless otherwise specified, the same symbol is defined same.

Compound (I) can be produced from compound (1) according to the following method.

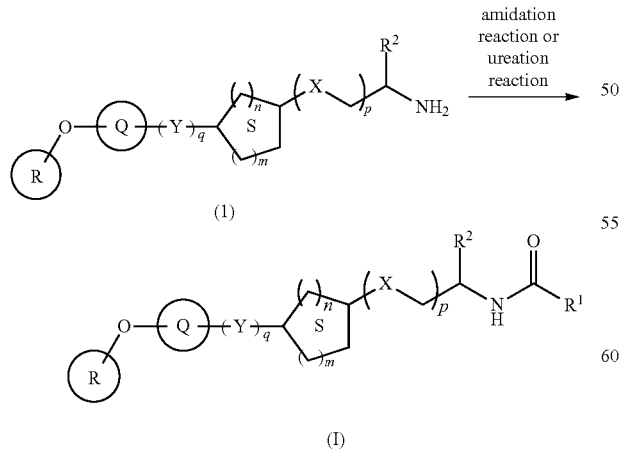

Compound (I-1) can be produced from compound (2) and compound (3) according to the following method.

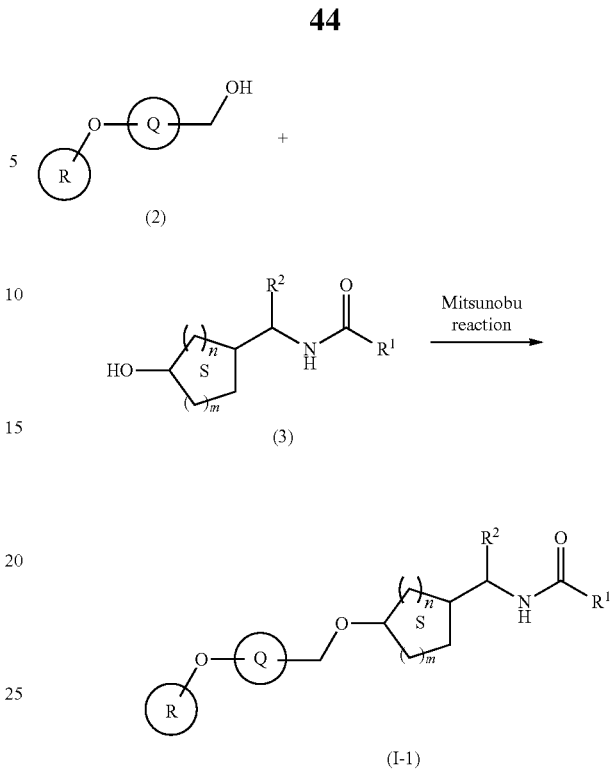

Compound (I-1) can also be produced from compound (2) and compound (4) according to the following method.

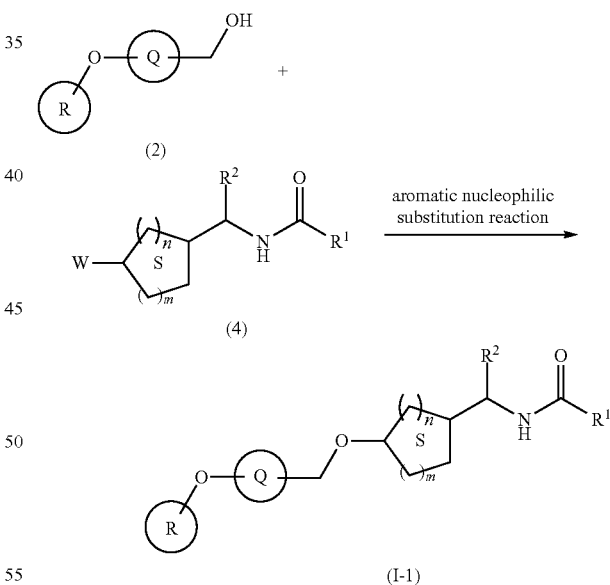

wherein W is a halogen atom or a sulfonyloxy group.

Examples of the "sulfonyloxy group" represented by W include optionally halogenated $C_{1-6}$ alkylsulfonyloxy groups (e.g., methylsulfonyloxy, trifluoromethylsulfonyloxy), $C_{6-14}$ arylsulfonyloxy groups optionally substituted by $C_{1-6}$ alkyl group(s) (e.g., phenylsulfonyloxy, p-toluenesulfonyloxy) and the like.

Compound (I-2) can be produced from compound (I-3) according to the following method.

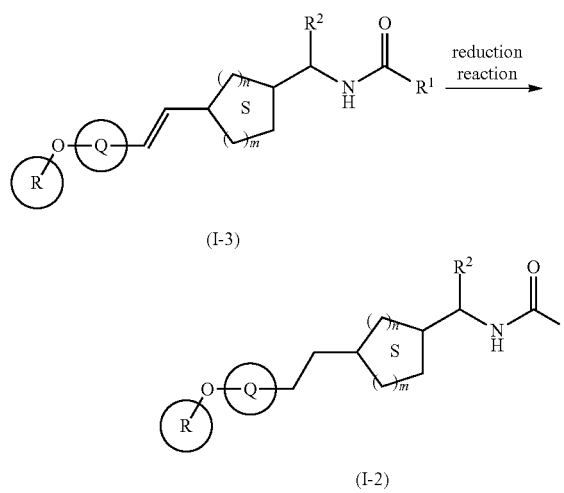

(I-3)

(I-2)

Compound (I-4) can be produced from compound (I-3) according to the following method.

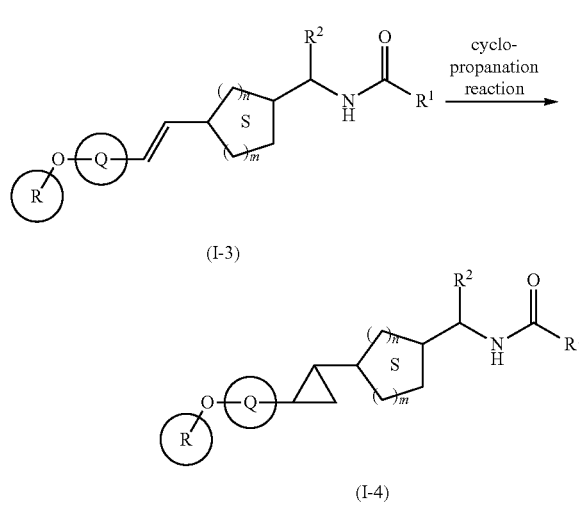

(I-3)

(I-4)

Compound (I-5) can be produced from compound (I-6) according to the following method.

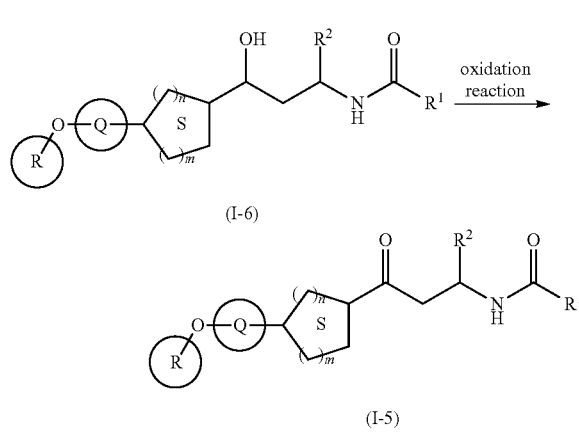

(I-6)

(I-5)

Compound (I-7) can be produced from compound (5) and compound (6) according to the following method.

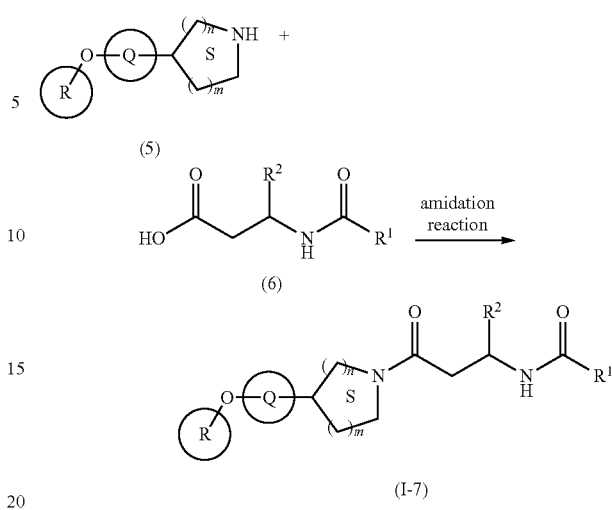

(5)

(6)

(I-7)

Compound (1) can be produced from compound (7) according to the following method.

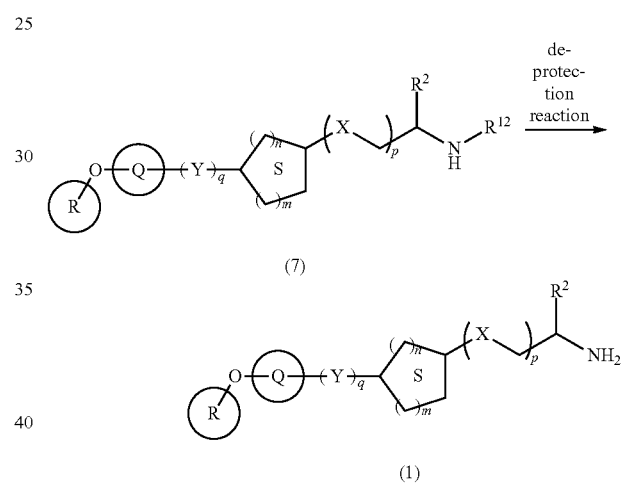

(7)

(1)

wherein $R^{12}$ is a protecting group of an amino group.

Examples of the protecting group of amino group include those similar to the above-mentioned protecting group of amino group.

Compound (1) can also be produced from compound (8) according to the following method.

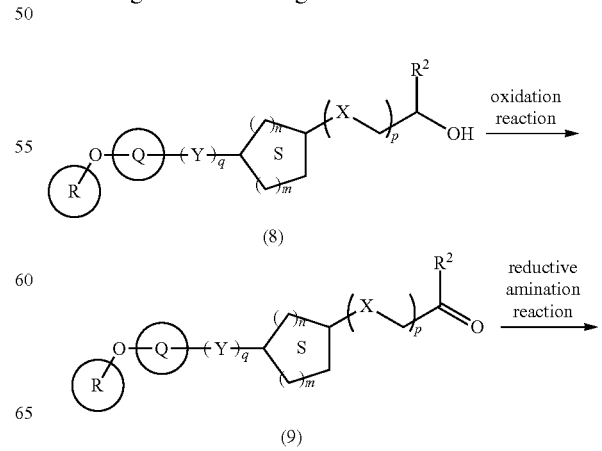

(8)

(9)

-continued

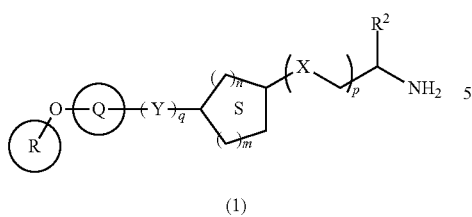

(1)

Compound (1) can also be produced from compound (8) according to the following method.

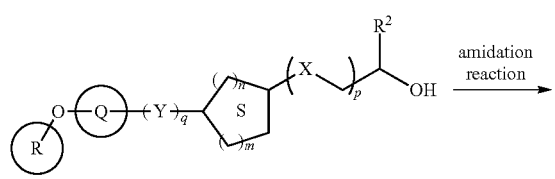

(8)

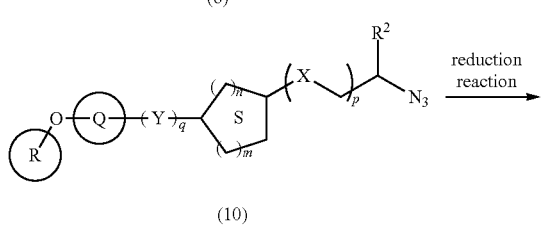

(10)

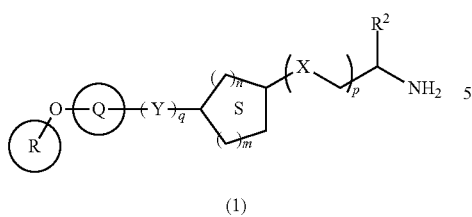

(1)

Compound (7-1) can be produced from compound (11) and compound (12) according to the following method.

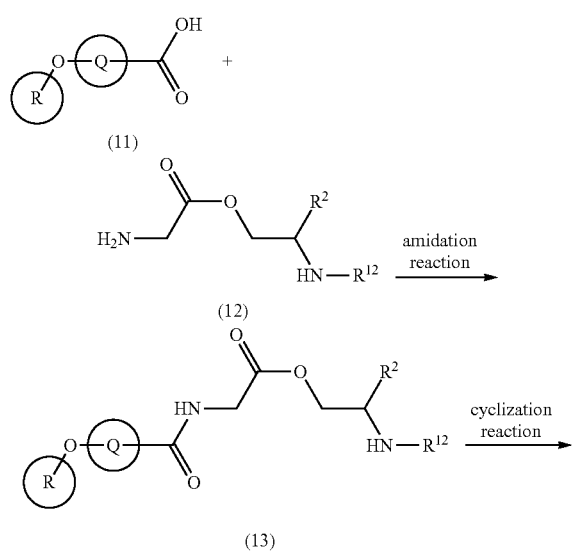

(13)

-continued

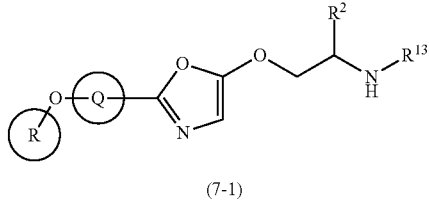

(7-1)

Compound (7-1) can be produced by subjecting compound (13) to a cyclization reaction with a dehydration condensing agent.

Examples of the dehydration condensing agent include a combination of iodine and triphenylphosphine; a combination of an azodicarboxylate and triphenylphosphine; phosphorus oxychloride, diphosphorus pentaoxide and the like.

Compound (7-1) can also be produced from compound (14) and compound (12) according to the following method.

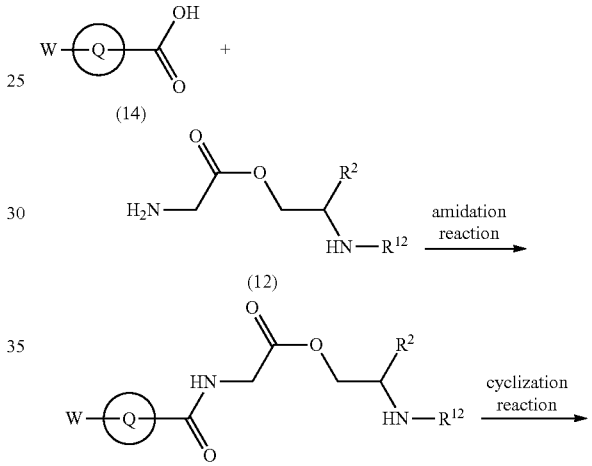

(15)

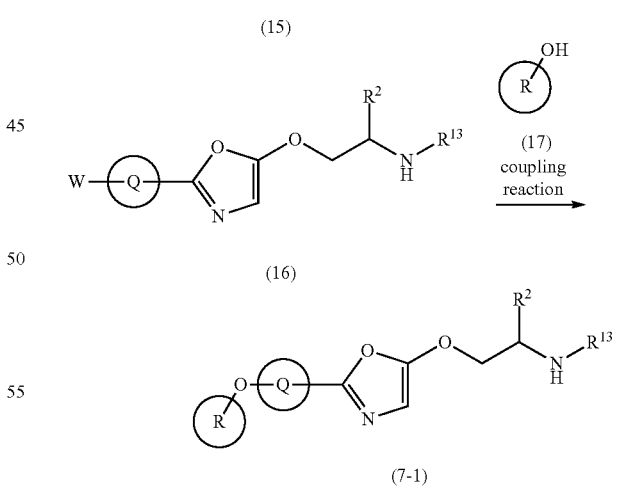

(7-1)

Compound (16) can be produced by subjecting compound (15) to a cyclization reaction with a dehydration condensing agent.

This reaction is carried out in the same manner as in the production of compound (7-1) from compound (13).

Compound (7-2) can be produced from compound (18) and compound (19) according to the following method.

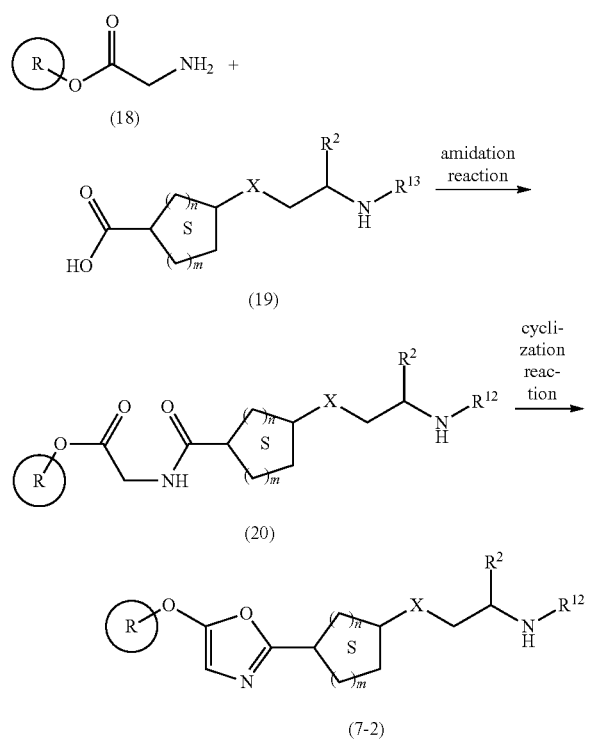

(18)

(19)

amidation reaction (20)

cyclization reaction (7-2)

Compound (7-2) can be produced by subjecting compound (20) to a cyclization reaction with a dehydration condensing agent.

This reaction is carried out in the same manner as in the production of compound (7-1) from compound (13).

Compound (7-3) can be produced from compound (21) and compound (22) according to the following method.

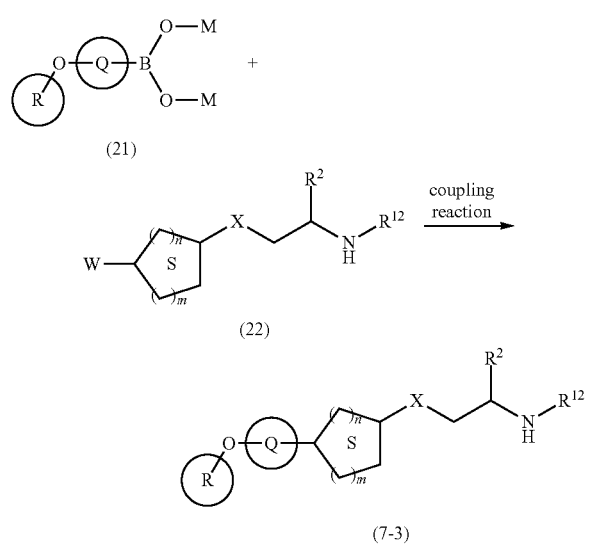

(21)

(22)

coupling reaction (7-3)

wherein M is a hydrogen atom or an optionally substituted $C_{1-6}$ alkyl group, or the two M in combination optionally form a ring.

Examples of the above-mentioned ring include heterocycles containing, as a ring-constituting atom besides carbon atom, a boron atom and an oxygen atom.

Compound (7-4) can be produced from compound (23) and compound (24) according to the following method.

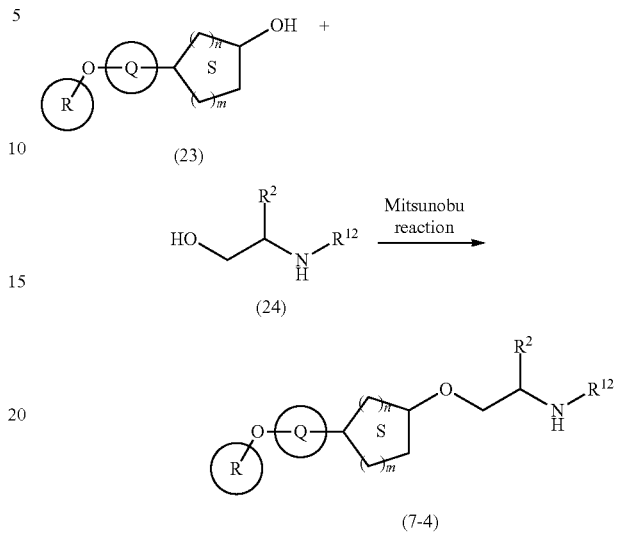

(23)

Mitsunobu reaction (24)

(7-4)

Compound (9) can be produced from compound (25) according to the following method.

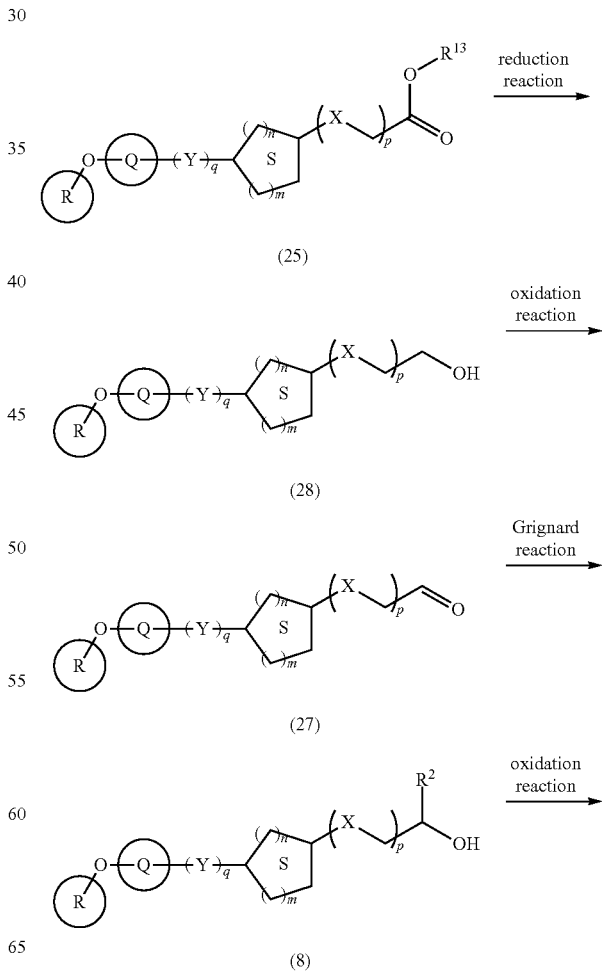

(25)

reduction reaction (28)

oxidation reaction (27)

Grignard reaction (8)

oxidation reaction

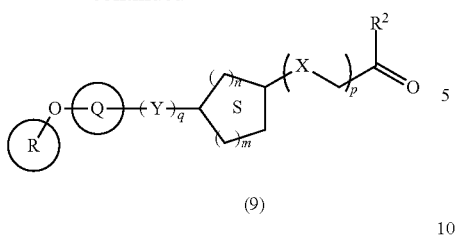

(9)

wherein R[13] is a substituent.

Compound (9) can also be produced from compound (25) according to the following method.

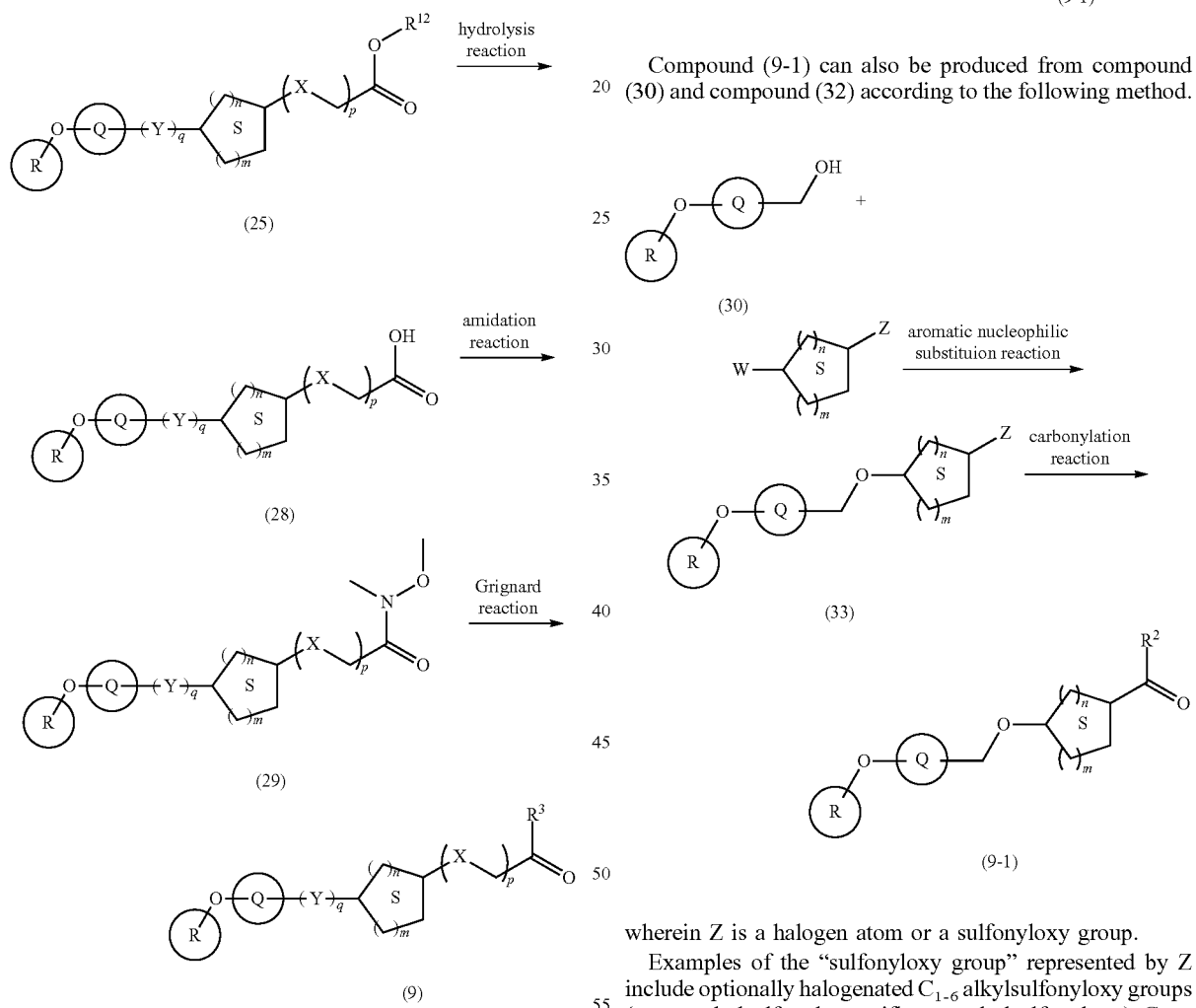

Compound (9-1) can be produced from compound (30) and compound (31) according to the following method.

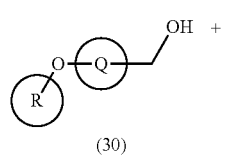

(30)

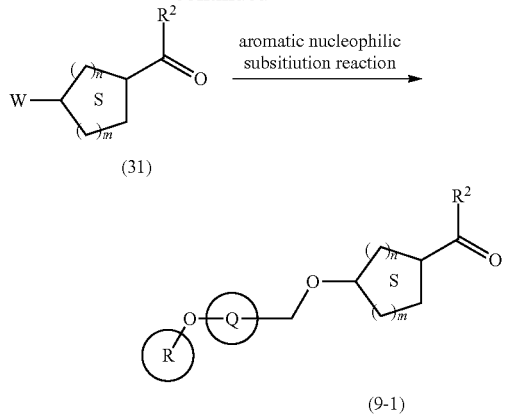

Compound (9-1) can also be produced from compound (30) and compound (32) according to the following method.

wherein Z is a halogen atom or a sulfonyloxy group.

Examples of the "sulfonyloxy group" represented by Z include optionally halogenated $C_{1-6}$ alkylsulfonyloxy groups (e.g., methylsulfonyloxy, trifluoromethylsulfonyloxy), $C_{6-14}$ arylsulfonyloxy groups optionally substituted by $C_{1-6}$ alkyl group(s) (e.g., phenylsulfonyloxy, p-toluenesulfonyloxy) and the like.

Compound (9-1) can be produced by subjecting compound (33) to a carbonylation reaction.

This reaction is carried out by vinyl etherification employing a coupling reaction, and then by a hydrolysis reaction.

Examples of the reagent to be used for the vinyl etherification employing a coupling reaction include tributyl(1-ethoxyvinyl)tin, ethoxyvinyl ether, butyl vinyl ether and the like.

Compound (9-2) can be produced from compound (34) and compound (31) according to the following method.

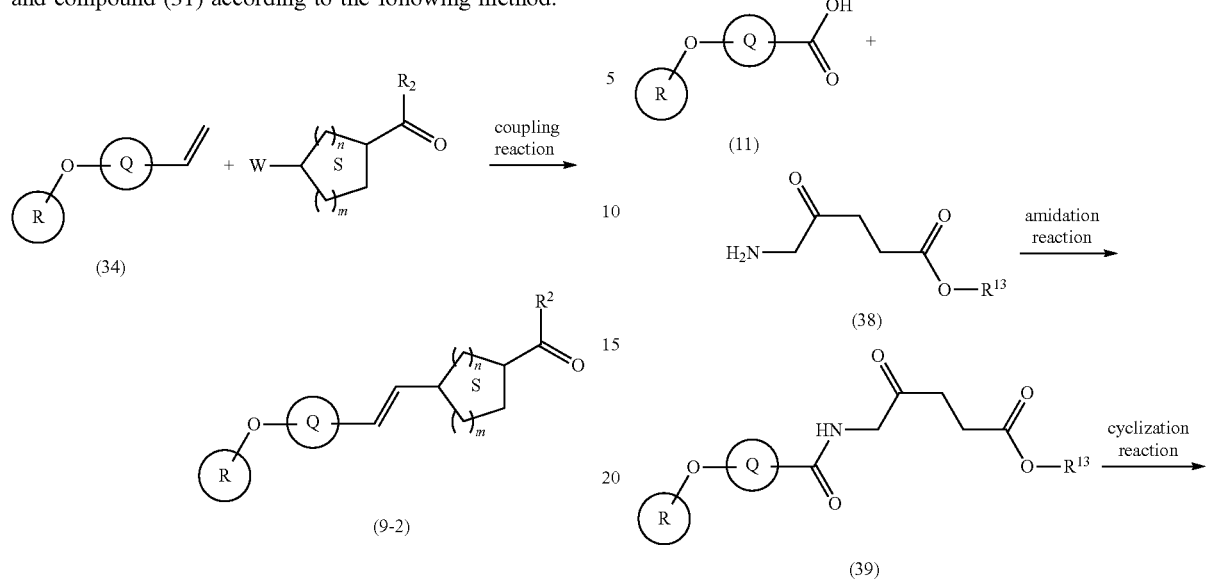

Compound (9-3) can be produced from compound (35) according to the following method.

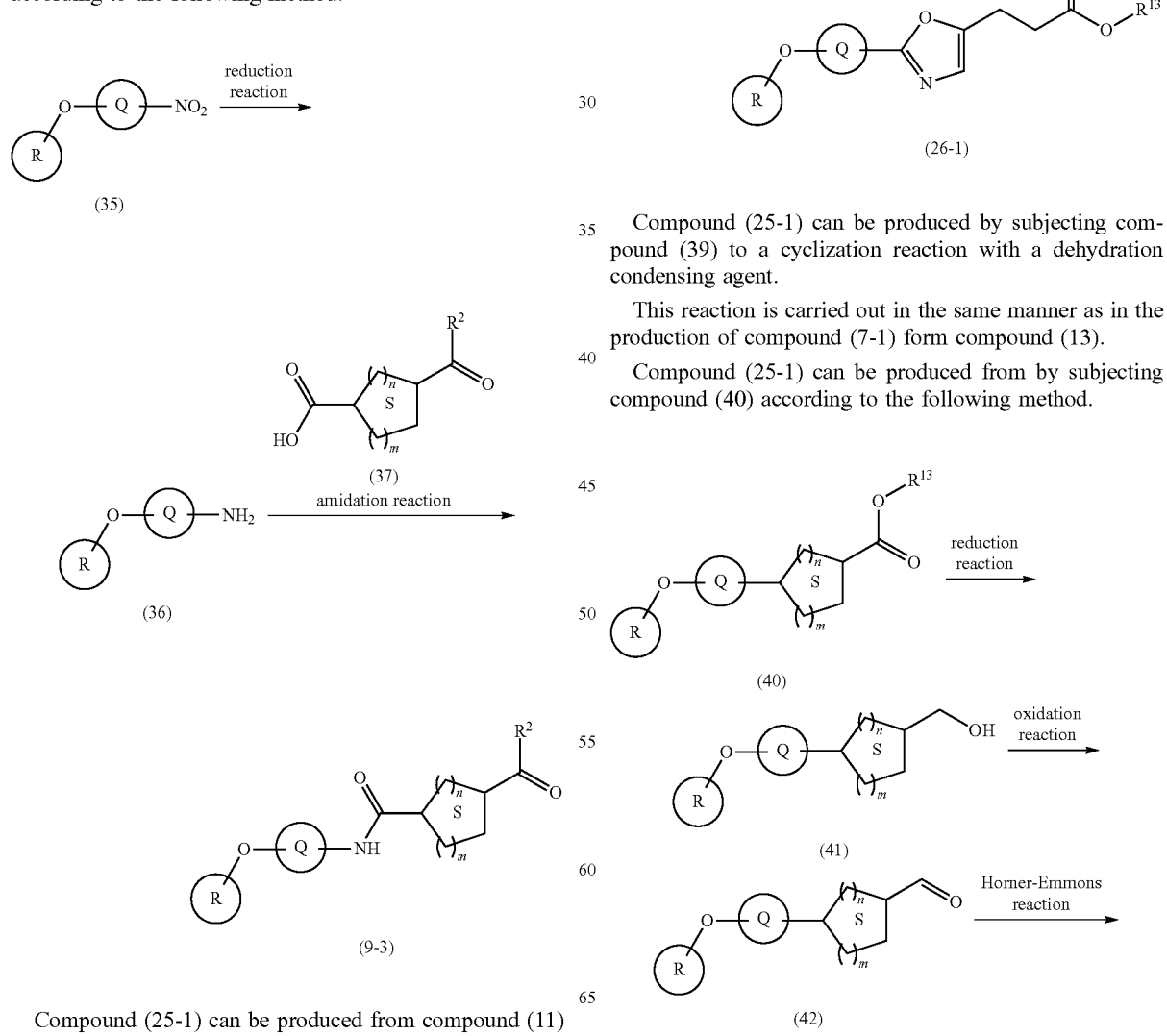

Compound (25-1) can be produced from compound (11) and compound (38) according to the following method.

Compound (25-1) can be produced by subjecting compound (39) to a cyclization reaction with a dehydration condensing agent.

This reaction is carried out in the same manner as in the production of compound (7-1) form compound (13).

Compound (25-1) can be produced from by subjecting compound (40) according to the following method.

-continued

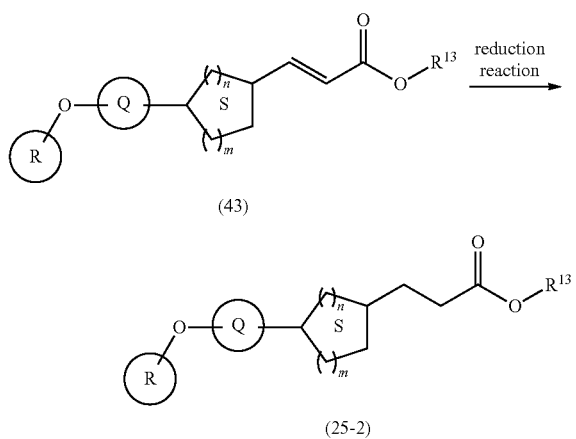

Compound (25-3) can be produced from compound (44) and compound (45) according to the following method.

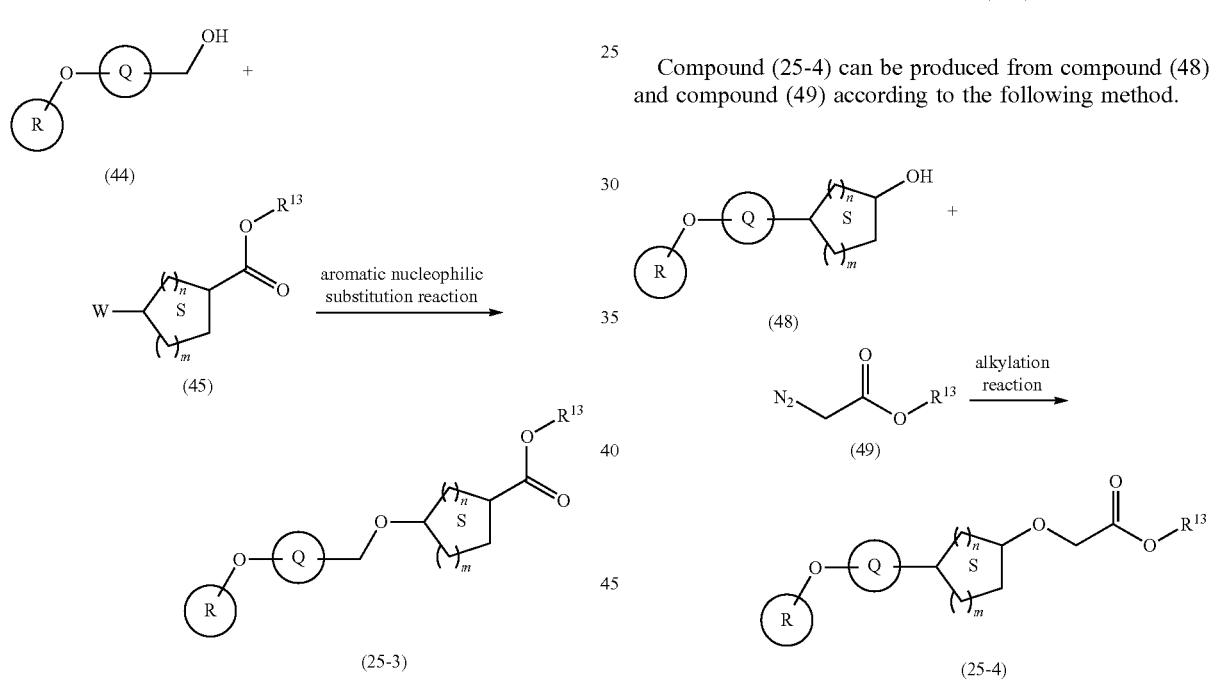

Compound (25-3) can also be produced from compound (46) and compound (45) according to the following method.

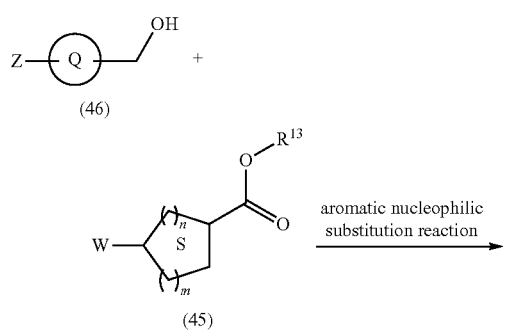

-continued

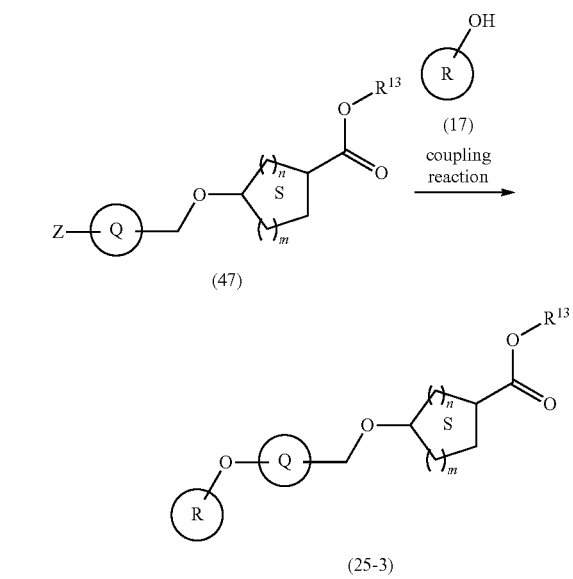

Compound (25-4) can be produced from compound (48) and compound (49) according to the following method.

Compound (25-43) can be produced by subjecting compound (48) and compound (49) to a alkylation reaction with a rhodium catalyst.

Examples of the rhodium catalyst include rhodium acetate dimer, rhodium trifluoroacetate dimer, rhodium benzoate dimer and the like.

Compound (25-5) can be produced from compound (50) and compound (51) according to the following method.

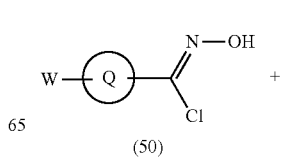

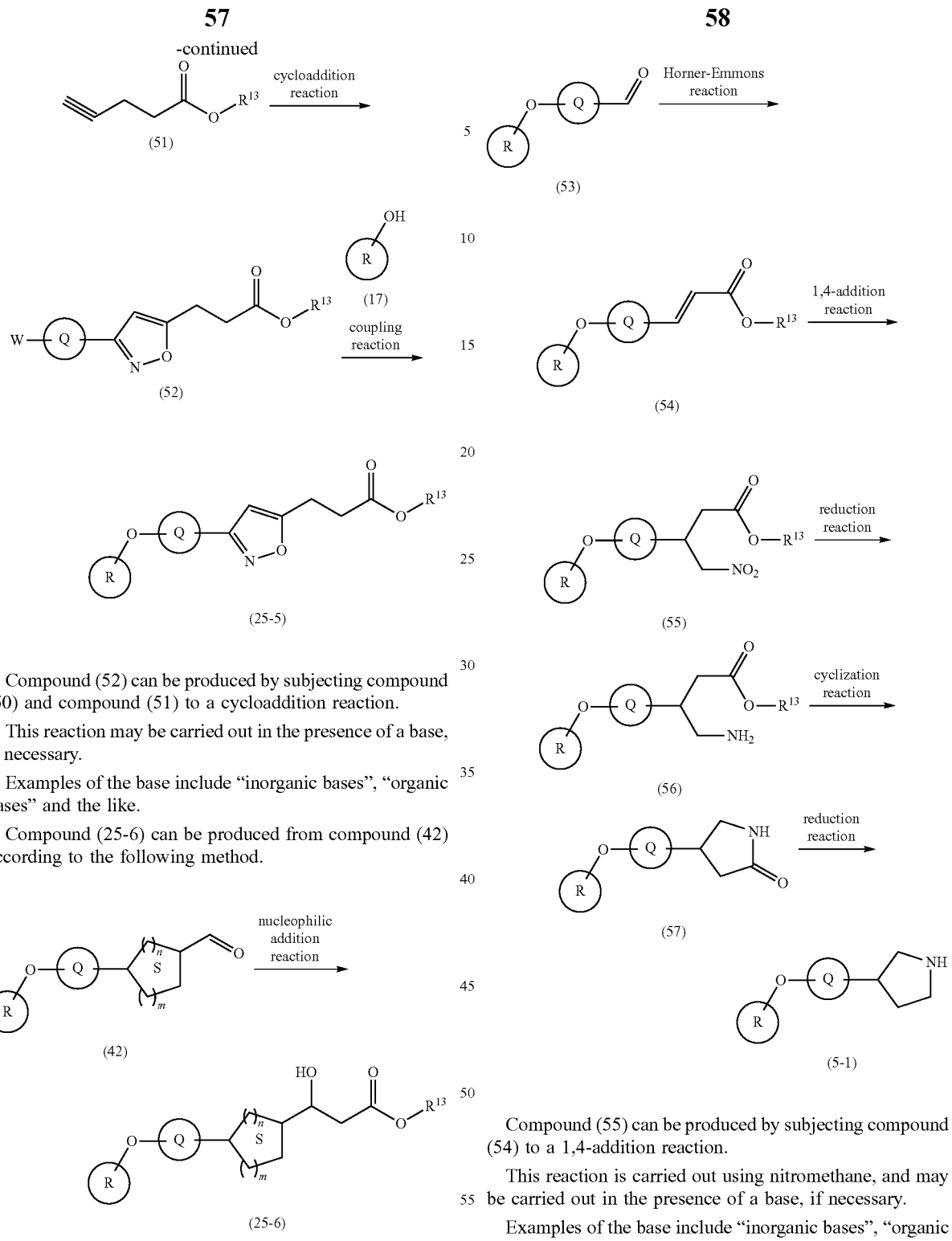

Compound (52) can be produced by subjecting compound (50) and compound (51) to a cycloaddition reaction.

This reaction may be carried out in the presence of a base, if necessary.

Examples of the base include "inorganic bases", "organic bases" and the like.

Compound (25-6) can be produced from compound (42) according to the following method.

Compound (25-6) can be produced by subjecting compound (42) to a nucleophilic addition reaction. This reaction is carried out using an organic zinc reagent.

Examples of the organic zinc reagent include (2-tert-butoxy-2-oxoethyl) (chloro)zinc, (2-ethoxy-2-oxoethyl) (chloro)zinc and the like.

Compound (5-1) can be produced from compound (53) according to the following method.

Compound (55) can be produced by subjecting compound (54) to a 1,4-addition reaction.

This reaction is carried out using nitromethane, and may be carried out in the presence of a base, if necessary.

Examples of the base include "inorganic bases", "organic bases" and the like.

Compound (57) can be produced by subjecting compound (56) to a cyclization reaction.

This reaction may be carried out in the presence of an acid, if necessary.

Examples of the acid include "organic acids", "inorganic acids" and the like.

Compound (40-1) can be produced from compound (58) and compound (59) according to the following method.

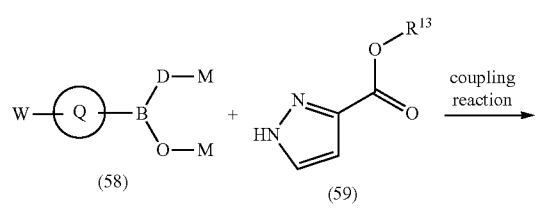

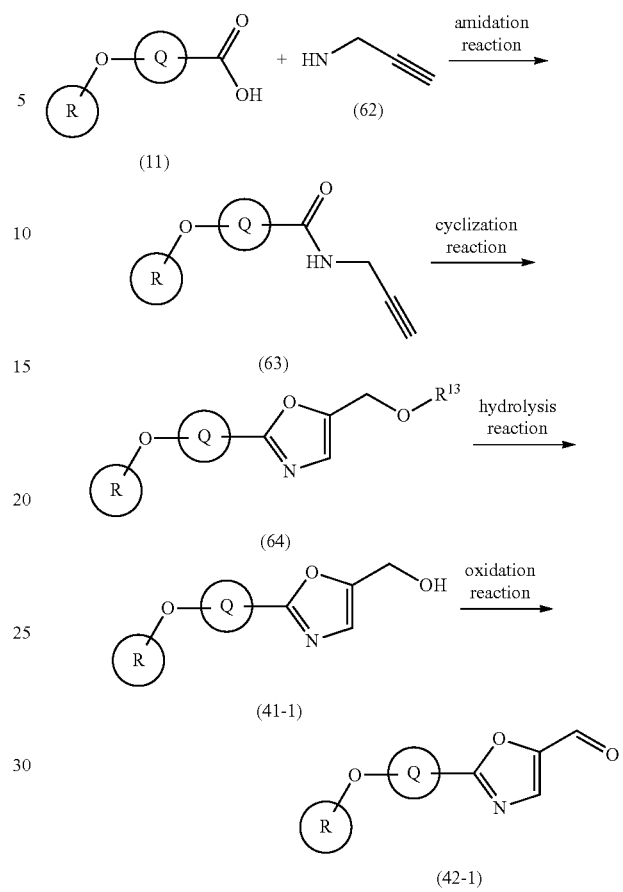

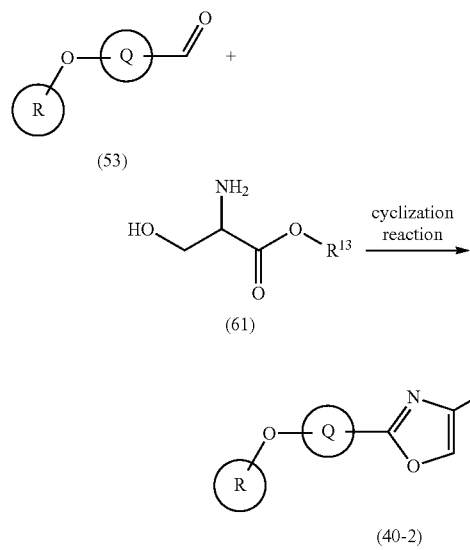

Compound (40-2) can be produced from compound (53) and compound (61) according to the following method.

Compound (40-2) can be produced by subjecting compound (53) and compound (61) to a cyclization reaction.

This reaction may be carried out in the presence of a base, if necessary.

Examples of the base include "inorganic bases", "organic bases" and the like.

Compound (42-1) can be produced from compound (11) and compound (62) according to the following method.

Compound (64) can be produced by subjecting compound (63) to a cyclization reaction with an oxidant.

Examples of the oxidant include iodobenzene diacetate, sodium hypochlorite and the like.

Compound (23-1) can be produced from compound (65) according to the following method.

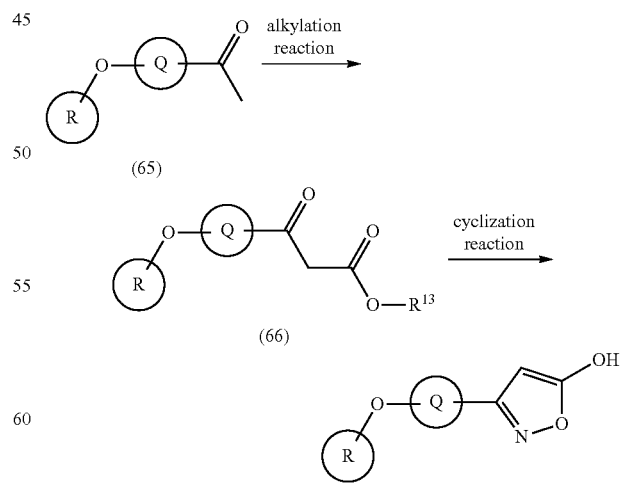

Compound (66) can be produced by subjecting compound (65) to an alkylation reaction with a base and a carbonate.

Examples of the base include "metal alkoxides" and "alkali metal hydrides".

Examples of the carbonate include dimethyl carbonate, diphenyl carbonate, ethyl chloroformate and the like.

Compound (23-1) can be produced by subjecting compound (66) to a cyclization reaction with hydroxylamine.

In compound (I) thus obtained, a functional group in a molecule can also be converted to a desired functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

Compound (I) obtained by the above-mentioned production methods can be isolated and purified according to a known means, for example, solvent extraction, pH control of solution, phase transfer, crystallization, recrystallization and chromatography.

When compound (I) contains an optical isomer, a stereoisomer, a regioisomer or a rotamer, these are also encompassed in compound (I), and can be obtained as a single product according to synthesis methods and separation methods known per se. For example, when compound (I) contains an optical isomer, an optical isomer resolved from this compound is also encompassed in compound (I).

The optical isomer can be produced according to a method known per se.

Compound (I) may be a crystal.

Crystals of compound (I) (hereinafter sometimes to be abbreviated as the crystals of the present invention) can be produced by crystallization according to crystallization methods known per se.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bonded silica gel. In HPLC (high performance liquid chromatography), C18 means use of octadecyl-bonded silica gel. The ratios of elution solvents are volume mixing ratios, unless otherwise specified.

In Examples, the following abbreviations are used.
mp: melting point
MS: mass spectrum
M: mol concentration
CDCl$_3$: deuterochloroform
DMSO-d$_G$: deuterodimethyl sulfoxide
$^1$H NMR: proton nuclear magnetic resonance
LC/MS: liquid chromatograph mass spectrometer
ESI: Electron Spray Ionization
APCI: atmospheric pressure chemical ionization
SFC: supercritical fluid liquid chromatography
THF: tetrahydrofuran
DMF: N,N-dimethylformamide
DME: 1,2-dimethoxyethane
DMA: N,N-dimethylacetamide
WSCD: 1-ethyl-3-(3-dimethylaminopropyl)carbodiimide hydrochloride
HATU: 2-(7-azabenzotriazol-1-yl)-1,1,3,3-tetramethyluronium hexafluorophosphate
HOBt: 1-hydroxybenzotriazole $^1$H NMR was measured by Fourier-transform type NMR. For the analysis, ACD/SpecManager (trade name) and the like were used. Peaks with very mild protons such as a hydroxy group, an amino group and the like are not described.

The other abbreviations used herein mean as follows.
s: singlet (singlet)
d: doublet(doublet)
t: triplet(triplet)
q: quartet (quartet)
m: multiplet (multiplet)
br: broad (broad)
J: coupling constant (coupling constant)
Hz: hertz (Hertz)
CDCl$_3$: deuterochloroform
DMSO-d$_6$: d$_6$-dimethyl sulfoxide
CD$_3$OD: deuteromethanol
$^1$H NMR: proton nuclear magnetic resonance
TFA: trifluoroacetic acid MS was measured by LC/MS. As ionization method, ESI method or APCI method was used. The data indicates actual measured value (found). Generally, molecular ion peaks ([M+H]$^+$, [M−H]$^−$ and the like) are observed. For example, in the case of a compound having a tert-butoxycarbonyl group, a peak after elimination of a tert-butoxycarbonyl group or a tert-butyl group may be observed as a fragment ion. In the case of a compound having a hydroxy group, a peak after elimination of H$_2$O may be observed as a fragment ion. In the case of a salt, a molecular ion peak or fragment ion peak of free form is generally observed.

Example 17

N-(1-(4-(2-(4-(3-(cyclopropylmethoxy)phenoxy) phenyl)ethyl)phenyl)ethyl)acetamide A)
1-(cyclopropylmethoxy)-3-(4-vinylphenoxy)benzene A mixture of 3-(cyclopropylmethoxy)phenol (5 g), 1-bromo-4-vinylbenzene (5.58 g), tripotassium phosphate (12.8 g), palladium acetate (137 mg), 2-di-tert-butylphosphino-3,4,5,6-tetramethyl-2',4'-6'-triisopropyl-1,1'-biphenyl (389 mg) and toluene (40 ml) was stirred under heating with reflux for 15 hr. The reaction mixture was poured into water, and extracted with ethyl acetate. The obtained organic layer was washed with saturated brine, dried over anhydrous sodium sulfate, and concentrated under reduced pressure. The obtained residue was purified by HPLC (water/acetonitrile, addition of 0.1% ammonium hydrogencarbonate) to give the title compound (4.8 g).

$^1$HNMR (400 MHz, DMSO-d$_6$) δ 0.22-0.35 (2H, m), 0.50-0.61 (2H, m), 1.13-1.25 (1H, m), 3.78 (2H, d, J=6.8 Hz), 5.11 (1H, d, J=10.8 Hz), 5.76 (1H, d, J=17.6 Hz), 6.51-6.60 (2H, m), 6.67-6.78 (2H, m), 6.98 (2H, d, J=8.8 Hz), 7.26 (1H, t, J=8.0 Hz), 7.49 (2H, d, J=8.8 Hz).

B) 1-(4-((E)-2-(4-(3-(cyclopropylmethoxy)phenoxy)phenyl)vinyl)phenyl)ethanone A mixture of 1-(cyclopropylmethoxy)-3-(4-vinylphenoxy)benzene (2.5 g), 1-(4-iodophenyl)ethanone (2.31 g), palladium acetate (84 mg), tri(2-methylphenyl)phosphine (171 mg) and triethylamine (25 ml) was stirred under nitrogen atmosphere at 80° C. for 5 hr. The reaction mixture was poured into water, and extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (2.65 g).

$^1$HNMR (400 MHz, DMSO-$d_6$) δ 0.25-0.34 (2H, m), 0.50-0.61 (2H, m), 1.15-1.25 (1H, m), 2.58 (3H, s), 3.80 (2H, d, J=7.2 Hz), 6.55-6.63 (2H, m), 6.70-6.78 (1H, m), 7.04 (2H, d, J=8.4 Hz), 7.23-7.33 (2H, m), 7.44 (1H, d, J=16.4 Hz), 7.67 (2H, d, J=8.4 Hz), 7.73 (2H, d, J=8.4 Hz), 7.96 (2H, d, J=8.4 Hz).

C) 1-(4-((E)-2-(4-(3-(cyclopropylmethoxy)phenoxy)phenyl)vinyl)phenyl)ethanamine A mixture of 1-(4-((E)-2-(4-(3-(cyclopropylmethoxy)phenoxy)phenyl)vinyl)phenyl)ethanone (2.65 g), ammonium acetate (5.31 g), sodium cyanoborohydride (867 mg) and methanol (30 ml) was stirred under heating with reflux for 20 hr. The reaction mixture was poured into water, and extracted with ethyl acetate. The obtained organic layer was washed with saturated brine, dried over anhydrous sodium sulfate, and concentrated under reduced pressure to give the title compound (2.5 g).

MS: [M+H]$^+$ 368.8.

D) N-(1-(4-((E)-2-(4-(3-(cyclopropylmethoxy)phenoxy)phenyl)vinyl)phenyl)ethyl)acetamide To a mixture of 1-(4-((E)-2-(4-(3-(cyclopropylmethoxy)phenoxy)phenyl)vinyl)phenyl)ethanamine (2.5 g) and THF (30 ml) was added acetic anhydride (1.41 g) at 0° C. The mixture was stirred at 0° C. for 1 hr. The reaction mixture was poured into water, and extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (800 mg).

MS: [M+H]$^+$ 427.8.

E) N-(1-(4-(2-(4-(3-(cyclopropylmethoxy)phenoxy)phenyl)ethyl)phenyl)ethyl)acetamide A mixture of N-(1-(4-((E)-2-(4-(3-(cyclopropylmethoxy)phenoxy)phenyl) vinyl)phenyl)ethyl)acetamide (300 mg), 10% palladium on carbon (30 mg) and methanol (10 ml) was stirred under hydrogen atmosphere at 8-16° C. for 15 hr. The reaction mixture was filtered, and the filtrate was concentrated under reduced pressure. The obtained residue was purified by HPLC (water/acetonitrile, addition of 0.1% ammonium hydrogencarbonate) to give the title compound (60 mg).

$^1$HNMR (400 MHz, DMSO-$d_6$) δ 0.25-0.35 (2H, m), 0.51-0.61 (2H, m), 1.13-1.24 (1H, m), 1.30 (3H, d, J=7.2 Hz), 1.82 (3H, s), 2.84 (4H, s), 3.77 (2H, d, J=6.8 Hz), 4.80-4.91 (1H, m), 6.45-6.52 (2H, m), 6.60-6.72 (1H, m), 6.93 (2H, d, J=8.4 Hz), 7.10-7.26 (7H, m), 8.23 (1H, d, J=7.6 Hz).

Example 19

N-(1-(4-((4-(3-(cyclopropylmethoxy)phenoxy)-2-fluorobenzyl)oxy)phenyl)ethyl)acetamide

A) N-(1-(4-hydroxyphenyl)ethyl)acetamide

A mixture of acetic anhydride (0.825 ml), 4-(1-aminoethyl)phenol (1 g) and THF (40 ml) was stirred at room temperature for 30 min. The mixture was extracted with water and ethyl acetate. The obtained organic layer was dried over magnesium sulfate, and concentrated under reduced pressure. The obtained residue was purified by silica gel column chromatography (ethyl acetate/hexane) to give the title compound (1.05 g).

MS: [M+H]$^+$ 180.2.

B) 4-(3-(cyclopropylmethoxy)phenoxy)-2-fluorobenzaldehyde

A mixture of 3-(cyclopropylmethoxy)phenol (849 mg), 2,4-difluorobenzaldehyde (700 mg), cesium carbonate (1.605 g) and DMF (10 ml) was stirred at 60° C. for 3 hr. To the mixture was added water at 0° C., and the mixture was extracted with ethyl acetate. The organic layer was separated, washed with saturated brine, dried over magnesium sulfate, and concentrated under reduced pressure. The obtained residue was purified by silica gel column chromatography (ethyl acetate/hexane) to give the title compound (852 mg) as a mixture with 2-(3-(cyclopropylmethoxy)phenoxy)-4-fluorobenzaldehyde.

MS: [M+H]$^+$ 286.9.

C) N-(1-(4-((4-(3-(cyclopropylmethoxy)phenoxy)-2-fluorobenzyl)oxy)phenyl)ethyl)acetamide To a mixture of 4-(3-(cyclopropylmethoxy)phenoxy)-2-fluorobenzaldehyde (300 mg) and 2-(3-(cyclopropylmethoxy)phenoxy)-4-fluorobenzaldehyde (150 mg) was added methanol (5 ml), and then sodium borohydride (119 mg) was added thereto at 0° C. The mixture was stirred at 0° C. for 3 hr, water was added thereto, and the mixture was extracted with ethyl acetate. The obtained organic layer was washed with saturated brine, dried over magnesium sulfate, and concentrated under reduced pressure. To a mixture of the obtained residue and N-(1-(4-hydroxyphenyl)ethyl)acetamide (282 mg) was added toluene (8 ml). The mixture was degassed, tributylphosphine (0.393 ml) was added thereto, and then (E)-diazene-1,2-diylbis(cyclohexylmethanone) (397 mg) was added thereto. The mixture was stirred overnight at room temperature. To the mixture was added a mixed solvent of ethyl acetate/hexane, and the precipitated solid was removed by filtration, and washed with a mixed solvent of ethyl acetate/hexane. The filtrate was concentrated under reduced pressure, and the residue was purified by silica gel column chromatography (ethyl acetate/hexane), and then purified by HPLC (acetonitrile/water, addition of 0.1% TFA), and crystallized from diisopropyl ether/hexane to give the title compound (142 mg).

$^1$H NMR (300 MHz, CD$_3$OD) δ 0.28-0.37 (2H, m), 0.54-0.64 (2H, m), 1.14-1.28 (1H, m), 1.41 (3H, d, J=7.0 Hz), 1.94 (3H, s), 3.79 (2H, d, J=6.8 Hz), 4.91-5.01 (1H, m), 5.06 (2H, s), 6.55-6.62 (2H, m), 6.68-6.83 (3H, m), 6.91-6.99 (2H, m), 7.19-7.32 (3H, m), 7.41-7.50 (1H, m), 8.36 (1H, d, J=7.9 Hz).

Example 28

N-((2S)-1-((4'-(3-(cyclopropylmethoxy)phenoxy) biphenyl-4-yl)oxy)propan-2-yl)acetamide A) tert-butyl ((2S)-1-(4-iodophenoxy)propan-2-yl) carbamate A mixture of 4-iodophenol (500 mg), tert-butyl ((2S)-1-hydroxypropan-2-yl)carbamate (438 mg), diisopropyl azodicarboxylate (40% toluene solution, 0.858 ml), triphenylphosphine (715 mg) and THF (10 ml) was stirred overnight at room temperature. The mixture was concentrated under reduced pressure. The obtained residue was purified by silica gel column chromatography (NH, ethyl acetate/hexane) to give the title compound (500 mg).
$^1$H NMR (300 MHz, DMSO-$d_6$) δ 1.10 (3H, d, J=6.2 Hz), 1.38 (9H, s), 3.67-3.92 (3H, m), 6.78 (2H, d, J=9.0 Hz), 6.83-6.93 (1H, m), 7.58 (2H, d, J=9.0 Hz).

B) N-((2S)-1-((4'-(3-(cyclopropylmethoxy)phenoxy) biphenyl-4-yl)oxy)propan-2-yl)acetamide A mixture of tert-butyl ((2S)-1-(4-iodophenoxy)propan-2-yl)carbamate (300 mg), tetrakis(triphenylphosphine)palladium (92 mg), 2M aqueous sodium carbonate solution (0.795 ml), 2-(4-(3-(cyclopropylmethoxy)phenoxy)phenyl)-4,4,5,5-tetramethyl-1,3,2-dioxaborolane (583 mg) and DME (6 ml) was stirred overnight at 80° C. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (ethyl acetate/hexane). A mixture of the obtained residue and hydrogen chloride (4M ethyl acetate solution, 4 ml) was stirred at room temperature for 1 hr. The mixture was concentrated under reduced pressure. To the obtained residue were added pyridine (2 ml) and acetic anhydride (0.377 ml). The reaction mixture was stirred at room temperature for 30 min, and concentrated under reduced pressure. The obtained residue was purified by silica gel column chromatography (NH, ethyl acetate/hexane), and crystallized from hexane/ethyl acetate to give the title compound (8 mg).
$^1$H NMR (300 MHz, DMSO-$d_6$) δ 0.25-0.36 (2H, m), 0.49-0.60 (2H, m), 1.16 (3H, d, J=6.7 Hz), 1.19-1.25 (1H, m), 1.82 (3H, s), 3.79 (2H, d, J=6.9 Hz), 3.82-3.87 (1H, m), 3.92-4.01 (1H, m), 4.04-4.17 (1H, m), 6.53-6.61 (2H, m), 6.67-6.75 (1H, m), 6.99-7.09 (4H, m), 7.27 (1H, t, J=8.4 Hz), 7.54-7.66 (4H, m), 7.93 (1H, d, J=7.8 Hz).

Example 30

N-((2S)-1-((2-(4-(3-(cyclopropylmethoxy)phenoxy) phenyl)-1,3-oxazol-5-yl)oxy)propan-2-yl)acetamide A) ethyl 4-(3-(cyclopropylmethoxy)phenoxy)benzoate A mixture of 3-(cyclopropylmethoxy)phenol (12.89 g), ethyl 4-fluorobenzoate (11 g), cesium carbonate (42.6 g) and DMF (100 ml) was stirred at 100° C. for 4 hr. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (13.3 g).
$^1$H NMR (300 MHz, DMSO-$d_6$) δ 0.23-0.36 (2H, m), 0.49-0.62 (2H, m), 1.19-1.25 (1H, m), 1.31 (3H, t, J=7.1 Hz), 3.80 (2H, d, J=7.0 Hz), 4.29 (2H, q, J=7.1 Hz), 6.61-6.69 (2H, m), 6.76-6.83 (1H, m), 7.01-7.09 (2H, m), 7.33 (1H, t, J=8.2 Hz), 7.92-8.00 (2H, m).

B) 4-(3-(cyclopropylmethoxy)phenoxy)benzoic acid

A mixture of ethyl 4-(3-(cyclopropylmethoxy)phenoxy) benzoate (13.3 g), 2N aqueous sodium hydroxide solution (85 ml), THF (80 ml) and methanol (80 ml) was stirred overnight at room temperature. The mixture was acidified with 2N hydrochloric acid, and stirred at room temperature for 30 min, and the precipitated solid was collected by filtration, and dried under reduced pressure to give the title compound (10.82 g).
$^1$H NMR (300 MHz, DMSO-$d_6$) δ 0.23-0.35 (2H, m), 0.45-0.61 (2H, m), 1.10-1.28 (1H, m), 3.80 (2H, d, J=7.0 Hz), 6.58-6.70 (2H, m), 6.73-6.85 (1H, m), 7.03 (2H, d, J=4.9 Hz), 7.32 (1H, t, J=8.2 Hz), 7.94 (2H, d, J=4.8 Hz), 12.81 (1H, brs).

C) (2S)-2-((tert-butoxycarbonyl) amino)propyl N-((benzyloxy)carbonyl)glycinate

A mixture of N-((benzyloxy)carbonyl)glycine (7.16 g), tert-butyl ((2S)-1-hydroxypropan-2-yl)carbamate (5 g), WSCD (8.21 g), N,N-dimethylpyridin-4-amine (0.349 g) and DMF (70 ml) was stirred overnight at room temperature. The mixture was extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (10.45 g).
$^1$H NMR (300 MHz, DMSO-$d_6$) δ 1.01 (3H, d, J=6.7 Hz), 1.38 (9H, s), 3.62-3.74 (1H, m), 3.77 (2H, d, J=6.0 Hz), 3.85-3.99 (2H, m), 5.04 (2H, s), 6.80 (1H, d, J=5.6 Hz), 7.23-7.43 (5H, m), 7.68 (1H, t, J=6.0 Hz).

D) (2S)-2-((tert-butoxycarbonyl)amino)propyl N-(4-(3-(cyclopropylmethoxy)phenoxy)benzoyl)glycinate A mixture of (2S)-2-((tert-butoxycarbonyl)amino)propyl N-((benzyloxy)carbonyl)glycinate (10.45 g), 10% palladium on carbon (50% hydrous, 1.518 g) and THF (200 ml) was stirred under hydrogen atmosphere at room temperature for 4 hr. The mixture was filtered through Celite, and the filtrate was concentrated under reduced pressure to give the corresponding amine. To a mixture of 4-(3-(cyclopropylmethoxy)phenoxy)benzoic acid (9.73 g), DMF (0.221 ml) and THF (100 ml) was added dropwise oxalyl chloride (4.99 ml) under ice-cooling. The mixture was stirred at room temperature for 1 hr, and concentrated under reduced pressure. To the obtained residue was added THF (100 ml), and then the amine previously obtained and triethylamine (7.95 ml) were added thereto. The reaction mixture was stirred overnight at room temperature. The mixture was extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (14.6 g).

$^1$H NMR (300 MHz, DMSO-d$_6$) δ 0.25-0.34 (2H, m), 0.51-0.60 (2H, m), 1.02 (3H, d, J=6.8 Hz), 1.19-1.27 (1H, m), 1.38 (9H, s), 3.65-3.76 (1H, m), 3.80 (2H, d, J=7.0 Hz), 3.86-4.03 (4H, m), 6.58-6.67 (2H, m), 6.73-6.84 (2H, m), 7.05 (2H, d, J=8.8 Hz), 7.31 (1H, t, J=8.2 Hz), 7.89 (2H, d, J=8.9 Hz), 8.87 (1H, t, J=5.9 Hz).

E) tert-butyl ((2S)-1-((2-(4-(3-(cyclopropylmethoxy)phenoxy)phenyl)-1,3-oxazol-5-yl)oxy)propan-2-yl)carbamate To a mixture of triphenylphosphine (15.36 g) and acetonitrile (100 ml) was added iodine (14.87 g) under ice-cooling, and then triethylamine (16.33 ml) was added dropwise thereto. The mixture was stirred at 0° C. for 10 min, and a mixture of (2S)-2-((tert-butoxycarbonyl)amino)propyl N-(4-(3-(cyclopropylmethoxy)phenoxy)benzoyl)glycinate (14.6 g) and acetonitrile (50 ml) was added thereto. The reaction mixture was stirred overnight at room temperature, and concentrated under reduced pressure. The obtained residue was purified by silica gel column chromatography (ethyl acetate/hexane) to give the title compound (10.4 g).

$^1$H NMR (300 MHz, DMSO-d$_6$) δ 0.26-0.34 (2H, m), 0.51-0.60 (2H, m), 1.11 (3H, d, J=6.8 Hz), 1.19-1.26 (1H, m), 1.38 (9H, s), 3.80 (2H, d, J=7.0 Hz), 3.83-3.92 (1H, m), 3.98-4.02 (1H, m), 6.44 (1H, s), 6.58-6.65 (2H, m), 6.72-6.80 (1H, m), 6.98 (1H, d, J=8.0 Hz), 7.08 (2H, d, J=8.9 Hz), 7.30 (1H, t, J=8.3 Hz), 7.83 (2H, d, J=9.0 Hz).

F) N-((2S)-1-((2-(4-(3-(cyclopropylmethoxy)phenoxy)phenyl)-1,3-oxazol-5-yl)oxy)propan-2-yl)acetamide A mixture of tert-butyl ((2S)-1-((2-(4-(3-(cyclopropylmethoxy)phenoxy)phenyl)-1,3-oxazol-5-yl)oxy)propan-2-yl)carbamate (10.4 g), TFA (16.67 ml) and toluene (50 ml) was stirred at room temperature for 30 min, and concentrated under reduced pressure. The obtained residue was subjected to azeotropic process twice with toluene. To the obtained residue was added pyridine (50 ml), and then acetic anhydride (6.13 ml) was added thereto. The mixture was stirred at room temperature for 30 min, and concentrated under reduced pressure. The obtained residue was purified by silica gel column chromatography (NH, ethyl acetate/hexane), and crystallized from hexane/ethyl acetate to give the title compound (3.72 g).

$^1$H NMR (300 MHz, DMSO-d$_6$) δ 0.25-0.35 (2H, m), 0.50-0.59 (2H, m), 1.15 (3H, d, J=6.7 Hz), 1.17-1.27 (1H, m), 1.81 (3H, s), 3.80 (2H, d, J=7.0 Hz), 3.98-4.06 (2H, m), 4.07-4.22 (1H, m), 6.45 (1H, s), 6.57-6.67 (2H, m), 6.73-6.80 (1H, m), 7.08 (2H, d, J=8.8 Hz), 7.31 (1H, t, J=8.2 Hz), 7.83 (2H, d, J=8.9 Hz), 7.99 (1H, d, J=7.6 Hz).

Example 32

N-(4-(2-(4-(3-(cyclopropylmethoxy)phenoxy)phenyl)-1,3-oxazol-5-yl) butan-2-yl)acetamide A) methyl 3-(2-(4-(3-(cyclopropylmethoxy)phenoxy)phenyl)-1,3-oxazol-5-yl)propanoate To a mixture of methyl 5-amino-4-oxopentanoate hydrochloride (11.9 g), 4-(3-(cyclopropylmethoxy)phenoxy)benzoic acid (18.5 g) and THF (300 ml) was added N,N-diisopropylethylamine (30.4 g), and then 2-chloro-1-methylpyridinium iodide (31.7 g) was added thereto at 12° C. The mixture was stirred at 12° C. for 2 hr, and water and ethyl acetate were added thereto. The organic layer was separated, and the aqueous layer was extracted three times with ethyl acetate. The combined organic layers were dried over anhydrous sodium sulfate, and concentrated under reduced pressure to give the corresponding amide. To a mixture of iodine (32 g) and dichloromethane (300 ml) was added triphenylphosphine (36 g). The mixture was stirred at 12° C. for 10 min, and triethylamine (28 g) was added thereto. To the mixture was added dropwise a mixture of the amide previously obtained and dichloromethane (100 ml). The mixture was stirred at 12° C. for 1 hr. The mixture was poured into ice water, and the organic layer was separated. The aqueous layer was extracted three times with dichloromethane. The combined organic layers were dried over anhydrous sodium sulfate, and concentrated under reduced pressure. The obtained residue was purified by silica gel column chromatography (ethyl acetate/petroleum ether) to give the title compound (2.3 g).

MS: [M+H]$^+$ 394.1.

B) 3-(2-(4-(3-(cyclopropylmethoxy)phenoxy)phenyl)-1,3-oxazol-5-yl)propanoic acid A mixture of methyl 3-(2-(4-(3-(cyclopropylmethoxy)phenoxy)phenyl)-1,3-oxazol-5-yl)propanoate (2 g), 1N aqueous sodium hydroxide solution (20.33 ml), THF (10 ml) and methanol (10 ml) was stirred overnight at room temperature. The mixture was acidified with 1N hydrochloric acid, and extracted with ethyl acetate. The obtained organic layer was washed with saturated brine, dried over magnesium sulfate, and concentrated under reduced pressure to give the title compound (1.4 g).

$^1$H NMR (300 MHz, DMSO-d$_6$) δ 0.26-0.35 (2H, m), 0.51-0.61 (2H, m), 1.12-1.27 (1H, m), 2.59-2.69 (2H, m), 2.91-3.01 (2H, m), 3.80 (2H, d, J=7.1 Hz), 6.57-6.68 (2H, m), 6.73-6.81 (1H, m), 6.96-7.03 (3H, m), 7.32-7.40 (1H, m), 7.93 (2H, d, J=8.8 Hz), 12.32 (1H, brs).

C) 3-(2-(4-(3-(cyclopropylmethoxy)phenoxy)phenyl)-1,3-oxazol-5-yl)-N-methoxy-N-methylpropanamide A mixture of 3-(2-(4-(3-(cyclopropylmethoxy)phenoxy)phenyl)-1,3-oxazol-5-yl)propanoic acid (1.4 g), N,O-dimethylhydroxylamine hydrochloride (0.72 g), WSCD (1.415 g), HOBt monohydrate (1.13 g), triethylamine (1.0 ml) and DMF (10 ml) was stirred overnight at room temperature. The mixture was extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (0.784 g).

$^1$H NMR (300 MHz, DMSO-d$_6$) δ 0.26-0.34 (2H, m), 0.51-0.61 (2H, m), 1.18-1.25 (1H, m), 2.76-2.84 (2H, m), 2.92-3.01 (2H, m), 3.11 (3H, s), 3.67 (3H, s), 3.80 (2H, d, J=7.0 Hz), 6.58-6.67 (2H, m), 6.73-6.81 (1H, m), 6.98 (1H, s), 7.10 (2H, d, J=8.9 Hz), 7.31 (1H, t, J=8.3 Hz), 7.93 (2H, d, J=8.9 Hz).

D) 4-(2-(4-(3-(cyclopropylmethoxy)phenoxy)phenyl)-1,3-oxazol-5-yl)butan-2-yl methanesulfonate To a mixture of 3-(2-(4-(3-(cyclopropylmethoxy)phenoxy)phenyl)-1,3-oxazol-5-yl)-N-methoxy-N-methylpropanamide (784 mg) and THF (10 ml) was added methylmagnesium bromide (1M THF solution, 3.71 ml) under ice-cooling. The mixture was stirred at 0° C. for 1 hr, and extracted with ethyl acetate and saturated aqueous ammonium chloride solution. The obtained organic layer was washed with saturated brine, dried over magnesium sulfate, and concentrated under reduced pressure. To a mixture of the obtained residue and ethanol (10 ml) was added sodium borohydride (0.141 g) under ice-cooling. The mixture was stirred at 0° C. for 30 min, and extracted with ethyl acetate and 1N hydrochloric acid. The obtained organic layer was washed with saturated brine, dried over magnesium sulfate, and concentrated under reduced pressure. A mixture of the obtained residue, methanesulfonyl chloride (0.432 ml), triethylamine (0.778 ml) and THF (10 ml) was stirred at room temperature for 1 hr. The mixture was extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (686 mg).

$^1$H NMR (300 MHz, DMSO-$d_6$) δ 0.26-0.34 (2H, m), 0.50-0.60 (2H, m), 1.19-1.25 (1H, m), 1.40 (3H, d, J=6.2 Hz), 1.99-2.06 (2H, m), 2.76-2.91 (2H, m), 3.31 (3H, s), 3.80 (2H, d, J=7.1 Hz), 4.75-4.89 (1H, m), 6.59-6.66 (2H, m), 6.73-6.80 (1H, m), 7.03 (1H, s), 7.10 (2H, d, J=8.9 Hz), 7.28 (1H, s), 7.92-7.97 (2H, m).

E) 5-(3-azidobutyl)-2-(4-(3-(cyclopropylmethoxy) phenoxy)phenyl)-1,3-oxazole

A mixture of 4-(2-(4-(3-(cyclopropylmethoxy)phenoxy) phenyl)-1,3-oxazol-5-yl)butan-2-yl methanesulfonate (686 mg), sodium azide (195 mg) and DMF (10 ml) was stirred at 80° C. for 2 hr. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (450 mg).

$^1$H NMR (300 MHz, DMSO-$d_6$) δ 0.26-0.34 (2H, m), 0.50-0.59 (2H, m), 1.20-1.24 (1H, m), 1.27 (3H, d, J=6.5 Hz), 1.70-1.91 (2H, m), 2.76-2.85 (2H, m), 3.59-3.74 (1H, m), 3.80 (2H, d, J=7.0 Hz), 6.58-6.67 (2H, m), 6.73-6.80 (1H, m), 7.03 (1H, s), 7.10 (2H, d, J=8.9 Hz), 7.31 (1H, t, J=8.3 Hz), 7.93 (2H, d, J=8.9 Hz).

F) 4-(2-(4-(3-(cyclopropylmethoxy)phenoxy)phenyl)-1,3-oxazol-5-yl)butan-2-amine

A mixture of 5-(3-azidobutyl)-2-(4-(3-(cyclopropylmethoxy)phenoxy)phenyl)-1,3-oxazole (450 mg), triphenylphosphine (584 mg), THF (8 ml) and water (4 ml) was stirred at 60° C. for 2 hr. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (NH, ethyl acetate/hexane) to give the title compound (346 mg).

$^1$H NMR (300 MHz, DMSO-$d_6$) δ 0.26-0.34 (2H, m), 0.50-0.60 (2H, m), 1.01 (3H, d, J=6.3 Hz), 1.11-1.27 (1H, m), 1.42-1.71 (4H, m), 2.65-2.86 (3H, m), 3.80 (2H, d, J=7.0 Hz), 6.59-6.67 (2H, m), 6.73-6.80 (1H, m), 6.97 (1H, s), 7.10 (2H, d, J=4.8 Hz), 7.31 (1H, t, J=8.3 Hz), 7.92 (2H, d, J=4.7 Hz).

G) N-(4-(2-(4-(3-(cyclopropylmethoxy)phenoxy) phenyl)-1,3-oxazol-5-yl)butan-2-yl)acetamide A mixture of 4-(2-(4-(3-(cyclopropylmethoxy)phenoxy) phenyl)-1,3-oxazol-5-yl)butan-2-amine (346 mg), acetic anhydride (0.431 ml) and pyridine (4 ml) was stirred at room temperature for 30 min. The mixture was concentrated under reduced pressure. The obtained residue was purified by silica gel column chromatography (NH, ethyl acetate/hexane), and crystallized from hexane/ethyl acetate to give the title compound (204 mg).

$^1$H NMR (300 MHz, DMSO-$d_6$) δ 0.26-0.35 (2H, m), 0.50-0.60 (2H, m), 1.07 (3H, d, J=6.6 Hz), 1.13-1.26 (1H, m), 1.67-1.77 (2H, m), 1.79 (3H, s), 2.64-2.76 (2H, m), 3.75-3.88 (3H, m, J=7.0 Hz), 6.59-6.67 (2H, m), 6.72-6.81 (1H, m), 6.98 (1H, s), 7.10 (2H, d, J=8.8 Hz), 7.25-7.36 (1H, m), 7.74 (1H, d, J=8.3 Hz), 7.92 (2H, d, J=8.8 Hz).

Example 35

N-(1-(5-((4-(3-(cyclopropylmethoxy)phenoxy)-2-fluorobenzyl)oxy)pyrazin-2-yl)ethyl)acetamide A) (4-(3-(cyclopropylmethoxy)phenoxy)-2-fluorophenyl)methanol A mixture of 3-(cyclopropylmethoxy)phenol (305 mg), (2-fluoro-4-iodophenyl)methanol (390 mg), copper(I) iodide (88 mg), N,N-dimethylglycine hydrochloride (194 mg), cesium carbonate (756 mg) and 1,2-dimethoxyethane (4.8 ml) was stirred under microwave irradiation at 135° C. for 2 hr. The mixture was filtered, and the filtrate was concentrated under reduced pressure. Then, a mixture of 3-(cyclopropylmethoxy)phenol (62.5 mg), (2-fluoro-4-iodophenyl) methanol (80 mg), copper(I) iodide (18.14 mg), N,N-dimethylglycine hydrochloride (39.9 mg), cesium carbonate (155 mg) and 1,2-dimethoxyethane (1 ml) was stirred under microwave irradiation at 135° C. for 2 hr. The mixture was filtered, and the filtrate was concentrated under reduced pressure. The obtained residues were combined, and purified by silica gel column chromatography (ethyl acetate/hexane) to give the title compound (114 mg).

$^1$H NMR (300 MHz, CD$_3$OD) δ 0.29-0.36 (2H, m), 0.56-0.63 (2H, m), 1.17-1.26 (1H, m), 3.78 (2H, d, J=6.8 Hz), 4.61 (2H, s), 6.52-6.59 (2H, m), 6.66-6.74 (2H, m), 6.78 (1H, dd, J=8.4, 2.4 Hz), 7.21-7.29 (1H, m), 7.40 (1H, t, J=8.5 Hz).

B) 1-(5-((4-(3-(cyclopropylmethoxy)phenoxy)-2-fluorobenzyl)oxy)pyrazin-2-yl)ethanone A mixture of (4-(3-(cyclopropylmethoxy)phenoxy)-2-fluorophenyl)methanol (200 mg), 1-(5-chloropyrazin-2-yl) ethanone (119 mg), sodium hydride (60% in oil, 41.6 mg) and THF (1 ml) was stirred at room temperature for 10 min, and heated under microwave irradiation at 100° C. for 1 hr. To the mixture was added water at 0° C., and the mixture was extracted with ethyl acetate. The organic layer was separated, washed with saturated brine, dried over magnesium sulfate, and concentrated under reduced pressure. The obtained residue was purified by silica gel column chromatography (ethyl acetate/hexane) to give the title compound (65 mg).

$^1$H NMR (300 MHz, CDCl$_3$) δ 0.27-0.39 (2H, m), 0.60-0.69 (2H, m), 1.19-1.31 (1H, m), 2.66 (3H, s), 3.77 (2H, d, J=6.9 Hz), 5.48 (2H, s), 6.57-6.65 (2H, m), 6.68-6.86 (3H, m), 7.19-7.29 (1H, m), 7.43 (1H, t, J=8.4 Hz), 8.23 (1H, d, J=1.2 Hz), 8.83 (1H, d, J=1.3 Hz).

C) N-(1-(5-((4-(3-(cyclopropylmethoxy)phenoxy)-2-fluorobenzyl)oxy)pyrazin-2-yl)ethyl)acetamide To a mixture of 1-(5-((4-(3-(cyclopropylmethoxy)phenoxy)-2-fluorobenzyl)oxy)pyrazin-2-yl)ethanone (65 mg), ammonium acetate (61.3 mg) and methanol (1 ml) was added sodium cyanoborohydride (20 mg). The mixture was stirred overnight at 60° C. To the mixture was added water at 0° C., and the mixture was extracted with ethyl acetate. The organic layer was separated, washed with saturated brine, dried over magnesium sulfate, and concentrated under reduced pressure. To a mixture of the obtained residue and THF (0.5 ml) was added acetic anhydride (6 µl). The mixture was stirred at room temperature for 2 hr, and concentrated under reduced pressure. The obtained residue was purified by silica gel column chromatography (ethyl acetate/hexane) to give the title compound (8 mg).
$^1$H NMR (300 MHz, CD$_3$OD) δ 0.31-0.40 (2H, m), 0.56-0.64 (2H, m), 1.20-1.27 (1H, m), 1.48 (3H, d, J=7.0 Hz), 1.98 (3H, s), 3.80 (2H, d, J=6.8 Hz), 5.06 (1H, d, J=7.0 Hz), 5.41 (2H, s), 6.54-6.63 (2H, m), 6.69-6.81 (3H, m), 7.27 (1H, t, J=8.5 Hz), 7.49 (1H, t, J=8.4 Hz), 8.11-8.21 (2H, m).

Example 39

N-(1-(4-((4-(3-(cyclopropylmethoxy)phenoxy)-2,6-difluorobenzyl)oxy)phenyl)ethyl)acetamide

A) (4-(3-(cyclopropylmethoxy)phenoxy)-2,6-difluorophenyl)methanol

To a mixture of 2,6-difluoro-4-iodobenzaldehyde (500 mg) and methanol (5 ml) was added sodium borohydride (92 mg) at 0° C. The mixture was stirred at room temperature for 1 hr. To the mixture was added water at 0° C., and the mixture was extracted with ethyl acetate. The organic layer was separated, washed with saturated brine, dried over magnesium sulfate, and concentrated under reduced pressure. A mixture of the obtained residue, 3-(cyclopropylmethoxy)phenol (365 mg), copper(I) iodide (106 mg), N,N-dimethylglycine hydrochloride (233 mg), cesium carbonate (905 mg) and DME (5 ml) was stirred under microwave irradiation at 100° C. for 2 hr. The mixture was filtered, and the filtrate was concentrated under reduced pressure. The obtained residue was purified by silica gel column chromatography (ethyl acetate/hexane) to give the title compound (166 mg).
MS: [M+H]$^+$ 288.9.

B) N-(1-(4-((4-(3-(cyclopropylmethoxy)phenoxy)-2,6-difluorobenzyl)oxy)phenyl)ethyl)acetamide To a mixture of (4-(3-(cyclopropylmethoxy)phenoxy)-2,6-difluorophenyl)methanol (150 mg) and N-(1-(4-hydroxyphenyl)ethyl)acetamide (132 mg) was added toluene (2 ml). The mixture was degassed, tributylphosphine (0.183 ml) was added thereto, and then (E)-diazene-1,2-diylbis(cyclohexylmethanone) (185 mg) was added thereto. The mixture was stirred overnight at room temperature. To the mixture was added a mixed solvent of ethyl acetate/hexane, and the mixture was filtered. The obtained solid was washed with a mixed solvent of ethyl acetate/hexane, and the filtrate was concentrated under reduced pressure. The obtained residue was purified by silica gel column chromatography (NH, ethyl acetate/hexane) to give the title compound (32 mg).
$^1$H NMR (300 MHz, DMSO-d$_6$) δ 0.28-0.35 (2H, m), 0.52-0.60 (2H, m), 1.17-1.34 (4H, m), 1.82 (3H, s), 3.82 (2H, d, J=7.0 Hz), 4.80-4.91 (1H, m), 5.02 (2H, s), 6.67-6.85 (5H, m), 6.93-7.01 (2H, m, J=8.7 Hz), 7.20-7.26 (2H, m, J=8.7 Hz), 7.34 (1H, t, J=8.1 Hz), 8.21 (1H, d, J=8.3 Hz).

Example 42

N-(1-(6-((4-(3-(cyclopropylmethoxy)phenoxy)-2-fluorobenzyl)oxy)pyridin-3-yl)ethyl)acetamide

A) methyl 6-((4-(3-(cyclopropylmethoxy)phenoxy)-2-fluorobenzyl)oxy)nicotinate A mixture of (4-(3-(cyclopropylmethoxy)phenoxy)-2-fluorophenyl)methanol (800 mg), methyl 6-bromonicotinate (599 mg), sodium hydride (60% in oil, 166 mg) and THF (10 ml) was stirred at room temperature for 10 min, and then stirred under microwave irradiation at 135° C. for 40 min. To the mixture was added water at 0° C., and the mixture was extracted with ethyl acetate. The organic layer was separated, washed with saturated brine, dried over magnesium sulfate, and concentrated under reduced pressure. The obtained residue was purified by silica gel column chromatography (ethyl acetate/hexane) to give the title compound (358 mg).
MS: [M+H]$^+$ 424.0.

B) N-(1-(6-((4-(3-(cyclopropylmethoxy)phenoxy)-2-fluorobenzyl)oxy)pyridin-3-yl)ethyl)acetamide A mixture of methyl 6-((4-(3-(cyclopropylmethoxy)phenoxy)-2-fluorobenzyl)oxy)nicotinate (350 mg) and THF (2 ml) was added to a mixture of lithium aluminium hydride (62.7 mg) and THF (3 ml) at 0° C. The mixture was stirred under nitrogen atmosphere at room temperature for 2 hr. To the mixture were successively added water (1 ml), 1N aqueous sodium hydroxide solution (1 ml) and water (1 ml) at 0° C., the mixture was filtered through Celite, and the filtrate was concentrated under reduced pressure. A mixture of the obtained residue, tetrapropyl perruthenate (80 mg), N-methylmorpholine N-oxide (89 mg), molecular sieve 4A (97 mg) and acetonitrile (3 ml) was stirred overnight at room temperature. The mixture was filtered through Celite, and the filtrate was concentrated under reduced pressure. To a mixture of the obtained residue and THF (2 ml) was added methylmagnesium bromide (3M diethyl ether solution, 0.132 ml) at 0° C., and the mixture was stirred at room temperature for 1 hr. To the mixture was added saturated aqueous ammonium chloride solution at 0° C., and the mixture was extracted with ethyl acetate. The organic layer was separated, washed with saturated brine, dried over magnesium sulfate, and concentrated under reduced pressure. A mixture of the obtained residue, manganese dioxide (143 mg) and acetonitrile (1 ml) was stirred overnight at room temperature. The mixture was filtered through Celite, and the filtrate was concentrated under reduced pressure. A mixture of the obtained residue, sodium cyanoborohydride (29.3 mg), ammonium acetate (90 mg) and methanol (1 ml) was stirred overnight at 65° C. To the mixture was added water at room temperature, and the mixture was extracted four times with ethyl acetate. The organic layer was separated, washed with saturated brine, dried over magnesium sulfate, and concentrated under reduced pressure. A mixture of the obtained residue, acetic anhydride (0.026 ml) and THF (1 ml) was stirred at room temperature for 1 hr. The mixture was concentrated under reduced pressure. The obtained residue was purified by silica gel column chromatography (ethyl acetate/hexane) to give the title compound (24 mg).

$^1$H NMR (300 MHz, CD$_3$OD) δ 0.29-0.38 (2H, m), 0.54-0.64 (2H, m), 1.16-1.28 (1H, m), 1.44 (3H, d, J=7.0 Hz), 1.94 (3H, s), 3.79 (2H, d, J=7.0 Hz), 4.92-5.03 (1H, m), 5.33 (2H, s), 6.53-6.64 (2H, m), 6.69-6.84 (4H, m), 7.19-7.31 (1H, m), 7.46 (1H, t, J=8.4 Hz), 7.66 (1H, dd, J=8.7, 2.4 Hz), 8.10 (1H, d, J=2.4 Hz).

Example 43

N-(1-(5-((4-(3-(cyclopropylmethoxy)phenoxy)-2,6-difluorobenzyl)oxy)pyrazin-2-yl)ethyl)acetamide A) 1-(5-((4-(3-(cyclopropylmethoxy)phenoxy)-2,6-difluorobenzyl)oxy)pyrazin-2-yl)ethanone A mixture of (4-(3-(cyclopropylmethoxy)phenoxy)-2,6-difluorophenyl)methanol (60 mg), 1-(5-chloropyrazin-2-yl)ethanone (33.7 mg), sodium hydride (60% in oil, 11.75 mg) and THF (1 ml) was stirred at room temperature for 10 min, and then stirred under microwave irradiation at 135° C. for 1 hr. To the mixture was added water at 0° C., and the mixture was extracted with ethyl acetate. The organic layer was separated, washed with saturated brine, dried over magnesium sulfate, and concentrated under reduced pressure. The obtained residue was purified by HPLC (acetonitrile/water, addition of 0.1% TFA) to give the title compound (20 mg).

$^1$H NMR (300 MHz, CDCl$_3$) δ 0.31-0.42 (2H, m), 0.61-0.70 (2H, m), 1.22-1.30 (1H, m), 2.66 (3H, s), 3.79 (2H, d, J=7.0 Hz), 5.47 (2H, s), 6.53-6.68 (4H, m), 6.76 (1H, ddd, J=8.3, 2.4, 0.8 Hz), 7.27-7.34 (1H, m), 8.18-8.23 (1H, m), 8.81-8.88 (1H, m).

B) N-(1-(5-((4-(3-(cyclopropylmethoxy)phenoxy)-2,6-difluorobenzyl)oxy)pyrazin-2-yl)ethyl)acetamide A mixture of 1-(5-((4-(3-(cyclopropylmethoxy)phenoxy)-2,6-difluorobenzyl)oxy)pyrazin-2-yl)ethanone (12 mg), sodium cyanoborohydride (3.54 mg), ammonium acetate (10.85 mg) and methanol (1 ml) was stirred overnight at 65° C. To the mixture was added water at room temperature, and the mixture was extracted four times with ethyl acetate. The organic layer was separated, washed with saturated brine, dried over magnesium sulfate, and concentrated under reduced pressure. To a mixture of the obtained residue and THF (1 ml) was added acetic anhydride (7.95 μl) at room temperature. The mixture was stirred at room temperature for 1 hr, water was added thereto at room temperature, and the mixture was extracted with ethyl acetate. The organic layer was separated, washed with saturated brine, dried over magnesium sulfate, and concentrated under reduced pressure. The obtained residue was purified by HPLC (acetonitrile/water, addition of 0.1% TFA). To the obtained residue was added ethyl acetate, and the mixture was washed with saturated aqueous sodium hydrogencarbonate solution. The obtained organic layer was concentrated under reduced pressure to give the title compound (7 mg).

$^1$H NMR (300 MHz, CD$_3$OD) δ 0.30-0.40 (2H, m), 0.56-0.67 (2H, m), 1.18-1.26 (1H, m), 1.47 (3H, d, J=7.2 Hz), 1.97 (3H, s), 3.81 (2H, d, J=6.8 Hz), 5.02-5.11 (1H, m), 5.40 (2H, s), 6.53-6.68 (4H, m), 6.77-6.85 (1H, m), 7.24-7.36 (1H, m), 8.14 (2H, s).

Example 44

N-((2S)-1-(4-(5-(3-(cyclopropylmethoxy)phenoxy)-1,3-oxazol-2-yl)phenoxy)propan-2-yl)acetamide A) 3-(cyclopropylmethoxy)phenyl N-(tert-butoxycarbonyl)glycinate A mixture of 3-(cyclopropylmethoxy)phenol (1 g), N-(tert-butoxycarbonyl)glycine (1.28 g), WSCD (1.401 g), N,N-dimethylpyridin-4-amine (0.893 g) and DMF (15 ml) was stirred overnight at room temperature. The mixture was extracted with ethyl acetate and water. The obtained organic layer was washed with saturated brine, dried over magnesium sulfate, and concentrated under reduced pressure. The obtained residue was purified by silica gel column chromatography (NH, ethyl acetate/hexane) to give the title compound (1.9 g).

$^1$H NMR (300 MHz, DMSO-d$_6$) δ 0.24-0.36 (2H, m), 0.49-0.63 (2H, m), 1.20-1.27 (1H, m), 1.40 (9H, s), 3.80 (2H, d, J=7.0 Hz), 3.94 (2H, d, J=6.0 Hz), 6.60-6.71 (2H, m), 6.74-6.89 (1H, m), 7.20-7.35 (1H, m), 7.36-7.44 (1H, m).

B) 3-(cyclopropylmethoxy)phenyl glycinate hydrochloride

A mixture of 3-(cyclopropylmethoxy)phenyl N-(tert-butoxycarbonyl)glycinate (1.9 g) and hydrogen chloride (4M ethyl acetate solution, 10 ml) was stirred at room temperature for 1 hr. The obtained solid was collected by filtration to give the title compound (1.11 g).

$^1$H NMR (300 MHz, DMSO-d$_6$) δ 0.24-0.40 (2H, m), 0.48-0.68 (2H, m), 1.11-1.31 (1H, m), 3.82 (2H, d, J=7.0 Hz), 4.08 (2H, s), 6.67-6.81 (2H, m), 6.82-6.95 (1H, m), 7.28-7.41 (1H, m), 8.46 (3H, s).

C) methyl 4-(((2S)-2-((tert-butoxycarbonyl)amino)propyl)oxy)benzoate

A mixture of tert-butyl ((2S)-1-hydroxypropan-2-yl)carbamate (2.53 g), triphenylphosphine (5.17 g), diisopropyl azodicarboxylate (1.9M toluene solution, 10.38 ml), methyl 4-hydroxybenzoate (2 g) and THF (30 ml) was stirred overnight at room temperature. The mixture was concentrated under reduced pressure. The obtained residue was purified by silica gel column chromatography (ethyl acetate/hexane) to give the title compound (2.74 g).

$^1$H NMR (300 MHz, DMSO-d$_6$) δ 1.12 (3H, d, J=6.5 Hz), 1.38 (9H, s), 3.81 (3H, s), 3.82-4.02 (3H, m), 6.83-6.95 (1H, m), 7.04 (2H, d, J=8.9 Hz), 7.90 (2H, d, J=8.9 Hz).

D) 4-(((2S)-2-((tert-butoxycarbonyl)amino)propyl)oxy)benzoic acid

A mixture of methyl 4-(((2S)-2-((tert-butoxycarbonyl)amino)propyl)oxy)benzoate (2.74 g), 1N aqueous sodium hydroxide solution (44.3 ml), THF (20 ml) and methanol (20 ml) was stirred at room temperature for 2 hr. The mixture was acidified with 1N hydrochloric acid. The mixture was stirred at room temperature for 30 min, and the obtained solid was collected by filtration to give the title compound (1.73 g).

$^1$H NMR (300 MHz, DMSO-d$_6$) δ 1.12 (3H, d, J=6.3 Hz), 1.38 (9H, s), 3.73-4.06 (3H, m), 6.82-6.93 (1H, m), 7.01 (2H, d, J=8.9 Hz), 7.87 (2H, d, J=8.9 Hz), 12.60 (1H, brs).

E) 3-(cyclopropylmethoxy)phenyl N-(4-(((2S)-2-((tert-butoxycarbonyl)amino)propyl)oxy)benzoyl)glycinate To a mixture of 4-(((2S)-2-((tert-butoxycarbonyl)amino)propyl)oxy)benzoic acid (1.272 g), DMF (0.033 ml) and THF (15 ml) was added dropwise oxalyl chloride (0.566 ml) under ice-cooling. The mixture was stirred at room temperature for 1 hr, and concentrated under reduced pressure. To the obtained residue was added THF (15 ml), and then 3-(cyclopropylmethoxy)phenyl glycinate hydrochloride (1.11 g) and triethylamine (1.501 ml) were added thereto. The reaction mixture was stirred overnight at room temperature. The mixture was extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (2 g).

$^1$H NMR (300 MHz, DMSO-$d_6$) δ 0.26-0.36 (2H, m), 0.50-0.61 (2H, m), 1.12 (3H, d, J=6.3 Hz), 1.18-1.27 (1H, m), 1.38 (9H, s), 3.81 (2H, d, J=7.0 Hz), 3.83-4.00 (3H, m), 4.23 (2H, d, J=5.8 Hz), 6.63-6.73 (2H, m), 6.79-6.87 (1H, m), 6.87-6.94 (1H, m), 7.02 (2H, d, J=8.9 Hz), 7.25-7.34 (1H, m), 7.86 (2H, d, J=8.9 Hz), 8.88-8.99 (1H, m).

F) tert-butyl((2S)-1-(4-(5-(3-(cyclopropylmethoxy)phenoxy)-1,3-oxazol-2-yl)phenoxy)propan-2-yl)carbamate To a mixture of triphenylphosphine (1.052 g) and acetonitrile (10 ml) was added iodine (1.018 g) under ice-cooling, and then triethylamine (1.18 ml) was added dropwise thereto. The mixture was stirred at 0° C. for 10 min, and a mixture of 3-(cyclopropylmethoxy)phenyl N-(4-(((2S)-2-((tert-butoxycarbonyl)amino)propyl)oxy)benzoyl)glycinate (1 g) and acetonitrile (5 ml) was added thereto. The reaction mixture was stirred overnight at room temperature. The mixture was concentrated under reduced pressure. The obtained residue was purified by silica gel column chromatography (ethyl acetate/hexane) to give the title compound (0.629 g).

$^1$H NMR (300 MHz, DMSO-$d_6$) δ 0.26-0.35 (2H, m), 0.50-0.60 (2H, m), 1.13 (3H, d, J=6.3 Hz), 1.18-1.27 (1H, m), 1.38 (9H, s), 3.77-3.99 (5H, m), 6.70-6.81 (3H, m), 6.82 (1H, s), 6.86-6.95 (1H, m), 7.05 (2H, d, J=9.0 Hz), 7.31 (1H, t, J=8.2 Hz), 7.81 (2H, d, J=8.9 Hz).

G) N-((2S)-1-(4-(5-(3-(cyclopropylmethoxy)phenoxy)-1,3-oxazol-2-yl)phenoxy)propan-2-yl)acetamide A mixture of tert-butyl ((2S)-1-(4-(5-(3-(cyclopropylmethoxy)phenoxy)-1,3-oxazol-2-yl)phenoxy)propan-2-yl)carbamate (629 mg) and formic acid (6 ml) was stirred at room temperature for 4 hr. The mixture was concentrated under reduced pressure. To the obtained residue were added pyridine (3 ml) and acetic anhydride (0.617 ml). The mixture was stirred at room temperature for 30 min, and concentrated under reduced pressure. The obtained residue was purified by silica gel column chromatography (ethyl acetate/hexane), and crystallized from hexane/ethyl acetate to give the title compound (100 mg).

$^1$H NMR (300 MHz, DMSO-$d_6$) δ 0.26-0.35 (2H, m), 0.50-0.61 (2H, m), 1.16 (3H, d, J=6.8 Hz), 1.18-1.25 (1H, m), 1.81 (3H, s), 3.83 (2H, d, J=7.0 Hz), 3.85-3.91 (1H, m), 3.93-4.02 (1H, m), 4.04-4.16 (1H, m), 6.70-6.85 (4H, m), 7.08 (2H, d, J=8.7 Hz), 7.31 (1H, t, J=7.8 Hz), 7.81 (2H, d, J=8.4 Hz), 7.94 (1H, d, J=8.7 Hz).

Example 45

N-(1-(((3R)-1-(4-(3-(cyclopropylmethoxy)phenoxy)phenyl)pyrrolidin-3-yl)oxy)propan-2-yl)acetamide

A) (4R)-4-((tert-butyl(dimethyl)silyl)oxy)pyrrolidin-2-one

A mixture of 1H-imidazole (3.03 g), tert-butyl(chloro)dimethylsilane (6.07 ml), (4R)-4-hydroxypyrrolidin-2-one (3 g) and DMF (30 ml) was stirred at room temperature for 48 hr. To the mixture was added water, and the obtained solid was collected by filtration to give the title compound (5.59 g).

$^1$H NMR (300 MHz, DMSO-$d_6$) δ 0.04 (6H, s), 0.85 (9H, s), 1.94-1.95 (1H, m), 2.41-2.47 (1H, m), 2.95-3.05 (1H, m), 3.45-3.50 (1H, m), 4.48-4.52 (1H, m), 7.55 (1H, brs).

B) (4R)-4-((tert-butyl(dimethyl)silyl)oxy)-1-(4-(3-(cyclopropylmethoxy)phenoxy)phenyl)pyrrolidin-2-one A mixture of (4R)-4-((tert-butyl(dimethyl)silyl)oxy)pyrrolidin-2-one (1.247 g), 1-(4-bromophenoxy)-3-(cyclopropylmethoxy)benzene (1.54 g), tris(dibenzylideneacetone)dipalladium (0.177 g), 5-(di-tert-butylphosphino)-1',3',5'-triphenyl-1'H-1,4'-bipyrazole (0.196 g), sodium tert-butoxide (0.51 g), tert-butanol (45 ml) and water (5 ml) was stirred at 80° C. for 3 hr. To the mixture were added saturated brine and ethyl acetate, and the mixture was filtered through Celite. The organic layer was separated, dried over magnesium sulfate, and concentrated under reduced pressure. The obtained residue was purified by silica gel column chromatography (ethyl acetate/hexane) to give the title compound (970 mg).

MS: [M+H]$^+$ 454.3.

C) (4R)-1-(4-(3-(cyclopropylmethoxy)phenoxy)phenyl)-4-hydroxypyrrolidin-2-one A mixture of (4R)-4-((tert-butyl(dimethyl)silyl)oxy)-1-(4-(3-(cyclopropylmethoxy)phenoxy)phenyl)pyrrolidin-2-one (970 mg), hydrogen chloride (4M cyclopentyl methyl ether solution, 15 ml) and ethyl acetate (15 ml) was stirred at room temperature for 5 hr. To the mixture was added saturated aqueous sodium hydrogencarbonate solution, and the mixture was extracted with ethyl acetate. The obtained organic layer was dried over magnesium sulfate, and concentrated under reduced pressure. The obtained residue was purified by silica gel column chromatography (ethyl acetate/hexane) to give the title compound (530 mg).

MS: [M+H]$^+$ 340.1.

D) 2-(((3R)-1-(4-(3-(cyclopropylmethoxy)phenoxy)phenyl)pyrrolidin-3-yl)oxy)ethanol To a mixture of (4R)-1-(4-(3-(cyclopropylmethoxy)phenoxy)phenyl)-4-hydroxypyrrolidin-2-one (334.7 mg), rhodium acetate dimer (21.79 mg) and toluene (20 ml) was added ethyl diazoacetate (4.19 ml) at 80° C. The mixture was stirred at 110° C. for 1.5 hr. The mixture was extracted with saturated brine and ethyl acetate. The obtained organic layer was dried over magnesium sulfate, and concentrated under reduced pressure. The obtained residue was purified by silica gel column chromatography (ethyl acetate/hexane). A mixture of the obtained residue, Red-Al (1.5M toluene solution, 1.78 ml) and THF (25 ml) was stirred at 60° C. for 1 hr. The mixture was extracted with water and ethyl acetate. The obtained organic layer was dried over magnesium sulfate, and concentrated under reduced pressure. The obtained residue was purified by silica gel column chromatography (NH, ethyl acetate/hexane) to give the title compound (78 mg).

E) 1-(((3R)-1-(4-(3-(cyclopropylmethoxy)phenoxy)phenyl)pyrrolidin-3-yl)oxy)propan-2-ol A mixture of triethylamine (0.294 ml), sulfur trioxide pyridine complex (224 mg), 2-(((3R)-1-(4-(3-(cyclopropylmethoxy)phenoxy)phenyl)pyrrolidin-3-yl)oxy)ethanol (78 mg) and DMSO (15 ml) was stirred at room temperature for 3 hr. To the mixture was added 1N hydrochloric acid, and the mixture was extracted with water and ethyl acetate. The obtained organic layer was washed with saturated brine, dried over magnesium sulfate, and concentrated under reduced pressure. To the obtained residue was added THF (20 ml), and then methylmagnesium bromide (3M diethyl ether solution, 1.056 ml) was added thereto. The mixture was stirred at room temperature for 1 hr. The mixture was extracted with water and ethyl acetate. The obtained organic layer was dried over magnesium sulfate, and concentrated under reduced pressure. The obtained residue was purified by silica gel column chromatography (NH, ethyl acetate/hexane) to give the title compound (23.5 mg).

$^1$H NMR (300 MHz, CDCl$_3$) δ 0.23-0.38 (2H, m), 0.52-0.67 (2H, m), 1.04-1.35 (4H, m), 2.06-2.22 (2H, m), 2.27-2.40 (1H, m), 3.17-3.60 (6H, m), 3.74 (2H, d, J=6.9 Hz), 3.88-4.06 (1H, m), 4.18-4.33 (1H, m), 6.37-6.66 (5H, m), 6.84-7.02 (2H, m), 7.08-7.20 (1H, m).

F) N-(1-(((3R)-1-(4-(3-(cyclopropylmethoxy)phenoxy)phenyl)pyrrolidin-3-yl)oxy)propan-2-yl)acetamide A mixture of 1-(((3R)-1-(4-(3-(cyclopropylmethoxy)phenoxy)phenyl) pyrrolidin-3-yl)oxy)propan-2-ol (23.5 mg), methanesulfonyl chloride (0.038 ml), triethylamine (0.085 ml) and THF (15 ml) was stirred at room temperature for 3 hr. The mixture was extracted with water and ethyl acetate. The obtained organic layer was dried over magnesium sulfate, and concentrated under reduced pressure. To the obtained residue was added DMF (15 ml), and then sodium azide (45 mg) was added thereto. The mixture was stirred at 100° C. for 2 hr. The mixture was extracted with water and ethyl acetate. The obtained organic layer was washed with saturated brine, dried over magnesium sulfate, and concentrated under reduced pressure. To the obtained residue were added THF (10 ml) and water (2 ml), and then triphenylphosphine (64.3 mg) was added thereto. The mixture was stirred at 60° C. for 2 hr. The mixture was extracted with water and ethyl acetate. The obtained organic layer was dried over magnesium sulfate, and concentrated under reduced pressure. A mixture of the obtained residue, triethylamine (0.042 ml), acetic anhydride (0.017 ml) and THF (10 ml) was stirred at room temperature for 1 hr. The mixture was extracted with water and ethyl acetate. The obtained organic layer was dried over magnesium sulfate, and concentrated under reduced pressure. The obtained residue was purified by silica gel column chromatography (methanol/ethyl acetate), and then purified by HPLC (water/acetonitrile, addition of 0.1% TFA) to give the title compound (1 mg).

$^1$H NMR (300 MHz, CDCl$_3$) δ 0.25-0.40 (2H, m), 0.54-0.68 (2H, m), 0.86-0.94 (1H, m), 1.18 (3H, dd, J=6.8, 2.1 Hz), 1.24 (3H, s), 2.09-2.17 (2H, m), 3.26-3.55 (6H, m), 3.74 (2H, d, J=7.0 Hz), 4.21 (1H, brs), 5.24-5.44 (1H, m), 5.64 (1H, brs), 6.43-6.58 (5H, m), 6.93-7.01 (2H, m), 7.10-7.18 (1H, m).

Example 46

N-(4-(3-(4-(3-(cyclopropylmethoxy)phenoxy)phenyl)-1,2-oxazol-5-yl)butan-2-yl)acetamide A) N-hydroxy-4-iodobenzenecarboxyimidoyl chloride A mixture of 4-iodobenzaldehyde (5 g), hydroxylamine hydrochloride (1.947 g), sodium hydrogencarbonate (2.353 g) and ethanol (50 ml) was stirred overnight at room temperature. The mixture was filtered, and the filtrate was concentrated under reduced pressure. The obtained residue was extracted with ethyl acetate and water. The obtained organic layer was washed with saturated brine, dried over magnesium sulfate, and concentrated under reduced pressure. A mixture of the obtained residue, N-chlorosuccinimide (3.45 g) and DMF (50 ml) was stirred at room temperature for 2 hr. The mixture was extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (5.15 g).

$^1$H NMR (300 MHz, DMSO-d$_6$) δ 7.46-7.67 (2H, m), 7.74-7.91 (2H, m), 12.51 (1H, s).

B) ethyl 3-(3-(4-iodophenyl)-1,2-oxazol-5-yl)propanoate

A mixture of N-hydroxy-4-iodobenzenecarboxyimidoyl chloride (2.86 g), ethyl pent-4-ynoate (1.28 g), triethylamine (2.83 ml) and THF (30 ml) was stirred at 60° C. for 2 hr. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (2.2 g).

$^1$H NMR (300 MHz, DMSO-d$_6$) δ 1.18 (3H, t, J=7.1 Hz), 2.72-2.82 (2H, m), 3.01-3.10 (2H, m), 4.09 (2H, q, J=7.1 Hz), 6.85 (1H, s), 7.63 (2H, d, J=8.5 Hz), 7.88 (2H, d, J=8.4 Hz).

C) ethyl 3-(3-(4-(3-(cyclopropylmethoxy)phenoxy)phenyl)-1,2-oxazol-5-yl)propanoate A mixture of ethyl 3-(3-(4-iodophenyl)-1,2-oxazol-5-yl)propanoate (2.2 g), 3-(cyclopropylmethoxy)phenol (1.265 g), pyridine-2-carboxylic acid (0.292 g), copper(I) iodide (0.226 g), tripotassium phosphate (3.77 g) and DMSO (20 ml) was stirred at 100° C. for 4 hr. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (1.74 g).

$^1$H NMR (300 MHz, DMSO-d$_6$) δ 0.26-0.34 (2H, m), 0.50-0.60 (2H, m), 1.17-1.20 (3H, m), 1.21-1.26 (1H, m), 2.71-2.82 (2H, m), 2.99-3.10 (2H, m), 3.80 (2H, d, J=7.0 Hz), 4.05-4.13 (2H, m), 6.56-6.67 (2H, m), 6.71-6.81 (2H, m), 7.10 (2H, d, J=8.8 Hz), 7.30 (1H, t, J=8.2 Hz), 7.83 (2H, d, J=8.8 Hz).

D) 3-(3-(4-(3-(cyclopropylmethoxy)phenoxy)phenyl)-1,2-oxazol-5-yl)propanoic acid A mixture of ethyl 3-(3-(4-(3-(cyclopropylmethoxy)phenoxy)phenyl)-1,2-oxazol-5-yl)propanoate (1.74 g), 1N aqueous sodium hydroxide solution (21.35 ml), methanol (15 ml) and THF (15 ml) was stirred at room temperature for 2 hr. The mixture was acidified with 1N hydrochloric acid, and extracted with ethyl acetate. The obtained organic layer was washed with saturated brine, dried over magnesium sulfate, and concentrated under reduced pressure to give the title compound (889 mg).

$^1$H NMR (300 MHz, DMSO-d$_6$) δ 0.26-0.35 (2H, m), 0.50-0.60 (2H, m), 1.12-1.26 (1H, m), 2.65-2.75 (2H, m), 2.96-3.07 (2H, m), 3.80 (2H, d, J=7.0 Hz), 6.54-6.68 (2H, m), 6.72-6.83 (2H, m), 7.10 (2H, d, J=8.8 Hz), 7.30 (1H, t, J=8.2 Hz), 7.84 (2H, d, J=8.8 Hz), 12.37 (1H, brs).

E) 4-(3-(4-(3-(cyclopropylmethoxy)phenoxy)phenyl)-1,2-oxazol-5-yl)butan-2-yl methanesulfonate A mixture of 3-(3-(4-(3-(cyclopropylmethoxy)phenoxy)phenyl)-1,2-oxazol-5-yl)propanoic acid (888 mg), N,O-dimethylhydroxylamine hydrochloride (342 mg), WSCD (637 mg), HOBt monohydrate (358 mg), N,N-diisopropylethylamine (0.613 ml) and DMF (10 ml) was stirred overnight at room temperature. The mixture was extracted with ethyl acetate and water. The obtained organic layer was washed with saturated brine, dried over magnesium sulfate, and concentrated under reduced pressure. The obtained residue was purified by silica gel column chromatography (ethyl acetate/hexane). To a mixture of the obtained residue and THF (10 ml) was added methylmagnesium bromide (1.0M THF solution, 4.68 ml) under ice-cooling. The mixture was stirred at 0° C. for 30 min, and extracted with ethyl acetate and saturated aqueous ammonium chloride solution. The obtained organic layer was washed with saturated brine, dried over magnesium sulfate, and concentrated under reduced pressure. To the obtained residue were added ethanol (10 ml) and THF (10 ml), and then sodium borohydride (177 mg) was added thereto at 0° C. The mixture was stirred at 0° C. for 30 min, and extracted with ethyl acetate and 1N hydrochloric acid. The obtained organic layer was washed with saturated brine, dried over magnesium sulfate, and concentrated under reduced pressure. To the obtained residue was added THF (10 ml), and then methanesulfonyl chloride (0.362 ml) and triethylamine (0.652 ml) were added thereto. The mixture was stirred at room temperature for 2 hr, and extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (692 mg).

$^1$H NMR (300 MHz, DMSO-d$_6$) δ 0.26-0.34 (2H, m), 0.50-0.59 (2H, m), 1.20-1.26 (1H, m), 1.40 (3H, d, J=6.2 Hz), 2.00-2.11 (2H, m, J=6.3 Hz), 2.82-2.98 (2H, m), 3.20 (3H, s), 3.80 (2H, d, J=7.0 Hz), 4.74-4.90 (1H, m), 6.58-6.66 (2H, m), 6.72-6.80 (1H, m), 6.83 (1H, s), 7.10 (2H, d, J=8.9 Hz), 7.30 (1H, t, J=7.9 Hz), 7.85 (2H, d, J=8.8 Hz).

F) N-(4-(3-(4-(3-(cyclopropylmethoxy)phenoxy)phenyl)-1,2-oxazol-5-yl)butan-2-yl)acetamide A mixture of 4-(3-(4-(3-(cyclopropylmethoxy)phenoxy)phenyl)-1,2-oxazol-5-yl)butan-2-yl methanesulfonate (691 mg), sodium azide (196 mg) and DMF (6 ml) was stirred at 80° C. for 2 hr. The mixture was allowed to cool to room temperature, and extracted with ethyl acetate and water. The obtained organic layer was washed with saturated brine, dried over magnesium sulfate, and concentrated under reduced pressure. To the obtained mixture were added THF (6 ml), water (3 ml) and triphenylphosphine (792 mg). The mixture was stirred at 60° C. for 1 hr. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (NH, ethyl acetate/hexane). A mixture of the obtained residue, acetic anhydride (0.712 ml) and pyridine (4 ml) was stirred at room temperature for 20 min. The mixture was concentrated under reduced pressure. The obtained residue was purified by silica gel column chromatography (NH, ethyl acetate/hexane), and crystallized from hexane/ethyl acetate to give the title compound (243 mg).

$^1$H NMR (300 MHz, DMSO-d$_6$) δ 0.25-0.35 (2H, m), 0.50-0.60 (2H, m), 1.07 (3H, d, J=6.8 Hz), 1.13-1.25 (1H, m), 1.71-1.84 (5H, m), 2.69-2.82 (2H, m), 3.75-3.90 (3H, m), 6.57-6.66 (2H, m), 6.70-6.80 (2H, m), 7.10 (2H, d, J=8.9 Hz), 7.30 (1H, t, J=8.3 Hz), 7.76 (1H, d, J=7.9 Hz), 7.84 (2H, d, J=8.7 Hz).

Example 48

N-(4-(1-(4-(3-(cyclopropylmethoxy)phenoxy)phenyl)-1H-pyrazol-3-yl) butan-2-yl)acetamide

A) ethyl 1-(4-iodophenyl)-1H-pyrazole-3-carboxylate

A mixture of (4-iodophenyl)boronic acid (5 g), ethyl 1H-pyrazole-3-carboxylate (3.08 g), copper(II) acetate (4 g), pyridine (2.9 g) and DMA (50 ml) was stirred overnight at room temperature. The mixture was extracted with ethyl acetate and saturated aqueous ammonium chloride solution. The obtained organic layer was washed with saturated brine, dried over magnesium sulfate, and concentrated under reduced pressure. The obtained residue was purified by silica gel column chromatography (ethyl acetate/hexane) to give the title compound (4.71 g).

$^1$H NMR (300 MHz, DMSO-d$_6$) δ 1.32 (3H, t, J=7.1 Hz), 4.33 (2H, q, J=7.1 Hz), 7.02 (1H, d, J=2.6 Hz), 7.68-7.77 (2H, m), 7.85-7.96 (2H, m), 8.65 (1H, d, J=2.6 Hz).

B) ethyl 1-(4-(3-(cyclopropylmethoxy)phenoxy)phenyl)-1H-pyrazole-3-carboxylate A mixture of 3-(cyclopropylmethoxy)phenol (2.71 g), ethyl 1-(4-iodophenyl)-1H-pyrazole-3-carboxylate (4.71 g), pyridine-2-carboxylic acid (0.678 g), tripotassium phosphate (8.77 g), copper(I) iodide (0.524 g) and DMSO (40 ml) was stirred at 100° C. for 4 hr. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (3.89 g).

$^1$H NMR (300 MHz, DMSO-d$_6$) δ 0.25-0.35 (2H, m), 0.50-0.60 (2H, m), 1.19-1.26 (1H, m), 1.28-1.37 (3H, m), 3.80 (2H, d, J=7.0 Hz), 4.23-4.41 (2H, m), 6.58-6.64 (2H, m), 6.70-6.80 (1H, m), 7.00 (1H, d, J=2.5 Hz), 7.13-7.19 (2H, m), 7.30 (1H, t, J=8.3 Hz), 7.81-7.95 (2H, m), 8.57 (1H, d, J=2.5 Hz).

C) (1-(4-(3-(cyclopropylmethoxy)phenoxy)phenyl)-1H-pyrazol-3-yl) methanol

To a mixture of lithium aluminium hydride (0.585 g) and THF (40 ml) was added a mixture of ethyl 1-(4-(3-(cyclopropylmethoxy)phenoxy)phenyl)-1H-pyrazole-3-carboxylate (3.10 g) and THF (20 ml) under ice-cooling. The mixture was stirred at 0° C. for 30 min, and water (0.6 ml) and 1N aqueous sodium hydroxide solution (0.6 ml) were successively added thereto. To the mixture was added water (1.8 ml), and the mixture was stirred at room temperature for 30 min. The mixture was filtered through Celite, and the filtrate was concentrated under reduced pressure. The obtained residue was purified by silica gel column chromatography (ethyl acetate/hexane) to give the title compound (3.1 g).

$^1$H NMR (300 MHz, DMSO-d$_6$) δ 0.25-0.35 (2H, m), 0.50-0.60 (2H, m), 1.18-1.27 (1H, m), 3.79 (2H, d, J=7.0 Hz), 4.50 (2H, d, J=5.9 Hz), 5.14 (1H, t, J=5.8 Hz), 6.47 (1H, d, J=2.4 Hz), 6.53-6.62 (2H, m), 6.67-6.75 (1H, m), 7.09-7.16 (2H, m), 7.27 (1H, t, J=8.0 Hz), 7.74-7.85 (2H, m), 8.36 (1H, d, J=2.5 Hz).

D) ethyl (2E)-3-(1-(4-(3-(cyclopropylmethoxy)phenoxy)phenyl)-1H-pyrazol-3-yl)acrylate A mixture of (1-(4-(3-(cyclopropylmethoxy)phenoxy)phenyl)-1H-pyrazol-3-yl)methanol (3.1 g), tetrapropyl perruthenate (0.162 g), N-methylmorpholine N-oxide (1.619 g), molecular sieve 4A (4.6 g) and acetonitrile (40 ml) was stirred at room temperature for 2 hr. The mixture was filtered, and the filtrate was concentrated under reduced pressure. The obtained residue was passed through silica gel short column (ethyl acetate) to give the corresponding aldehyde. To a mixture of sodium hydride (60% in oil, 0.487 g) and THF (20 ml) was added ethyl (diethoxyphosphoryl) acetate (2.0 ml) under ice-cooling. The mixture was stirred at 0° C. for 10 min, and a mixture of the aldehyde previously obtained and THF (10 ml) was added thereto. The reaction mixture was stirred at room temperature for 1 hr. The mixture was extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (1.85 g).

$^1$H NMR (300 MHz, DMSO-d$_6$) δ 0.27-0.34 (2H, m), 0.50-0.60 (2H, m), 1.17-1.22 (1H, m), 1.27 (3H, t, J=7.1 Hz), 3.80 (2H, d, J=7.0 Hz), 4.20 (2H, q, J=7.1 Hz), 6.55-6.61 (2H, m), 6.65 (1H, d, J=16.1 Hz), 6.70-6.76 (1H, m), 7.08 (1H, d, J=2.5 Hz), 7.16 (2H, d, J=9.0 Hz), 7.28 (1H, t, J=8.3 Hz), 7.58 (1H, d, J=16.1 Hz), 7.86 (2H, d, J=9.0 Hz), 8.51 (1H, d, J=2.3 Hz).

E) ethyl 3-(1-(4-(3-(cyclopropylmethoxy)phenoxy)phenyl)-1H-pyrazol-3-yl)propanoate A mixture of copper(I) chloride (0.045 g), 1,1'-bis(triphenylphosphine)binaphthyl (0.285 g), sodium tert-butoxide (0.044 g) and toluene (10 ml) was stirred at room temperature for 10 min. To the mixture was added a mixture of ethyl (2E)-3-(1-(4-(3-(cyclopropylmethoxy)phenoxy)phenyl)-1H-pyrazol-3-yl)acrylate (1.85 g), tert-butanol (1.695 g), polymethylhydrosiloxane (0.82 ml) and toluene (10 ml). The reaction mixture was stirred at room temperature for 2 hr. The mixture was extracted with toluene and water. The obtained organic layer was washed with saturated brine, dried over magnesium sulfate, and concentrated under reduced pressure. The obtained residue was purified by silica gel column chromatography (ethyl acetate/hexane) to give the title compound (1.76 g).

$^1$H NMR (300 MHz, DMSO-d$_6$) δ 0.25-0.34 (2H, m), 0.50-0.60 (2H, m), 1.17-1.24 (4H, m), 2.64-2.74 (2H, m), 2.84-2.94 (2H, m), 3.79 (2H, d, J=7.0 Hz), 4.03-4.12 (2H, m), 6.36 (1H, d, J=2.4 Hz), 6.51-6.59 (2H, m), 6.67-6.75 (1H, m), 7.12 (2H, d, J=9.0 Hz), 7.22-7.32 (1H, m), 7.78 (2H, d, J=9.1 Hz), 8.32 (1H, d, J=2.5 Hz).

F) 3-(1-(4-(3-(cyclopropylmethoxy)phenoxy)phenyl)-1H-pyrazol-3-yl)-N-methoxy-N-methylpropanamide A mixture of ethyl 3-(1-(4-(3-(cyclopropylmethoxy)phenoxy)phenyl)-1H-pyrazol-3-yl)propanoate (1.76 g), 2N aqueous sodium hydroxide solution (10.82 ml), THF (10 ml) and methanol (10 ml) was stirred at room temperature for 2 hr. The mixture was acidified with 1N hydrochloric acid, and extracted with ethyl acetate. The obtained organic layer was washed with saturated brine, dried over magnesium sulfate, and concentrated under reduced pressure. To the obtained mixture was added DMF (10 ml). To the mixture were added N,O-dimethylhydroxyamine hydrochloride (0.634 g), WSCD (1.245 g), HOBt monohydrate (0.995 g) and N,N-diisopropylethylamine (1.134 ml). The reaction mixture was stirred overnight at room temperature. The mixture was extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (1.73 g).

$^1$H NMR (300 MHz, DMSO-d$_6$) δ 0.25-0.34 (2H, m), 0.50-0.61 (2H, m), 1.18-1.26 (1H, m), 2.75-2.88 (4H, m), 3.10 (3H, s), 3.67 (3H, s), 3.79 (2H, d, J=7.0 Hz), 6.36 (1H, d, J=2.4 Hz), 6.50-6.61 (2H, m), 6.65-6.76 (1H, m), 7.12 (2H, d, J=9.0 Hz), 7.27 (1H, t, J=8.4 Hz), 7.78 (2H, d, J=9.1 Hz), 8.31 (1H, d, J=2.5 Hz).

G) 4-(1-(4-(3-(cyclopropylmethoxy)phenoxy)phenyl)-1H-pyrazol-3-yl)butan-2-yl methanesulfonate To a mixture of 3-(1-(4-(3-(cyclopropylmethoxy)phenoxy)phenyl)-1H-pyrazol-3-yl)-N-methoxy-N-methylpropanamide (1.73 g) and THF (15 ml) was added methylmagnesium bromide (1M THF solution, 8.21 ml) under ice-cooling. The mixture was stirred at 0° C. for 30 min, and extracted with ethyl acetate and saturated aqueous ammonium chloride solution. The obtained organic layer was washed with saturated brine, dried over magnesium sulfate, and concentrated under reduced pressure. To the obtained residue were added ethanol (7 ml) and THF (7 ml). To the mixture was added sodium borohydride (0.311 g) under ice-cooling. The mixture was stirred at 0° C. for 30 min, and extracted with ethyl acetate and saturated aqueous ammonium chloride solution. The obtained organic layer was washed with saturated brine, dried over magnesium sulfate, and concentrated under reduced pressure. To the obtained residue were added THF (15 ml), methanesulfonyl chloride (0.953 ml) and triethylamine (1.716 ml). The reaction mixture was stirred at room temperature for 1 hr. The mixture was extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (1.43 g).

$^1$H NMR (300 MHz, DMSO-$d_6$) δ 0.25-0.34 (2H, m), 0.50-0.60 (2H, m), 1.18-1.25 (1H, m), 1.39 (3H, d, J=6.2 Hz), 1.99-2.06 (2H, m), 2.64-2.81 (2H, m), 3.19 (3H, s), 3.79 (2H, d, J=7.0 Hz), 4.74-4.88 (1H, m), 6.39 (1H, d, J=2.5 Hz), 6.53-6.60 (2H, m), 6.66-6.75 (1H, m), 7.12 (2H, d, J=9.1 Hz), 7.27 (1H, t, J=8.4 Hz), 7.79 (2H, d, J=9.1 Hz), 8.34 (1H, d, J=2.5 Hz).

H) 4-(1-(4-(3-(cyclopropylmethoxy)phenoxy)phenyl)-1H-pyrazol-3-yl)butan-2-amine

A mixture of 4-(1-(4-(3-(cyclopropylmethoxy)phenoxy)phenyl)-1H-pyrazol-3-yl)butan-2-yl methanesulfonate (1.43 g), sodium azide (0.407 g) and DMF (10 ml) was stirred at 80° C. for 2 hr. The mixture was allowed to cool to room temperature, and extracted with ethyl acetate and water. The obtained organic layer was washed with saturated brine, dried over magnesium sulfate, and concentrated under reduced pressure. To the obtained residue were added THF (10 ml), water (5 ml) and triphenylphosphine (1.643 g). The reaction mixture was stirred at 60° C. for 1 hr. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (NH, methanol/ethyl acetate) to give the title compound (0.5 g).

$^1$H NMR (300 MHz, DMSO-$d_6$) δ 0.26-0.34 (2H, m), 0.50-0.59 (2H, m), 1.00 (3H, d, J=6.3 Hz), 1.18-1.25 (1H, m), 1.37-1.49 (2H, m), 1.52-1.64 (2H, m), 2.57-2.70 (2H, m), 2.72-2.85 (1H, m), 3.79 (2H, d, J=6.9 Hz), 6.33 (1H, d, J=2.4 Hz), 6.52-6.59 (2H, m), 6.66-6.74 (1H, m), 7.11 (2H, d, J=9.1 Hz), 7.22-7.31 (1H, m, J=16.8 Hz), 7.78 (2H, d, J=9.1 Hz), 8.30 (1H, d, J=2.5 Hz).

I) N-(4-(1-(4-(3-(cyclopropylmethoxy)phenoxy)phenyl)-1H-pyrazol-3-yl)butan-2-yl)acetamide A mixture of 4-(1-(4-(3-(cyclopropylmethoxy)phenoxy)phenyl)-1H-pyrazol-3-yl)butan-2-amine (500 mg), acetic anhydride (0.625 ml) and pyridine (5 ml) was stirred at room temperature for 30 min. The mixture was concentrated under reduced pressure. The obtained residue was purified by silica gel column chromatography (NH, ethyl acetate/hexane) to give the title compound (450 mg).

$^1$H NMR (300 MHz, DMSO-$d_6$) δ 0.25-0.35 (2H, m), 0.49-0.60 (2H, m), 1.06 (3H, d, J=6.6 Hz), 1.18-1.27 (1H, m), 1.66-1.78 (2H, m), 1.80 (3H, s), 2.55-2.66 (2H, m), 3.73-3.88 (3H, m), 6.34 (1H, d, J=2.5 Hz), 6.51-6.60 (2H, m), 6.67-6.75 (1H, m), 7.11 (2H, d, J=9.0 Hz), 7.27 (1H, t, J=8.4 Hz), 7.72 (1H, d, J=8.0 Hz), 7.78 (2H, d, J=9.1 Hz), 8.31 (1H, d, J=2.4 Hz).

Example 64

N-(4-(2-(4-(3-(cyclopropylmethoxy)phenoxy)phenyl)-1,3-oxazol-5-yl)-4-oxobutan-2-yl)acetamide A) 4-(3-(cyclopropylmethoxy)phenoxy)-N-(prop-2-yn-1-yl)benzamide A mixture of 4-(3-(cyclopropylmethoxy)phenoxy)benzoic acid (7.7 g), prop-2-yn-1-amine (1.49 g), WSCD (10.4 g) and pyridine (80 ml) was stirred at 26-39° C. for 20 hr. The mixture was concentrated under reduced pressure. To the obtained residue was added water, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (7 g).

$^1$H NMR (400 MHz, DMSO-$d_6$) δ 0.25-0.35 (2H, m), 0.50-0.60 (2H, m), 1.15-1.25 (1H, m), 3.12 (1H, t, J=2.4 Hz), 3.79 (2H, d, J=7.2 Hz), 4.00-4.07 (2H, m), 6.55-6.65 (2H, m), 6.77 (1H, d, J=8.0 Hz), 7.04 (2H, d, J=8.8 Hz), 7.31 (1H, t, J=8.0 Hz), 7.88 (2H, d, J=8.8 Hz), 8.87 (1H, t, J=5.6 Hz).

B) (2-(4-(3-(cyclopropylmethoxy)phenoxy)phenyl)-1,3-oxazol-5-yl)methyl acetate

A mixture of 4-(3-(cyclopropylmethoxy)phenoxy)-N-(prop-2-yn-1-yl)benzamide (7 g), iodobenzene diacetate (10.5 g) and acetic acid (70 ml) was stirred at 90° C. for 20 hr. The mixture was poured into water, and extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (5.4 g).

$^1$H NMR (400 MHz, DMSO-$d_6$) δ 0.25-0.35 (2H, m), 0.50-0.60 (2H, m), 1.15-1.25 (1H, m), 2.06 (3H, s), 3.80 (2H, d, J=7.2 Hz), 5.18 (2H, s), 6.60-6.70 (2H, m), 6.78 (1H, d, J=8.0 Hz), 7.12 (2H, d, J=8.8 Hz), 7.32 (1H, t, J=8.0 Hz), 7.36 (1H, s), 7.96 (2H, d, J=8.8 Hz).

C) (2-(4-(3-(cyclopropylmethoxy)phenoxy)phenyl)-1,3-oxazol-5-yl) methanol

A mixture of (2-(4-(3-(cyclopropylmethoxy)phenoxy)phenyl)-1,3-oxazol-5-yl)methyl acetate (5.4 g), potassium carbonate (3.92 g) and methanol (60 ml) was stirred at 28-39° C. for 20 hr. The reaction mixture was concentrated under reduced pressure. To the obtained residue was added water, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (4.4 g).

$^1$H NMR (400 MHz, DMSO-$d_6$) δ 0.25-0.35 (2H, m), 0.50-0.60 (2H, m), 1.15-1.25 (1H, m), 3.80 (2H, d, J=6.8 Hz), 4.52 (2H, d, J=5.6 Hz), 5.45 (1H, t, J=5.6 Hz), 6.60-6.70 (2H, m), 6.78 (1H, d, J=8.8 Hz), 7.05-7.15 (3H, m), 7.32 (1H, t, J=8.0 Hz), 7.95 (2H, d, J=8.8 Hz).

D) 2-(4-(3-(cyclopropylmethoxy)phenoxy)phenyl)-1,3-oxazole-5-carbaldehyde

A mixture of (2-(4-(3-(cyclopropylmethoxy)phenoxy)phenyl)-1,3-oxazol-5-yl)methanol (5.8 g), manganese dioxide (7.48 g) and dichloromethane (60 ml) was stirred under heating with reflux for 20 hr. The reaction mixture was concentrated under reduced pressure. The obtained residue was purified by silica gel column chromatography (ethyl acetate/petroleum ether) to give the title compound (4.78 g).

$^1$H NMR (400 MHz, DMSO-d$_6$) δ 0.25-0.35 (2H, m), 0.50-0.60 (2H, m), 1.15-1.25 (1H, m), 3.81 (2H, d, J=6.8 Hz), 6.60-6.70 (2H, m), 6.82 (1H, d, J=8.0 Hz), 7.15 (2H, d, J=8.8 Hz), 7.34 (1H, t, J=8.0 Hz), 8.10 (2H, d, J=9.2 Hz), 8.32 (1H, s), 9.78 (1H, s).

E) tert-butyl 3-(2-(4-(3-(cyclopropylmethoxy)phenoxy)phenyl)-1,3-oxazol-5-yl)-3-hydroxypropanoate To a mixture of 2-(4-(3-(cyclopropylmethoxy)phenoxy) phenyl)-1,3-oxazole-5-carbaldehyde (3.3 g) and THF (30 ml) was added (2-tert-butoxy-2-oxoethyl) (chloro)zinc (0.5M diethyl ether solution, 78.8 ml) at 0° C. The mixture was stirred under nitrogen atmosphere at 26-36° C. for 15 hr. The reaction mixture was poured into saturated aqueous ammonium chloride solution, and extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (4.4 g).

$^1$H NMR (400 MHz, DMSO-d$_6$) δ 0.25-0.35 (2H, m), 0.50-0.60 (2H, m), 1.15-1.25 (1H, m), 1.37 (9H, s), 2.65-2.80 (2H, m), 3.80 (2H, d, J=6.8 Hz), 4.95-5.05 (1H, m), 5.84 (1H, d, J=5.6 Hz), 6.60-6.68 (2H, m), 6.77 (1H, d, J=10.0 Hz), 7.08-7.15 (3H, m), 7.31 (1H, t, J=8.0 Hz), 7.95 (2H, d, J=8.8 Hz).

F) 3-(2-(4-(3-(cyclopropylmethoxy)phenoxy)phenyl)-1,3-oxazol-5-yl)-3-hydroxypropanoic acid A mixture of tert-butyl 3-(2-(4-(3-(cyclopropylmethoxy) phenoxy)phenyl)-1,3-oxazol-5-yl)-3-hydroxypropanoate (3.5 g), sodium hydroxide (1.24 g), THF (12 ml), methanol (12 ml) and water (12 ml) was stirred at 28-34° C. for 15 hr. The reaction mixture was concentrated under reduced pressure. To the mixture was added water, and the mixture was acidified with 4N hydrochloric acid, and extracted with ethyl acetate. The obtained organic layer was washed with saturated brine, dried over anhydrous sodium sulfate, and concentrated under reduced pressure to give the title compound (3 g).

MS: [M+H]$^+$ 396.0.

G) 3-(2-(4-(3-(cyclopropylmethoxy)phenoxy)phenyl)-1,3-oxazol-5-yl)-3-hydroxy-N-methoxy-N-methylpropanamide A mixture of 3-(2-(4-(3-(cyclopropylmethoxy)phenoxy) phenyl)-1,3-oxazol-5-yl)-3-hydroxypropanoic acid (3 g), N,O-dimethylhydroxylamine hydrochloride (889 mg), WSCD (2.19 g), HOBt monohydrate (1.54 g), triethylamine (2.31 g) and DMF (30 ml) was stirred at 27-32° C. for 15 hr. The reaction mixture was poured into water, and extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (2.4 g).

$^1$H NMR (400 MHz, DMSO-d$_6$) δ 0.25-0.35 (2H, m), 0.50-0.60 (2H, m), 1.15-1.25 (1H, m), 2.80-3.00 (2H, m), 3.11 (3H, s), 3.68 (3H, s), 3.80 (2H, d, J=7.2 Hz), 5.08-5.15 (1H, m), 5.76 (1H, d, J=5.6 Hz), 6.60-6.68 (2H, m), 6.78 (1H, d, J=8.0 Hz), 7.08-7.15 (3H, m), 7.31 (1H, t, J=8.4 Hz), 7.95 (2H, d, J=8.8 Hz).

H) 4-(2-(4-(3-(cyclopropylmethoxy)phenoxy)phenyl)-1,3-oxazol-5-yl)-4-hydroxybutan-2-one To a mixture of 3-(2-(4-(3-(cyclopropylmethoxy)phenoxy)phenyl)-1,3-oxazol-5-yl)-3-hydroxy-N-methoxy-N-methylpropanamide (2.4 g) and THF (30 ml) was added methylmagnesium bromide (3M diethyl ether solution, 9.2 ml) at 0° C. The mixture was stirred under nitrogen atmosphere at 0° C. for 1 hr. To the reaction mixture was added saturated aqueous ammonium chloride solution, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (1.4 g).

$^1$H NMR (400 MHz, DMSO-d$_6$) δ 0.25-0.35 (2H, m), 0.50-0.60 (2H, m), 1.15-1.25 (1H, m), 2.16 (3H, s), 2.88-3.00 (2H, m), 3.80 (2H, d, J=7.2 Hz), 5.08-5.15 (1H, m), 5.73 (1H, d, J=5.6 Hz), 6.60-6.68 (2H, m), 6.78 (1H, d, J=8.4 Hz), 7.08-7.15 (3H, m), 7.31 (1H, t, J=8.4 Hz), 7.95 (2H, d, J=8.8 Hz).

I) N-(4-(2-(4-(3-(cyclopropylmethoxy)phenoxy)phenyl)-1,3-oxazol-5-yl)-4-hydroxybutan-2-yl)acetamide A mixture of 4-(2-(4-(3-(cyclopropylmethoxy)phenoxy)phenyl)-1,3-oxazol-5-yl)-4-hydroxybutan-2-one (300 mg), ammonium acetate (118 mg), sodium cyanoborohydride (96 mg) and methanol (10 ml) was stirred under heating with reflux for 15 hr. To the mixture was added acetic anhydride (156 mg), and the mixture was stirred at 28° C. for 2 hr. The reaction mixture was poured into water, and extracted with ethyl acetate. The obtained organic layer was washed with saturated brine, dried over anhydrous sodium sulfate, and concentrated under reduced pressure. The obtained residue was purified by HPLC (water/acetonitrile, addition of 0.1% ammonium hydrogencarbonate) to give the title compound (130 mg).

$^1$H NMR (400 MHz, DMSO-d$_6$) δ 0.25-0.35 (2H, m), 0.50-0.60 (2H, m), 1.00-1.10 (3H, m), 1.15-1.25 (1H, m), 1.73-1.79 (3H, m), 1.79-2.00 (2H, m), 3.80 (2H, d, J=7.2 Hz), 3.80-4.00 (1H, m), 4.60-4.70 (1H, m), 5.55-5.58 (1H, m), 6.60-6.68 (2H, m), 6.77 (1H, d, J=7.6 Hz), 7.08-7.15 (3H, m), 7.31 (1H, t, J=8.0 Hz), 7.73-7.78 (1H, m), 7.95 (2H, d, J=8.8 Hz).

J) N-(4-(2-(4-(3-(cyclopropylmethoxy)phenoxy)phenyl)-1,3-oxazol-5-yl)-4-oxobutan-2-yl)acetamide A mixture of N-(4-(2-(4-(3-(cyclopropylmethoxy)phenoxy)phenyl)-1,3-oxazol-5-yl)-4-hydroxybutan-2-yl)acetamide (130 mg), manganese dioxide (130 mg) and dichloromethane (10 ml) was stirred under heating with reflux for 15 hr. The reaction mixture was concentrated under reduced pressure. The obtained residue was purified by silica gel column chromatography (ethyl acetate) to give the title compound (90 mg).

$^1$H NMR (400 MHz, DMSO-d$_6$) δ 0.25-0.35 (2H, m), 0.50-0.60 (2H, m), 1.11 (3H, d, J=6.8 Hz), 1.15-1.25 (1H, m), 1.73 (3H, s), 2.85-3.05 (2H, m), 3.79 (2H, d, J=6.8 Hz), 4.15-4.25 (1H, m), 6.60-6.68 (2H, m), 6.79 (1H, d, J=7.6 Hz), 7.14 (2H, d, J=8.8 Hz), 7.33 (1H, t, J=8.4 Hz), 7.92 (1H, d, J=7.6 Hz), 8.07 (2H, d, J=8.8 Hz), 8.24 (1H, s).

Example 67

N-((2S)-1-((3-(4-(3-(cyclopropylmethoxy)phenoxy) phenyl)-1,2-oxazol-5-yl)oxy)propan-2-yl)acetamide A) 1-(4-(3-(cyclopropylmethoxy)phenoxy)phenyl) ethanone A mixture of 1-(4-fluorophenyl) ethanone (5 g), 3-(cyclopropylmethoxy)phenol (6.54 g), potassium carbonate (10 g) and DMF (50 ml) was stirred overnight at 60° C. To the mixture was added cesium carbonate (17.69 g), and the mixture was stirred at 90° C. for 2 hr. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (9.55 g).
$^1$H NMR (300 MHz, DMSO-$d_6$) δ 0.26-0.34 (2H, m), 0.51-0.60 (2H, m), 1.20 (1H, s), 2.54 (3H, s), 3.81 (2H, d, J=7.0 Hz), 6.60-6.69 (2H, m), 6.76-6.84 (1H, m), 7.01-7.09 (2H, m), 7.29-7.37 (1H, m), 7.95-8.01 (2H, m).

B) ethyl 3-(4-(3-(cyclopropylmethoxy)phenoxy) phenyl)-3-oxopropanoate

To a mixture of sodium hydride (60% in oil, 3.38 g) and THF (50 ml) was added diethyl carbonate (4.51 ml). The mixture was heated to 60° C., and a mixture of 1-(4-(3-(cyclopropylmethoxy)phenoxy)phenyl)ethanone (9.55 g) and THF (50 ml) was added dropwise thereto. The mixture was stirred overnight at 60° C. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (9.14 g).
$^1$H NMR (300 MHz, DMSO-$d_6$) δ 0.23-0.37 (2H, m), 0.47-0.61 (2H, m), 1.14-1.24 (4H, m), 3.81 (2H, d, J=7.0 Hz), 4.06-4.26 (4H, m), 6.58-6.72 (2H, m), 6.82 (1H, ddd, J=8.3, 2.3, 0.9 Hz), 6.99-7.12 (2H, m), 7.25-7.43 (1H, m), 7.91-8.13 (2H, m).

C) 3-(4-(3-(cyclopropylmethoxy)phenoxy)phenyl)-1,2-oxazol-5-ol

A mixture of ethyl 3-(4-(3-(cyclopropylmethoxy)phenoxy)phenyl)-3-oxopropanoate (9.14 g), hydroxylamine hydrochloride (2.33 g), triethylamine (5.39 ml) and ethanol (80 ml) was stirred overnight at 80° C. The mixture was allowed to cool to room temperature, and concentrated under reduced pressure. The obtained residue was extracted with ethyl acetate and 1N hydrochloric acid. The obtained organic layer was washed with saturated brine, dried over magnesium sulfate, and concentrated under reduced pressure. The obtained residue was purified by silica gel column chromatography (ethyl acetate/hexane) to give the title compound (6 g).
MS: [M+H]$^+$ 323.9.

D) tert-butyl ((2S)-1-((3-(4-(3-(cyclopropylmethoxy)phenoxy)phenyl)-1,2-oxazol-5-yl)oxy) propan-2-yl)carbamate A mixture of 3-(4-(3-(cyclopropylmethoxy)phenoxy)phenyl)-1,2-oxazol-5-ol (500 mg), tert-butyl ((2S)-1-hydroxypropan-2-yl)carbamate (325 mg), triphenylphosphine (608 mg), diisopropyl azodicarboxylate (1.9M toluene solution, 1.221 ml) and THF (5 ml) was stirred overnight at room temperature. The mixture was concentrated under reduced pressure. The obtained residue was purified by silica gel column chromatography (ethyl acetate/hexane) to give the title compound (350 mg).
$^1$H NMR (300 MHz, DMSO-$d_6$) δ 0.22-0.36 (2H, m), 0.45-0.62 (2H, m), 1.08-1.16 (3H, m), 1.21-1.26 (1H, m), 1.37 (9H, s), 3.80 (2H, d, J=6.9 Hz), 3.85-3.95 (1H, m), 4.15 (2H, d, J=5.3 Hz), 6.16 (1H, s), 6.55-6.67 (2H, m), 6.72-6.81 (1H, m), 6.98-7.05 (1H, m), 7.10 (2H, d, J=8.5 Hz), 7.30 (1H, t, J=7.5 Hz), 7.79 (2H, d, J=8.8 Hz).

E) N-((2S)-1-((3-(4-(3-(cyclopropylmethoxy)phenoxy)phenyl)-1,2-oxazol-5-yl)oxy)propan-2-yl)acetamide A mixture of tert-butyl ((2S)-1-((3-(4-(3-(cyclopropylmethoxy)phenoxy)phenyl)-1,2-oxazol-5-yl)oxy)propan-2-yl)carbamate (500 mg) and hydrogen chloride (4M ethyl acetate solution, 5 ml) was stirred at room temperature for 1 hr. The mixture was concentrated under reduced pressure. To the obtained residue were added pyridine (3 ml) and acetic anhydride (0.491 ml). The mixture was stirred at room temperature for 30 min, and concentrated under reduced pressure. The obtained residue was purified by silica gel column chromatography (NH, ethyl acetate/hexane), and then purified by silica gel column chromatography (ethyl acetate/hexane), and crystallized from hexane/ethyl acetate to give the title compound (36.7 mg).
$^1$H NMR (300 MHz, DMSO-$d_6$) δ 0.26-0.35 (2H, m), 0.51-0.60 (2H, m), 1.16 (3H, d, J=6.6 Hz), 1.18-1.25 (1H, m), 1.82 (3H, s), 3.80 (2H, d, J=7.0 Hz), 4.09-4.23 (3H, m), 6.18 (1H, s), 6.57-6.66 (2H, m), 6.72-6.80 (1H, m), 7.10 (2H, d, J=8.8 Hz), 7.30 (1H, t, J=8.2 Hz), 7.79 (2H, d, J=8.9 Hz), 8.03 (1H, d, J=6.8 Hz).

Example 68

N-(1-(6-((4-(3-(cyclopropylmethoxy)phenoxy)-2,6-difluorobenzyl)oxy)pyridin-3-yl)ethyl)acetamide A) (2,6-difluoro-4-iodophenyl)methanol To a mixture of 2,6-difluoro-4-iodobenzaldehyde (16 g) and methanol (200 ml) was added sodium borohydride (3.39 g) at 0° C. The mixture was stirred at 28° C. for 1 hr. The mixture was concentrated under reduced pressure. To the obtained residue was added water, and the mixture was extracted with ethyl acetate. The obtained organic layer was washed with saturated brine, dried over anhydrous sodium sulfate, and concentrated under reduced pressure to give the title compound (16 g).
$^1$H NMR (400 MHz, DMSO-$d_6$) δ 4.44 (2H, d, J=5.2 Hz), 5.29 (1H, t, J=5.2 Hz), 7.53 (2H, d, J=6.8 Hz).

B) methyl 6-((2,6-difluoro-4-iodobenzyl)oxy)nicotinate

To a mixture of (2,6-difluoro-4-iodophenyl)methanol (2 g) and THF (20 ml) was added sodium hydride (60% in oil, 296 mg) at 30° C. The mixture was stirred at 30° C. for 30 min, methyl 6-fluoronicotinate (1.38 g) was added thereto, and the mixture was stirred at 30° C. for 2 hr. To the mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether). To the obtained solid was added a mixed solvent of petroleum ether/ethyl acetate, and the mixture was filtered. The obtained solid was washed with petroleum ether to give the title compound (1.07 g).

$^1$H NMR (400 MHz, CDCl$_3$) δ 3.91 (3H, s), 5.45 (2H, s), 6.76 (1H, d, J=8.4 Hz), 7.32 (2H, d, J=6.4 Hz), 8.16 (1H, dd, J=8.8, 2.4 Hz), 8.85 (1H, d, J=2.4 Hz).

C) methyl 6-((4-(3-(cyclopropylmethoxy)phenoxy)-2,6-difluorobenzyl)oxy)nicotinate To a mixture of methyl 6-((2,6-difluoro-4-iodobenzyl)oxy)nicotinate (870 mg) and DMSO (15 ml) were added 3-(cyclopropylmethoxy)phenol (423 mg), tripotassium phosphate (912 mg), copper(I) iodide (99 mg) and pyridine-2-carboxylic acid (127 mg) at 30° C. The mixture was stirred under nitrogen atmosphere at 90° C. for 24 hr. The mixture was allowed to cool to room temperature, water was added thereto, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (600 mg).

$^1$H NMR (400 MHz, CDCl$_3$) δ 0.25-0.40 (2H, m), 0.55-0.73 (2H, m), 1.15-1.35 (1H, m), 3.78 (2H, d, J=7.2 Hz), 3.91 (3H, s), 5.43 (2H, s), 6.50-6.70 (4H, m), 6.71-6.80 (2H, m), 7.28 (1H, t, J=8.0 Hz), 8.16 (1H, dd, J=8.8, 2.4 Hz), 8.86 (1H, d, J=2.0 Hz).

D) 6-((4-(3-(cyclopropylmethoxy)phenoxy)-2,6-difluorobenzyl)oxy)nicotinic acid

To a mixture of methyl 6-((4-(3-(cyclopropylmethoxy)phenoxy)-2,6-difluorobenzyl)oxy)nicotinate (600 mg), THF (6 ml) and methanol (6 ml) was added a mixture of lithium hydroxide monohydrate (100 mg) and water (6 ml) at 30° C. The mixture was stirred at 26-32° C. for 12 hr. The mixture was concentrated under reduced pressure, and water was added thereto. The mixture was acidified with 1N hydrochloric acid, and extracted with ethyl acetate. The obtained organic layer was washed with saturated brine, dried over anhydrous sodium sulfate, and concentrated under reduced pressure to give the title compound (590 mg).

$^1$H NMR (400 MHz, DMSO-d$_6$) δ 0.20-0.40 (2H, m), 0.45-0.63 (2H, m), 1.10-1.33 (1H, m), 3.81 (2H, d, J=6.8 Hz), 5.40 (2H, s), 6.62-6.89 (5H, m), 6.93 (1H, d, J=8.8 Hz), 7.34 (1H, t, J=8.0 Hz), 8.16 (1H, dd, J=8.8, 2.4 Hz), 8.75 (1H, d, J=2.0 Hz), 13.11 (1H, brs).

E) 6-((4-(3-(cyclopropylmethoxy)phenoxy)-2,6-difluorobenzyl)oxy)-N-methoxy-N-methylnicotinamide To a mixture of 6-((4-(3-(cyclopropylmethoxy)phenoxy)-2,6-difluorobenzyl)oxy)nicotinic acid (590 mg) and DMF (10 ml) were added N,O-dimethylhydroxylamine hydrochloride (191 mg), WSCD (621 mg), HOBt monohydrate (437 mg) and triethylamine (663 mg) at 30° C. The mixture was stirred at 30° C. for 3 hr. To the mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (530 mg).

$^1$H NMR (400 MHz, CDCl$_3$) δ 0.25-0.40 (2H, m), 0.55-0.73 (2H, m), 1.15-1.35 (1H, m), 3.38 (3H, s), 3.59 (3H, s), 3.78 (2H, d, J=6.8 Hz), 5.42 (2H, s), 6.55 (2H, d, J=8.8 Hz), 6.57-6.70 (2H, m), 6.71-6.80 (2H, m), 7.20-7.35 (1H, m), 8.00 (1H, dd, J=8.8, 2.4 Hz), 8.66 (1H, d, J=2.0 Hz).

F) 1-(6-((4-(3-(cyclopropylmethoxy)phenoxy)-2,6-difluorobenzyl)oxy)pyridin-3-yl)ethanone To a mixture of 6-((4-(3-(cyclopropylmethoxy)phenoxy)-2,6-difluorobenzyl)oxy)-N-methoxy-N-methylnicotinamide (530 mg) and THF (10 ml) was added methylmagnesium bromide (3M diethyl ether solution, 2.7 ml) at 0° C. The mixture was stirred at 0° C. for 1 hr. To the mixture was added saturated aqueous ammonium chloride solution, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (470 mg).

$^1$H NMR (400 MHz, CDCl$_3$) δ 0.25-0.40 (2H, m), 0.55-0.73 (2H, m), 1.17-1.41 (1H, m), 2.58 (3H, s), 3.78 (2H, d, J=6.8 Hz), 5.45 (2H, s), 6.51-6.68 (4H, m), 6.70-6.85 (2H, m), 7.28 (1H, t, J=8.4 Hz), 8.15 (1H, dd, J=8.8, 2.4 Hz), 8.81 (1H, d, J=2.0 Hz).

G) N-(1-(6-((4-(3-(cyclopropylmethoxy)phenoxy)-2,6-difluorobenzyl)oxy)pyridin-3-yl)ethyl)acetamide To a mixture of 1-(6-((4-(3-(cyclopropylmethoxy)phenoxy)-2,6-difluorobenzyl)oxy)pyridin-3-yl)ethanone (270 mg) and methanol (15 ml) were added ammonium acetate (500 mg) and sodium cyanoborohydride (82 mg) at 30° C. The mixture was stirred under heating with reflux for 12 hr. The mixture was allowed to cool to room temperature, and acetic anhydride (204 mg) was added thereto at 30° C. The mixture was stirred at 30° C. for 2 hr. The mixture was concentrated under reduced pressure, water was added thereto, and the mixture was extracted with ethyl acetate. The obtained organic layer was washed with saturated brine, dried over anhydrous sodium sulfate, and concentrated under reduced pressure. The obtained residue was purified by HPLC (water/acetonitrile, addition of 0.1% aqueous ammonia) to give the title compound (137 mg).

$^1$H NMR (400 MHz, DMSO-d$_6$) δ 0.22-0.45 (2H, m), 0.47-0.60 (2H, m), 1.10-1.30 (1H, m), 1.33 (3H, d, J=6.8 Hz), 1.82 (3H, s), 3.81 (2H, d, J=7.2 Hz), 4.80-4.95 (1H, m), 5.28 (2H, s), 6.62-6.74 (2H, m), 6.75-6.85 (4H, m), 7.33 (1H, t, J=8.4 Hz), 7.64 (1H, dd, J=8.4, 2.4 Hz), 8.10 (1H, d, J=2.0 Hz), 8.31 (1H, d, J=7.6 Hz).

Example 69

N-(1-(5-((4-(3-(cyclopropylmethoxy)phenoxy)-2,6-difluorobenzyl)oxy)pyridin-2-yl)ethyl)acetamide A) methyl 5-((2,6-difluoro-4-iodobenzyl)oxy)pyridine-2-carboxylate To a mixture of (2,6-difluoro-4-iodophenyl)methanol (3 g) and THF (30 ml) was added sodium hydride (60% in oil, 444 mg) at 30° C. The mixture was stirred at 30° C. for 30 min, and methyl 5-fluoropyridine-2-carboxylate (2.06 g) was added thereto. The mixture was stirred at 30° C. for 2 hr. To the mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (2.4 g).

$^1$H NMR (400 MHz, CDCl$_3$) δ 3.98 (3H, s), 5.17 (2H, s), 7.30-7.45 (3H, m), 8.12 (1H, d, J=8.8 Hz), 8.43 (1H, d, J=2.8 Hz).

B) methyl 5-((4-(3-(cyclopropylmethoxy)phenoxy)-2,6-difluorobenzyl)oxy)pyridine-2-carboxylate To a mixture of methyl 5-((2,6-difluoro-4-iodobenzyl)oxy)pyridine-2-carboxylate (1 g) and DMSO (20 ml) were added 3-(cyclopropylmethoxy)phenol (485 mg), tripotassium phosphate (1.05 g), copper(I) iodide (113 mg) and pyridine-2-carboxylic acid (146 mg) at 30° C. The mixture was stirred at 100° C. for 12 hr. The mixture was allowed to cool to room temperature, water was added thereto, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (900 mg).

$^1$H NMR (400 MHz, CDCl$_3$) δ 0.25-0.43 (2H, m), 0.55-0.73 (2H, m), 1.15-1.35 (1H, m), 3.78 (2H, d, J=6.8 Hz), 3.98 (3H, s), 5.17 (2H, s), 6.49-6.70 (3H, m), 6.77 (1H, dd, J=8.4, 2.0 Hz), 7.20-7.31 (1H, m), 7.32-7.47 (2H, m), 8.13 (1H, d, J=8.4 Hz), 8.45 (1H, d, J=2.8 Hz).

C) 5-((4-(3-(cyclopropylmethoxy)phenoxy)-2,6-difluorobenzyl)oxy)pyridine-2-carboxylic acid To a mixture of methyl 5-((4-(3-(cyclopropylmethoxy)phenoxy)-2,6-difluorobenzyl)oxy)pyridine-2-carboxylate (900 mg), THF (6 ml) and methanol (6 ml) was added a mixture of lithium hydroxide monohydrate (200 mg) and water (6 ml) at 30° C. The mixture was stirred at 30° C. for 2 hr. The mixture was concentrated under reduced pressure, and water was added thereto. The mixture was acidified with 1N hydrochloric acid, and extracted with ethyl acetate. The obtained organic layer was washed with saturated brine, dried over anhydrous sodium sulfate, and concentrated under reduced pressure to give the title compound (760 mg).

$^1$H NMR (400 MHz, DMSO-d$_6$) δ 0.20-0.40 (2H, m), 0.41-0.65 (2H, m), 1.10-1.40 (1H, m), 3.82 (2H, d, J=7.2 Hz), 5.24 (2H, s), 6.60-6.90 (4H, m), 7.25-7.40 (1H, m), 7.50-7.75 (2H, m), 8.05 (1H, d, J=8.8 Hz), 8.43 (1H, d, J=2.4 Hz), 12.86 (1H, brs).

D) 5-((4-(3-(cyclopropylmethoxy)phenoxy)-2,6-difluorobenzyl)oxy)-N-methoxy-N-methylpyridine-2-carboxamide To a mixture of 5-((4-(3-(cyclopropylmethoxy)phenoxy)-2,6-difluorobenzyl)oxy)pyridine-2-carboxylic acid (760 mg) and DMF (10 ml) were added N,O-dimethylhydroxylamine hydrochloride (250 mg), WSCD (807 mg), HOBt monohydrate (568 mg) and triethylamine (850 mg) at 30° C. The mixture was stirred at 30° C. for 3 hr. To the mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (780 mg).

$^1$H NMR (400 MHz, CDCl$_3$) δ 0.23-0.40 (2H, m), 0.55-0.70 (2H, m), 1.15-1.35 (1H, m), 3.42 (3H, s), 3.69-3.75 (5H, m), 5.14 (2H, s), 6.56 (2H, d, J=8.8 Hz), 6.60-6.82 (2H, m), 7.15-7.45 (3H, m), 7.74 (1H, d, J=8.4 Hz), 8.34 (1H, d, J=2.8 Hz).

E) 1-(5-((4-(3-(cyclopropylmethoxy)phenoxy)-2,6-difluorobenzyl)oxy)pyridin-2-yl)ethanone To a mixture of 5-((4-(3-(cyclopropylmethoxy)phenoxy)-2,6-difluorobenzyl)oxy)-N-methoxy-N-methylpyridine-2-carboxamide (780 mg) and THF (10 ml) was added methylmagnesium bromide (3M diethyl ether solution, 2.7 ml) at 0° C. The mixture was stirred at 0° C. for 1 hr. To the mixture was added saturated aqueous ammonium chloride solution, and the mixture was extracted with ethyl acetate. The obtained organic layer was washed with saturated brine, dried over anhydrous sodium sulfate, and concentrated under reduced pressure to give the title compound (450 mg).

MS: [M+H]$^+$ 426.0.

F) N-(1-(5-((4-(3-(cyclopropylmethoxy)phenoxy)-2,6-difluorobenzyl)oxy)pyridin-2-yl)ethyl)acetamide To a mixture of 1-(5-((4-(3-(cyclopropylmethoxy)phenoxy)-2,6-difluorobenzyl)oxy)pyridin-2-yl)ethanone (300 mg) and methanol (15 ml) were added ammonium acetate (550 mg) and sodium cyanoborohydride (90 mg) at 30° C. The mixture was stirred under heating with reflux for 12 hr. The mixture was allowed to cool to room temperature, and acetic anhydride (204 mg) was added thereto at 30° C. The mixture was stirred at 30° C. for 1 hr. The mixture was concentrated under reduced pressure, water was added thereto, and the mixture was extracted with ethyl acetate. The obtained organic layer was washed with saturated brine, dried over anhydrous sodium sulfate, and concentrated under reduced pressure. The obtained residue was purified by HPLC (water/acetonitrile, addition of 0.1% aqueous ammonia). The obtained solid was dissolved in ethyl acetate, and the solution was washed successively with saturated aqueous sodium carbonate solution and saturated brine, dried over anhydrous sodium sulfate, and concentrated under reduced pressure. The obtained residue was purified by silica gel column chromatography (ethyl acetate) to give the title compound (69 mg).

$^1$H NMR (400 MHz, DMSO-d$_6$) δ 0.20-0.36 (2H, m), 0.45-0.60 (2H, m), 1.10-1.30 (1H, m), 1.32 (3H, d, J=6.8 Hz), 1.84 (3H, s), 3.80 (2H, d, J=6.8 Hz), 4.80-4.99 (1H, m), 5.11 (2H, s), 6.65-6.71 (2H, m), 6.72-6.89 (3H, m), 7.25-7.40 (2H, m), 7.49 (1H, dd, J=8.4, 2.8 Hz), 8.27 (1H, d, J=2.8 Hz), 8.32 (1H, d, J=8.0 Hz).

Example 73

N-(1-(6-((4-(3-(cyclopropylmethoxy)phenoxy)-2,6-difluorobenzyl)oxy)-5-fluoropyridin-3-yl)ethyl)acetamide A) 5-bromo-2-((4-(3-(cyclopropylmethoxy)phenoxy)-2,6-difluorobenzyl)oxy)-3-fluoropyridine To a mixture of (4-(3-(cyclopropylmethoxy)phenoxy)-2,6-difluorophenyl)methanol (800 mg) and THF (10 ml) was added sodium hydride (60% in oil, 125 mg). The mixture was stirred at 25° C. for 30 min. To the mixture was added 5-bromo-2,3-difluoropyridine (507 mg), and the mixture was stirred at 25° C. for 2 hr. To the mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (780 mg).

$^1$H NMR (400 MHz, CDCl$_3$) δ 0.24-0.40 (2H, m), 0.57-0.63 (2H, m), 1.17-1.35 (1H, m), 3.79 (2H, d, J=6.8 Hz), 5.42 (2H, s), 6.55 (2H, d, J=8.8 Hz), 6.56-6.70 (2H, m), 6.76 (1H, dd, J=8.4, 2.4 Hz), 7.28 (1H, t, J=8.4 Hz), 7.49 (1H, dd, J=9.2, 2.0 Hz), 8.02 (1H, d, J=2.0 Hz).

B) 1-(6-((4-(3-(cyclopropylmethoxy)phenoxy)-2,6-difluorobenzyl)oxy)-5-fluoropyridin-3-yl)ethanone To a mixture of 5-bromo-2-((4-(3-(cyclopropylmethoxy)phenoxy)-2,6-difluorobenzyl)oxy)-3-fluoropyridine (480 mg) and DMF (3 ml) were added tributyl(1-ethoxyvinyl)stannane (397 mg) and bis(triphenylphosphine)dichloropalladium (14 mg), and the mixture was stirred at 70° C. for 2 hr. The mixture was allowed to cool to room temperature, saturated aqueous potassium fluoride solution was added thereto, and the mixture was stirred at 25° C. for 30 min, and extracted with ethyl acetate. The obtained organic layer was washed with saturated brine, dried over anhydrous sodium sulfate, and concentrated under reduced pressure. To a mixture of the obtained residue and acetone (50 ml) was added 1N hydrochloric acid (30 ml) at 25° C., and the mixture was stirred at 25° C. for 1 hr. The mixture was basified with 1N aqueous sodium hydroxide solution, and extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (440 mg).

$^1$H NMR (400 MHz, CDCl$_3$) δ 0.28-0.40 (2H, m), 0.57-0.61 (2H, m), 1.15-1.40 (1H, m), 2.59 (3H, s), 3.78 (2H, d, J=6.8 Hz), 5.52 (2H, s), 6.55 (2H, d, J=8.4 Hz), 6.57-6.70 (2H, m), 6.76 (1H, dd, J=8.0, 2.0 Hz), 7.28 (1H, t, J=8.4 Hz), 7.88 (1H, dd, J=10.4, 2.0 Hz), 8.57 (1H, d, J=2.0 Hz).

C) N-(1-(6-((4-(3-(cyclopropylmethoxy)phenoxy)-2,6-difluorobenzyl)oxy)-5-fluoropyridin-3-yl)ethyl)acetamide To a mixture of 1-(6-((4-(3-(cyclopropylmethoxy)phenoxy)-2,6-difluorobenzyl)oxy)-5-fluoropyridin-3-yl)ethanone (300 mg) and methanol (30 ml) were added ammonium acetate (580 mg) and sodium cyanoborohydride (90 mg). The mixture was stirred under heating with reflux for 12 hr. The mixture was allowed to cool to room temperature, and acetic anhydride (204 mg) was added thereto. The mixture was stirred at 25° C. for 2 hr. The mixture was concentrated under reduced pressure, to the obtained residue was added water, and the mixture was extracted with ethyl acetate. The obtained organic layer was washed with saturated brine, dried over anhydrous sodium sulfate, and concentrated under reduced pressure. The obtained residue was purified by HPLC (water/acetonitrile, addition of 0.1% ammonium hydrogencarbonate) to give the title compound (117 mg).

$^1$H NMR (400 MHz, DMSO-d$_6$) δ 0.25-0.40 (2H, m), 0.47-0.60 (2H, m), 1.10-1.30 (1H, m), 1.34 (3H, d, J=6.8 Hz), 1.83 (3H, s), 3.81 (2H, d, J=7.2 Hz), 4.80-4.97 (1H, m), 5.38 (2H, s), 6.65-6.72 (2H, m), 6.73-6.83 (3H, m), 7.33 (1H, t, J=8.0 Hz), 7.63 (1H, dd, J=11.6, 1.6 Hz), 7.94 (1H, d, J=1.6 Hz), 8.31 (1H, d, J=7.6 Hz).

Example 78

N-(1-(6-((4-(3-(cyclopropylmethoxy)phenoxy)-2,6-difluorobenzyl)oxy)pyridazin-3-yl)ethyl)acetamide A) (4-(3-(cyclopropylmethoxy)phenoxy)-2,6-difluorophenyl)methanol A mixture of (2,6-difluoro-4-iodophenyl)methanol (6 g), 3-(cyclopropylmethoxy)phenol (3.65 g), copper(I) iodide (423 mg), pyridine-2-carboxylic acid (546 mg), tripotassium phosphate (9.41 g) and DMSO (60 ml) was stirred under nitrogen atmosphere at 90° C. for 15 hr. The reaction mixture was poured into water, and extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (3.7 g).

$^1$H NMR (400 MHz, DMSO-d$_6$) δ 0.25-0.35 (2H, m), 0.50-0.60 (2H, m), 1.15-1.25 (1H, m), 3.80 (2H, d, J=6.8 Hz), 4.44 (2H, d, J=5.6 Hz), 5.20 (1H, t, J=5.6 Hz), 6.60-6.68 (2H, m), 6.71 (2H, d, J=8.8 Hz), 6.80 (1H, d, J=7.6 Hz), 7.32 (1H, t, J=8.0 Hz).

B) 3-bromo-6-((4-(3-(cyclopropylmethoxy)phenoxy)-2,6-difluorobenzyl)oxy)pyridazine To a mixture of (4-(3-(cyclopropylmethoxy)phenoxy)-2,6-difluorophenyl)methanol (500 mg) and THF (10 ml) was added sodium hydride (60% in oil, 65 mg), and the mixture was stirred at 15° C. for 30 min. To the mixture was added 3,6-dibromopyridazine (388 mg), and the mixture was stirred at 18° C. for 4 hr. The reaction mixture was poured into water, and extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (570 mg).

$^1$H NMR (400 MHz, DMSO-d$_6$) δ 0.25-0.35 (2H, m), 0.50-0.60 (2H, m), 1.15-1.25 (1H, m), 3.81 (2H, d, J=7.2 Hz), 5.47 (2H, s), 6.65-6.73 (2H, m), 6.75-6.85 (3H, m), 7.28 (1H, d, J=9.2 Hz), 7.34 (1H, t, J=8.0 Hz), 7.91 (1H, d, J=9.2 Hz).

C) 1-(6-((4-(3-(cyclopropylmethoxy)phenoxy)-2,6-difluorobenzyl)oxy)pyridazin-3-yl) ethanone A mixture of 3-bromo-6-((4-(3-(cyclopropylmethoxy)phenoxy)-2,6-difluorobenzyl)oxy)pyridazine (570 mg), tributyl(1-ethoxyvinyl)stannane (535 mg), bis(triphenylphosphine)dichloropalladium (18 mg) and DMF (15 ml) was stirred under nitrogen atmosphere at 80° C. for 15 hr. To the mixture was added saturated aqueous potassium fluoride solution, and the mixture was stirred at 20° C. for 1 hr. The reaction mixture was poured into water, and extracted with ethyl acetate. The obtained organic layer was washed with saturated brine, dried over anhydrous sodium sulfate, and concentrated under reduced pressure. To the obtained residue were added 1N hydrochloric acid (20 ml) and acetone (20 ml), and the mixture was stirred at 20° C. for 1 hr. The mixture was neutralized with saturated aqueous sodium hydrogencarbonate solution, and extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (300 mg).

$^1$H NMR (400 MHz, DMSO-$d_6$) δ 0.25-0.35 (2H, m), 0.50-0.60 (2H, m), 1.15-1.25 (1H, m), 2.72 (3H, s), 3.81 (2H, d, J=6.8 Hz), 5.63 (2H, s), 6.65-6.73 (2H, m), 6.75-6.85 (3H, m), 7.30-7.41 (2H, m), 8.05 (1H, d, J=8.8 Hz).

D) 1-(6-((4-(3-(cyclopropylmethoxy)phenoxy)-2,6-difluorobenzyl)oxy)pyridazin-3-yl)ethanol To a mixture of 1-(6-((4-(3-(cyclopropylmethoxy)phenoxy)-2,6-difluorobenzyl)oxy)pyridazin-3-yl)ethanone (300 mg) and methanol (10 ml) was added sodium borohydride (53 mg), and the mixture was stirred at 20° C. for 30 min. The mixture was poured into water, and extracted with ethyl acetate. The obtained organic layer was washed with saturated brine, dried over anhydrous sodium sulfate, and concentrated under reduced pressure to give the title compound (280 mg).

$^1$H NMR (400 MHz, DMSO-$d_6$) δ 0.25-0.35 (2H, m), 0.50-0.60 (2H, m), 1.15-1.25 (1H, m), 1.40 (3H, d, J=6.8 Hz), 3.82 (2H, d, J=7.2 Hz), 4.85-4.95 (1H, m), 5.48 (2H, s), 5.55 (1H, d, J=4.8 Hz), 6.65-6.73 (2H, m), 6.75-6.88 (3H, m), 7.24 (1H, d, J=9.2 Hz), 7.34 (1H, t, J=8.0 Hz), 7.70 (1H, d, J=8.8 Hz).

E) 3-(1-azidoethyl)-6-((4-(3-(cyclopropylmethoxy)phenoxy)-2,6-difluorobenzyl)oxy)pyridazine To a mixture of 1-(6-((4-(3-(cyclopropylmethoxy)phenoxy)-2,6-difluorobenzyl)oxy)pyridazin-3-yl)ethanol (280 mg), triethylamine (198 mg) and dichloromethane (10 ml) was added methanesulfonyl chloride (150 mg) at 0° C. The mixture was stirred at 20° C. for 1 hr. The reaction mixture was poured into water, and extracted with dichloromethane. The obtained organic layer was washed with water, dried over anhydrous sodium sulfate, and concentrated under reduced pressure. To a mixture of the obtained residue and DMF (10 ml) was added sodium azide (213 mg), and the mixture was stirred at 60° C. for 2 hr. The reaction mixture was poured into water, and extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (230 mg).

$^1$H NMR (400 MHz, DMSO-$d_6$) δ 0.25-0.35 (2H, m), 0.50-0.60 (2H, m), 1.15-1.25 (1H, m), 1.57 (3H, d, J=6.8 Hz), 3.81 (2H, d, J=7.2 Hz), 4.94-5.00 (1H, m), 5.51 (2H, s), 6.65-6.73 (2H, m), 6.78-6.88 (3H, m), 7.30-7.29 (2H, m), 7.74 (1H, d, J=9.2 Hz).

F) N-(1-(6-((4-(3-(cyclopropylmethoxy)phenoxy)-2,6-difluorobenzyl)oxy)pyridazin-3-yl)ethyl)acetamide A mixture of 3-(1-azidoethyl)-6-((4-(3-(cyclopropylmethoxy)phenoxy)-2,6-difluorobenzyl)oxy)pyridazine (230 mg), triphenylphosphine (200 mg), THF (10 ml) and water (1 ml) was stirred under heating with reflux for 15 hr. To the reaction mixture was added acetic anhydride (104 mg), and the mixture was stirred at 20° C. for 1 hr. The reaction mixture was poured into water, and extracted with ethyl acetate. The obtained organic layer was washed with saturated brine, dried over anhydrous sodium sulfate, and concentrated under reduced pressure. The obtained residue was purified by HPLC (water/acetonitrile, addition of 0.1% ammonium hydrogencarbonate) to give the title compound (123 mg).

$^1$H NMR (400 MHz, DMSO-$d_6$) δ 0.25-0.35 (2H, m), 0.50-0.60 (2H, m), 1.15-1.25 (1H, m), 1.41 (3H, d, J=7.2 Hz), 1.85 (3H, s), 3.81 (2H, d, J=6.8 Hz), 5.02-5.11 (1H, m), 5.48 (2H, s), 6.65-6.73 (2H, m), 6.75-6.86 (3H, m), 7.21 (1H, d, J=9.2 Hz), 7.34 (1H, t, J=8.0 Hz), 7.56 (1H, d, J=8.8 Hz), 8.42 (1H, d, J=8.0 Hz).

Example 82

1-((2S)-1-((2-(4-(3-(cyclopropylmethoxy)phenoxy)phenyl)-1,3-oxazol-5-yl)oxy)propan-2-yl)urea A mixture of tert-butyl ((2S)-1-((2-(4-(3-(cyclopropylmethoxy)phenoxy)phenyl)-1,3-oxazol-5-yl)oxy)propan-2-yl)carbamate (28 g) and formic acid (150 ml) was stirred at 40° C. for 30 min. The mixture was allowed to cool to room temperature, and concentrated under reduced pressure. The obtained residue was extracted with ethyl acetate and saturated aqueous sodium hydrogencarbonate solution. The obtained organic layer was washed with saturated brine, dried over magnesium sulfate, and concentrated under reduced pressure. To the obtained residue was added THF (200 ml), and triethylamine (13 ml) and 4-nitrophenyl chlorocarbonate (15 g) were added thereto. The mixture was stirred at 0° C. for 1 hr, and 28% aqueous ammonia (50 ml) was added thereto. The mixture was stirred at room temperature for 30 min, and extracted with ethyl acetate. The obtained organic layer was washed with saturated brine, dried over anhydrous magnesium sulfate, and concentrated under reduced pressure. The obtained residue was purified by silica gel column chromatography (NH, ethyl acetate/hexane), and crystallized from hexane/ethyl acetate to give the title compound (10 g).

$^1$H NMR (300 MHz, DMSO-$d_6$) δ 0.24-0.37 (2H, m), 0.50-0.59 (2H, m), 1.14 (3H, d, J=6.7 Hz), 1.18 (1H, d, J=5.8 Hz), 3.80 (2H, d, J=7.0 Hz), 3.90-4.10 (3H, m), 5.49 (2H, s), 6.10 (1H, d, J=7.6 Hz), 6.45 (1H, s), 6.56-6.67 (2H, m), 6.72-6.81 (1H, m), 7.01-7.11 (2H, m), 7.31 (1H, t, J=8.3 Hz), 7.79-7.88 (2H, m).

Example 83

N-(4-(2-(4-(3-(cyclopropylmethoxy)phenoxy)phenyl)-1,3-oxazol-4-yl)butan-2-yl)acetamide A)
4-(3-(cyclopropylmethoxy)phenoxy)benzaldehyde A mixture of 3-(cyclopropylmethoxy)phenol (1.5 g), 4-fluorobenzaldehyde (1 g), cesium carbonate (5 g) and DMF (15 ml) was stirred overnight at 80° C. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (2.12 g).

$^1$H NMR (300 MHz, DMSO-$d_6$) δ 0.26-0.34 (2H, m), 0.51-0.60 (2H, m), 1.20-1.25 (1H, m), 3.81 (2H, d, J=7.1

Hz), 6.63-6.72 (2H, m), 6.79-6.86 (1H, m), 7.09-7.16 (2H, m), 7.30-7.39 (1H, m), 7.88-7.96 (2H, m), 9.92 (1H, s).

B) methyl 2-(4-(3-(cyclopropylmethoxy)phenoxy)phenyl)-1,3-oxazole-4-carboxylate

A mixture of 4-(3-(cyclopropylmethoxy)phenoxy)benzaldehyde (2.12 g), methyl L-serinate hydrochloride (1.3 g), tripotassium phosphate (3.4 g) and DMA (20 ml) was stirred overnight at room temperature. To the mixture were added bromotrichloromethane (4.7 g) and DBU (3.6 ml). The reaction mixture was stirred overnight at room temperature. The mixture was extracted with ethyl acetate and water. The obtained organic layer was washed with saturated brine, dried over magnesium sulfate, and concentrated under reduced pressure. The obtained residue was purified by silica gel column chromatography (NH, ethyl acetate/hexane) to give the title compound (1.88 g).
$^1$H NMR (300 MHz, DMSO-$d_6$) δ 0.25-0.34 (2H, m), 0.50-0.60 (2H, m), 1.19-1.26 (1H, m), 3.81 (2H, d, J=7.0 Hz), 3.84 (3H, s), 6.63-6.70 (2H, m), 6.76-6.84 (1H, m), 7.08-7.18 (2H, m), 7.33 (1H, t, J=8.3 Hz), 7.97-8.05 (2H, m), 8.94 (1H, s).

C) ethyl (2E)-3-(2-(4-(3-(cyclopropylmethoxy)phenoxy)phenyl)-1,3-oxazol-4-yl) acrylate To a mixture of lithium aluminium hydride (0.293 g) and THF (10 ml) was added dropwise a mixture of methyl 2-(4-(3-(cyclopropylmethoxy)phenoxy)phenyl)-1,3-oxazole-4-carboxylate (1.88 g) and THF (10 ml) under ice-cooling. The mixture was stirred at 0° C. for 30 min, and water (0.3 ml) and 1N aqueous sodium hydroxide solution (0.3 ml) were successively added thereto. To the mixture was added water (0.9 ml), and the mixture was stirred at room temperature for 30 min. The mixture was filtered through Celite, and the filtrate was concentrated under reduced pressure. To the obtained residue were added acetonitrile (10 ml), molecular sieve 4A (3 g), tetrapropyl perruthenate (200 mg) and N-methylmorpholine N-oxide (1 g). The mixture was stirred at room temperature for 1 hr. The mixture was passed through silica gel short column (ethyl acetate/hexane), and concentrated under reduced pressure. The obtained residue was added to a mixture of ethyl (diethoxyphosphoryl)acetate (1.5 ml), sodium hydride (60% in oil, 0.5 g) and THF (10 ml) at 0° C. The mixture was stirred at room temperature for 1 hr, and extracted with saturated aqueous ammonium chloride solution and ethyl acetate. The obtained organic layer was washed with saturated brine, dried over magnesium sulfate, and concentrated under reduced pressure. The obtained residue was purified by silica gel column chromatography (NH, ethyl acetate/hexane) to give the title compound (0.536 g).
$^1$H NMR (300 MHz, DMSO-$d_6$) δ 0.26-0.34 (2H, m), 0.51-0.60 (2H, m), 1.18-1.22 (1H, m), 1.26 (3H, t, J=7.1 Hz), 3.81 (2H, d, J=7.0 Hz), 4.19 (2H, q, J=7.1 Hz), 6.53 (1H, dd, J=15.7, 0.6 Hz), 6.62-6.70 (2H, m), 6.76-6.83 (1H, m), 7.14 (2H, d, J=9.0 Hz), 7.33 (1H, t, J=7.9 Hz), 7.58 (1H, d, J=15.3 Hz), 8.02 (2H, d, J=8.9 Hz), 8.53 (1H, s).

D) 3-(2-(4-(3-(cyclopropylmethoxy)phenoxy)phenyl)-1,3-oxazol-4-yl)-N-methoxy-N-methylpropanamide A mixture of copper(I) chloride (13 mg), 1,1'-bis(triphenylphosphine)binaphthyl (82 mg), sodium tert-butoxide (13 mg) and toluene (3 ml) was stirred at room temperature for 10 min. To the mixture was added a mixture of ethyl (2E)-3-(2-(4-(3-(cyclopropylmethoxy)phenoxy)phenyl)-1,3-oxazol-4-yl)acrylate (536 mg), tert-butanol (490 mg), polymethylhydrosiloxane (0.24 ml) and toluene (30 ml). The reaction mixture was stirred at room temperature for 2 hr. The mixture was extracted with toluene and water. The obtained organic layer was washed with saturated brine, dried over magnesium sulfate, and concentrated under reduced pressure. The obtained residue was purified by silica gel column chromatography (ethyl acetate/hexane). To the obtained residue were added 1N aqueous sodium hydroxide solution (6 ml), THF (3 ml) and methanol (3 ml). The mixture was stirred at room temperature for 2 hr, acidified with 1N hydrochloric acid, and extracted with ethyl acetate. The obtained organic layer was washed with saturated brine, dried over magnesium sulfate, and concentrated under reduced pressure. To the obtained residue were added DMF (3 ml), N,O-dimethylhydroxylamine hydrochloride (258 mg), WSCD (506 mg), HOBt monohydrate (404 m) and triethylamine (0.736 ml). The mixture was stirred overnight at room temperature. The mixture was extracted with water and ethyl acetate. The obtained organic layer was washed with saturated brine, dried over magnesium sulfate, and concentrated under reduced pressure. The obtained residue was purified by silica gel column chromatography (NH, ethyl acetate/hexane) to give the title compound (298 mg).
$^1$H NMR (300 MHz, DMSO-$d_6$) δ 0.26-0.34 (2H, m), 0.50-0.60 (2H, m), 1.18-1.26 (1H, m), 2.75 (4H, s), 3.10 (3H, s), 3.67 (3H, s), 3.80 (2H, d, J=7.0 Hz), 6.60-6.68 (2H, m), 6.74-6.81 (1H, m), 7.10 (2H, d, J=8.9 Hz), 7.32 (1H, t, J=8.3 Hz), 7.89 (1H, s), 7.94 (2H, d, J=6.9 Hz).

E) 4-(2-(4-(3-(cyclopropylmethoxy)phenoxy)phenyl)-1,3-oxazol-4-yl)butan-2-yl methanesulfonate To a mixture of 3-(2-(4-(3-(cyclopropylmethoxy)phenoxy)phenyl)-1,3-oxazol-4-yl)-N-methoxy-N-methylpropanamide (298 mg) and THF (3 ml) was added methylmagnesium bromide (1M THF solution, 1.4 ml) under ice-cooling. The mixture was stirred at 0° C. for 30 min, and extracted with ethyl acetate and saturated aqueous ammonium chloride solution. The obtained organic layer was washed with saturated brine, dried over magnesium sulfate, and concentrated under reduced pressure. To the obtained residue were added THF (3 ml) and ethanol (3 ml). To the mixture was added sodium borohydride (60 mg) at 0° C. The mixture was stirred at 0° C. for 30 min, and extracted with ethyl acetate and 1N hydrochloric acid. The obtained organic layer was washed with saturated brine, dried over magnesium sulfate, and concentrated under reduced pressure. To the obtained residue were added THF (3 ml), triethylamine (0.2 ml) and methanesulfonyl chloride (0.1 ml). The mixture was stirred at room temperature for 1 hr, and extracted with ethyl acetate and saturated aqueous sodium hydrogencarbonate solution. The obtained organic layer was washed with saturated brine, dried over magnesium sulfate, and concentrated under reduced pressure. The obtained residue was purified by silica gel column chromatography (ethyl acetate/hexane) to give the title compound (137 mg).
$^1$H NMR (300 MHz, DMSO-$d_6$) δ 0.26-0.35 (2H, m), 0.51-0.60 (2H, m), 1.19-1.25 (1H, m), 1.39 (3H, d, J=6.2 Hz), 1.90-1.99 (2H, m), 2.57-2.70 (2H, m), 3.20 (3H, s), 3.80 (2H, d, J=7.0 Hz), 4.74-4.88 (1H, m), 6.60-6.68 (2H, m), 6.74-6.81 (1H, m), 7.10 (2H, d, J=8.9 Hz), 7.32 (1H, t, J=8.3 Hz), 7.90-7.98 (3H, m).

F) N-(4-(2-(4-(3-(cyclopropylmethoxy)phenoxy)phenyl)-1,3-oxazol-4-yl)butan-2-yl)acetamide A mixture of 4-(2-(4-(3-(cyclopropylmethoxy)phenoxy)phenyl)-1,3-oxazol-4-yl)butan-2-yl methanesulfonate (137 mg), sodium azide (40 mg) and DMF (3 ml) was stirred at 60° C. for 2 hr. The mixture was allowed to cool to room temperature, and extracted with ethyl acetate and water. The obtained organic layer was washed with saturated brine, dried over magnesium sulfate, and concentrated under reduced pressure. To the obtained residue were added THF (4 ml), water (2 ml) and triphenylphosphine (160 mg). The mixture was stirred at 60° C. for 1 hr. The mixture was allowed to cool to room temperature, and extracted with ethyl acetate and water. The obtained organic layer was washed with saturated brine, dried over magnesium sulfate, and concentrated under reduced pressure. To the obtained residue were added pyridine (2 ml) and acetic anhydride (0.15 ml). The mixture was stirred at room temperature for 30 min. The mixture was concentrated under reduced pressure. The obtained residue was purified by silica gel column chromatography (NH, ethyl acetate/hexane) to give the title compound (50 mg).
$^1$H NMR (300 MHz, DMSO-$d_6$) δ 0.26-0.35 (2H, m), 0.50-0.61 (2H, m), 1.06 (3H, d, J=6.6 Hz), 1.20-1.27 (1H, m), 1.64-1.75 (2H, m), 1.80 (3H, s), 2.43-2.49 (2H, m), 3.75-3.86 (3H, m), 6.60-6.67 (2H, m), 6.74-6.81 (1H, m), 7.10 (2H, d, J=8.9 Hz), 7.32 (1H, t, J=7.8 Hz), 7.74 (1H, d, J=8.1 Hz), 7.88 (1H, s), 7.94 (2H, d, J=9.0 Hz).

Example 89

N-(4-(3-(4-(3-(cyclopropylmethoxy)phenoxy)phenyl)pyrrolidin-1-yl)-4-oxobutan-2-yl)acetamide A)
4-(3-(cyclopropylmethoxy)phenoxy)benzaldehyde To a mixture of 3-(cyclopropylmethoxy)phenol (27.1 g), 4-fluorobenzaldehyde (20.5 g) and DMF (200 ml) was added cesium carbonate (108 g). The mixture was stirred at 80-85° C. for 16 hr. The mixture was allowed to cool to room temperature, water was added thereto, and the mixture was extracted with ethyl acetate. The obtained organic layer was washed successively with water and saturated brine, dried over anhydrous sodium sulfate, and concentrated under reduced pressure. The obtained residue was purified by silica gel column chromatography (ethyl acetate/petroleum ether) to give the title compound (28.1 g).
$^1$H NMR (400 MHz, CDCl$_3$) δ 0.30-0.36 (2H, m), 0.60-0.66 (2H, m), 1.19-1.27 (1H, m), 3.78 (2H, d, J=6.8 Hz), 6.57-6.66 (2H, m), 6.76 (1H, d, J=8.4 Hz), 7.07 (2H, d, J=8.4 Hz), 7.28 (1H, t, J=8.4 Hz), 7.84 (2H, d, J=8.8 Hz), 9.92 (1H, brs).

B) ethyl (2E)-3-(4-(3-(cyclopropylmethoxy)phenoxy)phenyl) acrylate

To a mixture of ethyl (diethoxyphosphoryl)acetate (26.5 g) and THF (300 ml) was added sodium hydride (60% in oil, 4.72 g) at 0° C., and the mixture was stirred at 0° C. for 1 hr. To the mixture was added 4-(3-(cyclopropylmethoxy)phenoxy)benzaldehyde (31.7 g), and the mixture was stirred at 19° C. for 2 hr. To the mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (34.7 g).
$^1$H NMR (400 MHz, CDCl$_3$) δ 0.31-0.37 (2H, m), 0.60-0.68 (2H, m), 1.20-1.27 (1H, m), 1.33 (3H, t, J=7.2 Hz), 3.76 (2H, d, J=6.8 Hz), 4.26 (2H, q, J=7.2 Hz), 6.34 (1H, d, J=16.0 Hz), 6.57-6.62 (2H, m), 6.70 (1H, d, J=8.0 Hz), 6.99 (2H, d, J=8.4 Hz), 7.24 (1H, t, J=8.0 Hz), 7.48 (2H, d, J=8.4 Hz), 7.65 (1H, d, J=16.4 Hz).

C) ethyl 3-(4-(3-(cyclopropylmethoxy)phenoxy)phenyl)-4-nitrobutanoate

To a mixture of ethyl (2E)-3-(4-(3-(cyclopropylmethoxy)phenoxy)phenyl)acrylate (29.7 g) and nitromethane (200 mL) was added dropwise DBU (80.2 g). The mixture was stirred at 11-14° C. for 16 hr. To the mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (28.8 g).
$^1$H NMR (400 MHz, CDCl$_3$) δ 0.34-0.40 (2H, m), 0.63-0.70 (2H, m), 1.25-1.33 (4H, m), 2.72-2.80 (2H, m), 3.79 (2H, d, J=7.2 Hz), 3.96-4.05 (1H, m), 4.10-4.15 (2H, m), 4.63-4.69 (1H, m), 4.72-4.80 (1H, m), 6.56-6.62 (2H, m), 6.69 (1H, d, J=7.2 Hz), 7.00 (2H, d, J=8.4 Hz), 7.18-7.27 (3H, m).

D) 4-(4-(3-(cyclopropylmethoxy)phenoxy)phenyl)pyrrolidin-2-one

To a mixture of ethyl 3-(4-(3-(cyclopropylmethoxy)phenoxy)phenyl)-4-nitrobutanoate (28.8 g) and ethanol (360 ml) was added 10% palladium on carbon (2.88 g), and the mixture was stirred under hydrogen atmosphere at 12-15° C. for 16 hr. The mixture was filtered through Celite, and the obtained residue was washed with ethanol. The filtrate was concentrated under reduced pressure. To a mixture of the obtained residue and toluene (280 ml) was added acetic acid (0.4 ml), and the mixture was stirred at 80° C. for 4 hr. The mixture was concentrated under reduced pressure. The obtained residue was purified by silica gel column chromatography (ethyl acetate) to give the title compound (3.2 g).
$^1$H NMR (400 MHz, DMSO-$d_6$) δ 0.25-0.33 (2H, m), 0.50-0.57 (2H, m), 1.10-1.17 (1H, m), 2.25-2.34 (1H, m), 2.44-2.50 (1H, m), 3.15-3.24 (1H, m), 3.56-3.64 (2H, m), 3.78 (2H, d, J=6.8 Hz), 6.45-6.55 (2H, m), 6.68 (1H, d, J=8.4 Hz), 6.97 (2H, d, J=8.4 Hz), 7.24 (1H, t, J=8.4 Hz), 7.32 (2H, d, J=8.4 Hz), 7.72 (1H, brs).

E) N-(4-(3-(4-(3-(cyclopropylmethoxy)phenoxy)phenyl)pyrrolidin-1-yl)-4-oxobutan-2-yl)acetamide To a mixture of 4-(4-(3-(cyclopropylmethoxy)phenoxy)phenyl)pyrrolidin-2-one (2 g) and THF (20 ml) was added lithium aluminium hydride (471 mg) at 0° C. The mixture was stirred under heating with reflux for 12 hr. To the reaction mixture were successively added water (1 ml), 10% aqueous sodium hydroxide solution (1 ml) and water (3 ml), and filtered. To the filtrate was added water, and the mixture was extracted with ethyl acetate. The obtained organic layer was washed with saturated brine, dried over anhydrous sodium sulfate, and concentrated under reduced pressure to give a residue (1.81 g). A mixture of the obtained residue (1.36 g), 3-acetamidobutanoic acid (640 mg), WSCD (1.01 g) and pyridine (15 ml) was stirred at 8-17° C. for 12 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by HPLC (water/acetonitrile, addition of 0.1% ammonium hydrogencarbonate) to give the title compound (350 mg).

$^1$H NMR (400 MHz, DMSO-$d_6$) δ 0.25-0.35 (2H, m), 0.50-0.60 (2H, m), 1.05-1.15 (3H, m), 1.16-1.25 (1H, m), 1.72-1.82 (3H, m), 1.85-2.05 (1H, m), 2.15-2.35 (2H, m), 2.45-2.52 (1H, m), 3.10-3.20 (0.5H, m), 3.25-3.35 (1H, m), 3.36-3.55 (1.5H, m), 3.57-3.70 (1H, m), 3.75-4.00 (3H, m), 4.05-4.15 (1H, m), 6.45-6.55 (2H, m), 6.68 (1H, dd, J=8.0, 1.6 Hz), 6.93-7.04 (2H, m), 7.24 (1H, t, J=8.0 Hz), 7.27-7.40 (2H, m), 7.70-7.80 (1H, m).

Example 99

N-((2S)-1-((2-(6-(3-(cyclopropylmethoxy)phenoxy)pyridin-3-yl)-1,3-oxazol-5-yl)oxy)propan-2-yl)acetamide A) (2S)-2-((tert-butoxycarbonyl)amino)propyl glycinate A mixture of (2S)-2-((tert-butoxycarbonyl)amino)propyl N-((benzyloxy)carbonyl)glycinate (5 g), 10% palladium on carbon (500 mg) and THF (100 ml) was stirred under hydrogen atmosphere at 10-15° C. for 4 hr. The mixture was filtered through Celite, and washed three times with THF. The filtrate was concentrated under reduced pressure to give the title compound (3.16 g).

$^1$H NMR (400 MHz, DMSO-$d_6$) δ 1.00 (3H, d, J=6.8 Hz), 1.37 (9H, s), 1.50-1.60 (2H, m), 3.30-3.45 (2H, m), 3.65-4.00 (3H, m), 6.82 (1H, d, J=8.0 Hz).

B) (2S)-2-((tert-butoxycarbonyl)amino)propyl N-((6-chloropyridin-3-yl)carbonyl)glycinate To a mixture of 6-chloronicotinic acid (3 g) and THF (100 ml) was added oxalyl chloride (4.85 g) under ice-cooling, and then DMF (5 drops) was added thereto. The mixture was stirred at 0° C. for 5 hr, and concentrated under reduced pressure to give the corresponding acid chloride. To a mixture of (2S)-2-((tert-butoxycarbonyl)amino)propyl glycinate (4.43 g) and THF (80 ml) was added triethylamine (3.86 g), and a mixture of the acid chloride previously obtained and THF (20 ml) was added dropwise thereto under nitrogen atmosphere at 0° C. The reaction mixture was stirred at 10-15° C. for 16 hr. To the mixture was added ethyl acetate, and the mixture was washed successively with water and saturated brine, dried over anhydrous sodium sulfate, and concentrated under reduced pressure. The obtained residue was purified by silica gel column chromatography (ethyl acetate/petroleum ether) to give the title compound (5.9 g).

$^1$H NMR (400 MHz, DMSO-$d_6$) δ 1.03 (3H, d, J=6.8 Hz), 1.38 (9H, s), 3.70-3.80 (1H, m), 3.90-4.10 (4H, m), 6.82 (1H, d, J=8.0 Hz), 7.69 (1H, d, J=8.4 Hz), 8.26 (1H, dd, J=8.4, 2.4 Hz), 8.86 (1H, d, J=2.4 Hz), 9.26 (1H, t, J=5.2 Hz).

C) tert-butyl ((2S)-1-((2-(6-chloropyridin-3-yl)-1,3-oxazol-5-yl)oxy)propan-2-yl)carbamate To a mixture of iodine (5.75 g), triphenylphosphine (5.92 g) and dichloromethane (100 ml) was added triethylamine (4.56 g) under nitrogen atmosphere at 10-15° C., and the mixture was stirred for 30 min. To the mixture was added a mixture of (2S)-2-((tert-butoxycarbonyl)amino)propyl N-((6-chloropyridin-3-yl)carbonyl)glycinate (4.2 g) and dichloromethane (50 ml), and the mixture was stirred at 10-15° C. for 16 hr. To the mixture was added dichloromethane, and the mixture was washed successively with saturated aqueous sodium hydrogencarbonate solution and saturated brine, dried over anhydrous sodium sulfate, and concentrated under reduced pressure. The obtained residue was purified by silica gel column chromatography (ethyl acetate/petroleum ether) to give the title compound (2.4 g).

MS: [M+H]$^+$ 353.9.

D) tert-butyl ((2S)-1-((2-(6-(3-(cyclopropylmethoxy)phenoxy)pyridin-3-yl)-1,3-oxazol-5-yl)oxy)propan-2-yl)carbamate A mixture of tert-butyl ((2S)-1-((2-(6-chloropyridin-3-yl)-1,3-oxazol-5-yl)oxy)propan-2-yl)carbamate (1 g), 3-(cyclopropylmethoxy)phenol (465 mg), cesium carbonate (1.38 g) and DMF (20 ml) was stirred under nitrogen atmosphere at 60-70° C. for 7 days. To the reaction mixture was added ethyl acetate, and the mixture was washed successively with 2N aqueous sodium hydroxide solution, water and saturated brine, dried over anhydrous sodium sulfate, and concentrated under reduced pressure. The obtained residue was purified by silica gel column chromatography (ethyl acetate/petroleum ether), and then purified by HPLC (water/acetonitrile, addition of 0.1% TFA) to give the title compound (200 mg).

$^1$H NMR (400 MHz, DMSO-$d_6$) δ 0.25-0.35 (2H, m), 0.50-0.60 (2H, m), 1.11 (3H, d, J=6.8 Hz), 1.15-1.25 (1H, m), 1.37 (9H, s), 3.80 (2H, d, J=6.8 Hz), 3.80-3.90 (1H, m), 4.01 (2H, d, J=5.6 Hz), 6.49 (1H, s), 6.65-6.75 (2H, m), 6.80 (1H, dd, J=8.0, 2.0 Hz), 7.00 (1H, d, J=7.6 Hz), 7.10 (1H, d, J=8.8 Hz), 7.31 (1H, t, J=8.4 Hz), 8.22 (1H, dd, J=8.8, 2.4 Hz), 8.59 (1H, d, J=2.4 Hz).

E) N-((2S)-1-((2-(6-(3-(cyclopropylmethoxy)phenoxy)pyridin-3-yl)-1,3-oxazol-5-yl)oxy)propan-2-yl)acetamide A mixture of tert-butyl ((2S)-1-((2-(6-(3-(cyclopropylmethoxy)phenoxy)pyridin-3-yl)-1,3-oxazol-5-yl)oxy)propan-2-yl)carbamate (216 mg) and hydrogen chloride (4M ethyl acetate solution, 2 ml) was stirred at 10-15° C. for 12 hr. The mixture was concentrated under reduced pressure. To a mixture of the obtained residue and pyridine (3 ml) was added acetic anhydride (69 mg). The mixture was stirred 10-15° C. for 16 hr. The mixture was concentrated under reduced pressure. The obtained residue was purified by preparative TLC (ethyl acetate), and then purified by HPLC (water/acetonitrile) to give the title compound (25 mg).

$^1$H NMR (400 MHz, CDCl$_3$) δ 0.30-0.40 (2H, m), 0.50-0.60 (2H, m), 1.20-1.40 (4H, m), 2.01 (3H, s), 3.79 (2H, d, J=6.8 Hz), 4.00-4.20 (2H, m), 4.35-4.45 (1H, m), 5.75 (1H, d, J=6.4 Hz), 6.22 (1H, s), 6.65-6.85 (3H, m), 6.93 (1H, d, J=8.4 Hz), 7.25-7.35 (1H, m), 8.17 (1H, d, J=7.6 Hz), 8.71 (1H, s).

Example 101

1-((2S)-1-((2-(6-(3-(cyclopropylmethoxy)phenoxy)pyridin-3-yl)-1,3-oxazol-5-yl)oxy)propan-2-yl)urea A mixture of tert-butyl ((2S)-1-((2-(6-(3-(cyclopropylmethoxy)phenoxy)pyridin-3-yl)-1,3-oxazol-5-yl)oxy)propan-2-yl)carbamate (100 mg) and formic acid (5 ml) was stirred under nitrogen atmosphere at 15-20° C. for 16 hr. The mixture was concentrated under reduced pressure. To a mixture of the obtained residue, triethylamine (63 mg) and dichloromethane (4 ml) was added trimethylsilyl isocyanate (60 mg) at 0° C. The mixture was stirred at 15-20° C. for 16 hr, 1N hydrochloric acid (4 ml) was added thereto, and the mixture was stirred at 30° C. for 30 min. The mixture was neutralized with saturated aqueous sodium hydrogencarbonate solution, and extracted with dichloromethane. The obtained organic layer was washed with saturated brine, dried over anhydrous sodium sulfate, and concentrated under reduced pressure. The obtained residue was purified by HPLC (water/acetonitrile) to give the title compound (19 mg).
$^1$H NMR (400 MHz, CDCl$_3$) δ 0.30-0.40 (2H, m), 0.50-0.60 (2H, m), 1.20-1.30 (4H, m), 3.78 (2H, d, J=6.8 Hz), 4.00-4.30 (3H, m), 4.61 (2H, s), 5.16 (1H, d, J=8.0 Hz), 6.20 (1H, s), 6.69-6.73 (2H, m), 6.78 (1H, dd, J=8.8, 1.6 Hz), 6.92 (1H, d, J=8.8 Hz), 7.29 (1H, t, J=8.4 Hz), 8.14 (1H, dd, J=8.4, 2.4 Hz), 8.67 (1H, d, J=2.0 Hz).

Example 102

N-((2S)-1-((2-(5-(3-(cyclopropylmethoxy)phenoxy)pyridin-2-yl)-1,3-oxazol-5-yl)oxy)propan-2-yl)acetamide A) (2S)-2-((tert-butoxycarbonyl)amino)propyl N-((5-bromopyridin-2-yl)carbonyl)glycinate To a mixture of 5-bromopyridine-2-carboxylic acid (3.85 g) and THF (100 ml) was added dropwise oxalyl chloride (4.85 ml) under ice-cooling, and then DMF (5 drops) was added thereto. The reaction mixture was stirred at 0° C. for 5 hr, and concentrated under reduced pressure to give the corresponding acid chloride. To a mixture of (2S)-2-((tert-butoxycarbonyl)amino)propyl glycinate (4.43 g) and THF (80 ml) was added triethylamine (3.86 g), and then a mixture of the acid chloride previously obtained and THF (20 ml) was added dropwise thereto under nitrogen atmosphere at 0° C. The reaction mixture was stirred at 10-15° C. for 16 hr. To the reaction mixture was added ethyl acetate, and the mixture was washed successively with water and saturated brine, dried over anhydrous sodium sulfate, and concentrated under reduced pressure. The obtained residue was purified by silica gel column chromatography (ethyl acetate/petroleum ether) to give the title compound (4.2 g).
MS: [M+Na]$^+$ 439.9.

B) tert-butyl ((2S)-1-((2-(5-bromopyridin-2-yl)-1,3-oxazol-5-yl)oxy)propan-2-yl)carbamate To a mixture of iodine (5.12 g), triphenylphosphine (5.29 g) and dichloromethane (150 ml) was added triethylamine (4.08 g) under nitrogen atmosphere at 10-15° C., and the mixture was stirred for 30 min. To the mixture was added a mixture of (2S)-2-((tert-butoxycarbonyl)amino)propyl N-((5-bromopyridin-2-yl)carbonyl)glycinate (4.2 g) and dichloromethane (150 ml). The reaction mixture was stirred at 10-15° C. for 16 hr. To the reaction mixture was added dichloromethane, and the mixture was washed successively with saturated aqueous sodium hydrogencarbonate solution and saturated brine, dried over anhydrous sodium sulfate, and concentrated under reduced pressure. The obtained residue was purified by silica gel column chromatography (ethyl acetate/petroleum ether), and then purified by HPLC (water/acetonitrile, addition of 0.1% TFA) to give the title compound (800 mg).
$^1$H NMR (400 MHz, DMSO-d$_6$) 1.12 (3H, d, J=6.8 Hz), 1.37 (9H, s), 3.85-3.95 (1H, m), 4.05 (2H, d, J=5.6 Hz), 6.61 (1H, s), 7.01 (1H, d, J=8.0 Hz), 7.90 (1H, d, J=8.4 Hz), 8.18 (1H, dd, J=8.4, 2.4 Hz), 8.76 (1H, d, J=2.0 Hz).

C) tert-butyl ((2S)-1-((2-(5-(3-(cyclopropylmethoxy)phenoxy)pyridin-2-yl)-1,3-oxazol-5-yl)oxy)propan-2-yl)carbamate A mixture of tert-butyl ((2S)-1-((2-(5-bromopyridin-2-yl)-1,3-oxazol-5-yl)oxy)propan-2-yl)carbamate (374 mg), 3-(cyclopropylmethoxy)phenol (170 mg), tripotassium phosphate (399 mg), copper(I) iodide (17.89 mg), pyridine-2-carboxylic acid (23 mg) and DMSO (5 ml) was stirred under nitrogen atmosphere at 80-90° C. for 16 hr. The mixture was cooled to 10-15° C., water was added thereto, and the mixture was extracted with dichloromethane. The obtained organic layer was dried over anhydrous sodium sulfate, and concentrated under reduced pressure. The obtained residue was purified by silica gel column chromatography (ethyl acetate/petroleum ether) to give the title compound (200 mg).
MS: [M+H]$^+$ 482.2.

D) (2S)-1-((2-(5-(3-(cyclopropylmethoxy)phenoxy)pyridin-2-yl)-1,3-oxazol-5-yl)oxy)propan-2-amine A mixture of tert-butyl ((2S)-1-((2-(5-(3-(cyclopropylmethoxy)phenoxy)pyridin-2-yl)-1,3-oxazol-5-yl)oxy)propan-2-yl)carbamate (200 mg) and formic acid (5 ml) was stirred under nitrogen atmosphere at 10-15° C. for 5 hr. The formic acid was removed by blowing nitrogen gas to the mixture, water was added thereto, and the mixture was freeze-dried to give the title compound (165 mg).
MS: [M+H]$^+$ 382.1.

E) N-((2S)-1-((2-(5-(3-(cyclopropylmethoxy)phenoxy)pyridin-2-yl)-1,3-oxazol-5-yl)oxy)propan-2-yl)acetamide To a mixture of (2S)-1-((2-(5-(3-(cyclopropylmethoxy)phenoxy)pyridin-2-yl)-1,3-oxazol-5-yl)oxy)propan-2-amine (130 mg) and pyridine (5 ml) was added dropwise acetic anhydride (52 mg) at 0° C. The mixture was stirred at 15-20° C. for 16 hr. The mixture was concentrated under reduced pressure. The obtained residue was purified by HPLC (water/acetonitrile) to give the title compound (38 mg).
$^1$H NMR (400 MHz, CDCl$_3$) δ 50.30-0.40 (2H, m), 0.60-0.70 (2H, m), 1.20-1.30 (1H, m), 1.33 (3H, d, J=6.8 Hz), 2.00 (3H, s), 3.78 (1H, d, J=6.8 Hz), 4.12 (1H, dd, J=9.2, 3.2 Hz), 4.18 (1H, dd, J=9.2, 3.6 Hz), 4.35-4.45 (1H, m), 5.73 (1H, d, J=8.0 Hz), 6.29 (1H, s), 6.60-6.65 (2H, m), 6.70-6.75 (1H, m), 7.25-7.29 (2H, m), 7.35 (1H, dd, J=8.8, 2.8 Hz), 7.96 (1H, d, J=8.8 Hz), 8.44 (1H, d, J=2.4 Hz).

Example 103

N-(4-(1-(6-(3-(cyclopropylmethoxy)phenoxy)pyridin-3-yl)-1H-pyrazol-4-yl)-4-oxobutan-2-yl)acetamide A)
5-bromo-2-(3-(cyclopropylmethoxy)phenoxy)pyridine A mixture of 3-(cyclopropylmethoxy)phenol (32.8 g), 5-bromo-2-fluoropyridine (35 g), potassium carbonate (55.2 g) and DMF (600 ml) was stirred at 80° C. for 72 hr. The mixture was allowed to cool to room temperature, and filtered, and the filtrate was concentrated under reduced pressure. The obtained residue was purified by silica gel column chromatography (ethyl acetate/petroleum ether) to give the title compound (29.3 g).
$^1$H NMR (400 MHz, CDCl$_3$) δ 0.30-0.38 (2H, m), 0.60-0.68 (2H, m), 1.20-1.31 (1H, m), 3.78 (2H, d, J=6.8 Hz), 6.65-6.70 (2H, m), 6.74-6.78 (1H, m), 6.81 (1H, d, J=8.8 Hz), 7.22-7.32 (1H, m), 7.75 (1H, dd, J=8.6, 2.6 Hz), 8.23 (1H, d, J=2.0 Hz).

B) 2-(3-(cyclopropylmethoxy)phenoxy)-5-(4,4,5,5-tetramethyl-1,3,2-dioxaborolan-2-yl)pyridine To a mixture of 5-bromo-2-(3-(cyclopropylmethoxy)phenoxy)pyridine (29.3 g), 4,4,4',4',5,5,5',5'-octamethyl-2,2'-bi-1,3,2-dioxaborolane (35 g), potassium acetate (13.5 g) and 1,4-dioxane (600 ml) was added (bis(1,1'-diphenylphosphino)ferrocene)dichloropalladium (3.36 g) under nitrogen atmosphere. The mixture was subjected to nitrogen substitution, and stirred under nitrogen atmosphere at 80° C. for 16 hr. The mixture was allowed to cool to room temperature, and filtered through Celite, and the residue was washed with ethyl acetate. The filtrate was concentrated under reduced pressure to give the title compound (33.7 g).
MS: [M+H]$^+$ 368.4.

C) ethyl 1-(6-(3-(cyclopropylmethoxy)phenoxy)pyridin-3-yl)-1H-pyrazole-4-carboxylate To a mixture of 2-(3-(cyclopropylmethoxy)phenoxy)-5-(4,4,5,5-tetramethyl-1,3,2-dioxaborolan-2-yl)pyridine (6.55 g), ethyl 1H-pyrazole-4-carboxylate (2.5 g), copper(II) acetate (3.24 g) and DMF (50 ml) was added pyridine (7.07 g) at 12° C. The mixture was stirred under oxygen atmosphere at 80-90° C. for 10 days. The mixture was allowed to cool to room temperature, and filtered through Celite, and the residue was washed with ethyl acetate. The filtrate was concentrated under reduced pressure. The obtained residue was purified by silica gel column chromatography (ethyl acetate/petroleum ether), and the obtained residue was washed with hexane/ethyl acetate to give the title compound (2.7 g).
$^1$H NMR (400 MHz, DMSO-d$_6$) δ 0.26-0.36 (2H, m), 0.50-0.60 (2H, m), 1.12-1.25 (1H, m), 1.31 (3H, t, J=7.0 Hz), 3.81 (2H, d, J=6.8 Hz), 4.28 (2H, d, J=7.2 Hz), 6.67-6.75 (2H, m), 6.81 (1H, d, J=8.4 Hz), 7.18 (1H, d, J=8.0 Hz), 7.32 (1H, t, J=8.0 Hz), 8.17 (1H, s), 8.37 (1H, dd, J=8.8, 2.8 Hz), 8.72 (1H, d, J=2.8 Hz), 9.11 (1H, s).

D) (1-(6-(3-(cyclopropylmethoxy)phenoxy)pyridin-3-yl)-1H-pyrazol-4-yl)methanol

To a mixture of ethyl 1-(6-(3-(cyclopropylmethoxy)phenoxy)pyridin-3-yl)-1H-pyrazole-4-carboxylate (2.7 g) and dichloromethane (50 ml) was added dropwise diisobutylaluminium hydride (1M hexane solution, 14.8 ml) at −78° C., and the mixture was stirred for 1 hr. To the mixture was added methanol at −78° C., and the mixture was stirred at 20° C. for 2 hr. The mixture was filtered, and the filtrate was concentrated under reduced pressure to give the title compound (2.1 g).
$^1$H NMR (400 MHz, CDCl$_3$) δ 0.30-0.36 (2H, m), 0.60-0.67 (2H, m), 1.20-1.32 (1H, m), 3.74 (1H, t, J=6.4 Hz), 3.79 (2H, d, J=6.8 Hz), 4.62-4.70 (2H, m), 6.68-6.80 (3H, m), 6.99 (1H, d, J=8.8 Hz), 7.30 (1H, t, J=8.2 Hz), 7.73 (1H, s), 7.85 (1H, s), 8.03 (1H, dd, J=8.8, 2.8 Hz), 8.46 (1H, d, J=2.4 Hz).

E) 1-(6-(3-(cyclopropylmethoxy)phenoxy)pyridin-3-yl)-1H-pyrazole-4-carbaldehyde

To a mixture of (1-(6-(3-(cyclopropylmethoxy)phenoxy)pyridin-3-yl)-1H-pyrazol-4-yl)methanol (2.1 g) and dichloromethane (50 ml) was added manganese dioxide (5.41 g), and the mixture was stirred at 20° C. for 16 hr. The mixture was filtered, and the filtrate was concentrated under reduced pressure. The obtained residue was purified by silica gel column chromatography (methanol/dichloromethane) to give the title compound (1.7 g).
$^1$H NMR (400 MHz, CDCl$_3$) δ 0.29-0.37 (2H, m), 0.60-0.68 (2H, m), 1.19-1.32 (1H, m), 3.80 (2H, d, J=6.8 Hz), 6.70-6.82 (3H, m), 7.05 (1H, dd, J=0.6 Hz), 7.32 (1H, t, J=8.2 Hz), 8.07 (1H, dd, J=8.8, 2.8 Hz), 8.19 (1H, s), 8.36 (1H, s), 8.53 (1H, d, J=2.8 Hz), 9.98 (1H, s).

F) tert-butyl 3-(1-(6-(3-(cyclopropylmethoxy)phenoxy)pyridin-3-yl)-1H-pyrazol-4-yl)-3-hydroxypropanoate To a mixture of 1-(6-(3-(cyclopropylmethoxy)phenoxy)pyridin-3-yl)-1H-pyrazole-4-carbaldehyde (1.6 g) and THF (20 ml) was added (2-tert-butoxy-2-oxoethyl)(chloro)zinc (0.5M diethyl ether solution, 47.7 ml) at 0° C. The mixture was stirred under nitrogen atmosphere at 20° C. for 72 hr. The reaction mixture was poured into water, and extracted with ethyl acetate. The obtained organic layer was dried over anhydrous sodium sulfate, and concentrated under reduced pressure to give the title compound (2.1 g).
MS: [M+H]$^+$ 452.1.

G) 3-(1-(6-(3-(cyclopropylmethoxy)phenoxy)pyridin-3-yl)-1H-pyrazol-4-yl)-3-hydroxypropanoic acid To a mixture of tert-butyl 3-(1-(6-(3-(cyclopropylmethoxy)phenoxy)pyridin-3-yl)-1H-pyrazol-4-yl)-3-hydroxypropanoate (2.1 g), methanol (20 ml) and water (20 ml) was added sodium hydroxide (744 mg), and the mixture was stirred at 20° C. for 16 hr. The mixture was concentrated under reduced pressure, to the obtained residue was added water, and the mixture was extracted with methyl tert-butyl ether. The obtained aqueous layer was acidified with 2N hydrochloric acid, and extracted with ethyl acetate. The obtained organic layer was washed with saturated brine, dried over anhydrous sodium sulfate, and concentrated under reduced pressure to give the title compound (1.8 g).
MS: [M+H]$^+$ 396.2.

H) 3-(1-(6-(3-(cyclopropylmethoxy)phenoxy)pyridin-3-yl)-1H-pyrazol-4-yl)-3-hydroxy-N-methoxy-N-methylpropanamide A mixture of 3-(1-(6-(3-(cyclopropylmethoxy)phenoxy)pyridin-3-yl)-1H-pyrazol-4-yl)-3-hydroxypropanoic acid (1.8 g), N,O-dimethylhydroxylamine hydrochloride (666 mg), HATU (2.6 g), triethylamine (1.9 ml) and dichloromethane (25 ml) was stirred at 20° C. for 16 hr. To the reaction mixture was added dichloromethane, and the mixture was washed successively with water and saturated brine, dried over anhydrous sodium sulfate, and concentrated under reduced pressure. The obtained residue was purified by silica gel column chromatography (ethyl acetate/dichloromethane) to give the title compound (1.21 g).

$^1$H NMR (400 MHz, CDCl$_3$) δ 0.32-0.40 (2H, m), 0.60-0.67 (2H, m), 1.20-1.32 (1H, m), 2.82-3.02 (2H, m), 3.25 (3H, s), 3.73 (3H, s), 3.81 (2H, d, J=7.2 Hz), 4.33 (1H, d, J=3.2 Hz), 5.20-5.30 (1H, m), 6.69-6.81 (3H, m), 7.01 (1H, d, J=8.8 Hz), 7.32 (1H, t, J=8.0 Hz), 7.73 (1H, s), 7.90 (1H, s), 8.05 (1H, dd, J=8.8, 2.8 Hz), 8.51 (1H, d, J=2.4 Hz).

I) 4-(1-(6-(3-(cyclopropylmethoxy)phenoxy)pyridin-3-yl)-1H-pyrazol-4-yl)-4-hydroxybutan-2-one To a mixture of 3-(1-(6-(3-(cyclopropylmethoxy)phenoxy)pyridin-3-yl)-1H-pyrazol-4-yl)-3-hydroxy-N-methoxy-N-methylpropanamide (1.2 g) and THF (25 ml) was added methylmagnesium bromide (3M THF solution, 2.74 ml) at 0° C., and the mixture was stirred under nitrogen atmosphere at 20° C. for 16 hr. To the reaction mixture was added saturated aqueous ammonium chloride solution, the mixture was extracted with ethyl acetate, and the organic layer was dried over anhydrous sodium sulfate, and concentrated under reduced pressure. The obtained residue was purified by silica gel column chromatography (ethyl acetate/dichloromethane) to give the title compound (930 mg).

$^1$H NMR (400 MHz, CDCl$_3$) δ 0.30-0.37 (2H, m), 0.60-0.67 (2H, m), 1.20-1.32 (1H, m), 2.24 (3H, s), 2.92-2.98 (2H, m), 3.41 (1H, d, J=3.6 Hz), 3.79 (2H, d, J=6.8 Hz), 5.20-5.28 (1H, m), 6.68-6.80 (3H, m), 6.99 (1H, d, J=8.8 Hz), 7.29 (1H, t, J=8.2 Hz), 7.68 (1H, s), 7.84 (1H, s), 8.02 (1H, dd, J=8.8, 2.8 Hz), 8.47 (1H, d, J=2.4 Hz).

J) N-(4-(1-(6-(3-(cyclopropylmethoxy)phenoxy)pyridin-3-yl)-1H-pyrazol-4-yl)-4-hydroxybutan-2-yl)acetamide To a mixture of 4-(1-(6-(3-(cyclopropylmethoxy)phenoxy)pyridin-3-yl)-1H-pyrazol-4-yl)-4-hydroxybutan-2-one (900 mg), ammonium acetate (3.53 g) and methanol (20 ml) was added sodium cyanoborohydride (576 mg). The mixture was stirred under heating with reflux for 16 hr. The mixture was allowed to cool to room temperature, and concentrated under reduced pressure. To a mixture of the obtained residue and dichloromethane (30 ml) was added acetic anhydride (3 ml), and the mixture was stirred at 20° C. for 2 hr. The mixture was concentrated under reduced pressure, and ethyl acetate was added thereto. The obtained organic layer was washed successively with water and saturated brine, dried over anhydrous sodium sulfate, and concentrated under reduced pressure. The obtained residue was purified by preparative TLC (dichloromethane/methanol) to give the title compound (201 mg).

$^1$H NMR (400 MHz, CDCl$_3$) δ 0.30-0.37 (2H, m), 0.60-0.67 (2H, m), 1.20-1.32 (4H, m), 1.89 (3H, s), 1.92-1.98 (2H, m), 3.49 (1H, brs), 3.79 (2H, d, J=6.8 Hz), 4.09-4.11 (1H, m), 4.90 (1H, t, J=6.0 Hz), 5.52 (1H, brd, J=8.0 Hz), 6.68-6.80 (3H, m), 6.98 (1H, d, J=8.8 Hz), 7.29 (1H, t, J=8.2 Hz), 7.66 (1H, s), 7.85 (1H, s), 8.01 (1H, dd, J=8.8, 2.8 Hz), 8.48 (1H, d, J=2.8 Hz).

K) N-(4-(1-(6-(3-(cyclopropylmethoxy)phenoxy)pyridin-3-yl)-1H-pyrazol-4-yl)-4-oxobutan-2-yl)acetamide To a mixture of N-(4-(1-(6-(3-(cyclopropylmethoxy)phenoxy)pyridin-3-yl)-1H-pyrazol-4-yl)-4-hydroxybutan-2-yl)acetamide (201 mg) and dichloromethane (20 ml) was added manganese dioxide (400 mg), and the mixture was stirred at 20° C. for 16 hr. The mixture was filtered, and the filtrate was concentrated under reduced pressure. The obtained residue was purified by preparative TLC (dichloromethane/methanol) to give the title compound (128 mg).

$^1$H NMR (400 MHz, CDCl$_3$) δ 0.30-0.37 (2H, m), 0.60-0.67 (2H, m), 1.20-1.32 (4H, m), 1.98 (3H, s), 2.84 (1H, dd, J=15.2, 6.8 Hz), 3.22 (1H, dd, J=15.2, 4.0 Hz), 3.80 (2H, d, J=6.8 Hz), 4.31-4.45 (1H, m), 6.04 (1H, brd, J=8.0 Hz), 6.70-6.81 (3H, m), 7.03 (1H, d, J=8.8 Hz), 7.31 (1H, t, J=8.0 Hz), 8.06 (1H, dd, J=8.8, 2.8 Hz), 8.15 (1H, s), 8.51-8.59 (2H, m).

Example 104

1-((2S)-1-((2-(5-(3-(cyclopropylmethoxy)phenoxy)pyridin-2-yl)-1,3-oxazol-5-yl)oxy)propan-2-yl)urea To a mixture of (2S)-1-((2-(5-(3-(cyclopropylmethoxy)phenoxy)pyridin-2-yl)-1,3-oxazol-5-yl)oxy)propan-2-amine (165 mg), triethylamine (78.1 mg) and dichloromethane (4 ml) was added trimethylsilyl isocyanate (67 mg) at 0° C. The mixture was stirred at 15-20° C. for 16 hr. To the mixture was added 1N hydrochloric acid, and the mixture was stirred at 15-20° C. for 30 min. The reaction mixture was neutralized with saturated aqueous sodium hydrogencarbonate solution, and extracted with dichloromethane. The obtained organic layer was washed with saturated brine, dried over anhydrous sodium sulfate, and concentrated under reduced pressure. The obtained residue was purified by HPLC (water/acetonitrile) to give the title compound (34 mg).

$^1$H NMR (400 MHz, CDCl$_3$) δ 0.30-0.40 (2H, m), 0.60-0.70 (2H, m), 1.20-1.40 (4H, m), 3.76 (2H, d, J=7.2 Hz), 4.09-4.30 (3H, m), 4.57 (2H, s), 5.11 (1H, d, J=8.0 Hz), 6.27 (1H, s), 6.55-6.65 (2H, m), 6.72 (1H, d, J=8.0 Hz), 7.20-7.30 (1H, m), 7.33 (1H, dd, J=8.8, 2.4 Hz), 7.93 (1H, d, J=8.4 Hz), 8.40 (1H, d, J=2.4 Hz).

Example 105

N-(4-(2-(6-(3-(cyclopropylmethoxy)phenoxy)pyridin-3-yl)-1,3-oxazol-5-yl)-4-oxobutan-2-yl)acetamide A) 6-chloro-N-(prop-2-yn-1-yl)nicotinamide To a mixture of 6-chloronicotinoyl chloride (50 g), prop-2-yn-1-amine (15.7 g) and THF (500 ml) was added triethylamine (86.2 g), and the mixture was stirred at 15-17° C. for 16 hr. To the mixture was added water, and the mixture was extracted with ethyl acetate. The obtained organic layer was washed with saturated brine, dried over anhydrous sodium sulfate, and concentrated under reduced pressure. To the obtained residue was added a mixed solvent of petroleum ether/ethyl acetate, and the mixture was stirred at 15° C. for 1 hr. The mixture was filtered, and the obtained solid was washed with petroleum ether to give the title compound (25.5 g).

¹H NMR (400 MHz, DMSO-d$_6$) δ 3.19 (1H, t, J=2.4 Hz), 4.09 (2H, dd, J=5.2, 2.8 Hz), 7.67 (1H, d, J=8.0 Hz), 8.25 (1H, dd, J=8.4, 2.4 Hz), 8.84 (1H, d, J=2.0 Hz), 9.24 (1H, t, J=5.6 Hz).

B) (2-(6-chloropyridin-3-yl)-1,3-oxazol-5-yl)methyl acetate

A mixture of 6-chloro-N-(prop-2-yn-1-yl)nicotinamide (25.5 g), iodobenzene diacetate (63.3 g) and acetic acid (300 ml) was stirred at 90° C. for 16 hr. To the mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (23.9 g).
¹H NMR (400 MHz, CDCl$_3$) δ 2.13 (3H, s), 5.18 (2H, s), 7.27 (1H, s), 7.45 (1H, d, J=8.8 Hz), 8.28 (1H, dd, J=8.4, 2.4 Hz), 9.05 (1H, d, J=2.0 Hz).

C) (2-(6-chloropyridin-3-yl)-1,3-oxazol-5-yl)methanol

To a mixture of (2-(6-chloropyridin-3-yl)-1,3-oxazol-5-yl)methyl acetate (23.9 g) and methanol (350 ml) was added potassium carbonate (13.1 g), and the mixture was stirred at 17-19° C. for 16 hr. The mixture was concentrated under reduced pressure. To the obtained residue was added water, and the mixture was extracted with ethyl acetate. The obtained organic layer was washed with saturated brine, dried over anhydrous sodium sulfate, and concentrated under reduced pressure to give the title compound (18.8 g).
¹H NMR (400 MHz, DMSO-d$_6$) δ 4.57 (2H, d, J=5.2 Hz), 5.55 (1H, t, J=5.2 Hz), 7.28 (1H, s), 7.70 (1H, d, J=8.4 Hz), 8.33 (1H, dd, J=8.4, 2.4 Hz), 8.95 (1H, d, J=2.0 Hz).

D) 2-(6-chloropyridin-3-yl)-1,3-oxazole-5-carbaldehyde

To a mixture of (2-(6-chloropyridin-3-yl)-1,3-oxazol-5-yl)methanol (18.8 g) and dichloromethane (200 ml) was added manganese dioxide (38.8 g), and the mixture was stirred at 40° C. for 16 hr. The mixture was filtered, and the residue was washed with dichloromethane. The obtained organic layer was concentrated under reduced pressure. To the obtained residue was added a mixed solvent of petroleum ether/ethyl acetate, and the mixture was stirred at 20° C. for 2 hr. The mixture was filtered, and the obtained solid was washed with petroleum ether to give the title compound (12 g).
¹H NMR (400 MHz, DMSO-d$_6$) δ 7.78 (1H, d, J=8.4 Hz), 8.42 (1H, s), 8.48 (1H, dd, J=8.0, 2.4 Hz), 9.09 (1H, d, J=2.4 Hz), 9.85 (1H, s).

E) tert-butyl 3-(2-(6-chloropyridin-3-yl)-1,3-oxazol-5-yl)-3-hydroxypropanoate

To a mixture of 2-(6-chloropyridin-3-yl)-1,3-oxazole-5-carbaldehyde (12 g), zinc (11.3 g) and THF (140 ml) was added dropwise tert-butyl 2-bromoacetate (14.6 ml) over 30 min at 66° C. The mixture was stirred at 66° C. for 20 hr. The mixture was allowed to cool to room temperature, and saturated aqueous ammonium chloride solution was added thereto. The mixture was filtered, and the filtrate was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (9.3 g).
¹H NMR (400 MHz, DMSO-d$_6$) δ 1.39 (9H, s), 2.65-2.85 (2H, m), 5.03-5.11 (1H, m), 5.93 (1H, d, J=6.0 Hz), 7.29 (1H, s), 7.72 (1H, d, J=8.4 Hz), 8.36 (1H, dd, J=8.4, 2.4 Hz), 8.97 (1H, s).

F) 3-(2-(6-chloropyridin-3-yl)-1,3-oxazol-5-yl)-3-hydroxypropanoic acid

To a mixture of tert-butyl 3-(2-(6-chloropyridin-3-yl)-1,3-oxazol-5-yl)-3-hydroxypropanoate (9.3 g) and dichloromethane (80 ml) was added TFA (15 ml), and the mixture was stirred at 15-25° C. for 12 hr. The mixture was concentrated under reduced pressure. To the obtained residue was added water, and the mixture was adjusted to pH=5-6 with saturated sodium hydrogencarbonate. The mixture was extracted with ethyl acetate. The obtained organic layer was washed with saturated brine, dried over anhydrous sodium sulfate, and concentrated under reduced pressure to give the title compound (7.5 g).
¹H NMR (400 MHz, DMSO-d$_6$) δ 2.72 (1H, dd, J=15.6, 8.4 Hz), 2.82 (1H, dd, J=15.6, 8.4 Hz), 5.08 (1H, dd, J=8.4, 5.2 Hz), 5.91 (1H, brs), 7.27 (1H, s), 7.69 (1H, d, J=8.4 Hz), 8.33 (1H, dd, J=8.4, 2.4 Hz), 8.95 (1H, d, J=2.0 Hz), 12.34 (1H, brs).

G) 3-(2-(6-chloropyridin-3-yl)-1,3-oxazol-5-yl)-3-hydroxy-N-methoxy-N-methylpropanamide To a mixture of 3-(2-(6-chloropyridin-3-yl)-1,3-oxazol-5-yl)-3-hydroxypropanoic acid (7.6 g), N,O-dimethylhydroxylamine hydrochloride (3.86 g) and DMF (80 ml) were added triethylamine (14.3 g), HOBt monohydrate (5.73 g) and WSCD (8.13 g). The mixture was stirred at 30° C. for 12 hr. To the mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether) to give the title compound (5.05 g).
¹H NMR (400 MHz, DMSO-d$_6$) δ 2.75-3.08 (2H, m), 3.11 (3H, s), 3.69 (3H, s), 5.05-5.20 (1H, m), 5.84 (1H, d, J=5.6 Hz), 7.27 (1H, s), 7.70 (1H, d, J=8.0 Hz), 8.25-8.39 (1H, m), 8.95 (1H, d, J=1.6 Hz).

H) 4-(2-(6-chloropyridin-3-yl)-1,3-oxazol-5-yl)-4-hydroxybutan-2-one

To a mixture of 3-(2-(6-chloropyridin-3-yl)-1,3-oxazol-5-yl)-3-hydroxy-N-methoxy-N-methylpropanamide (2 g) and THF (30 ml) was added methylmagnesium bromide (3M diethyl ether solution, 25 ml), and the mixture was stirred at 15° C. for 30 min. To the mixture was added saturated aqueous ammonium chloride solution, and the mixture was extracted with ethyl acetate. The obtained organic layer was washed with saturated brine, dried over anhydrous sodium sulfate, and concentrated under reduced pressure to give the title compound (1.65 g).
MS: [M+H]$^+$ 266.9.

I) N-(4-(2-(6-chloropyridin-3-yl)-1,3-oxazol-5-yl)-4-hydroxybutan-2-yl)acetamide To a mixture of 4-(2-(6-chloropyridin-3-yl)-1,3-oxazol-5-yl)-4-hydroxybutan-2-one (1.1 g) and methanol (40 ml)

were added ammonium acetate (4.76 g) and sodium cyanoborohydride (518 mg) at 20° C. The mixture was stirred at 50° C. for 1.5 hr. The mixture was concentrated under reduced pressure. To a mixture of the obtained residue and THF (20 ml) was added acetic anhydride (2.5 g), and the mixture was stirred at 20° C. for 1 hr. To the mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (methanol/dichloromethane) to give the title compound (300 mg).

MS: [M+Na]$^+$331.9.

J) N-(4-(2-(6-(3-(cyclopropylmethoxy)phenoxy)pyridin-3-yl)-1,3-oxazol-5-yl)-4-hydroxybutan-2-yl)acetamide To a mixture of N-(4-(2-(6-chloropyridin-3-yl)-1,3-oxazol-5-yl)-4-hydroxybutan-2-yl)acetamide (300 mg) and DMF (8 ml) were added 3-(cyclopropylmethoxy)phenol (99 mg) and cesium carbonate (293 mg). The mixture was stirred at 70° C. for 12 hr. The mixture was cooled to 20° C., water was added thereto, and the mixture was extracted with ethyl acetate. The obtained organic layer was washed with saturated brine, dried over anhydrous sodium sulfate, and concentrated under reduced pressure. The obtained residue was purified by silica gel column chromatography (methanol/dichloromethane) to give the title compound (50 mg).

MS: [M+H]+ 438.1.

K) N-(4-(2-(6-(3-(cyclopropylmethoxy)phenoxy)pyridin-3-yl)-1,3-oxazol-5-yl)-4-oxobutan-2-yl)acetamide To a mixture of N-(4-(2-(6-(3-(cyclopropylmethoxy)phenoxy)pyridin-3-yl)-1,3-oxazol-5-yl)-4-hydroxybutan-2-yl)acetamide (50 mg) and dichloromethane (10 ml) was added manganese dioxide (84 mg), and the mixture was stirred at 40° C. for 24 hr. The mixture was cooled to 30° C., methanol was added thereto, and the mixture was filtered. The obtained residue was washed with dichloromethane. The filtrate was concentrated under reduced pressure. The obtained residue was purified by HPLC (water/acetonitrile, addition of 0.1% aqueous ammonia) to give the title compound (10 mg).

$^1$H NMR (400 MHz, DMSO-d$_6$) δ 0.25-0.35 (2H, m), 0.50-0.61 (2H, m), 1.12 (3H, d, J=6.8 Hz), 1.15-1.25 (1H, m), 1.74 (3H, s), 2.85-2.95 (1H, m), 2.96-3.10 (1H, m), 3.81 (2H, d, J=6.8 Hz), 4.10-4.25 (1H, m), 6.70-6.90 (3H, m), 7.19 (1H, d, J=8.8 Hz), 7.34 (1H, t, J=8.0 Hz), 7.90 (1H, d, J=7.6 Hz), 8.31 (1H, s), 8.44 (1H, dd, J=8.8, 2.4 Hz), 8.85 (1H, d, J=2.0 Hz).

Example 106

N-((2S)-1-((2-(6-(3-(cyclopropylmethoxy)phenoxy)-4-methylpyridin-3-yl)-1,3-oxazol-5-yl)oxy)propan-2-yl)acetamide A) (2S)-2-((tert-butoxycarbonyl)amino)propyl N-((6-chloro-4-methylpyridin-3-yl)carbonyl)glycinate To a mixture of 6-chloro-4-methylnicotinic acid (1 g) and THF (20 ml) was added dropwise oxalyl chloride (1.48 g) at 0° C., and then DMF (5 drops) was added thereto. The mixture was stirred at 10-15° C. for 16 hr. The mixture was concentrated under reduced pressure to give the corresponding acid chloride. To a mixture of (2S)-2-((tert-butoxycarbonyl)amino)propyl glycinate (1.58 g) and THF (20 ml) was added triethylamine (2.36 g), and then a mixture of the acid chloride previously obtained and THF (20 ml) was added dropwise thereto under nitrogen atmosphere at 0° C. The reaction mixture was stirred at 10-15° C. for 16 hr. To the reaction mixture was added ethyl acetate, and the mixture was washed successively with water and saturated brine, dried over anhydrous sodium sulfate, and concentrated under reduced pressure. The obtained residue was purified by silica gel column chromatography (ethyl acetate/petroleum ether) to give the title compound (1 g).

$^1$H NMR (400 MHz, DMSO-d$_6$) δ 1.03 (3H, d, J=6.8 Hz), 1.37 (9H, s), 2.39 (3H, m), 3.65-3.75 (1H, m), 3.90-4.10 (4H, m), 6.84 (1H, d, J=8.4 Hz), 7.51 (1H, s), 8.35 (1H, s), 9.01 (1H, t, J=5.6 Hz).

B) tert-butyl ((2S)-1-((2-(6-chloro-4-methylpyridin-3-yl)-1,3-oxazol-5-yl)oxy)propan-2-yl)carbamate To a mixture of iodine (1.84 g), triphenylphosphine (1.9 g) and dichloromethane (40 ml) was added triethylamine (1.47 g) under nitrogen atmosphere at 20-25° C., and the mixture was stirred for 30 min. To the mixture was added a mixture of (2S)-2-((tert-butoxycarbonyl)amino)propyl N-((6-chloro-4-methylpyridin-3-yl)carbonyl)glycinate (1.4 g) and dichloromethane (20 ml). The reaction mixture was stirred at 20-25° C. for 16 hr. The mixture was concentrated under reduced pressure. The obtained residue was purified by silica gel column chromatography (ethyl acetate/petroleum ether) to give the title compound (720 mg).

$^1$H NMR (400 MHz, DMSO-d$_6$) δ 1.11 (3H, d, J=6.8 Hz), 1.36 (9H, s), 2.60 (3H, s), 3.80-3.90 (1H, m), 4.00-4.10 (2H, m), 6.60 (1H, s), 7.00 (1H, d, J=8.0 Hz), 7.57 (1H, s), 8.72 (1H, s).

C) tert-butyl ((2S)-1-((2-(6-(3-(cyclopropylmethoxy)phenoxy)-4-methylpyridin-3-yl)-1,3-oxazol-5-yl)oxy)propan-2-yl)carbamate A mixture of tert-butyl ((2S)-1-((2-(6-chloro-4-methylpyridin-3-yl)-1,3-oxazol-5-yl)oxy)propan-2-yl)carbamate (200 mg), 3-(cyclopropylmethoxy)phenol (134 mg), copper (I) iodide (10 mg), pyridine-2-carboxylic acid (13 mg), tripotassium phosphate (231 mg) and DMSO (3 ml) was stirred under nitrogen atmosphere at 80-90° C. for 16 hr. This reaction was again performed under the same condition, and the obtained mixtures were combined. To the mixture was added water, and the mixture was extracted with ethyl acetate. The obtained organic layer was dried over anhydrous sodium sulfate, and concentrated under reduced pressure. The obtained residue was purified by silica gel column chromatography (ethyl acetate/petroleum ether), and then purified by HPLC (water/acetonitrile) to give the title compound (20 mg).

$^1$H NMR (400 MHz, CDCl$_3$) δ 0.30-0.40 (2H, m), 0.60-0.70 (2H, m), 1.25-1.35 (4H, m), 1.32 (9H, s), 2.64 (3H, s), 3.79 (2H, d, J=7.2 Hz), 4.00-4.10 (3H, m), 4.70 (1H, brs), 6.26 (1H, s), 6.65-6.75 (4H, m), 7.29 (1H, t, J=8.4 Hz), 8.64 (1H, s).

D) N-((2S)-1-((2-(6-(3-(cyclopropylmethoxy)phenoxy)-4-methylpyridin-3-yl)-1,3-oxazol-5-yl)oxy)propan-2-yl)acetamide A mixture of tert-butyl ((2S)-1-((2-(6-(3-(cyclopropylmethoxy)phenoxy)-4-methylpyridin-3-yl)-1,3-oxazol-5-yl)

oxy)propan-2-yl)carbamate (40 mg) and formic acid (2 ml) was stirred at 25-30° C. for 16 hr. The formic acid was removed by blowing nitrogen to the mixture, and then by freeze-drying the mixture. To a mixture of the obtained residue and pyridine (1 ml) was added acetic anhydride (17 mg), and the mixture was stirred at 25-30° C. for 16 hr. The mixture was purified by HPLC (water/acetonitrile) to give the title compound (16 mg).

$^1$H NMR (400 MHz, CDCl$_3$) δ 0.30-0.40 (2H, m), 0.60-0.70 (2H, m), 1.20-1.30 (1H, m), 1.32-1.42 (3H, m), 2.01 (3H, s), 2.64 (3H, s), 3.79 (2H, d, J=6.8 Hz). 4.05-4.15 (2H, m), 4.35-4.55 (1H, m), 5.65-5.85 (1H, m), 6.26-6.29 (1H, m), 6.65-6.70 (4H, m), 7.29 (1H, t, J=8.0 Hz), 8.63 (1H, s).

Example 111

N-(1-(4-(2-(4-(3-(cyclopropylmethoxy)phenoxy)phenyl)cyclopropyl)phenyl)ethyl)acetamide To a mixture of diethylzinc (1M toluene solution, 4.68 ml) and dichloromethane (5 ml) was added dropwise a mixture of trifluoroacetic acid (534 mg) and dichloromethane (5 ml) under nitrogen atmosphere at 0° C. The mixture was stirred at 0° C. for 20 min, and a mixture of diiodomethane (1.25 g) and dichloromethane (2 ml) was added thereto. The mixture was stirred for 20 min, and a mixture of N-(1-(4-((E)-2-(4-(3-(cyclopropylmethoxy)phenoxy)phenyl)vinyl)phenyl)ethyl)acetamide (400 mg) and dichloromethane (2 ml) was added thereto. The mixture was stirred under nitrogen atmosphere at 6-16° C. for 15 hr. To the reaction mixture was added saturated aqueous ammonium chloride solution, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/petroleum ether), and then purified by SFC (2-propanol/carbon dioxide, addition of 0.1% aqueous ammonia) to give the title compound (41 mg).

$^1$HNMR (400 MHz, DMSO-d$_6$) δ 0.25-0.35 (2H, m), 0.50-0.62 (2H, m), 1.15-1.26 (1H, m), 1.31 (3H, d, J=7.2 Hz), 1.42 (2H, t, J=7.2 Hz), 1.82 (3H, s), 2.10-2.22 (2H, m), 3.78 (2H, d, J=6.8 Hz), 4.80-4.92 (1H, m), 6.45-6.55 (2H, m), 6.65-6.75 (1H, m), 6.94 (2H, d, J=8.4 Hz), 7.11 (2H, d, J=8.4 Hz), 7.15-7.30 (5H, m), 8.24 (1H, d, J=8.0 Hz).

Example 113

4-(1-acetamidoethyl)-N-(6-(3-(cyclopropylmethoxy)phenoxy)pyridin-3-yl)-N-methylbenzamide A) 2-(3-(benzyloxy)phenoxy)-5-nitropyridine A mixture of 3-(benzyloxy)phenol (1.389 g), 2-chloro-5-nitropyridine (1 g), cesium carbonate (3.08 g) and DMF (15 ml) was stirred at 60° C. for 4 hr. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (2 g).

$^1$HNMR (300 MHz, DMSO-d$_6$) δ 5.11 (2H, s), 6.81 (1H, ddd, J=8.1, 2.1, 0.8 Hz), 6.89-7.01 (2H, m), 7.20-7.26 (1H, m), 7.32-7.49 (6H, m), 8.62 (1H, dd, J=9.1, 2.9 Hz), 9.04 (1H, d, J=2.5 Hz).

B) 4-acetyl-N-(6-(3-hydroxyphenoxy)pyridin-3-yl)benzamide

A mixture of 2-(3-(benzyloxy)phenoxy)-5-nitropyridine (2 g), 10% palladium on carbon (50% hydrous, 0.33 g) and THF (30 ml) was stirred under hydrogen atmosphere at room temperature for 4 hr. The mixture was filtered through Celite, and the filtrate was concentrated under reduced pressure. A mixture of the obtained residue, 4-acetyl benzoic acid (1.019 g), HATU (2.83 g), N,N-diisopropylethylamine (1.627 ml) and DMF (15 ml) was stirred overnight at room temperature. The mixture was extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (1.19 g).

$^1$HNMR (300 MHz, DMSO-d$_6$) δ 2.65 (3H, s), 6.43-6.55 (2H, m), 6.56-6.66 (1H, m), 6.98-7.09 (1H, m), 7.12-7.24 (1H, m), 8.10 (4H, s), 8.17-8.27 (1H, m), 8.49-8.60 (1H, m), 9.55-9.65 (1H, m), 10.52-10.64 (1H, m).

C) 4-acetyl-N-(6-(3-(cyclopropylmethoxy)phenoxy)pyridin-3-yl)benzamide

A mixture of 4-acetyl-N-(6-(3-hydroxyphenoxy)pyridin-3-yl)benzamide (1.19 g), (bromomethyl)cyclopropane (0.992 g), potassium carbonate (1.416 g) and DMF (10 ml) was stirred at 80° C. for 2 hr. The mixture was allowed to cool to room temperature, and extracted with ethyl acetate and water. The obtained organic layer was washed with saturated brine, dried over magnesium sulfate, and concentrated under reduced pressure. The obtained residue was purified by silica gel column chromatography (ethyl acetate/hexane) to give the title compound (0.56 g).

$^1$HNMR (300 MHz, DMSO-d$_6$) δ 0.27-0.35 (2H, m), 0.51-0.61 (2H, m), 1.14-1.29 (1H, m), 2.65 (3H, s), 3.80 (2H, d, J=7.0 Hz), 6.60-6.69 (2H, m), 6.73-6.80 (1H, m), 7.02-7.10 (1H, m), 7.24-7.34 (1H, m), 8.04-8.16 (4H, m), 8.18-8.27 (1H, m), 8.49-8.56 (1H, m), 10.55-10.63 (1H, m).

D) 4-(1-acetamidoethyl)-N-(6-(3-(cyclopropylmethoxy)phenoxy)pyridin-3-yl)-N-methylbenzamide To a mixture of sodium hydride (60% in oil, 59.6 mg) and THF (5 ml) was added 4-acetyl-N-(6-(3-(cyclopropylmethoxy)phenoxy)pyridin-3-yl)benzamide (300 mg) under ice-cooling. The mixture was stirred at 0° C. for 30 min, and methyl iodide (0.093 ml) was added thereto. The mixture was stirred at room temperature for 1 hr, and extracted with ethyl acetate and water. The obtained organic layer was washed with saturated brine, dried over magnesium sulfate, and concentrated under reduced pressure. A mixture of the obtained residue, ammonium acetate (1.156 g), sodium cyanoborohydride (0.471 g) and methanol (20 ml) was stirred overnight at 60° C. The mixture was allowed to cool to room temperature, and extracted with ethyl acetate and water. The obtained organic layer was washed with saturated brine, dried over magnesium sulfate, and concentrated under reduced pressure. A mixture of the obtained residue, acetic anhydride (0.708 ml) and pyridine (2 ml) was stirred at room temperature for 30 min. The mixture was concentrated under reduced pressure. The obtained residue was purified by silica gel column chromatography (NH, ethyl acetate/hexane) to give the title compound (50 mg).

$^1$HNMR (300 MHz, DMSO-d$_6$) δ 0.30 (2H, dd, J=4.7, 1.5 Hz), 0.49-0.59 (2H, m), 1.19-1.23 (1H, m), 1.27 (3H, d, J=7.1 Hz), 1.82 (3H, s), 3.34 (3H, s), 3.78 (2H, d, J=7.1 Hz), 4.77-4.92 (1H, m), 6.52-6.58 (1H, m), 6.61 (1H, s), 6.75 (1H, dd, J=8.0, 2.7 Hz), 6.96 (1H, d, J=8.8 Hz), 7.15-7.30 (5H, m), 7.79 (1H, dd, J=8.7, 2.8 Hz), 7.88-7.96 (1H, m), 8.26 (1H, d, J=8.0 Hz).

The compounds of Examples 1 to 16, 18, 20 to 27, 29, 31, 33, 34, 36 to 38, 40, 41, 47, 49 to 63, 65, 66, 70 to 72, 74 to 77, 79 to 81, 84 to 88, 90 to 98, 100, 107 to 110, 112, 114 and 115 in the following tables were produced according to the methods described in the above-mentioned Examples, or methods analogous thereto. The compounds of Examples are shown in the following tables. MS in the tables means actual measured value.

TABLE 1-1

| Ex. No. | IUPACNAME | STRUCTURE | ADDITIVE | MS |
|---|---|---|---|---|
| 1 | N-(1-(4-((5-(3-(cyclopropylmethoxy)phenoxy)pyridin-2-yl)methoxy)phenyl)ethyl)acetamide | 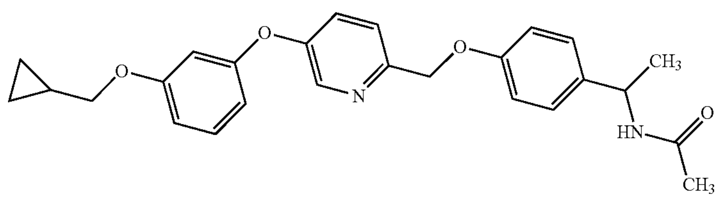 | | 433.1 |
| 2 | N-(1-(3-((5-(3-(cyclopropylmethoxy)phenoxy)pyridin-2-yl)methoxy)phenyl)ethyl)acetamide | 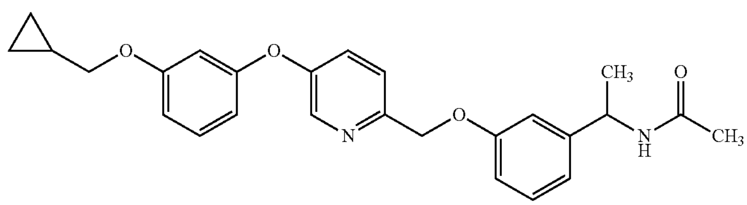 [SMILES: CC(=O)NC(C)c1cccc(OCc2ccc(Oc3cccc(OCC4CC4)c3)cn2)c1] | | 433.1 |
| 3 | N-(1-(4-((5-(3-(cyclopropylmethoxy)phenoxy)pyridin-2-yl)methoxy)-3-methylphenyl)ethyl)acetamide | 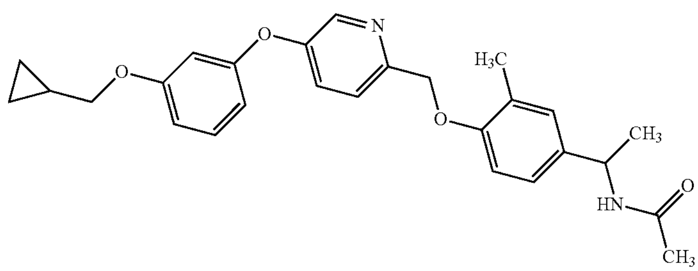 [SMILES: CC(=O)NC(C)c1ccc(OCc2ccc(Oc3cccc(OCC4CC4)c3)cn2)c(C)c1] | | 447.1 |
| 4 | N-(1-(4-((5-(3-(cyclopropylmethoxy)phenoxy)pyridin-2-yl)methoxy)-3-fluorophenyl)ethyl)acetamide | 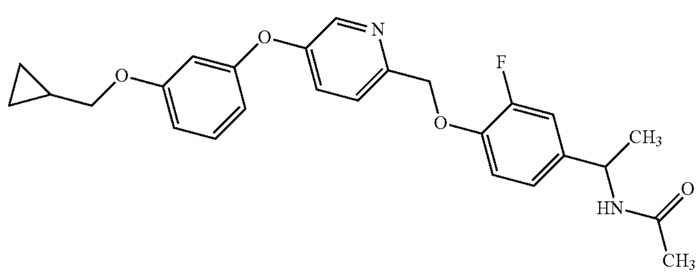 [SMILES: CC(=O)NC(C)c1ccc(OCc2ccc(Oc3cccc(OCC4CC4)c3)cn2)c(F)c1] | | 451.1 |
| 5 | N-(1-(4-((5-(3-(cyclopropylmethoxy)phenoxy)pyridin-2-yl)methoxy)-2-methylphenyl)ethyl)acetamide | 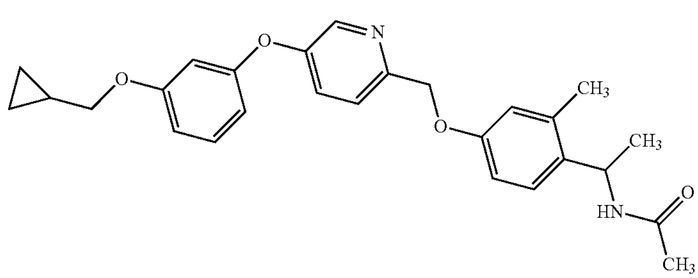 [SMILES: CC(=O)NC(C)c1ccc(OCc2ccc(Oc3cccc(OCC4CC4)c3)cn2)cc1C] | | 447.1 |

TABLE 1-1-continued

| Ex. No. | IUPACNAME | STRUCTURE | ADDITIVE | MS |
|---|---|---|---|---|
| 6 | N-(1-(4-((5-(3-(cyclopropylmethoxy)phenoxy)pyridin-2-yl)methoxy)-3-methoxyphenyl)ethyl)acetamide | 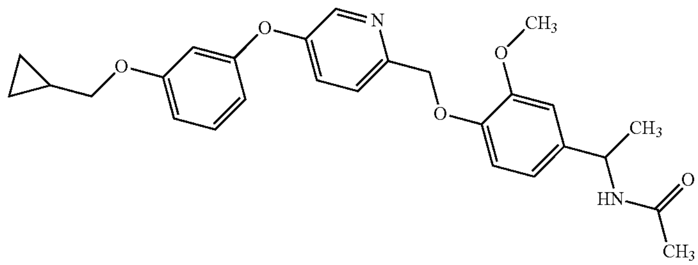 [SMILES: COc1cc(C(C)NC(C)=O)ccc1OCc1ccc(Oc2cccc(OCC3CC3)c2)cn1] | | 463.1 |
| 7 | N-(1-(4-((5-(3-(cyclopropylmethoxy)phenoxy)pyridin-2-yl)methoxy)-2-fluorophenyl)ethyl)acetamide | 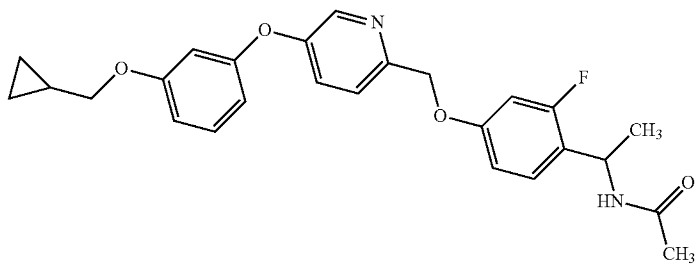 [SMILES: CC(=O)NC(C)c1ccc(OCc2ccc(Oc3cccc(OCC4CC4)c3)cn2)cc1F] | | 451.1 |
| 8 | N-(1-(6-((5-(3-(cyclopropylmethoxy)phenoxy)pyridin-2-yl)methoxy)pyridin-3-yl)ethyl)acetamide | 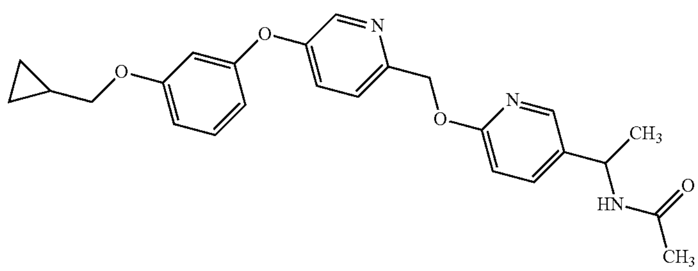 [SMILES: CC(=O)NC(C)c1ccc(OCc2ccc(Oc3cccc(OCC4CC4)c3)cn2)nc1] | | 434.2 |
| 9 | N-(1-(4-((6-(3-(cyclopropylmethoxy)phenoxy)pyridin-3-yl)methoxy)phenyl)ethyl)acetamide | 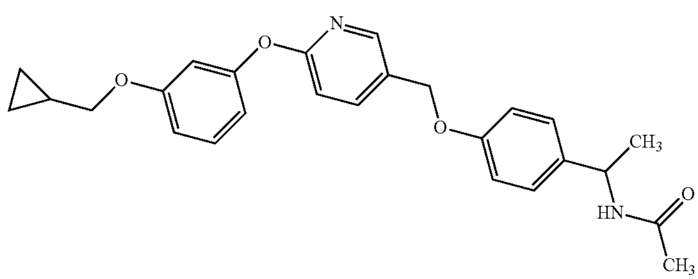 [SMILES: CC(=O)NC(C)c1ccc(OCc2ccc(Oc3cccc(OCC4CC4)c3)nc2)cc1] | | 433.1 |
| 10 | N-(1-(3-chloro-4-((5-(3-(cyclopropylmethoxy)phenoxy)pyridin-2-yl)methoxy)phenyl)ethyl)acetamide | 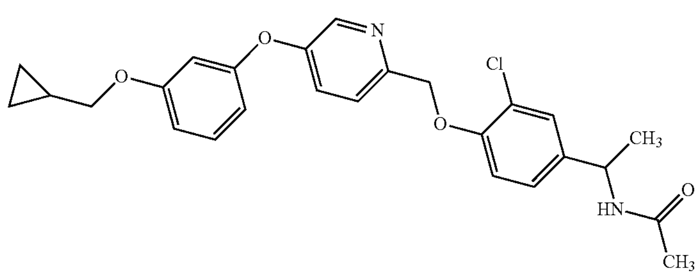 [SMILES: CC(=O)NC(C)c1ccc(OCc2ccc(Oc3cccc(OCC4CC4)c3)cn2)c(Cl)c1] | | 467.1 |

TABLE 1-2

| Ex. No. | IUPAC NAME | STRUCTURE | ADDITIVE | MS |
|---|---|---|---|---|
| 11 | N-(1-(4-((4-(3-(cyclopropylmethoxy)phenoxy)-2-methylbenzyl)oxy)phenyl)ethyl)acetamide | 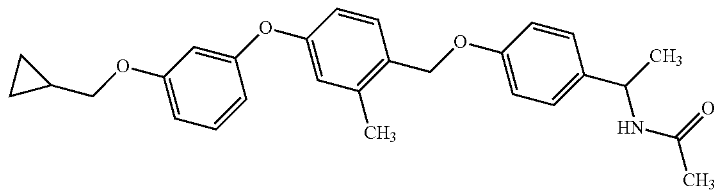 | | 446.2 |
| 12 | N-(1-(4-((4-(3-(cyclopropylmethoxy)phenoxy)benzyl)oxy)phenyl)ethyl)acetamide | 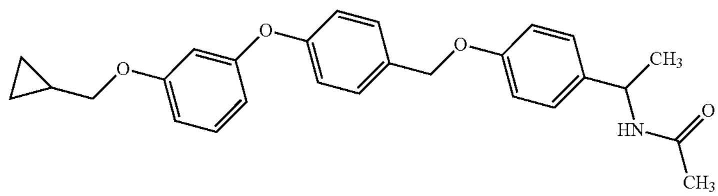 [SMILES: CC(=O)NC(C)c1ccc(OCc2ccc(Oc3cccc(OCC4CC4)c3)cc2)cc1] | | 432.1 |
| 13 | N-(1-(4-((4-(3-(cyclopropylmethoxy)phenoxy)phenoxy)methyl)phenyl)ethyl)acetamide | 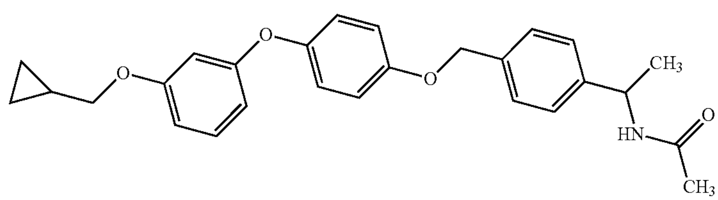 [SMILES: CC(=O)NC(C)c1ccc(COc2ccc(Oc3cccc(OCC4CC4)c3)cc2)cc1] | | 432.1 |
| 14 | N-(1-(5-((5-(3-(cyclopropylmethoxy)phenoxy)pyridin-2-yl)methoxy)pyridin-2-yl)ethyl)acetamide | 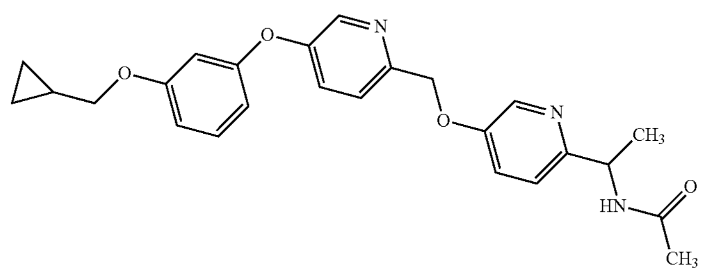 [SMILES: CC(=O)NC(C)c1ccc(OCc2ccc(Oc3cccc(OCC4CC4)c3)cn2)cn1] | | 434.1 |
| 15 | N-(1-(4-((2-chloro-4-(3-(cyclopropylmethoxy)phenoxy)benzyl)oxy)phenyl)ethyl)acetamide | 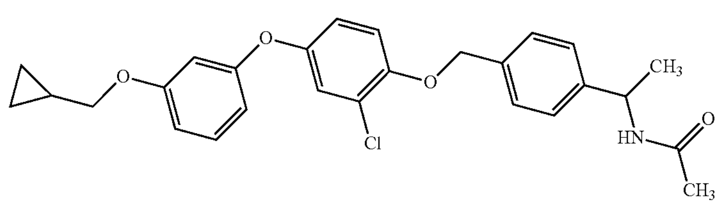 [SMILES: CC(=O)NC(C)c1ccc(COc2ccc(Oc3cccc(OCC4CC4)c3)cc2Cl)cc1] | | 466.2 |
| 16 | N-(1-(4-((4-(3-(cyclopropylmethoxy)phenoxy)cyclohexyl)methoxy)phenyl)ethyl)acetamide | 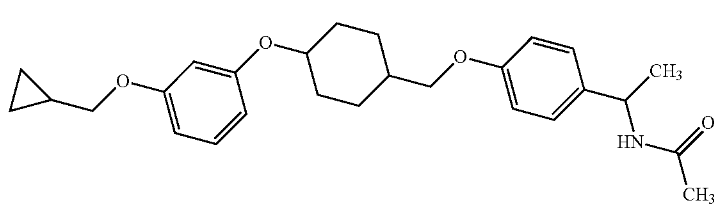 [SMILES: CC(=O)NC(C)c1ccc(OCC2CCC(Oc3cccc(OCC4CC4)c3)CC2)cc1] | | 438.2 |

TABLE 1-2-continued

| Ex. No. | IUPACNAME | STRUCTURE | ADDITIVE | MS |
|---|---|---|---|---|
| 17 | N-(1-(4-(2-(4-(3-(cyclopropylmethoxy)phenoxy)phenyl)ethyl)phenyl)ethyl)acetamide | 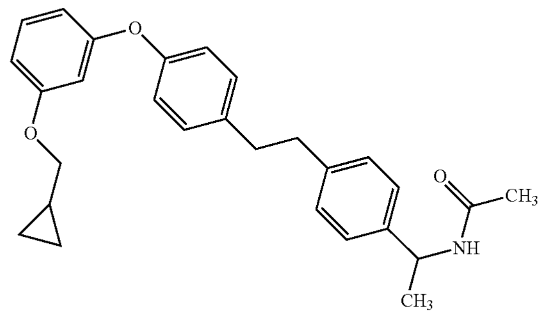 [SMILES: CC(=O)NC(C)c1ccc(CCc2ccc(Oc3cccc(OCC4CC4)c3)cc2)cc1] | | 430.1 |
| 18 | N-(1-(4-((5-(3-(cyclopropylmethoxy)phenoxy)pyridin-2-yl)methoxy)-3-(trifluoromethyl)phenyl)ethyl)acetamide | 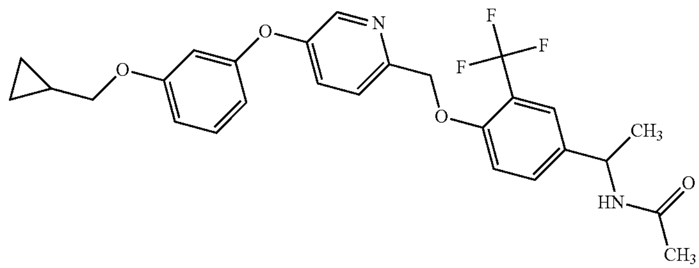 [SMILES: CC(=O)NC(C)c1ccc(OCc2ccc(Oc3cccc(OCC4CC4)c3)cn2)c(C(F)(F)F)c1] | | 501.2 |
| 19 | N-(1-(4-((4-(3-(cyclopropylmethoxy)phenoxy)-2-fluorobenzyl)oxy)phenyl)ethyl)acetamide | 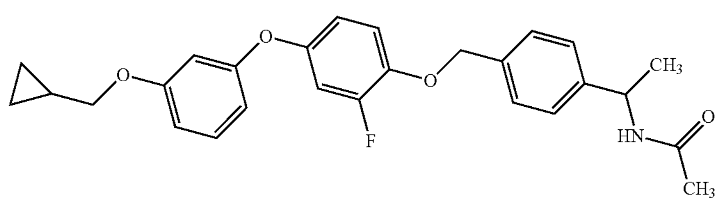 [SMILES: CC(=O)NC(C)c1ccc(COc2ccc(Oc3cccc(OCC4CC4)c3)cc2F)cc1] | | 450.1 |
| 20 | N-(1-(3-((4-(3-(cyclopropylmethoxy)phenoxy)benzyl)oxy)phenyl)ethyl)acetamide | 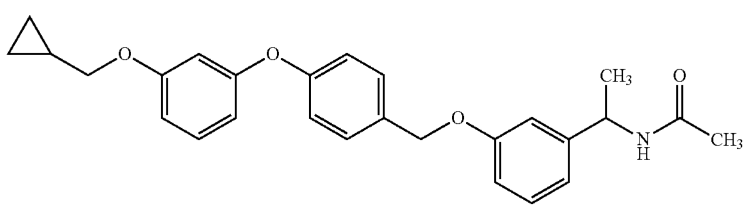 [SMILES: CC(=O)NC(C)c1cccc(OCc2ccc(Oc3cccc(OCC4CC4)c3)cc2)c1] | | 432.1 |

TABLE 1-3

| Ex. No. | IUPACNAME | STRUCTURE | ADDITIVE | MS |
|---|---|---|---|---|
| 21 | N-(1-(4-(2-(4-(3-(cyclopropylmethoxy)phenoxy)phenyl)propyl)phenyl)ethyl)acetamide | 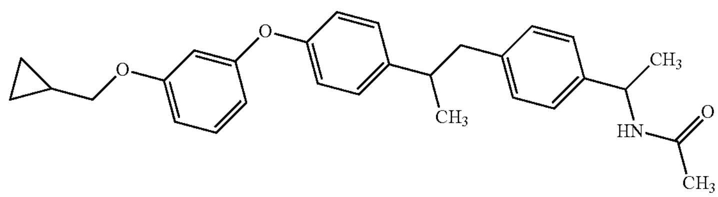 [SMILES: CC(=O)NC(C)c1ccc(CC(C)c2ccc(Oc3cccc(OCC4CC4)c3)cc2)cc1] | | 444.3 |

TABLE 1-3-continued

| Ex. No. | IUPACNAME | STRUCTURE | ADDITIVE | MS |
|---|---|---|---|---|
| 22 | N-(1-(4-((4-(3-(cyclopropylmethoxy)phenoxy)benzyl)oxy)-2-fluorophenyl)ethyl)acetamide | 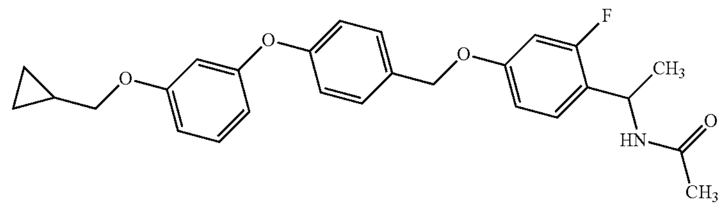 [SMILES: CC(=O)NC(C)c1ccc(OCc2ccc(Oc3cccc(OCC4CC4)c3)cc2)cc1F] | | 450.1 |
| 23 | N-(1-(3-((4-(3-(cyclopropylmethoxy)phenoxy)benzyl)oxy)-2-fluorophenyl)ethyl)acetamide | 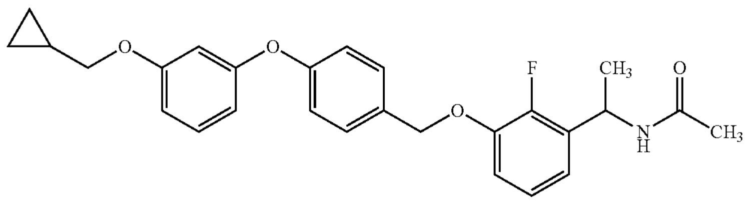 [SMILES: CC(=O)NC(C)c1cccc(OCc2ccc(Oc3cccc(OCC4CC4)c3)cc2)c1F] | | 450.1 |
| 24 | N-(1-(4-((4-(3-(cyclopropylmethoxy)phenoxy)-2-fluorobenzyl)oxy)-2-fluorophenyl)ethyl)acetamide | 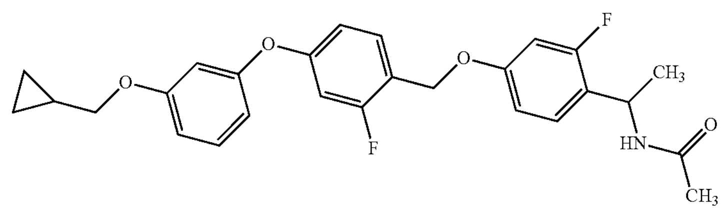 [SMILES: CC(=O)NC(C)c1ccc(OCc2ccc(Oc3cccc(OCC4CC4)c3)cc2F)cc1F] | | 468.1 |
| 25 | N-(1-(6-((5-(3-(cyclopropylmethoxy)phenoxy)pyridin-2-yl)methoxy)-5-methylpyridin-3-yl)ethyl)acetamide | 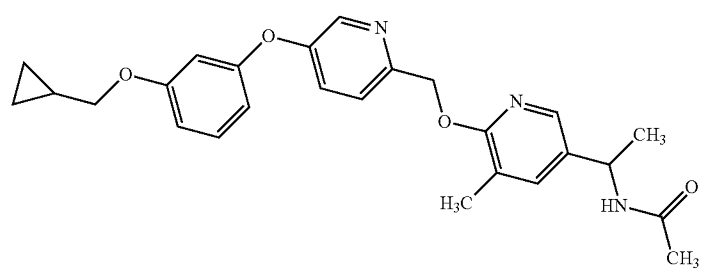 [SMILES: CC(=O)NC(C)c1cnc(OCc2ccc(Oc3cccc(OCC4CC4)c3)cn2)c(C)c1] | | 448.1 |
| 26 | N-(1-(4-((2-cyano-4-(3-(cyclopropylmethoxy)phenoxy)benzyl)oxy)phenyl)ethyl)acetamide | 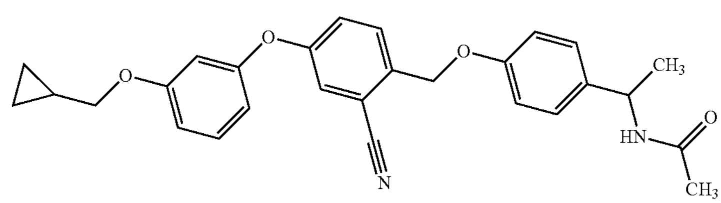 [SMILES: CC(=O)NC(C)c1ccc(OCc2ccc(Oc3cccc(OCC4CC4)c3)cc2C#N)cc1] | | 457.1 |
| 27 | N-(1-(4-((4-((5-(cyclopropylmethoxy)pyridin-3-yl)oxy)-2-fluorobenzyl)oxy)phenyl)ethyl)acetamide | 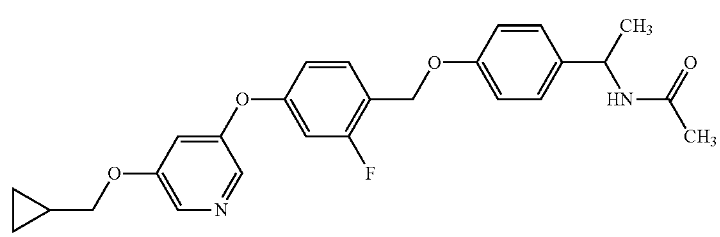 | | 451.1 |
| 28 | N-((2S)-1-((4'-(3-(cyclopropylmethoxy)phenoxy)biphenyl-4-yl)oxy)propan-2-yl)acetamide | 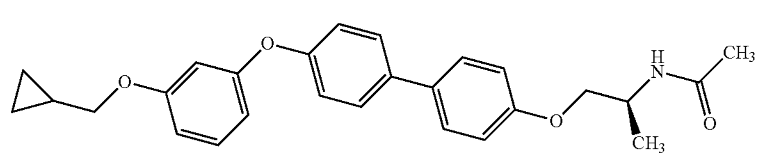 [SMILES: CC(=O)N[C@@H](C)COc1ccc(-c2ccc(Oc3cccc(OCC4CC4)c3)cc2)cc1] | | 432.3 |

TABLE 1-3-continued

| Ex. No. | IUPACNAME | STRUCTURE | ADDITIVE | MS |
|---|---|---|---|---|
| 29 | N-((2S)-1-((4'-(3-(cyclopropylmethoxy)phenoxy)biphenyl-3-yl)oxy)propan-2-yl)acetamide | 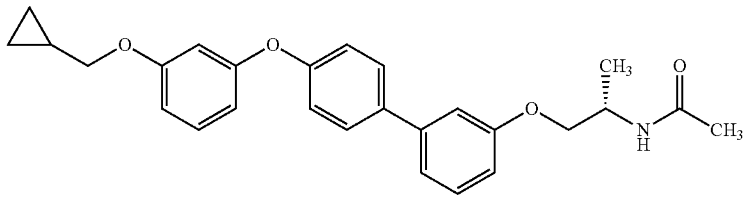 [SMILES: CC(=O)N[C@@H](C)COc1cccc(-c2ccc(Oc3cccc(OCC4CC4)c3)cc2)c1] | | 432.1 |
| 30 | N-((2S)-1-((2-(4-(3-(cyclopropylmethoxy)phenoxy)phenyl)-1,3-oxazol-5-yl)oxy)propan-2-yl)acetamide | 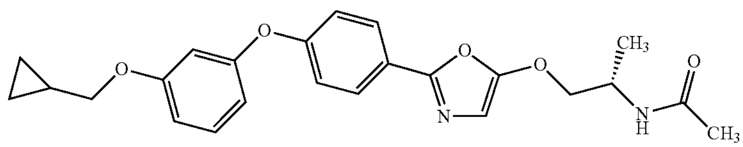 [SMILES: CC(=O)N[C@@H](C)COc1cnc(-c2ccc(Oc3cccc(OCC4CC4)c3)cc2)o1] | | 423.2 |

TABLE 1-4

| Ex. No. | IUPACNAME | STRUCTURE | ADDITIVE | MS |
|---|---|---|---|---|
| 31 | N-((2R)-1-((2-(4-(3-(cyclopropylmethoxy)phenoxy)phenyl)-1,3-oxazol-5-yl)oxy)propan-2-yl)acetamide | 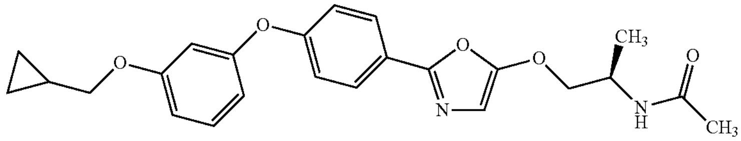 [SMILES: CC(=O)N[C@H](C)COc1cnc(-c2ccc(Oc3cccc(OCC4CC4)c3)cc2)o1] | | 423.1 |
| 32 | N-(4-(2-(4-(3-(cyclopropylmethoxy)phenoxy)phenyl)-1,3-oxazol-5-yl)butan-2-yl)acetamide | 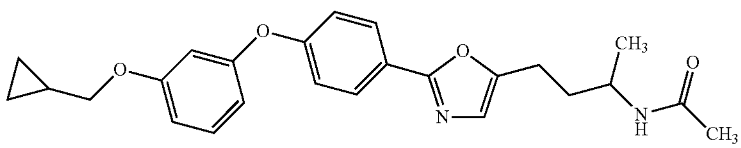 [SMILES: CC(=O)NC(C)CCc1cnc(-c2ccc(Oc3cccc(OCC4CC4)c3)cc2)o1] | | 421.2 |
| 33 | N-(4-(3-(5-(3-(cyclopropylmethoxy)phenoxy)pyridin-2-yl)-1,2,4-oxadiazol-5-yl)butan-2-yl)acetamide | 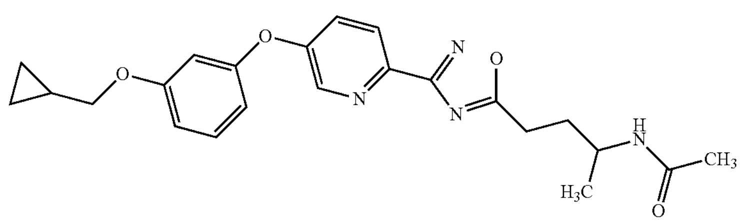 [SMILES: CC(=O)NC(C)CC/C(O)=N/C(=N)c1ccc(Oc2cccc(OCC3CC3)c2)cn1] | | 423.1 |
| 34 | N-(1-(2-((4-(3-(cyclopropylmethoxy)phenoxy)-2-fluorobenzyl)oxy)pyrimidin-5-yl)ethyl)acetamide | 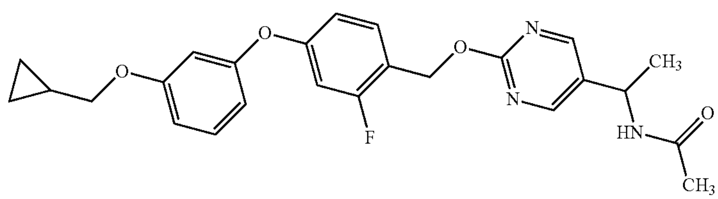 | | 452.2 |
| 35 | N-(1-(5-((4-(3-(cyclopropylmethoxy)phenoxy)-2-fluorobenzyl)oxy)pyrazin-2-yl)ethyl)acetamide | 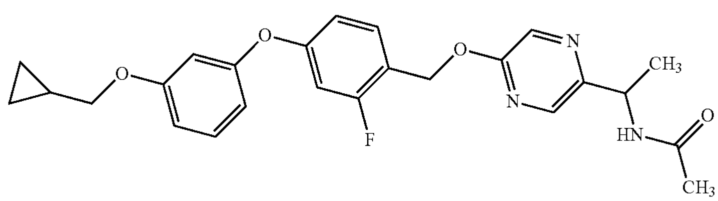 | | 452.1 |

TABLE 1-4-continued

| Ex. No. | IUPACNAME | STRUCTURE | ADDITIVE | MS |
|---|---|---|---|---|
| 36 | N-((2S)-1-((6-(4-(3-(cyclopropylmethoxy)phenoxy)phenyl)pyridin-3-yl)oxy)propan-2-yl)acetamide | 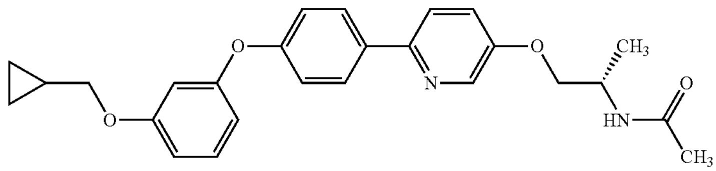 [SMILES: CC(=O)N[C@@H](C)COc1ccc(-c2ccc(Oc3cccc(OCC4CC4)c3)cc2)nc1] | | 433.0 |
| 37 | N-((2S)-1-((2-(4-(3-(cyclopropylmethoxy)phenoxy)phenyl)pyrimidin-5-yl)oxy)propan-2-yl)acetamide | 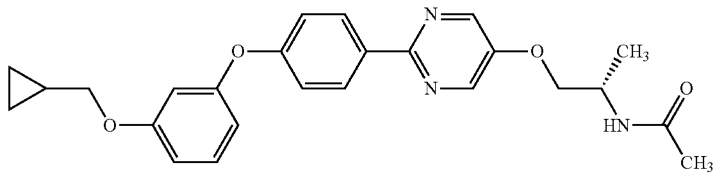 [SMILES: CC(=O)N[C@@H](C)COc1cnc(-c2ccc(Oc3cccc(OCC4CC4)c3)cc2)nc1] | | 434.2 |
| 38 | N-(1-(4-((2-(3-(cyclopropylmethoxy)phenoxy)-1,3-thiazol-5-yl)methoxy)phenyl)ethyl)acetamide | 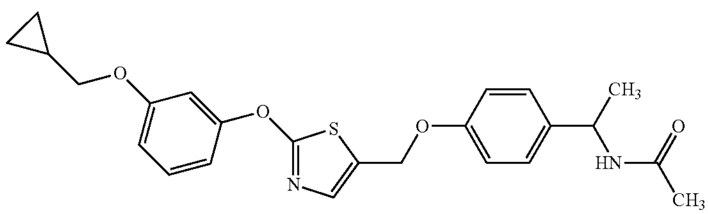 [SMILES: CC(=O)NC(C)c1ccc(OCc2cnc(Oc3cccc(OCC4CC4)c3)s2)cc1] | | 439.1 |
| 39 | N-(1-(4-((4-(3-(cyclopropylmethoxy)phenoxy)-2,6-difluorobenzyl)oxy)phenyl)ethyl)acetamide | 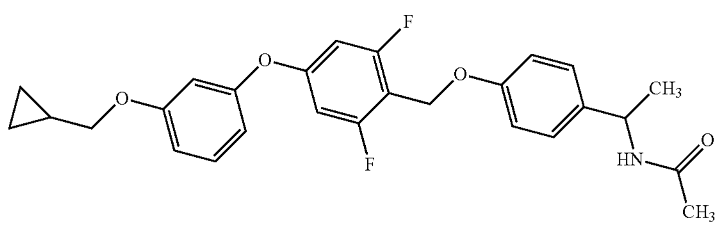 [SMILES: CC(=O)NC(C)c1ccc(OCc2c(F)cc(Oc3cccc(OCC4CC4)c3)cc2F)cc1] | | 468.1 |
| 40 | N-(1-(4-((4-((4-(cyclopropylmethoxy)pyridin-2-yl)oxy)-2-fluorobenzyl)oxy)phenyl)ethyl)acetamide | 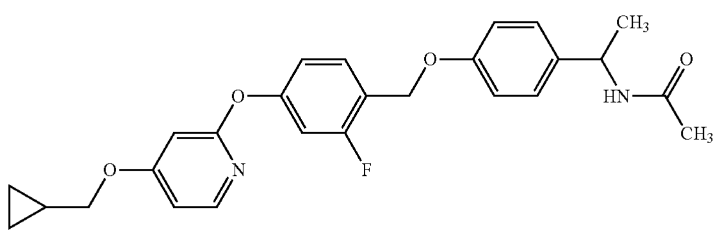 [SMILES: CC(=O)NC(C)c1ccc(OCc2ccc(Oc3cc(OCC4CC4)ccn3)cc2F)cc1] | | 451.1 |

TABLE 1-5

| Ex. No. | IUPACNAME | STRUCTURE | ADDITIVE | MS |
|---|---|---|---|---|
| 41 | N-(4-(1-(4-(3-(cyclopropylmethoxy)phenoxy)phenyl)-1H-pyrazol-4-yl)butan-2-yl)acetamide | 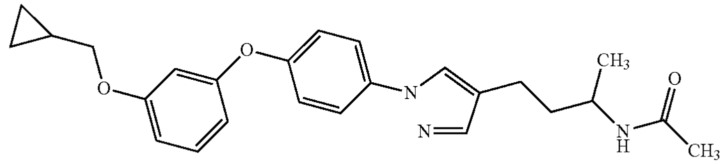 [SMILES: CC(=O)NC(C)CC/C(C=N)=C/Nc1ccc(Oc2cccc(OCC3CC3)c2)cc1] | | 420.2 |

TABLE 1-5-continued

| Ex. No. | IUPACNAME | STRUCTURE | ADDITIVE | MS |
|---|---|---|---|---|
| 42 | N-(1-(6-((4-(3-(cyclopropylmethoxy)phenoxy)-2-fluorobenzyl)oxy)pyridin-3-yl)ethyl)acetamide | 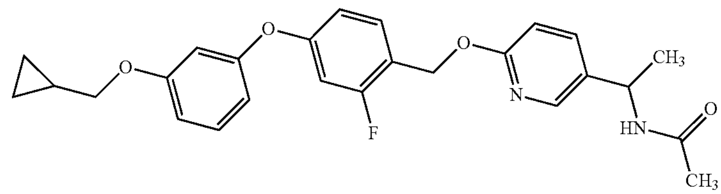 [SMILES: CC(=O)NC(C)c1ccc(OCc2ccc(Oc3cccc(OCC4CC4)c3)cc2F)nc1] | | 451.1 |
| 43 | N-(1-(5-((4-(3-(cyclopropylmethoxy)phenoxy)-2,6-difluorobenzyl)oxy)pyrazin-2-yl)ethyl)acetamide | 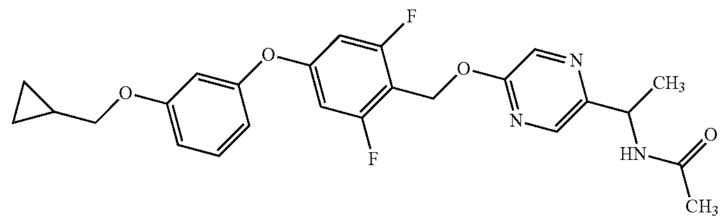 [SMILES: CC(=O)NC(C)c1cnc(OCc2c(F)cc(Oc3cccc(OCC4CC4)c3)cc2F)cn1] | | 470.1 |
| 44 | N-((2S)-1-(4-(5-(3-(cyclopropylmethoxy)phenoxy)-1,3-oxazol-2-yl)phenoxy)propan-2-yl)acetamide | 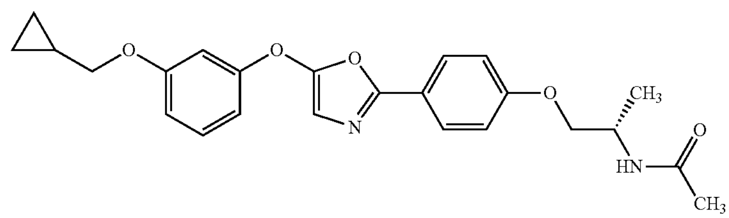 | | 423.1 |
| 45 | N-(1-(((3R)-1-(4-(3-(cyclopropylmethoxy)phenoxy)phenyl)pyrrolidin-3-yl)oxy)propan-2-yl)acetamide | 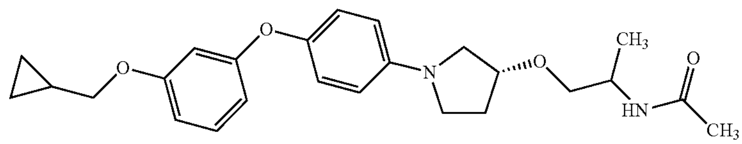 [SMILES: CC(=O)NC(C)CO[C@@H]1CCN(c2ccc(Oc3cccc(OCC4CC4)c3)cc2)C1] | | 425.3 |
| 46 | N-(4-(3-(4-(3-(cyclopropylmethoxy)phenoxy)phenyl)-1,2-oxazol-5-yl)butan-2-yl)acetamide | 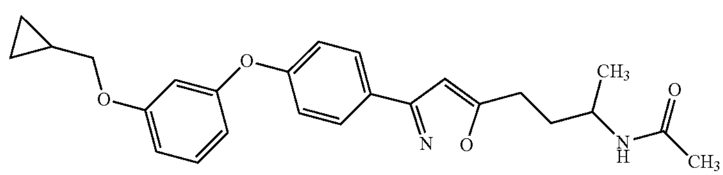 [SMILES: CC(=O)NC(C)CC/C(O)=C/C(=N)c1ccc(Oc2cccc(OCC3CC3)c2)cc1] | | 421.1 |
| 47 | N-((2S)-1-(4-(5-(3-(cyclopropylmethoxy)phenoxy)-1,3-thiazol-2-yl)phenoxy)propan-2-yl)acetamide | 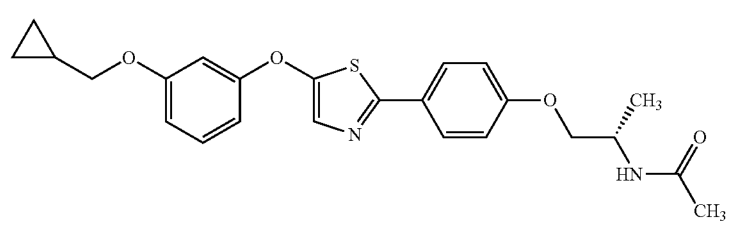 | | 439.1 |
| 48 | N-(4-(1-(4-(3-(cyclopropylmethoxy)phenoxy)phenyl)-1H-pyrazol-3-yl)butan-2-yl)acetamide | 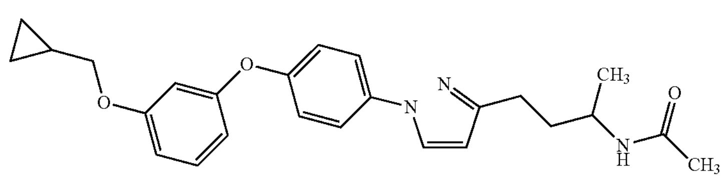 [SMILES: CC(=O)NC(C)CCC(=N)/C=C\Nc1ccc(Oc2cccc(OCC3CC3)c2)cc1] | | 420.2 |
| 49 | N-(1-(4-(2-(6-(3-(cyclopropylmethoxy)phenoxy)pyridin-3-yl)ethyl)phenyl)ethyl)acetamide | 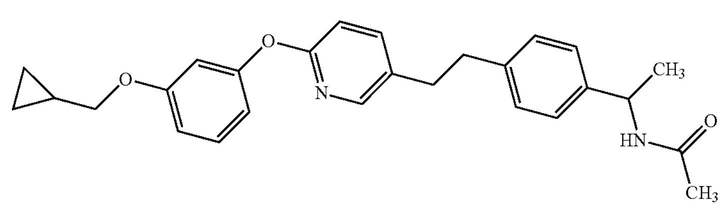 | | 431.2 |

TABLE 1-5-continued

| Ex. No. | IUPACNAME | STRUCTURE | ADDITIVE | MS |
|---|---|---|---|---|
| 50 | N-(1-(4-(2-(6-(3-(cyclopropylmethoxy)phenoxy)-4-methylpyridin-3-yl)ethyl)phenyl)ethyl)acetamide | 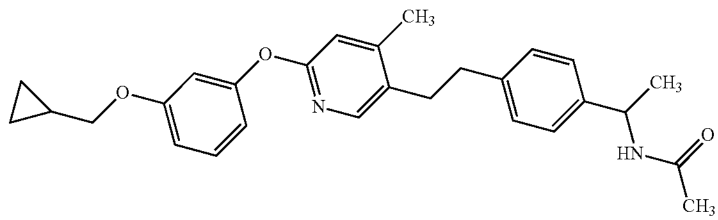 [SMILES: CC(=O)NC(C)c1ccc(CCc2cnc(Oc3cccc(OCC4CC4)c3)cc2C)cc1] | | 445.2 |

TABLE 1-6

| Ex. No. | IUPACNAME | STRUCTURE | ADDITIVE | MS |
|---|---|---|---|---|
| 51 | N-(1-(4-(2-(6-(3-(cyclopropylmethoxy)phenoxy)-2-methylpyridin-3-yl)ethyl)phenyl)ethyl)acetamide | 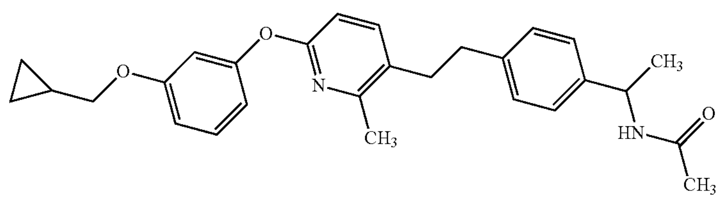 [SMILES: CC(=O)NC(C)c1ccc(CCc2ccc(Oc3cccc(OCC4CC4)c3)nc2C)cc1] | | 445.2 |
| 52 | N-((2S)-1-((2-(4-(3-(((1S)-2,2-difluorocyclopropyl)methoxy)phenoxy)phenyl)-1,3-oxazol-5-yl)oxy)propan-2-yl)acetamide | 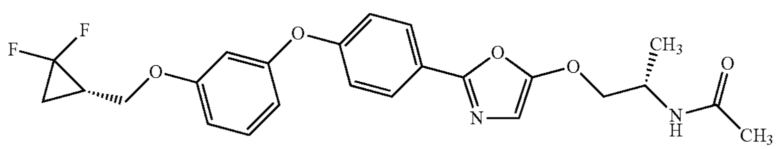 [SMILES: CC(=O)N[C@@H](C)COc1cnc(-c2ccc(Oc3cccc(OC[C@@H]4CC4(F)F)c3)cc2)o1] | | 459.1 |
| 53 | N-(1-(4-(2-(6-(3-(cyclopropylmethoxy)phenoxy)pyridin-3-yl)ethyl)-2-fluorophenyl)ethyl)acetamide | 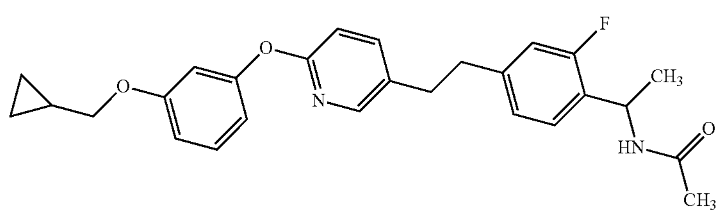 [SMILES: CC(=O)NC(C)c1ccc(CCc2ccc(Oc3cccc(OCC4CC4)c3)nc2)cc1F] | | 449.1 |
| 54 | N-(1-(6-(2-(6-(3-(cyclopropylmethoxy)phenoxy)pyridin-3-yl)ethyl)pyridin-3-yl)ethyl)acetamide | 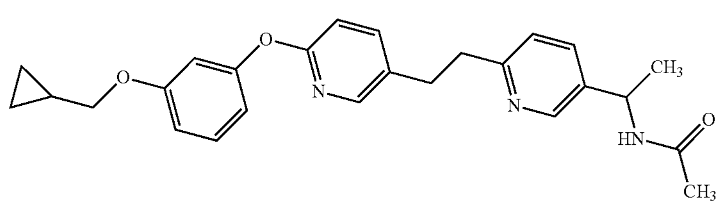 [SMILES: CC(=O)NC(C)c1ccc(CCc2ccc(Oc3cccc(OCC4CC4)c3)nc2)nc1] | | 432.1 |
| 55 | N-((2S)-1-((2-(5-(3-(cyclopropylmethoxy)phenoxy)pyridin-2-yl)-1,3-thiazol-5-yl)oxy)propan-2-yl)acetamide | 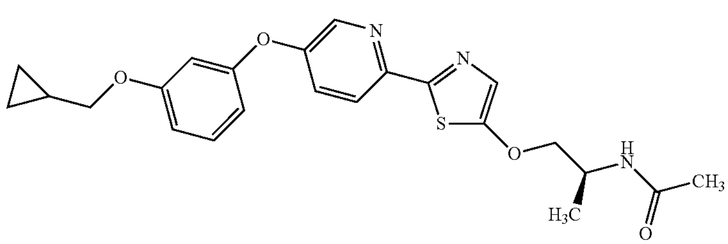 [SMILES: CC(=O)N[C@@H](C)COc1cnc(-c2ccc(Oc3cccc(OCC4CC4)c3)cn2)s1] | | 440.1 |

TABLE 1-6-continued

| Ex. No. | IUPACNAME | STRUCTURE | ADDITIVE | MS |
|---|---|---|---|---|
| 56 | N-(1-((6-(4-(3-(cyclopropylmethoxy)phenoxy)phenyl)pyridazin-3-yl)oxy)propan-2-yl)acetamide | 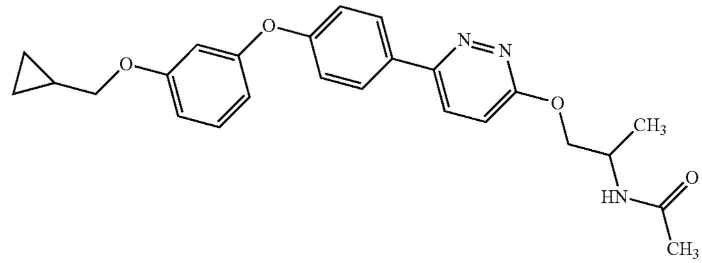 [SMILES: CC(=O)NC(C)COc1ccc(-c2ccc(Oc3cccc(OCC4CC4)c3)cc2)nn1] | | 434.1 |
| 57 | N-(1-((5-(4-(3-(cyclopropylmethoxy)phenoxy)phenyl)pyrimidin-2-yl)oxy)propan-2-yl)acetamide | 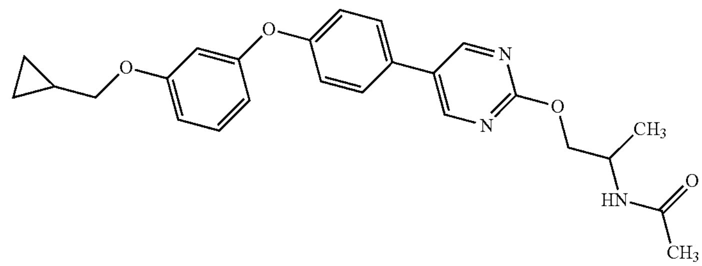 [SMILES: CC(=O)NC(C)COc1ncc(-c2ccc(Oc3cccc(OCC4CC4)c3)cc2)cn1] | | 434.1 |
| 58 | N-((2S)-1-((2-(6-(3-(cyclopropylmethoxy)phenoxy)-4-methylpyridin-3-yl)-1,3-thiazol-5-yl)oxy)propan-2-yl)acetamide | 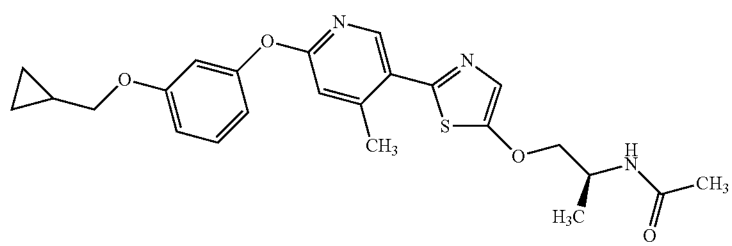 [SMILES: CC(=O)N[C@@H](C)COc1cnc(-c2cnc(Oc3cccc(OCC4CC4)c3)cc2C)s1] | | 454.1 |
| 59 | N-((2S)-1-((2-(4-(3-(cyclopropylmethoxy)phenoxy)phenyl)-1,3-thaizol-5-yl)oxy)propan-2-yl)acetamide | 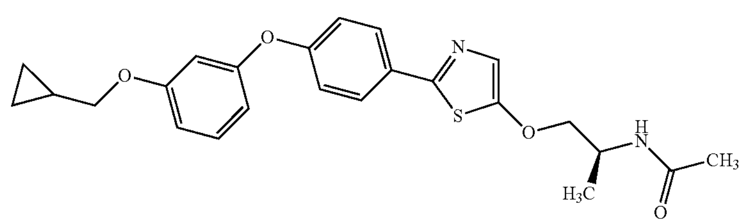 [SMILES: CC(=O)N[C@@H](C)COc1cnc(-c2ccc(Oc3cccc(OCC4CC4)c3)cc2)s1] | | 439.1 |
| 60 | N-((2S)-1-((1-(4-(3-(cyclopropylmethoxy)phenoxy)phenyl)piperidin-4-yl)oxy)propan-2-yl)acetamide | 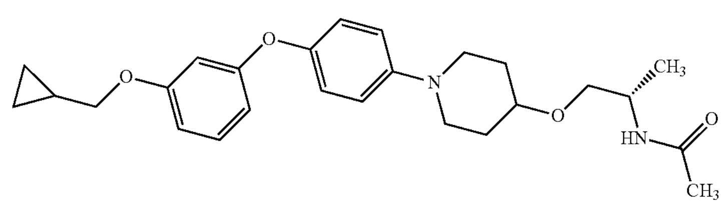 [SMILES: CC(=O)N[C@@H](C)COC1CCN(c2ccc(Oc3cccc(OCC4CC4)c3)cc2)CC1] | | 439.2 |

TABLE 1-7

| Ex. No. | IUPAC NAME | STRUCTURE | ADDITIVE | MS |
|---|---|---|---|---|
| 61 | N-((2S)-1-((2-(2-bromo-4-(3-(cyclopropylmethoxy)phenoxy)phenyl)-1,3-thiazol-5-yl)oxy)propan-2-yl)acetamide | 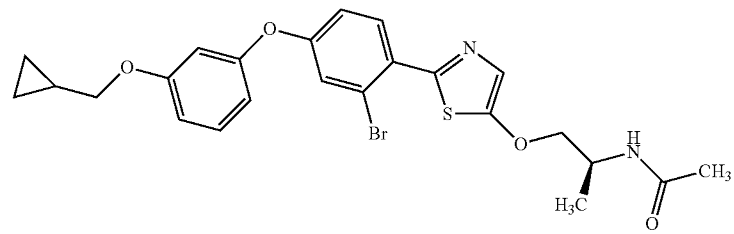 [SMILES: CC(=O)N[C@@H](C)COc1cnc(-c2ccc(Oc3cccc(OCC4CC4)c3)cc2Br)s1] | | 517.0 |
| 62 | N-((2S)-1-((2-(2-cyano-4-(3-(cyclopropylmethoxy)phenoxy)phenyl)-1,3-thiazol-5-yl)oxy)propan-2-yl)acetamide | 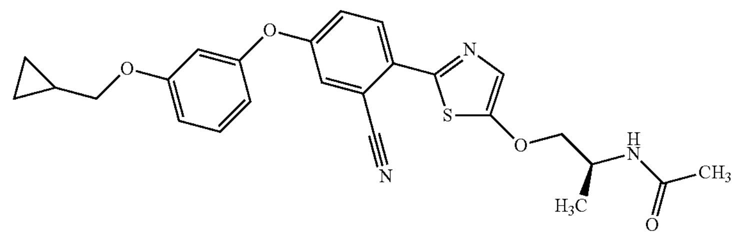 [SMILES: CC(=O)N[C@@H](C)COc1cnc(-c2ccc(Oc3cccc(OCC4CC4)c3)cc2C#N)s1] | | 464.1 |
| 63 | N-(4-(2-(4-(3-(cyclopropylmethoxy)phenoxy)phenyl)-1,3-oxazol-5-yl)-4-hydroxybutan-2-yl)acetamide | 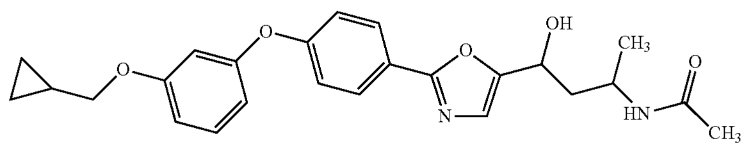 [SMILES: CC(=O)NC(C)CC(O)c1cnc(-c2ccc(Oc3cccc(OCC4CC4)c3)cc2)o1] | | 437.1 |
| 64 | N-(4-(2-(4-(3-(cyclopropylmethoxy)phenoxy)phenyl)-1,3-oxazol-5-yl)-4-oxobutan-2-yl)acetamide | 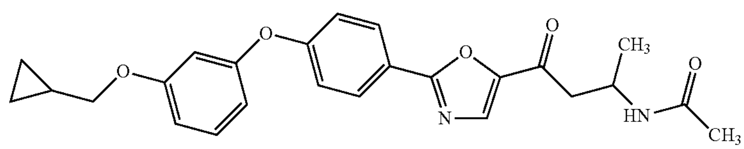 [SMILES: CC(=O)NC(C)CC(=O)c1cnc(-c2ccc(Oc3cccc(OCC4CC4)c3)cc2)o1] | | 435.0 |
| 65 | N-((2S)-1-((2-(6-(3-(cyclopropylmethoxy)phenoxy)pyridazin-3-yl)-1,3-thiazol-5-yl)oxy)propan-2-yl)acetamide | 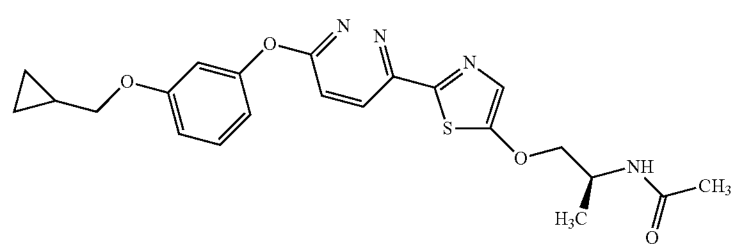 [SMILES: CC(=O)N[C@@H](C)COc1cnc(C(=N)/C=C\C(=N)Oc2cccc(OCC3CC3)c2)s1] | | 441.1 |
| 66 | N-(1-((2-(2-(3-(cyclopropylmethoxy)phenoxy)pyrimidin-5-yl)-1,3-thiazol-5-yl)oxy)propan-2-yl)acetamide | 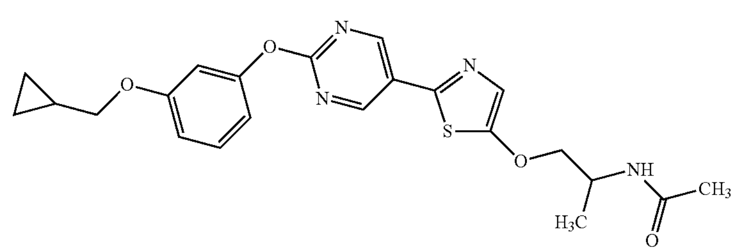 [SMILES: CC(=O)NC(C)COc1cnc(-c2cnc(Oc3cccc(OCC4CC4)c3)nc2)s1] | | 441.1 |
| 67 | N-((2S)-1-((3-(4-(3-(cyclopropylmethoxy)phenoxy)phenyl)-1,2-oxazol-5-yl)oxy)propan-2-yl)acetamide | 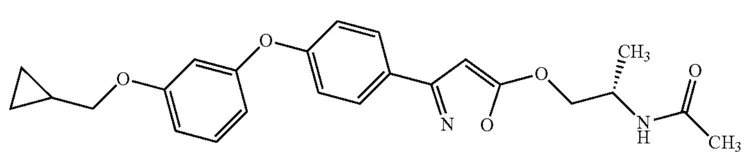 [SMILES: CC(=O)N[C@@H](C)CO/C(O)=C/C(=N)c1ccc(Oc2cccc(OCC3CC3)c2)cc1] | | 423.0 |

TABLE 1-7-continued

| Ex. No. | IUPACNAME | STRUCTURE | ADDITIVE | MS |
|---|---|---|---|---|
| 68 | N-(1-(6-((4-(3-(cyclopropylmethoxy)phenoxy)-2,6-difluorobenzyl)oxy)pyridin-3-yl)ethyl)acetamide | 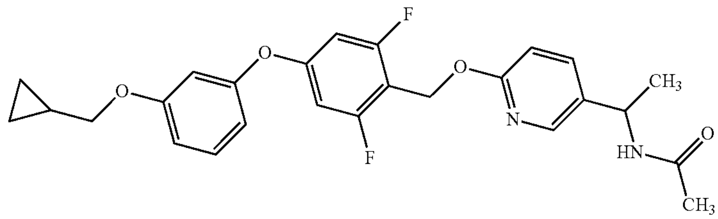 [SMILES: CC(=O)NC(C)c1ccc(OCc2c(F)cc(Oc3cccc(OCC4CC4)c3)cc2F)nc1] | | 469.1 |
| 69 | N-(1-(5-((4-(3-(cyclopropylmethoxy)phenoxy)-2,6-difluorobenzyl)oxy)pyridin-2-yl)ethyl)acetamide | 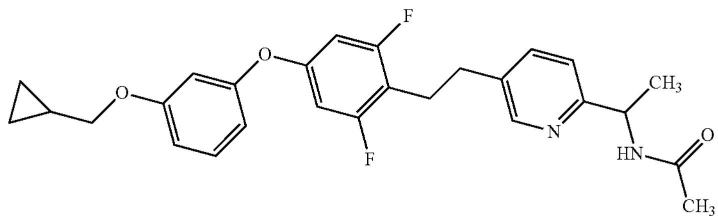 [SMILES: CC(=O)NC(C)c1ccc(CCc2c(F)cc(Oc3cccc(OCC4CC4)c3)cc2F)cn1] | | 469.1 |
| 70 | N-(1-((1-(4-(3-(cyclopropylmethoxy)phenoxy)phenyl)pyrrolidin-3-yl)oxy)propan-2-yl)acetamide | 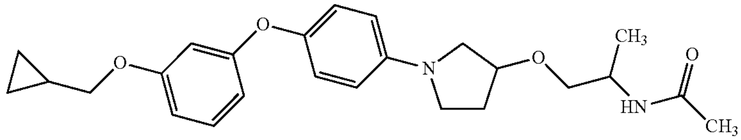 | | 425.1 |

TABLE 1-8

| Ex. No. | IUPACNAME | STRUCTURE | ADDITIVE | MS |
|---|---|---|---|---|
| 71 | N-(1-(6-((4-(3-(cyclopropylmethoxy)phenoxy)-2,6-difluorobenzyl)oxy)-5-(trifluoromethyl)pyridin-3-yl)ethyl)acetamide | 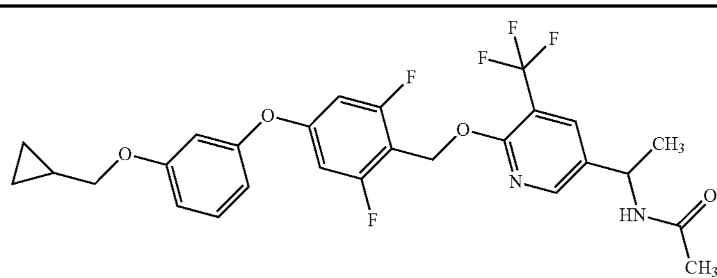 | | 535.1 |
| 72 | N-(1-((cis-4-(4-(3-(cyclopropylmethoxy)phenoxy)phenyl)cyclohexyl)oxy)propan-2-yl)acetamide | 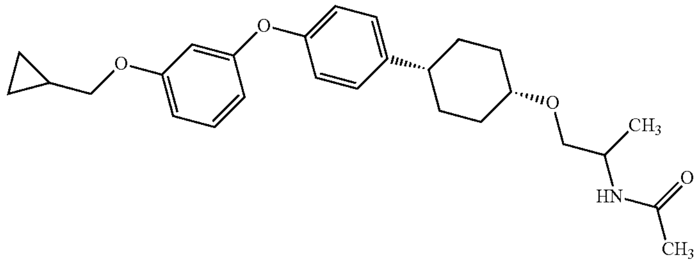 [SMILES: CC(=O)NC(C)CO[C@H]1CC[C@@H](c2ccc(Oc3cccc(OCC4CC4)c3)cc2)CC1] | | 438.1 |
| 73 | N-(1-(6-((4-(3-(cyclopropylmethoxy)phenoxy)-2,6-difluorobenzyl)oxy)-5-fluoropyridin-3-yl)ethyl)acetamide | 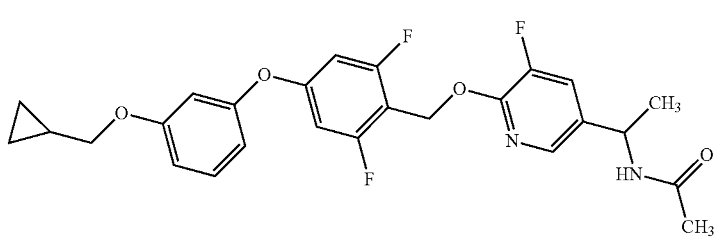 [SMILES: CC(=O)NC(C)c1cnc(OCc2c(F)cc(Oc3cccc(OCC4CC4)c3)cc2F)c(F)c1] | | 484.8 |

TABLE 1-8-continued

| Ex. No. | IUPAC NAME | STRUCTURE | ADDITIVE | MS |
|---|---|---|---|---|
| 74 | N-(4-(4-(4-(3-(cyclopropylmethoxy)phenoxy)phenyl)-1H-pyrazol-1-yl)butan-2-yl)acetamide | 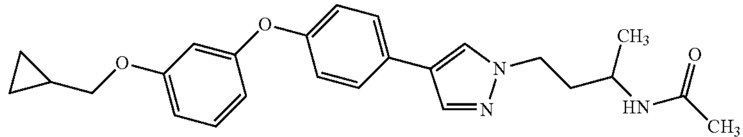 [SMILES: CC(=O)NC(C)CCn1cc(-c2ccc(Oc3cccc(OCC4CC4)c3)cc2)cn1] | | 420.1 |
| 75 | N-(4-(2-(4-(3-(cyclopropylmethoxy)phenoxy)piperidin-1-yl)-1,3-oxazol-5-yl)butan-2-yl)acetamide | 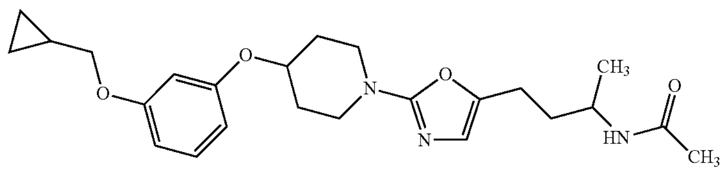 [SMILES: CC(=O)NC(C)CCc1cnc(N2CCC(Oc3cccc(OCC4CC4)c3)CC2)o1] | | 428.2 |
| 76 | N-((2S)-1-((2-(2-(3-(cyclopropylmethoxy)phenoxy)-1,3-thiazol-5-yl)-1,3-oxazol-5-yl)oxy)propan-2-yl)acetamide | 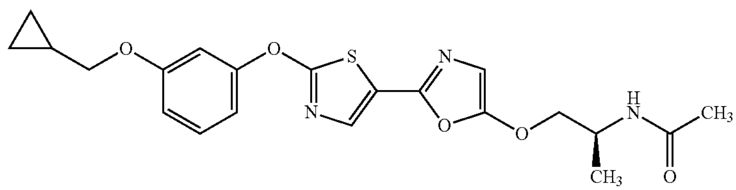 [SMILES: CC(=O)N[C@@H](C)COc1cnc(-c2cnc(Oc3cccc(OCC4CC4)c3)s2)o1] | | 430.0 |
| 77 | N-(1-(6-((4-(3-((2,2-difluorocyclopropyl)methoxy)phenoxy)-2,6-difluorobenzyl)oxy)pyridin-3-yl)ethyl)acetamide | 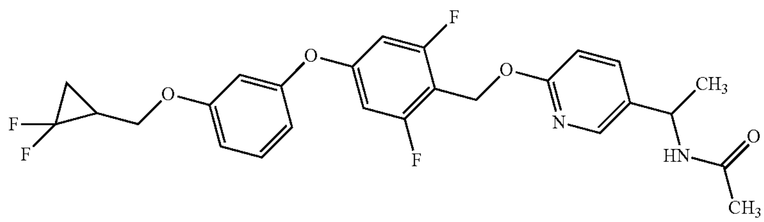 [SMILES: CC(=O)NC(C)c1ccc(OCc2c(F)cc(Oc3cccc(OCC4CC4(F)F)c3)cc2F)nc1] | | 505.0 |
| 78 | N-(1-(6-((4-(3-(cyclopropylmethoxy)phenoxy)-2,6-difluorobenzyl)oxy)pyridazin-3-yl)ethyl)acetamide | 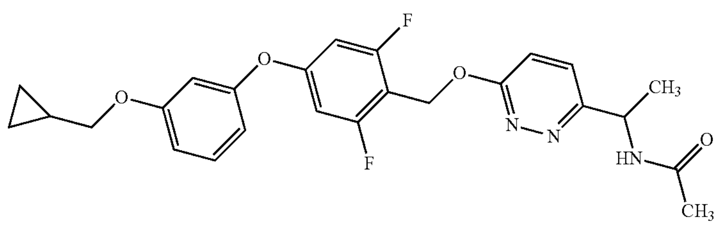 | | 470.0 |
| 79 | N-(4-(5-(4-(3-(cyclopropylmethoxy)phenoxy)phenyl)-3-thienyl)butan-2-yl)acetamide | 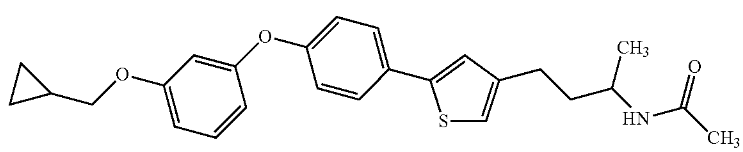 [SMILES: CC(=O)NC(C)CCc1csc(-c2ccc(Oc3cccc(OCC4CC4)c3)cc2)c1] | | 436.0 |
| 80 | N-(1-((trans-4-(4-(3-(cyclopropylmethoxy)phenoxy)phenyl)cyclohexyl)oxy)propan-2-yl)acetamide | 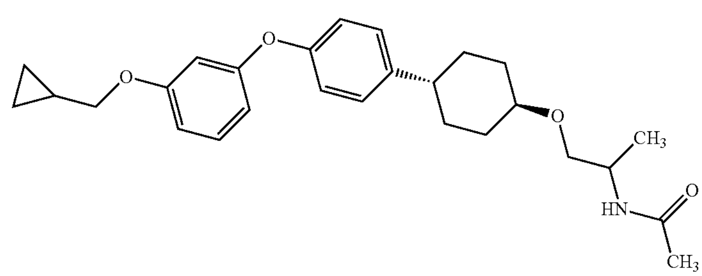 [SMILES: CC(=O)NC(C)CO[C@H]1CC[C@H](c2ccc(Oc3cccc(OCC4CC4)c3)cc2)CC1] | | 438.1 |

TABLE 1-9

| Ex. No. | IUPAC NAME | STRUCTURE | ADDITIVE | MS |
|---|---|---|---|---|
| 81 | N-(4-(5-(4-(3-(cyclopropylmethoxy)phenoxy)phenyl)-2-thienyl)butan-2-yl)acetamide | 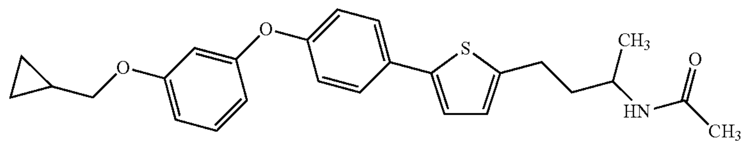 | | 436.0 |
| 82 | 1-((2S)-1-((2-(4-(3-(cyclopropylmethoxy)phenoxy)phenyl)-1,3-oxazol-5-yl)oxy)propan-2-yl)urea | 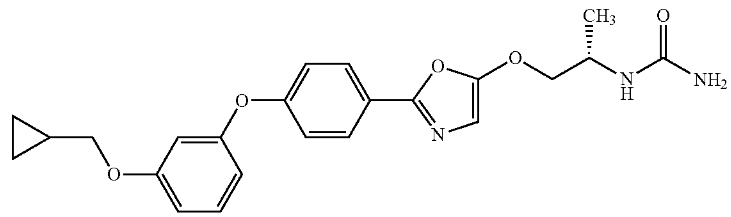 | | 424.0 |
| 83 | N-(4-(2-(4-(3-(cyclopropylmethoxy)phenoxy)phenyl)-1,3-oxazol-4-yl)butan-2-yl)acetamide | 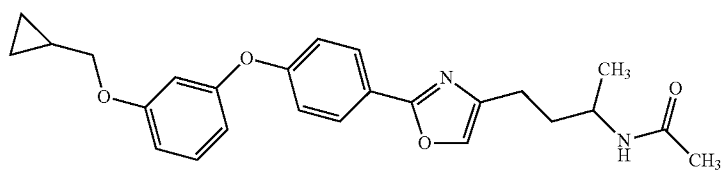 [SMILES: CC(=O)NC(C)CCc1coc(-c2ccc(Oc3cccc(OCC4CC4)c3)cc2)n1] | 421.0 | |
| 84 | N-(1-(4-((4-(3-(cyclopropylmethoxy)-4-fluorophenoxy)-2,6-difluorobenzyl)oxy)phenyl)ethyl)acetamide | 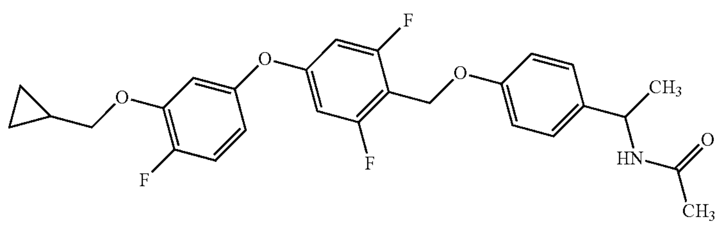 [SMILES: CC(=O)NC(C)c1ccc(OCc2c(F)cc(Oc3ccc(F)c(OCC4CC4)c3)cc2F)cc1] | | 486.0 |
| 85 | N-(1-(4-((4-((5-(cyclopropylmethoxy)pyridin-3-yl)oxy)-2,6-difluorobenzyl)oxy)phenyl)ethyl)acetamide | 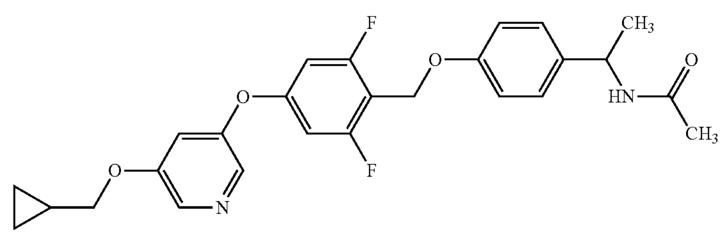 | | 469.0 |
| 86 | N-(1-(4-((4-((6-(cyclopropylmethoxy)pyridin-2-yl)oxy)-2,6-difluorobenzyl)oxy)phenyl)ethyl)acetamide | 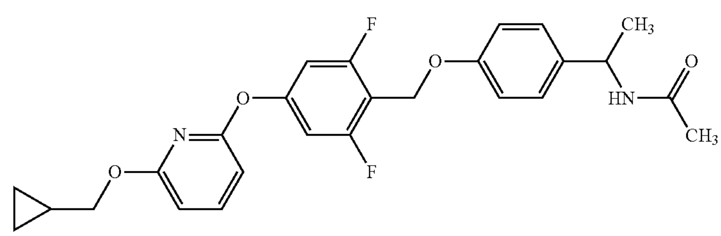 | | 469.2 |
| 87 | N-(1-(4-((4-(3-(cyclopropylmethoxy)-2-fluorophenoxy)-2,6-difluorobenzyl)oxy)phenyl)ethyl)acetamide | 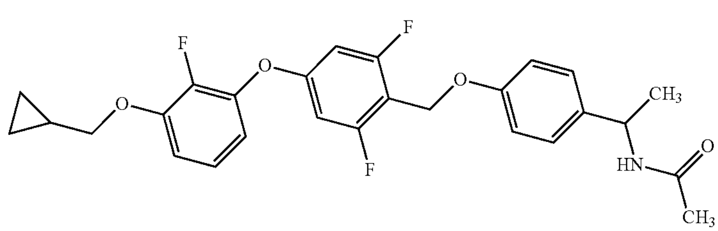 [SMILES: CC(=O)NC(C)c1ccc(OCc2c(F)cc(Oc3cccc(OCC4CC4)c3F)cc2F)cc1] | | 486.1 |

TABLE 1-9-continued

| Ex. No. | IUPACNAME | STRUCTURE | ADDITIVE | MS |
|---|---|---|---|---|
| 88 | N-(1-(4-((4-(5-(cyclopropylmethoxy)-2-fluorophenoxy)-2,6-difluorobenzyl)oxy)phenyl)ethyl)acetamide | 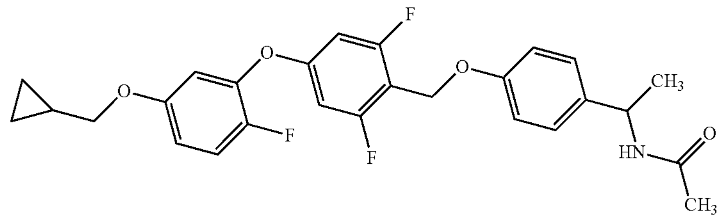 [SMILES: CC(=O)NC(C)c1ccc(OCc2c(F)cc(Oc3cc(OCC4CC4)ccc3F)cc2F)cc1] | | 486.1 |
| 89 | N-(4-(3-(4-(3-(cyclopropylmethoxy)phenoxy)phenyl)pyrrolidin-1-yl)-4-oxobutan-2-yl)acetamide | 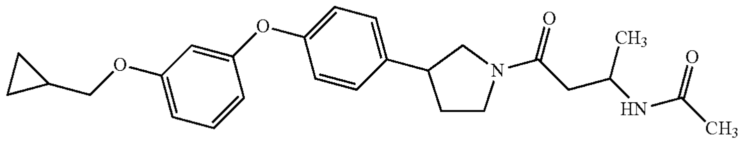 | | 437.2 |
| 90 | N-(1-(4-((4-((4-(cyclopropylmethoxy)pyridin-2-yl)oxy)-2,6-difluorobenzyl)oxy)phenyl)ethyl)acetamide | 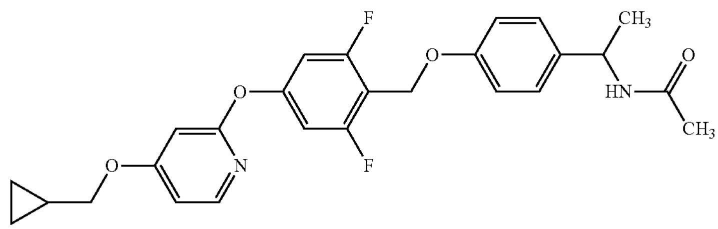 | | 469.2 |

TABLE 1-10

| Ex. No. | IUPACNAME | STRUCTURE | ADDITIVE | MS |
|---|---|---|---|---|
| 91 | N-(1-(4-((2,6-difluoro-4-((6-oxo-1-pentyl-1,6-dihydropyridin-3-yl)oxy)benzyl)oxy)phenyl)ethyl)acetamide | 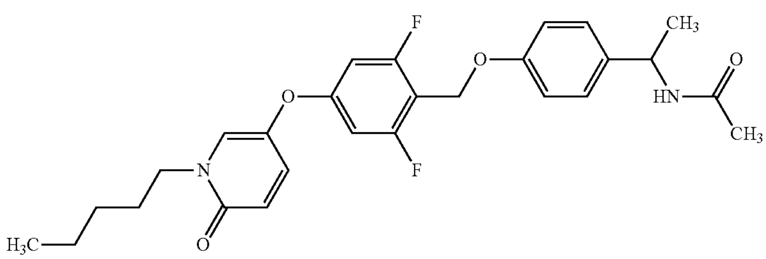 [SMILES: CCCCCn1cc(Oc2cc(F)c(COc3ccc(C(C)NC(C)=O)cc3)c(F)c2)ccc1=O] | | 485.2 |
| 92 | N-(4-(4'-(3-(cyclopropylmethoxy)phenoxy)biphenyl-4-yl)butan-2-yl)acetamide | 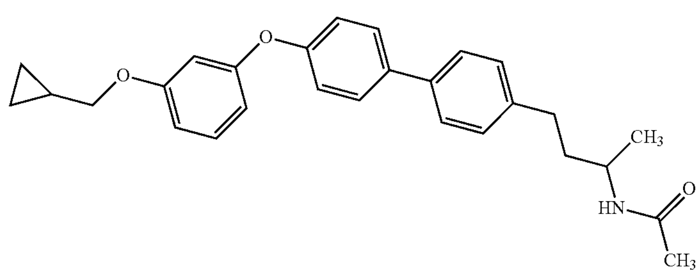 [SMILES: CC(=O)NC(C)CCc1ccc(-c2ccc(Oc3cccc(OCC4CC4)c3)cc2)cc1] | | 430.2 |
| 93 | N-(4-(5-(6-(3-(cyclopropylmethoxy)phenoxy)pyridin-3-yl)-2-thienyl)-4-oxobutan-2-yl)acetamide | 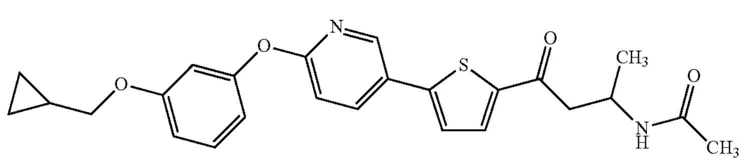 | | 451.0 |

TABLE 1-10-continued

| Ex. No. | IUPAC NAME | STRUCTURE | ADDITIVE | MS |
|---|---|---|---|---|
| 94 | N-(4-(2-(6-(3-(cyclopropylmethoxy)phenoxy)pyridin-3-yl)-1,3-thiazol-4-yl)-4-oxobutan-2-yl)acetamide | 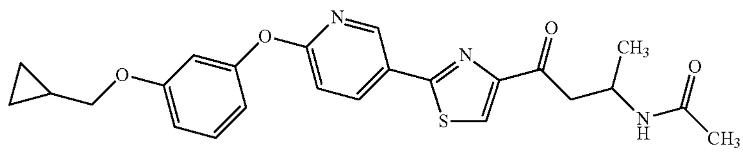 [SMILES: CC(=O)NC(C)CC(=O)c1csc(-c2ccc(Oc3cccc(OCC4CC4)c3)nc2)n1] | | 452.0 |
| 95 | N-(4-(1-(6-(3-(cyclopropylmethoxy)phenoxy)pyridin-3-yl)-1H-pyrazol-3-yl)-4-oxobutan-2-yl)acetamide | 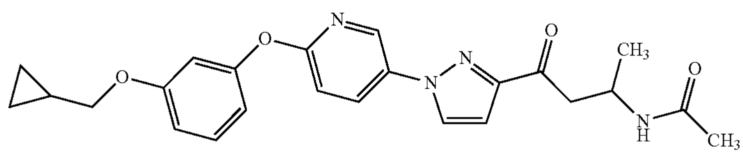 | | 435.0 |
| 96 | N-((2S)-1-((2-(4-(3-(cyclopropylmethoxy)phenoxy)phenyl)-4-methyl-1,3-oxazol-5-yl)oxy)propan-2-yl)acetamide | 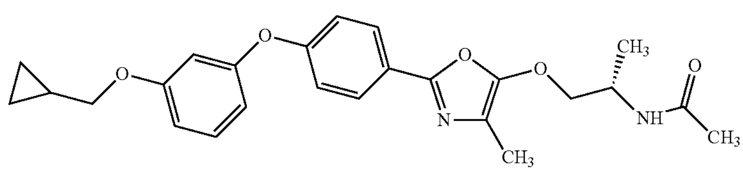 [SMILES: CC(=O)N[C@@H](C)COc1oc(-c2ccc(Oc3cccc(OCC4CC4)c3)cc2)nc1C] | | 437.0 |
| 97 | N-(4-(4'-(3-(cyclopropylmethoxy)phenoxy)biphenyl-4-yl)-4-oxobutan-2-yl)acetamide | 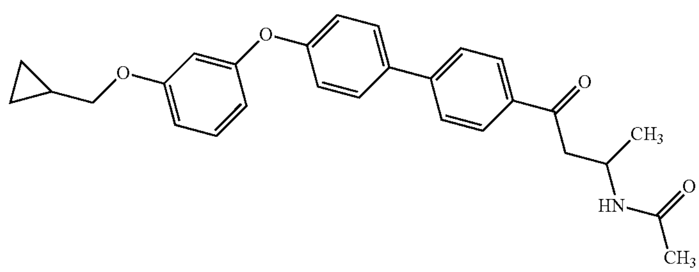 [SMILES: CC(=O)NC(C)CC(=O)c1ccc(-c2ccc(Oc3cccc(OCC4CC4)c3)cc2)cc1] | | 444.1 |
| 98 | N-(4-(5-(6-(3-(cyclopropylmethoxy)phenoxy)pyridin-3-yl)-3-thienyl)-4-oxobutan-2-yl)acetamide | 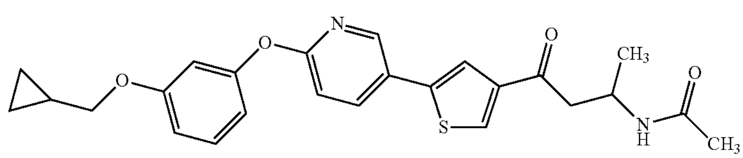 [SMILES: CC(=O)NC(C)CC(=O)c1csc(-c2ccc(Oc3cccc(OCC4CC4)c3)nc2)c1] | | 451.0 |
| 99 | N-((2S)-1-((2-(6-(3-(cyclopropylmethoxy)phenoxy)pyridin-3-yl)-1,3-oxazol-5-yl)oxy)propan-2-yl)acetamide | 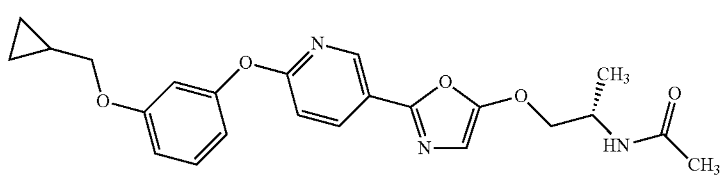 [SMILES: CC(=O)N[C@@H](C)COc1cnc(-c2ccc(Oc3cccc(OCC4CC4)c3)nc2)o1] | | 424.1 |
| 100 | N-(4-(2-(6-(3-(cyclopropylmethoxy)phenoxy)pyridin-3-yl)-1,3-thiazol-5-yl)-4-oxobutan-2-yl)acetamide | 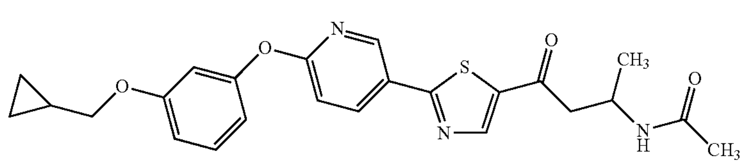 [SMILES: CC(=O)NC(C)CC(=O)c1cnc(-c2ccc(Oc3cccc(OCC4CC4)c3)nc2)s1] | | 452.0 |

TABLE 1-11

| Ex. No. | IUPAC NAME | STRUCTURE | ADDITIVE | MS |
|---|---|---|---|---|
| 101 | 1-((2S)-1-((2-(6-(3-(cyclopropylmethoxy)phenoxy)pyridin-3-yl)-1,3-oxazol-5-yl)oxy)propan-2-yl)urea | 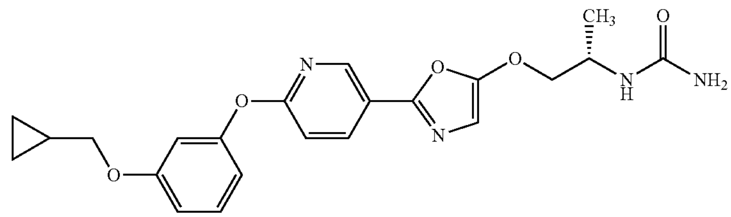 [SMILES: C[C@@H](COc1cnc(-c2ccc(Oc3cccc(OCC4CC4)c3)nc2)o1)NC(N)=O] | | 425.0 |
| 102 | N-((2S)-1-((2-(5-(3-(cyclopropylmethoxy)phenoxy)pyridin-2-yl)-1,3-oxazol-5-yl)oxy)propan-2-yl)acetamide | 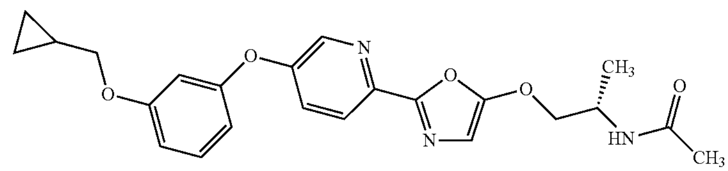 [SMILES: CC(=O)N[C@@H](C)COc1cnc(-c2ccc(Oc3cccc(OCC4CC4)c3)cn2)o1] | | 424.0 |
| 103 | N-(4-(1-(6-(3-(cyclopropylmethoxy)phenoxy)pyridin-3-yl)-1H-pyrazol-4-yl)-4-oxobutan-2-yl)acetamide | 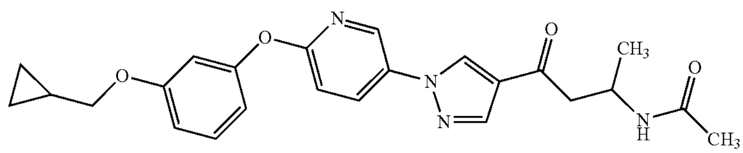 [SMILES: CC(=O)NC(C)CC(=O)c1cnn(-c2ccc(Oc3cccc(OCC4CC4)c3)nc2)c1] | | 435.0 |
| 104 | 1-((2S)-1-((2-(5-(3-(cyclopropylmethoxy)phenoxy)pyridin-2-yl)-1,3-oxazol-5-yl)oxy)propan-2-yl)urea | 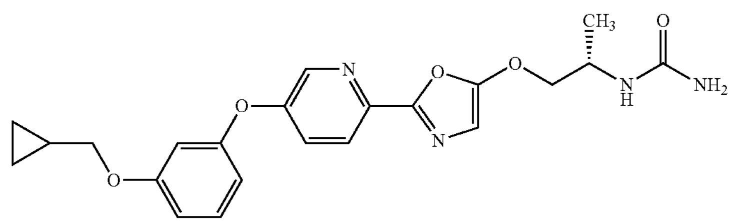 | | 425.0 |
| 105 | N-(4-(2-(6-(3-(cyclopropylmethoxy)phenoxy)pyridin-3-yl)-1,3-oxazol-5-yl)-4-oxobutan-2-yl)acetamide | 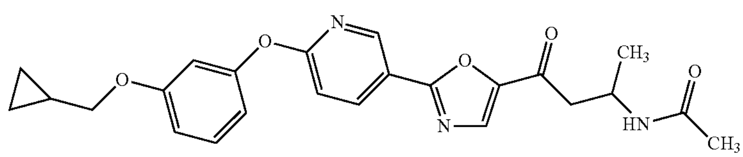 [SMILES: CC(=O)NC(C)CC(=O)c1cnc(-c2ccc(Oc3cccc(OCC4CC4)c3)nc2)o1] | | 436.1 |
| 106 | N-((2S)-1-((2-(6-(3-(cyclopropylmethoxy)phenoxy)-4-methylpyridin-3-yl)-1,3-oxazol-5-yl)oxy)propan-2-yl)acetamide | 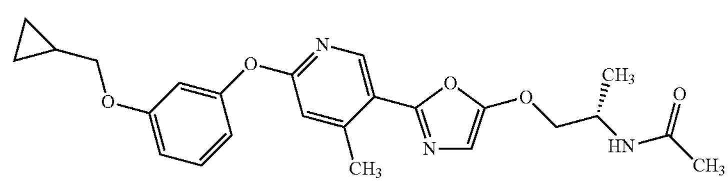 | | 438.0 |
| 107 | N-(4-(2-(6-(3-((2,2-difluorocyclopropyl)methoxy)phenoxy)pyridin-3-yl)-1,3-oxazol-5-yl)-4-oxobutan-2-yl)acetamide | 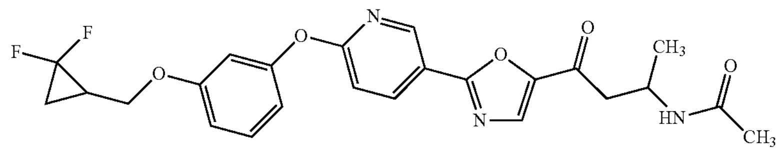 [SMILES: CC(=O)NC(C)CC(=O)c1cnc(-c2ccc(Oc3cccc(OCC4CC4(F)F)c3)nc2)o1] | | 472.1 |
| 108 | N-(4-(2-(6-(3-(2,2-difluoropropoxy)phenoxy)pyridin-3-yl)-1,3-oxazol-5-yl)-4-oxobutan-2-yl)acetamide | 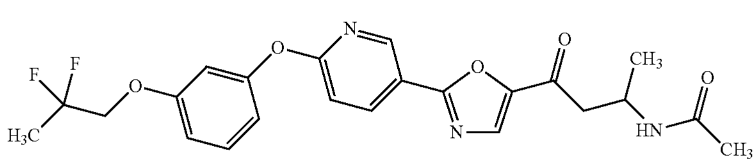 [SMILES: CC(=O)NC(C)CC(=O)c1cnc(-c2ccc(Oc3cccc(OCC(C)(F)F)c3)nc2)o1] | | 460.1 |

TABLE 1-12

| Ex. No. | IUPACNAME | STRUCTURE | ADDITIVE | MS |
|---|---|---|---|---|
| 109 | N-(1-(4-((1E)-2-(4-(3-(cyclopropylmethoxy)phenoxy)phenyl)prop-1-en-1-yl)phenyl)ethyl)acetamide | 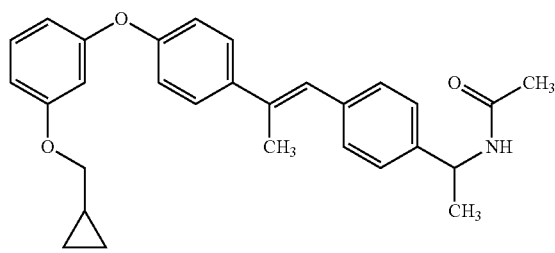 [SMILES: CC(=O)NC(C)c1ccc(/C=C(\C)c2ccc(Oc3cccc(OCC4CC4)c3)cc2)cc1] | | 442.2 |
| 110 | N-(1-(4-((E)-2-(4-(3-(cyclopropylmethoxy)phenoxy)phenyl)vinyl)phenyl)ethyl)acetamide | 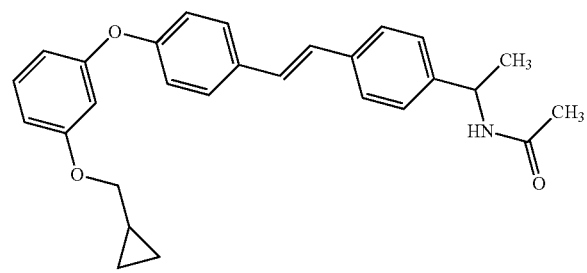 [SMILES: CC(=O)NC(C)c1ccc(/C=C/c2ccc(Oc3cccc(OCC4CC4)c3)cc2)cc1] | | 428.2 |
| 111 | N-(1-(4-(2-(4-(3-(cyclopropylmethoxy)phenoxy)phenyl)cyclopropyl)phenyl)ethyl)acetamide | 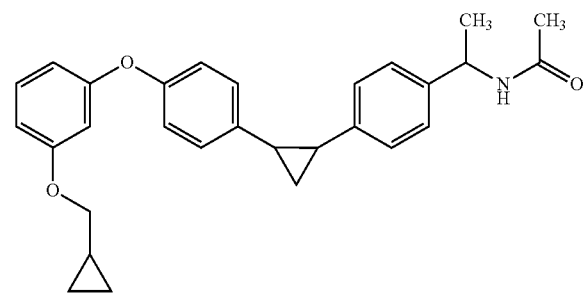 [SMILES: CC(=O)NC(C)c1ccc(C2CC2c2ccc(Oc3cccc(OCC4CC4)c3)cc2)cc1] | | 442.1 |
| 112 | N-(5-(1-acetamidoethyl)pyridin-2-yl)-4-(3-(cyclopropylmethoxy)phenoxy)benzamide | 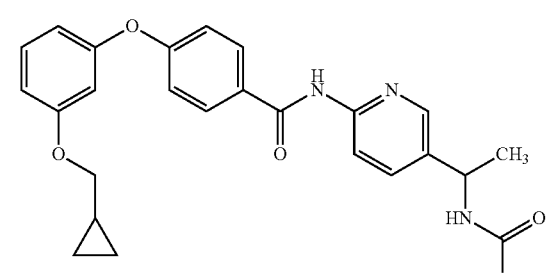 | | 446.1 |
| 113 | 4-(1-acetamidoethyl)-N-(6-(3-(cyclopropylmethoxy)phenoxy)pyridin-3-yl)-N-methylbenzamide | 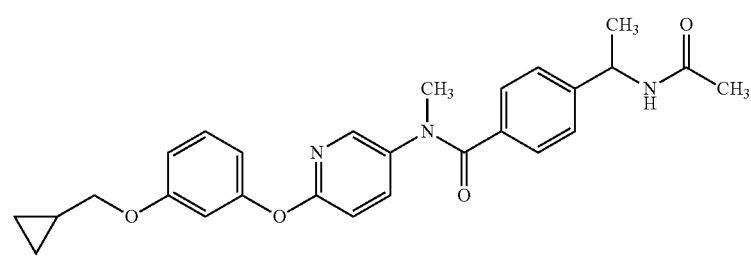 [SMILES: CC(=O)NC(C)c1ccc(C(=O)N(C)c2ccc(Oc3cccc(OCC4CC4)c3)nc2)cc1] | | 460.3 |

TABLE 1-12-continued

| Ex. No. | IUPACNAME | STRUCTURE | ADDITIVE | MS |
|---|---|---|---|---|
| 114 | N-(4-(1-acetamido-ethyl)phenyl)-5-(3-(cyclopropylmethoxy)phenoxy)pyridine-2-carboxamide | 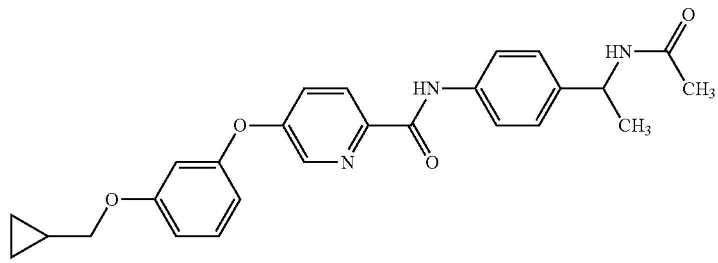 [SMILES: CC(=O)NC(C)c1ccc(NC(=O)c2ccc(Oc3cccc(OCC4CC4)c3)cn2)cc1] | | 446.2 |
| 115 | 4-(1-acetamido-ethyl)-N-(4-(3-(cyclopropylmethoxy)phenoxy)phenyl)benzamide | 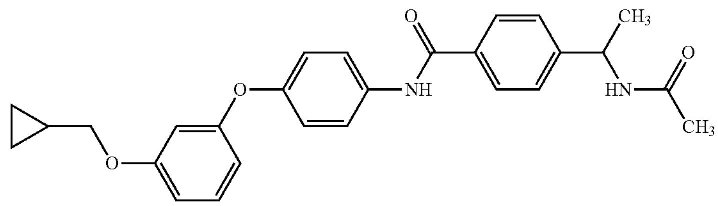 [SMILES: CC(=O)NC(C)c1ccc(C(=O)Nc2ccc(Oc3cccc(OCC4CC4)c3)cc2)cc1] | | 445.1 |

Experimental Example 1

The ACC2 inhibitory action of the compound of the present invention was evaluated by the following method.
(1) Cloning of Human ACC1 Gene and Preparation of Recombinant Baculovirus Human ACC1 gene was cloned by PCR using a human liver cDNA library (Clontech) as a template and Primer 1 and Primer 2 shown below. Primer 1 and Primer 2 were prepared by adding SalI, NotI restriction enzyme recognition sequences based on the information of the base sequence of human ACC1 gene (Genbank Accession U19822).

```
Primer 1:
                                     (SEQ ID NO: 1)
5'-AAAAGTCGACCCACCATGGATGAACCTTCTCCCTTGGCCC-3'

Primer 2:
                                     (SEQ ID NO: 2)
5'-AAAAGCGGCCGCCTACGTAGAAGGGGAGTCCATAGTG-3'
```

PCR was performed using Pyrobest DNA polymerase (TAKARA BIO INC.). The obtained PCR product was cloned to pT7 Blue vector (Novagen) and after confirmation of the base sequence, digested with restriction enzymes SalI and XbaI. The obtained DNA fragment was inserted into pFAST-BacHTc (Invitrogen) digested with restriction enzymes SalI and XbaI to give expression plasmid ACC1/pFAST-BacHTc.

Using the expression plasmid ACC1/pFAST-BacHTc and BAC-TO-BAC Baculovirus Expression System (Invitrogen), virus stock BAC-ACC1 of recombinant Baculovirus was prepared.
(2) Preparation of ACC1 Protein SF-9 cells (Invitrogen) were inoculated to a medium (10 L) for insect cells (Sf-900IISFM medium (Invitrogen) containing 5% fetal bovine serum (Trace), 50 mg/L Gentamicin (Wako Pure Chemical Industries, Ltd.) and 0.1% Pluronic F-68 (Invitrogen)) at $1.0 \times 10^6$ cells/mL, and cultured with shaking in Wave Bioreactor (GE Healthcare) at 27° C., 20 rpm, rocking angle 100, oxygen concentration 30%.

On day 2 of the culture, recombinant Baculovirus BAC-ACC1 was added, and the cells were cultured for 3 days. The culture medium was centrifuged at 4000×g for 10 min to give virus-infected cells. The cells were washed with phosphate buffered saline (Invitrogen) and centrifuged under the same conditions. The obtained cells were cryopreserved at −80° C.

The cryopreserved cells were thawed in ice, and suspended in 800 mL of 25 mM HEPES buffer (pH 7.5) containing 10% Glycerol, 0.3 M NaCl, 1 mM EDTA, 25 mM Sodium β-Glycerophosphate and 1 mM Sodium Orthovanadate, and supplemented with Complete Protease Inhibitor (Roche). The obtained suspension was homogenized two times in a polytron homogenizer (Kinematica) at 20,000 rpm for 20 sec. The obtained cell disruption solution was clarified by centrifugation at 186,000×g for 60 min, and the supernatant was passed through Ni-NTA Superflow Cartridges (5 mL) (QUIAGEN). Furthermore, it was washed with 25 mM HEPES buffer (pH 7.5) containing 20 mM Imidazole and 0.3 M NaCl, and eluted with 25 mM HEPES buffer (pH 7.5) containing 250 mM Imidazol and 0.3 M NaCl. The eluate was concentrated by Amicon Ultra-15 (Nihon Millipore K.K.) having a fraction molecular weight of 50K. The obtained concentrate was subjected to gel filtration with 50 mM HEPES buffer (pH 7.5) containing 10 mM $MgCl_2$, 2 mM dithiothreitol, 10 mM tripotassium citrate and 0.3 M NaCl by using HiLoad 26/60 Superdex200 prep grade gel filtration column (GE Healthcare) to give ACC1. The obtained ACC1 was cryopreserved at −80° C.
(3) Measurement of ACC1 Inhibitory Activity ACC1 obtained in the above-mentioned (2) was diluted with an enzyme reaction buffer (50 mM HEPES (pH 7.5), 10 mM $MgCl_2$, 10 mM Tripottasium Citrate, 2 mM Dithiothreitol, 0.001% Fatty acid free BSA) to a concentration of 0.2 μg/ml, and the mixture was added to each well of a 384 well assay plate by 10 μl. A test compound dissolved in dimethyl sulfoxide (DMSO) was diluted with an enzyme reaction buffer, and the resulting solution (5 μl) was added to each well. The mixture was incubated at room temperature for 60 min. Then, a substrate solution (50 mM $KHCO_3$, 200 μM ATP, 200 μM Acetyl-CoA, 5 μl) was added to each well, and the mixture was reacted at room temperature for 30 min. The reaction was quenched by adding a reaction quenching liquid (1.3% formic acid, 0.2 μM Malonyl-$^{13}C_3$-CoA) by 60 μL each to the obtained reaction mixtures (test compound addition group).

In addition, a reaction was performed in the same manner as above and without adding the test compound (test compound non-addition group).

Furthermore, a reaction was performed in the same manner as above without adding the test compound and adding ACC1 after addition of a reaction quenching liquid (control group).

The amount of Malonyl-CoA produced was measured by RapidFire-mass spectrometry, and determined by normalizing by the amount of Malonyl-$^{13}C_3$-CoA.

High throughput online solid phase extraction was performed using the RapidFire300™ system (Agilent Technologies). A sample was loaded and desalted in an SPE C4 cartridge (Agilent Technologies) at a flow rate of 1.5 mL/min with 5 mM dibutyl ammonium acetate in ultrapure water, eluted with 5 mM dibutyl ammonium acetate dissolved in acetonitrile/ultrapure water (90/10, v/v), at a flow rate of 1.0 mL/min, and introduced into a mass spectrometry part. The injection needle was washed with ultrapure water (500 milliseconds) and acetonitrile (500 milliseconds) to minimize carryover. The suction time (injection loop 5 μL), load/washing time, elution time and re-equilibration time were adjusted to 350, 3000, 4500 and 500 milliseconds, respectively, and the total cycle time was adjusted to about 10.0 seconds. The RapidFire300 system was controlled by RapidFire UI software version 3.6 (Agilent Technologies).

Mass spectrometry of the resultant product was performed using API4000™ triple quadrupole mass spectrometer (AB SCIEX) equipped with an electrospray ion sauce (Turbolon Spray™) on a positive selected reaction monitoring (SRM) mode. The conditions of SRM are shown in Table 2. The parameter of instrument was optimized as follows: capillary temperature 650° C., ion spray voltage 5.5 kV, collision gas 10, curtain gas 15 psi, ion source gas 1 60 psi, ion source gas 2 60 psi. The mass spectrometer was controlled by Analyst™ software version 1.5.1 (AB SCIEX). The peak area integration was analyzed using RapidFire integrator software version 3.6 (Agilent Technologies).

TABLE 2

| Analyte | Q1 --> Q3 (m/z) | DP (V) | CE (V) | CXP (V) |
|---|---|---|---|---|
| Malonyl-CoA (Product) | 854.2 --> 245.1 | 116 | 43 | 16 |
| Malonyl-$^{13}C_3$-CoA (Internal Standard) | 857.2 --> 248.3 | 116 | 43 | 16 |

DP: declustering potential,
CE: collision energy,
CXP: collision cell exit potential ACC1 inhibitory rate (%) was determined according to the following calculation formula.

(1−(produced amount of Malonyl-CoA of test compound addition group−produced amount of Malonyl-CoA of control group)÷(produced amount of Malonyl-CoA of test compound non-addition group−produced amount of Malonyl-CoA of control group))×100

The inhibitory rates (%) against ACC1 at 10 μM of the test compound are shown below.

TABLE 3

| Example No. | ACC1 inhibitory rate (%) at 10 μM |
|---|---|
| 19 | 83 |
| 30 | 99 |
| 32 | 97 |
| 35 | 78 |
| 39 | 82 |
| 42 | 85 |
| 43 | 94 |
| 46 | 95 |
| 48 | 96 |
| 64 | 99 |
| 67 | 92 |
| 68 | 96 |
| 69 | 96 |
| 73 | 98 |
| 78 | 97 |
| 82 | 96 |
| 83 | 97 |
| 99 | 100 |
| 101 | 98 |
| 102 | 100 |
| 103 | 98 |
| 104 | 95 |
| 105 | 100 |
| 106 | 98 |

As shown in Table 3, the compound of the present invention has a superior ACC1 inhibitory activity.

Experimental Example 2

The growth inhibitory activity of the compound on HCT116 cell was evaluated by the following method.

HCT116 cells were seeded in a 384 well blackplate at 900 cells/30 mL/well, and maintained in an assay medium (RPMI medium (Wako) containing 2% fetal bovine serum, 50 Unit/mL penicillin and 50 mg/mL streptomycin (Invitrogen)). The next day, a test compound dissolved in dimethyl sulfoxide (DMSO) was diluted with the assay medium, and the obtained compound solution was added by 10 mL to each well of a plate containing HCT116 cells, and incubated at 37° C., 5% $CO_2$ (test compound addition group).

A similar reaction was performed without adding a test compound (test compound non-addition group).

Furthermore, a similar reaction was performed under the conditions without adding HCT116 cell and a test compound (control group).

After 3 days, 20 mL of a CellTiter-Glo reagent (Promega KK) was added to the well, and the mixture was stirred for 10 min. Thereafter, the luminescence value of each well was measured by the EnVision™ multilabel counter (Perkin Elmer Inc.).

The HCT116 cell proliferation inhibitory rate (%) of the test compound was determined by the following calculation formula.

(1−(luminescence of test compound addition group−luminescence of control group)÷(luminescence of test compound non-addition group−luminescence of control group))×100

The HCT116 cell proliferation inhibitory rates (%) of the test compound (1 μM) are shown below.

TABLE 4

| Example No. | HCT116 cell proliferation inhibitory rate (%) at 1 μM |
|---|---|
| 19 | 15 |
| 30 | 28 |

TABLE 4-continued

| Example No. | HCT116 cell proliferation inhibitory rate (%) at 1 μM |
|---|---|
| 32 | 30 |
| 39 | 26 |
| 42 | 10 |
| 46 | 20 |
| 48 | 14 |
| 64 | 35 |
| 67 | 29 |
| 68 | 25 |
| 69 | 28 |
| 73 | 31 |
| 78 | 12 |
| 82 | 33 |
| 83 | 28 |

As shown in Table 4, the compound of the present invention has a superior cell proliferation inhibitory activity against colorectal cancer cells.

Experimental Example 3 (Inhibitory Effect on Liver Fibrosis Caused by NASH)

The action on liver fibrosis caused by non-alcoholic steatohepatitis (NASH) was verified by the following method.

For efficacy evaluation of action on the above-mentioned fibrosis, 9-week-old, male, homo low-density lipoprotein receptor deficient mouse (Jackson Laboratories (Bar Harbor Me., USA)) was used. Specifically, a choline-deficient amino acid diet (A08111307, Research Diets, New Brunswick, N.J., USA) was fed to the above-mentioned mouse for one week, and a drug was administered for three weeks, and then the collagen I gene expression level in liver after the drug administration was measured.

For the above-mentioned drug administration group, the test compound suspended in 0.5% methylcellulose solution was orally administered by gavage using a stomach gavage needle once per day (n=8). For control group, 0.5% methylcellulose solution was administered (normal diet group n=4, choline-deficient amino acid diet group n=8). The choline-deficient amino acid diet was continuously fed during the period for drug administration.

The measurement of the collagen I gene expression level in liver was performed by the following method. Specifically, after drug administration for 3 weeks, the mouse was sacrificed by euthanasia under isoflurane anesthesia under non-fasting, and the liver was removed. A part of the isolated liver was preserved in RNAlater (Ambion, Austin, Tex., USA). The total RNA was purified using RNeasy Mini Kit (Qiagen, Valencia, Calif., USA), and cDNA was prepared using High Capacity cDNA Reverse Transcription Kit (PN4368814, Applied Biosystems, Foster City, Calif., USA), and the collagen I gene expression level was measured (collagen type I alpha 1, Part Number 4351370, Applied Biosystems) by the quantitative PCR method (TaqMan Gene Expression Master Mix, PN4369016, Applied Biosystems).

The collagen I gene expression level was normalized by GAPDH, and statistical analysis with the choline-deficient amino acid diet control group was performed by two-tailed Williams' test (#P<0.05 vs. control value). The results are shown in FIG. 1.

As shown in FIG. 1, the test compound (specifically, the compound shown in Example 82) has a superior inhibitory effect on liver fibrosis caused by non-alcoholic steatohepatitis.

Experimental Example 4 (Anti-Fatty Liver Effect)

As representative examples of anti-fatty liver effect, the action on fatty liver caused by non-alcoholic steatohepatitis was verified by the following method.

For efficacy evaluation of action on the above-mentioned fibrosis, 9-week-old, male, homo low-density lipoprotein receptor deficient mouse (Jackson Laboratories (Bar Harbor Me., USA)) was used. Specifically, a choline-deficient amino acid diet (A08111307, Research Diets, New Brunswick, N.J., USA) was fed to the above-mentioned mouse for one week, and a drug was administered for three weeks, and then the triglyceride amount in liver after the drug administration was measured.

For the above-mentioned drug administration group, the test compound suspended in 0.5% methylcellulose solution was orally administered by gavage using a stomach gavage needle once per day (n=8). For control group, 0.5% methylcellulose solution was administered (normal diet group n=4, choline-deficient amino acid diet group n=8). The choline-deficient amino acid diet was continuously fed during the period for drug administration.

The measurement of the triglyceride amount in liver was performed by the following method. Specifically, after drug administration for 3 weeks, the mouse was sacrificed by euthanasia under isoflurane anesthesia under non-fasting, and the liver was removed. The total weight of the isolated liver was measured, and a part of the liver was immediately cryopreserved using dry ice. The cryopreserved liver sample was homogenized in 3.35% sodium sulfate solution, and the homogenized solution was mixed with hexane/2-propanol (3/2, v/v) solution. The centrifuged organic layer was evaporated to dryness in the presence of nitrogen gas. The dried substance was dissolved in 2-propanol, and the triglyceride concentration in the solution was measured by autoanalyzer (Hitachi 7180 type). The total triglyceride amount in the liver (mg/liver) was calculated from the weight of the liver used for the measurement and the total liver weight.

For the triglyceride amount in the liver, statistical analysis with the choline-deficient amino acid diet control group was performed by two-tailed Williams' test (#P<0.05 vs. control value). The results are shown in FIG. 2.

Figure 2:
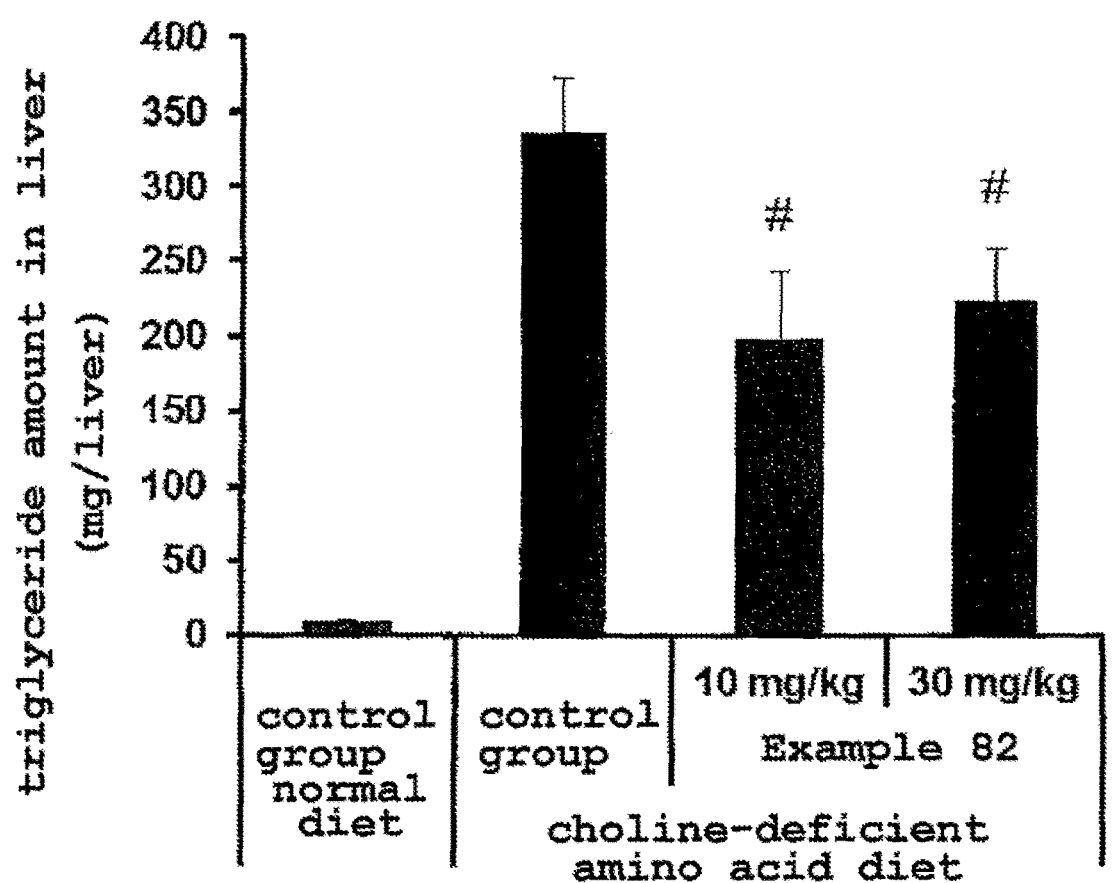
FIG. 2 shows the inhibitory effect of the present compound on fatty liver caused by non-alcoholic steatohepatitis.

As shown in FIG. 2, the test compound (specifically, the compound shown in Example 82) has a superior inhibitory effect on fatty liver caused by non-alcoholic steatohepatitis.

Formulation Example 1 (Production of Capsule)

| 1) compound of Example 1 | 30 mg |
| 2) finely-powdered cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2 (Production of Tablets)

| 1) compound of Example 1 | 30 g |
| 2) lactose | 50 g |
| 3) cornstarch | 15 g |

-continued

| | |
|---|---|
| 4) calcium carboxymethylcellulose | 44 g |
| 5) magnesium stearate | 1 g |
| 1000 tablets | total 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention has ACC (acetyl-CoA carboxylase) inhibitory action, and may be useful for the prophylaxis or treatment of cancer, hepatitis, hepatic fibrosis, fatty liver and the like.

This application is based on patent application No. 2015-071614 filed on Mar. 31, 2015 in Japan, the contents of which are encompassed in full herein.

Ring Q is benzene, a 6-membered monocyclic aromatic heterocycle or a 6-membered monocyclic non-aromatic heterocycle, each optionally substituted by 1 to 3 substituents selected from (a) a halogen atom, (b) a cyano group and (c) a $C_{1-6}$ alkyl group;

Ring R is benzene, a 5- or 6-membered monocyclic aromatic heterocycle or a 5- or 6-membered monocyclic non-aromatic heterocycle, each optionally substituted by 1 to 3 substituents selected from (a) a halogen atom, (b) an oxo group, (c) a $C_{1-6}$ alkyl group, and (d) a $C_{1-6}$ alkoxy group optionally substituted by 1 to 3 substituents selected from (i) a halogen atom and (ii) a $C_{3-10}$ cycloalkyl group optionally substituted by 1 to 3 halogen atoms:

Ring S is a 5-membered monocyclic aromatic heterocycle or a 5-membered monocyclic non-aromatic heterocycle, each optionally substituted by 1 to 3 substituents selected from

The invention claimed is:

1. A compound represented by the formula (I):

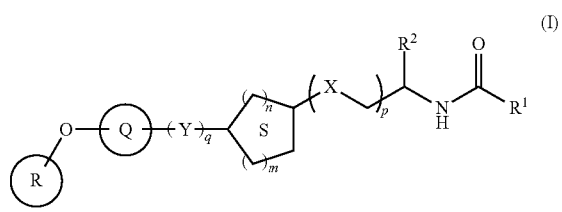

wherein $R^1$ is a $C_{1-6}$ alkyl group or an amino group;

$R^2$ is a $C_{1-6}$ alkyl group;

X is $-C(R^3)(R^4)-$, or $-O-$;

$R^3$ and $R^4$ are each independently a hydrogen atom or a hydroxy group;

(a) a halogen atom, (b) an optionally halogenated $C_{1-6}$ alkyl group, and (c) a $C_{1-6}$ alkoxy group;

p is 1; and q is 0, or a salt thereof.

2. The compound or salt according to claim 1, wherein X is $-O-$.

3. N((-2S)-1-((2-(4-(3-(Cyclopropylmethoxy)phenoxy)phenyl)-1,3-oxazol-5-yl)oxy)propan-2-yl)acetamide or a salt thereof.

4. 1-((2S)-1-((2-(4-(3-(Cyclopropylmethoxy)phenoxy)phenyl)-1,3-oxazol-5-yl)oxy)propan-2-yl)urea or a salt thereof.

5. A pharmaceutical composition comprising the compound or salt according to claim 1, and a pharmaceutically acceptable carrier.

6. A method for treatment of hepatitis, hepatic fibrosis or fatty liver in a mammal, which comprises administering an effective amount of the compound or salt according to claim 1 to the mammal.

* * * * *

SEQUENCE LISTING

```
<160> NUMBER OF SEQ ID NOS: 2

<210> SEQ ID NO 1
<211> LENGTH: 40
<212> TYPE: DNA
<213> ORGANISM: Artificial
<220> FEATURE:
<223> OTHER INFORMATION: PCR primer

<400> SEQUENCE: 1
aaaagtcgac ccaccatgga tgaaccttct cccttggccc                            40

<210> SEQ ID NO 2
<211> LENGTH: 37
<212> TYPE: DNA
<213> ORGANISM: Artificial
<220> FEATURE:
<223> OTHER INFORMATION: PCR primer

<400> SEQUENCE: 2
aaaagcggcc gcctacgtag aagggagtc catagtg                               37
```